(12) United States Patent
Cochrane et al.

(10) Patent No.: US 7,959,917 B2
(45) Date of Patent: Jun. 14, 2011

(54) BINDING MEMBERS FOR IGE MOLECULES

(75) Inventors: Duncan Cochrane, Cambridge (GB);
Suzanne Cohen, Cambridge (GB);
Claire Louise Dobson, Cambridge (GB); Per-Olof Eriksson, Lund (SE);
Karin Von Wachenfeldt, Lund (SE);
Phillip David Monk, Southampton (GB)

(73) Assignee: MedImmune Limited, Cambridge (GB)

( * ) Notice: Subject to any disclaimer, the term of this patent is extended or adjusted under 35 U.S.C. 154(b) by 356 days.

(21) Appl. No.: 12/032,061

(22) Filed: Feb. 15, 2008

(65) Prior Publication Data

US 2009/0060919 A1 Mar. 5, 2009

Related U.S. Application Data

(60) Provisional application No. 60/901,304, filed on Feb. 15, 2007.

(51) Int. Cl.
*A61K 39/00* (2006.01)

(52) U.S. Cl. ............... 424/139.1; 424/133.1; 424/141.1; 424/144.1; 424/805; 424/810; 530/387.3; 530/387.9; 530/388.1; 530/388.25; 530/862

(58) Field of Classification Search .................. None
See application file for complete search history.

(56) References Cited

U.S. PATENT DOCUMENTS

| 5,693,762 A * | 12/1997 | Queen et al. ............... 530/387.3 |
| 5,994,511 A * | 11/1999 | Lowman et al. ............ 530/387.3 |
| 6,172,213 B1 | 1/2001 | Lowman et al. |
| 2005/0169909 A1* | 8/2005 | Singh et al. ................ 424/130.1 |

FOREIGN PATENT DOCUMENTS

| WO | 8906138 A1 | 7/1989 |
| WO | 9111456 A1 | 8/1991 |
| WO | 9304173 A1 | 3/1993 |
| WO | 9421676 A1 | 9/1994 |
| WO | 9704807 A1 | 2/1997 |
| WO | 9901556 A2 | 1/1999 |
| WO | 200050460 A1 | 8/2000 |
| WO | 2003030833 A2 | 4/2003 |
| WO | 2004000217 A2 | 12/2003 |
| WO | 2004070010 A2 | 8/2004 |
| WO | 2004070011 A2 | 8/2004 |
| WO | 2005075504 A1 | 8/2005 |
| WO | 2008099188 A1 | 8/2008 |

OTHER PUBLICATIONS

Janeway et al., Immunobiology, 3rd edition, 1997, Garland Press, pp. 3:1 to 3:11.*
William E. Paul, M.D. ed., Fundamental Immunology, 3d ed. 1993, p. 242.*
Portolano et al., J Immunol. Feb. 1, 1993;150(3):880-7.*
Rudikoff et al., Proc Natl Acad Sci U S A. Mar. 1982;79(6):1979-83.*
Zheng et al., Biochem Biophys Res Commun. Oct. 31, 2008;375(4):619-22. Epub Aug. 24, 2008.*
Barbas et al., Proc Natl Acad Sci U S A. Mar. 28, 1995;92(7):2529-33.*
Clemens et al., Int Immunol. Dec. 1998;10(12):1931-42.*
Wurzburg B A et al: "Structure of the human IgE-Fc Cepsilon3-Cepsilon4 reveals conformational flexibility in the antibody effector domains" Immunity, Cell Press, US, vol. 13, No. 3, Sep. 1, 2000, pp. 375-385, ISSN: 1074-7613.
Holt L J et al: "Domain antibodies: proteins for therapy" Trends in Biotechnology, Elsevier Publications, Cambridge, GB, vol. 21, No. 11, Nov. 1, 2003, pp. 484-490, ISSN: 0167-7799.
Davies J et al: "Affinity improvement of single antibody VH domains: residues in all three hypervariable regions affect antigen binding" Immunotechnology, Elsevier Science Publishers BV, NL, vol. 2, No. 3, Sep. 1, 1996, pp. 169-179, ISSN: 1380-2933.

* cited by examiner

*Primary Examiner* — Michael Szperka

(57) ABSTRACT

This invention relates to binding members, especially antibody molecules, for IgE. The binding members are useful for, inter alia, treatment of disorders mediated by IgE including allergies and asthma.

13 Claims, 23 Drawing Sheets

Figure 2

Figure 1:
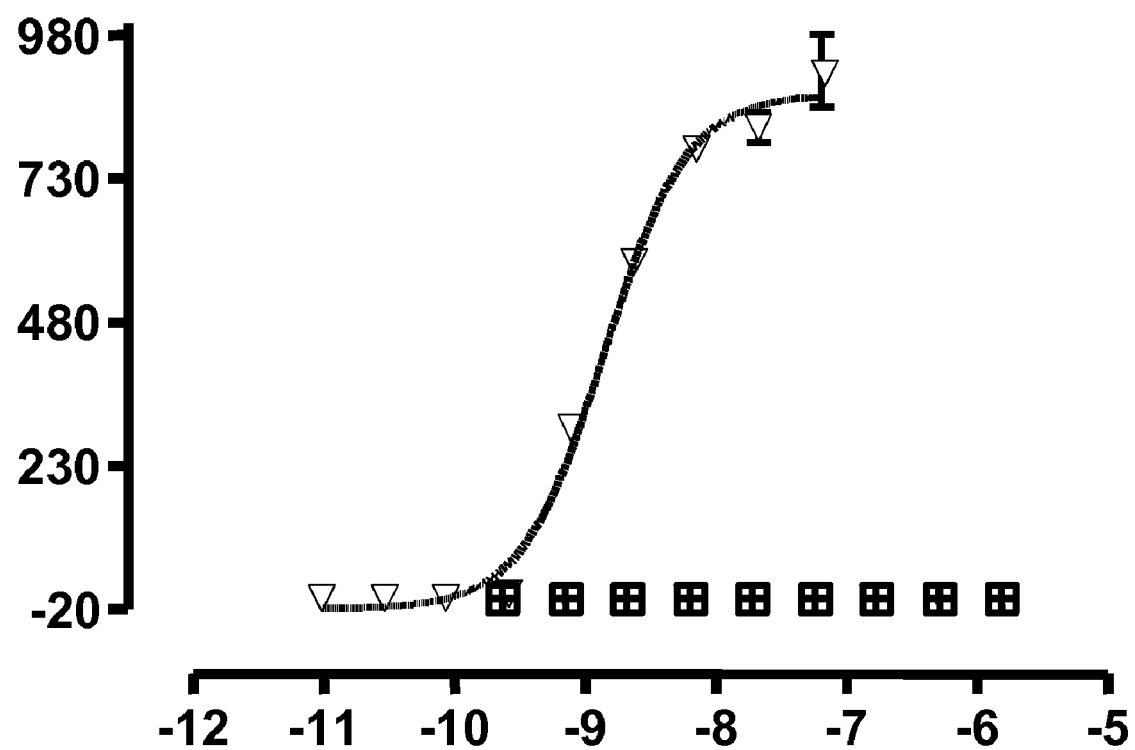

```
           10         20         30         40         50
ATGGGATGGAGTTGCATTATACTGTTTTTGGTTGCCACCGCTACTGGTGC
 M  G  W  S  C  I  I  L  F  L  V  A  T  A  T  G  A
           60         70         80         90        100
GCACTCTGCGGACCCCTGTGACTCTAATCCCAGGGGAGTGAGCGCATATC
 H  S  A  D  P  C  D  S  N  P  R  G  V  S  A  Y
          110        120        130        140        150
TCAGCAGGCCATCCCCTTTCGATCTTTTCATCAGCAAGAGCCCAACAATA
 L  S  R  P  S  P  F  D  L  F  I  S  K  S  P  T  I
          160        170        180        190        200
ACTTGCCTGGTAGTCGATCTCGCACCATCCAAGGAAACCGTCAATCTTAC
 T  C  L  V  V  D  L  A  P  S  K  E  T  V  N  L  T
          210        220        230        240        250
ATGGAGCAGAGCATCAGGTAAGCCTGTTCCTCACATACCTGCAACTGAAA
 W  S  R  A  S  G  K  P  V  P  H  I  P  A  T  E
          260        270        280        290        300
AAAAACAGCAGAGGAACGGTACTCTCACGGTGACTAGTATCCTTCCGGTG
 K  K  Q  R  N  G  T  L  T  V  T  S  I  L  P  V
          310        320        330        340        350
GTCACCCAGGATTGGATTGAGGGAGAGACTTACCAGTGCCGGGTCACACA
 V  T  Q  D  W  I  E  G  E  T  Y  Q  C  R  V  T  H
          360        370        380        390        400
CCCTCACCTGCCGCGAGCACTGGTGCGCTCCATGACAAAGACGTCCGGGC
 P  H  L  P  R  A  L  V  R  S  M  T  K  T  S  G
          410        420        430        440        450
CACGCGCGGCTCCCGAGGTGTACGTTTTTGCCACCCCCGAGAAACTCGAG
 P  R  A  A  P  E  V  Y  V  F  A  T  P  E  K  L  E
          460        470        480        490        500
AGCCGCGACAAGCGGACACTTGCCTGCCTGATCGAGAACTTTATGCCTGA
 S  R  D  K  R  T  L  A  C  L  I  E  N  F  M  P  E
          510        520        530        540        550
AGATATCTCTGTTCAGTGGCTGCACAGTGATGTGCAACTTCCCGATGCAC
 D  I  S  V  Q  W  L  H  S  D  V  Q  L  P  D  A
          560        570        580        590        600
GCCACAGTGTTACCCAGCCCAGGAAGACCAAAGGTAGTGGCTTCTTCGTG
 R  H  S  V  T  Q  P  R  K  T  K  G  S  G  F  F  V
          610        620        630        640        650
TTTTCCCGCCTCGAGGTGACCAAGGCAGAATGGGAGCAAAAGGATGAATT
 F  S  R  L  E  V  T  K  A  E  W  E  Q  K  D  E  F
          660        670        680        690        700
TATCTGCAGAGCGGTGCATGAAGCCGCGTCCCCTTCCTGGATCGTACAGC
 I  C  R  A  V  H  E  A  A  S  P  S  W  I  V  Q
          710        720        730        740        750
AGGCCGTCAGTGTGAATCCTGGGAAGGACTATAAGGATGATGACGACAAG
 Q  A  V  S  V  N  P  G  K  D  Y  K  D  D  D  D  K
          760        770        780
GCCGCACACCACCATCACCATCATCATCACCATCACTAG
 A  A  H  H  H  H  H  H  H  H  H  H  *
```

Figure 3A

```
         10         20         30         40         50
ATGGGATGGAGCTGTATCATCCTCTTCTTGGTAGCAACAGCTACAGGCGC
 M  G  W  S  C  I  I  L  F  L  V  A  T  A  T  G  A 60         70         80         90        100
GCACTCCGAGGTGCAGCTGGTGGAGTCTGGGGGAGGCTTGGTACAGCCTG
  H  S  E  V  Q  L  V  E  S  G  G  G  L  V  Q  P 110        120        130        140        150
GGAGGTCCCTGAGACTCTCCTGTGCAGCCTCTGGAGTCACCTTTAGCAGC
 G  R  S  L  R  L  S  C  A  A  S  G  V  T  F  S  S 160        170        180        190        200
CATGCCATGACCTGGGTCCGCCAGGCTCCAGGGAAGGGGCTGGAATGGGT
 H  A  M  T  W  V  R  Q  A  P  G  K  G  L  E  W  V 210        220        230        240        250
CTCAGGTATCAGTGGTAGTGGTGGTGACACATACCACGCAGACTCCGTGA
  S  G  I  S  G  S  G  G  D  T  Y  H  A  D  S  V 260        270        280        290        300
AGGGCCGGTTCACCATCTCCAGGGACAATTCCAAGAACACGGTGTATCTG
 K  G  R  F  T  I  S  R  D  N  S  K  N  T  V  Y  L 310        320        330        340        350
CAAATGAACAGCCTGCGAGCCGAGGACACGGCCATATATTACTGTGCGAT
 Q  M  N  S  L  R  A  E  D  T  A  I  Y  Y  C  A  I 360        370        380        390        400
TTTAGGAGTACTAAATGGTTTTGATATCTGGGGCCAAGGGACAATGGTCA
 L  G  V  L  N  G  F  D  I  W  G  Q  G  T  M  V 410        420        430        440        450
CCGTCTCCTCAGCCTCCATACAGAGCCCCTTCGTCTTCCCCTTGATCCCC
 T  V  S  S  A  S  I  Q  S  P  F  V  F  P  L  I  P 460        470        480        490        500
TGCTGCAAACACATTGCCTCCAATGCCACCTCCGTGACCCTGGGCTGCCT
 C  C  K  H  I  A  S  N  A  T  S  V  T  L  G  C  L 510        520        530        540        550
GGCCACGGGCTACTTCCCGGAGCCGGTGATGGTGACCTGGGACGCAGGCT
  A  T  G  Y  F  P  E  P  V  M  V  T  W  D  A  G 560        570        580        590        600
CCCTCAACAGAAGCACTATGACCTTACCAGCCACCACCTTCACGCCCTCC
 S  L  N  R  S  T  M  T  L  P  A  T  T  F  T  P  S 610        620        630        640        650
GGTCACTATGCCACCATCAGCTTGCTGACCGTCTCGGGTGCGTGGGCCAA
 G  H  Y  A  T  I  S  L  L  T  V  S  G  A  W  A  K 660        670        680        690        700
```

Figure 3B

```
GGAGACGTTCACCTGCCATGTGGTGCACACTCCATCGTCCGCAGACAAAG
 E  T  F  T  C  H  V  V  H  T  P  S  S  A  D  K 710       720       730       740       750
AGGTCAACAAAACCTTTGGCGTCTGCTCCAGGAACTTCACCCCACCTACC
 E  V  N  K  T  F  G  V  C  S  R  N  F  T  P  P  T 760       770       780       790       800
GTGAAGATCTTACAGTCATCCTGCGATGACGACGGGCACTTTCCCCCGAC
 V  K  I  L  Q  S  S  C  D  D  D  G  H  F  P  P  T 810       820       830       840       850
CATCCAGCTCCTGTGCCTCATCTCCGGGTACACCCCAGGGGCCATCAATG
  I  Q  L  L  C  L  I  S  G  Y  T  P  G  A  I  N 860       870       880       890       900
TCACCTGGCTGGAGAACGGGCAGGTCATGAAAGTGAACTCGCCCACCCCT
 V  T  W  L  E  N  G  Q  V  M  K  V  N  S  P  T  P 910       920       930       940       950
CCTGCCACGCAGGAGGGTGAGCTGGCCTCCACACAAAGTGAGTTCACCCT
 P  A  T  Q  E  G  E  L  A  S  T  Q  S  E  F  T  L 960       970       980       990      1000
CGCCCAGAAGCACTGGCTGTCGGACCGCACTTACACCTGCCAGGTCACCT
 A  Q  K  H  W  L  S  D  R  T  Y  T  C  Q  V  T 1010      1020      1030      1040      1050
ATCAAGGTACCACCTATAACGACAGCACCAAGAAGTGTGCAGATTCCAAC
 Y  Q  G  T  T  Y  N  D  S  T  K  K  C  A  D  S  N 1060      1070      1080      1090      1100
CCGAGAGGGGTGAGTGCCTACCTAAGCCGGCCCAGCCCGTTTGACCTGTT
 P  R  G  V  S  A  Y  L  S  R  P  S  P  F  D  L  F 1110      1120      1130      1140      1150
CATCAGCAAGTCGCCCACGATCACCTGTCTGGTGGTGGACCTGGCACCCA
 I  S  K  S  P  T  I  T  C  L  V  V  D  L  A  P 1160      1170      1180      1190      1200
GCAAGGAGACCGTGAACCTGACCTGGTCCCGGGCCAGTGGGAAGCCTGTG
 S  K  E  T  V  N  L  T  W  S  R  A  S  G  K  P  V 1210      1220      1230      1240      1250
CCCCACATCCCCGCAACGGAGAAGAAGCAGCAGCGCAATGGCACGTTAAC
 P  H  I  P  A  T  E  K  K  Q  Q  R  N  G  T  L  T 1260      1270      1280      1290      1300
CGTTACGTCCATCCTGCCGGTGGTCACCCAAGACTGGATCGAGGGGGAGA
  V  T  S  I  L  P  V  V  T  Q  D  W  I  E  G  E 1310      1320      1330      1340      1350
CCTACCAGTGCAGGGTGACCCACCCCCACCTCCCCAGGGCCCTCGTGCGG
 T  Y  Q  C  R  V  T  H  P  H  L  P  R  A  L  V  R 1360      1370      1380      1390      1400
```

Figure 3C

```
TCCATGACCAAGACCAGCGGCCCGCGTGCTGCCCCGGAAGTCTATGTGTT
 S  M  T  K  T  S  G  P  R  A  A  P  E  V  Y  V  F 1410      1420      1430      1440      1450
TGCAACGCCAGAGAAGCTAGAGAGCCGGACAAGCGCACCCTCGCCTGCC
  A  T  P  E  K  L  E  S  R  D  K  R  T  L  A  C 1460      1470      1480      1490      1500
TGATCCAGAACTTCATGCCTGAGGACATATCGGTGCAGTGGCTGCACAGC
 L  I  Q  N  F  M  P  E  D  I  S  V  Q  W  L  H  S 1510      1520      1530      1540      1550
GACGTGCAGCTCCCGGACGCCCGGCACAGCGTGACGCAGCCCCGCAAGAC
 D  V  Q  L  P  D  A  R  H  S  V  T  Q  P  R  K  T 1560      1570      1580      1590      1600
CAAGGGCTCCGGCTTCTTCGTCTTCAGCCGCCTGGAGGTGACCAAGGCCG
  K  G  S  G  F  F  V  F  S  R  L  E  V  T  K  A 1610      1620      1630      1640      1650
AATGGGAGCAGAAAGACGAGTTCATCTGCCGTGCAGTCCATGAGGCAGCG
 E  W  E  Q  K  D  E  F  I  C  R  A  V  H  E  A  A 1660      1670      1680      1690      1700
AGCCCCTCATGGATCGTCCAGCAAGCGGTGTCTGTAAATCCCGGTAAATGA
  S  P  S  W  I  V  Q  Q  A  V  S  V  N  P  G  K  *
```

Figure 4A

```
         10         20         30         40         50
ATGGGATGGAGCTGTATCATCCTCTTCTTGGTAGCAACAGCTACAGGCGC
 M  G  W  S  C  I  I  L  F  L  V  A  T  A  T  G  A 60         70         80         90        100
GCACTCCGAGGTGCAGCTGGTGGAGTCTGGGGGAGGCTTGGTACAGCCTG
  H  S  E  V  Q  L  V  E  S  G  G  G  L  V  Q  P 110        120        130        140        150
GGAGGTCCCTGAGACTCTCCTGTGCAGCCTCTGGAGTCACCTTTAGCAGC
 G  R  S  L  R  L  S  C  A  A  S  G  V  T  F  S  S 160        170        180        190        200
CATGCCATGACCTGGGTCCGCCAGGCTCCAGGGAAGGGGCTGGAATGGGT
  H  A  M  T  W  V  R  Q  A  P  G  K  G  L  E  W  V 210        220        230        240        250
CTCAGGTATCAGTGGTAGTGGTGGTGACACATACCACGCAGACTCCGTGA
  S  G  I  S  G  S  G  G  D  T  Y  H  A  D  S  V 260        270        280        290        300
AGGGCCGGTTCACCATCTCCAGGGACAATTCCAAGAACACGGTGTATCTG
 K  G  R  F  T  I  S  R  D  N  S  K  N  T  V  Y  L 310        320        330        340        350
CAAATGAACAGCCTGCGAGCCGAGGACACGGCCATATATTACTGTGCGAT
 Q  M  N  S  L  R  A  E  D  T  A  I  Y  Y  C  A  I 360        370        380        390        400
TTTAGGAGTACTAAATGGTTTTGATATCTGGGGCCAAGGGACAATGGTCA
 L  G  V  L  N  G  F  D  I  W  G  Q  G  T  M  V 410        420        430        440        450
CCGTCTCCTCAGCCTCCATACAGAGCCCCTTCGTCTTCCCCTTGATCCCC
 T  V  S  S  A  S  I  Q  S  P  F  V  F  P  L  I  P 460        470        480        490        500
TGCTGCAAACACATTGCCTCCAATGCCACCTCCGTGACCCTGGGCTGCCT
 C  C  K  H  I  A  S  N  A  T  S  V  T  L  G  C  L 510        520        530        540        550
GGCCACGGGCTACTTCCCGGAGCCGGTGATGGTGACCTGGGACGCAGGCT
  A  T  G  Y  F  P  E  P  V  M  V  T  W  D  A  G 560        570        580        590        600
CCCTCAACAGAAGCACTATGACCTTACCAGCCACCACCTTCACGCCCTCC
  S  L  N  R  S  T  M  T  L  P  A  T  T  F  T  P  S 610        620        630        640        650
GGTCACTATGCCACCATCAGCTTGCTGACCGTCTCGGGTGCGTGGGCCAA
 G  H  Y  A  T  I  S  L  L  T  V  S  G  A  W  A  K
```

Figure 4B

```
       660        670        680        690        700
GGAGATGTTCACCTGCCATGTGGTGCACACTCCATCGTCCGCAGACAAAG
 E  M  F  T  C  H  V  V  H  T  P  S  S  A  D  K 710        720        730        740        750
AGGTCAACAAAACCTTTGGCGTCTGCTCCAGGAACTTCACCCCACCTACC
 E  V  N  K  T  F  G  V  C  S  R  N  F  T  P  P  T 760        770        780        790        800
GTGAAGATCTTACAGTCATCCTGCGATGACGACGGGCACTTTCCCCCGAC
 V  K  I  L  Q  S  S  C  D  D  D  G  H  F  P  P  T 810        820        830        840        850
CATCCAGCTCCTGTGCCTCATCTCCGGGTACACCCCAGGGGCCATCAATG
 I  Q  L  L  C  L  I  S  G  Y  T  P  G  A  I  N 860        870        880        890        900
TCACCTGGCTGGAGAACGGGCAGGTCATGAAAGTGAACTCGCCCACCCCT
 V  T  W  L  E  N  G  Q  V  M  K  V  N  S  P  T  P 910        920        930        940        950
CCTGCCACGCAGGAGGGTGAGCTGGCCTCCACACAAAGTGAGTTCACCCT
 P  A  T  Q  E  G  E  L  A  S  T  Q  S  E  F  T  L 960        970        980        990       1000
CGCCCAGAAGCACTGGCTGTCGGACCGCACTTACACCTGCCAGGTCACCT
 A  Q  K  H  W  L  S  D  R  T  Y  T  C  Q  V  T 1010       1020       1030       1040       1050
ATCAAGGTACCACCTATAACGACAGCACCAAGAAGTGTGCAGATTCCAAC
 Y  Q  G  T  T  Y  N  D  S  T  K  K  C  A  D  S  N 1060       1070       1080       1090       1100
CCGAGAGGGGTGAGTGCCTACCTAAGCCGGCCCAGCCCGTTTGACCTGTT
 P  R  G  V  S  A  Y  L  S  R  P  S  P  F  D  L  F 1110       1120       1130       1140       1150
CATCAGCAAGTCGCCCACGATCACCTGTCTGGTGGTGGACCTGGCACCCA
 I  S  K  S  P  T  I  T  C  L  V  V  D  L  A  P 1160       1170       1180       1190       1200
GCAAGGAGACCGTGAACCTGACCTGGTCCCGGGCCAGTGGGAAGCCTGTG
 S  K  E  T  V  N  L  T  W  S  R  A  S  G  K  P  V 1210       1220       1230       1240       1250
CCCCACATCCCCGCAACGGAGAAGAAGCAGCAGCGCAATGGCACGTTAAC
 P  H  I  P  A  T  E  K  K  Q  Q  R  N  G  T  L  T 1260       1270       1280       1290       1300
CGTTACGTCCATCCTGCCGGTGGTCACCCAAGACTGGATCGAGGGGGAGA
 V  T  S  I  L  P  V  V  T  Q  D  W  I  E  G  E 1310       1320       1330       1340       1350
CCTACCAGTGCAGGGTGACCCACCCCCACCTCCCCAGGGCCCTCGTGCGG
 T  Y  Q  C  R  V  T  H  P  H  L  P  R  A  L  V  R
```

Figure 4C

```
         1360       1370       1380       1390       1400
TCCATGACCAAGACCAGCGGCCCGCGTGCTGCCCCGGAAGTCTATGTGTT
  S  M  T  K  T  S  G  P  R  A  A  P  E  V  Y  V  F 1410       1420       1430       1440       1450
TGCAACGCCAGAGAAGCTAGAGAGCCGGGACAAGCGCACCCTCGCCTGCC
  A  T  P  E  K  L  E  S  R  D  K  R  T  L  A  C 1460       1470       1480       1490       1500
TGATCGAGAACTTCATGCCTGAGGACATATCGGTGCAGTGGCTGCACAGC
  L  I  E  N  F  M  P  E  D  I  S  V  Q  W  L  H  S 1510       1520       1530       1540       1550
GACGTGCAGCTCCCGGACGCCCGGCACAGCGTGACGCAGCCCCGCAAGAC
  D  V  Q  L  P  D  A  R  H  S  V  T  Q  P  R  K  T 1560       1570       1580       1590       1600
CAAGGGCTCCGGCTTCTTCGTCTTCAGCCGCCTGGAGGTGACCAAGGCCG
  K  G  S  G  F  F  V  F  S  R  L  E  V  T  K  A 1610       1620       1630       1640       1650
AATGGGAGCAGAAAGACGAGTTCATCTGCCGTGCAGTCCATGAGGCAGCG
  E  W  E  Q  K  D  E  F  I  C  R  A  V  H  E  A  A 1660       1670       1680       1690       1700
AGCCCCTCATGGATCGTCCAGCAAGCGGTGTCTGTAAATCCCGGTAAATG A
  S  P  S  W  I  V  Q  Q  A  V  S  V  N  P  G  K  *
                                                    a
```

Figure 5A

```
           10         20         30         40         50
    ATGGGTTGGAGTTGTATAATTCTCTTTCTGGTGGCTACCGCTACCGGTGT
     M  G  W  S  C  I  I  L  F  L  V  A  T  A  T  G  V 60         70         80         90        100
    GCACTCCCAGTCAGCTCTGACGCAACCAGCTTCCGTTTCAGGGAGCCCAG
      H  S  Q  S  A  L  T  Q  P  A  S  V  S  G  S  P 110        120        130        140        150
    GGCAGAGTATAACCATCAGTTGCACTGGCACTAGCTCCGACGTTGGCGGA
     G  Q  S  I  T  I  S  C  T  G  T  S  S  D  V  G  G 160        170        180        190        200
    TACAAGTACGTATCTTGGTATCAACAGCACCCCGGAAAAGCTCCTAAGCT
     Y  K  Y  V  S  W  Y  Q  Q  H  P  G  K  A  P  K  L 210        220        230        240        250
    GATGATTTTCGAGGTTTCCAACAGACCCAGCGGTGTACCTAATCGGTTCT
      M  I  F  E  V  S  N  R  P  S  G  V  P  N  R  F 260        270        280        290        300
    CTGGCTCTAAATCCGGGAACACTGCCTCACTCACCATCAGCGGACTGCAG
      S  G  S  K  S  G  N  T  A  S  L  T  I  S  G  L  Q 310        320        330        340        350
    GTGGAAGACGAGGCGGACTATTATTGCAGCTCTCTCACCAGACGCGTTAC
     V  E  D  E  A  D  Y  Y  C  S  S  L  T  R  R  V  T 360        370        380        390        400
    CGTCATTTTTGGCGGAGGCACTAAGCTGACCGTTCTCGGCCAACCTAAAG
      V  I  F  G  G  G  T  K  L  T  V  L  G  Q  P  K 410        420        430        440        450
    CCGCCCCATCTGTGACCCTTTTTCCTCCCAGCAGCGAGGAACTGCAGGCC
      A  A  P  S  V  T  L  F  P  P  S  S  E  E  L  Q  A 460        470        480        490        500
    AATAAGGCCACTCTCGTGTGCCTCATGTCAGACTTTTACCCAGGGATCCT
      N  K  A  T  L  V  C  L  M  S  D  F  Y  P  G  I  L 510        520        530        540        550
    GACCGTGACCTGGAAGGCCGACGGAACCCCCATCACACAGGGCGTGGAAA
      T  V  T  W  K  A  D  G  T  P  I  T  Q  G  V  E 560        570        580        590        600
    TGACCACGCCAAGTAAGCAGTCTAACAACAAATACGCCGCATCTAGCTAC
      M  T  T  P  S  K  Q  S  N  N  K  Y  A  A  S  S  Y 610        620        630        640        650
    TTGAGCCTGACCCCAGAGCAGTGGCGGAGTCACAATAGCTACAGCTGCCA
      L  S  L  T  P  E  Q  W  R  S  H  N  S  Y  S  C  Q
```

Figure 5B

```
         660       670       680       690       700
AGTGATGCACGAGGGATCAATCGTGGAGAAGACTGTTGCTCCAGCCGAGT
  V  M  H  E  G  S  I  V  E  K  T  V  A  P  A  E

GCTCCTAA
 C  S  *
```

Figure 6A

```
         10        20        30        40        50
ATGGGTTGGAGTTGTATAATTCTCTTTCTGGTGGCTACCGCTACCGGTGT
 M  G  W  S  C  I  I  L  F  L  V  A  T  A  T  G  V 60        70        80        90       100
GCACTCCCAGTCAGCTCTGACGCAACCAGCTTCCGTTTCAGGGAGCCCAG
 H  S  Q  S  A  L  T  Q  P  A  S  V  S  G  S  P 110       120       130       140       150
GGCAGAGTATAACCATCAGTTGCACTGGCACTAGCTCCGACGTTGGCGGA
 G  Q  S  I  T  I  S  C  T  G  T  S  S  D  V  G  G 160       170       180       190       200
TACAAGTACGTATCTTGGTATCAACAGCACCCCGGAAAAGCTCCTAAGCT
 Y  K  Y  V  S  W  Y  Q  Q  H  P  G  K  A  P  K  L 210       220       230       240       250
GATGATTTTCGAGGTTTCCAACAGACCCAGCGGTGTACCTAATCGGTTCT
 M  I  F  E  V  S  N  R  P  S  G  V  P  N  R  F 260       270       280       290       300
CTGGCTCTAAATCCGGGAACACTGCCTCACTCACCATCAGCGGACTGCAG
 S  G  S  K  S  G  N  T  A  S  L  T  I  S  G  L  Q 310       320       330       340       350
GTGGAAGACGAGGCGGACTATTATTGCAGCTCTCTCACCAGACGCGTTAC
 V  E  D  E  A  D  Y  Y  C  S  S  L  T  R  R  V  T 360       370       380       390       400
CGTCATTTTTGGCGGGGGGACTAAGCTGACCGTTCTCGGCCAACCTAAAG
 V  I  F  G  G  G  T  K  L  T  V  L  G  Q  P  K 410       420       430       440       450
CCGCCCCCTCTGTGACCCTTTTTCCCCCTAGCAGCGAGGAACTGCAGGCC
 A  A  P  S  V  T  L  F  P  P  S  S  E  E  L  Q  A 460       470       480       490       500
AATAAGGCCACTCTCGTGTGCCTCATCTCAGACTTTTACCCAGGGGCCGT
 N  K  A  T  L  V  C  L  I  S  D  F  Y  P  G  A  V 510       520       530       540       550
GGAGGTGGCCTGGAAGGCCGACGGAAGCGCCGTCAACGCGGGCGTGGAAA
 E  V  A  W  K  A  D  G  S  A  V  N  A  G  V  E 560       570       580       590       600
CGACCAAGCCAAGTAAGCAGTCTAACAACAAATACGCCGCATCTAGCTAC
 T  T  K  P  S  K  Q  S  N  N  K  Y  A  A  S  S  Y 610       620       630       640       650
TTGAGCCTGACCTCAGACCAGTGGAAGAGTCACAAGAGCTACAGCTGCCA
 L  S  L  T  S  D  Q  W  K  S  H  K  S  Y  S  C  Q
```

Figure 6B

```
         660       670       680       690       700
AGTGACACACGAGGGATCAACCGTGGAGAAGACTGTTGCTCCAACCGAGT
  V  T  H  E  G  S  T  V  E  K  T  V  A  P  T  E

GCTCCTAA
 C  S  *
```

Figure 10
a)
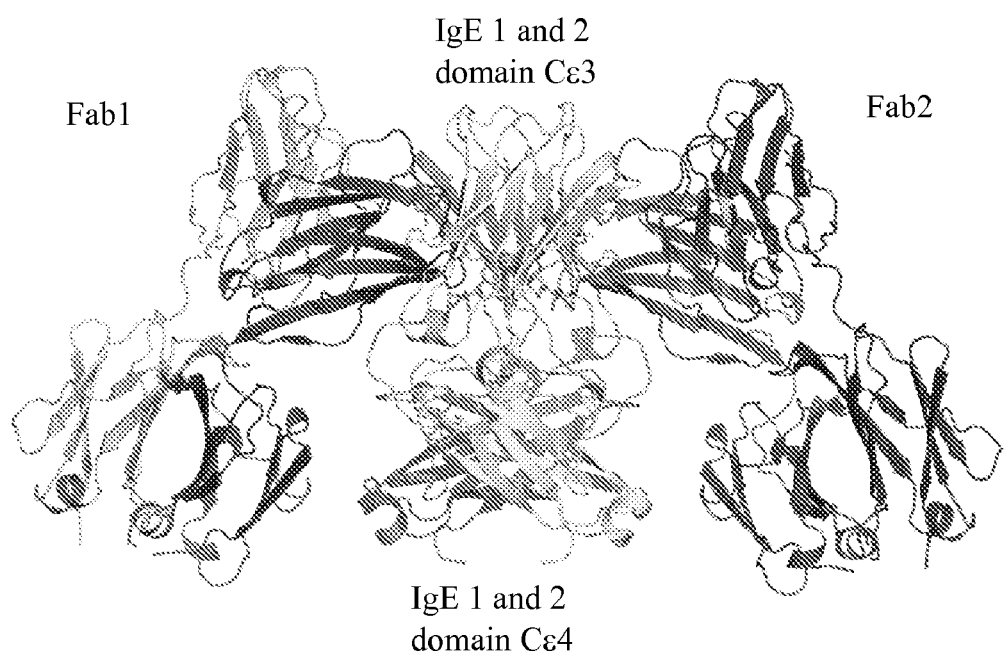
b)
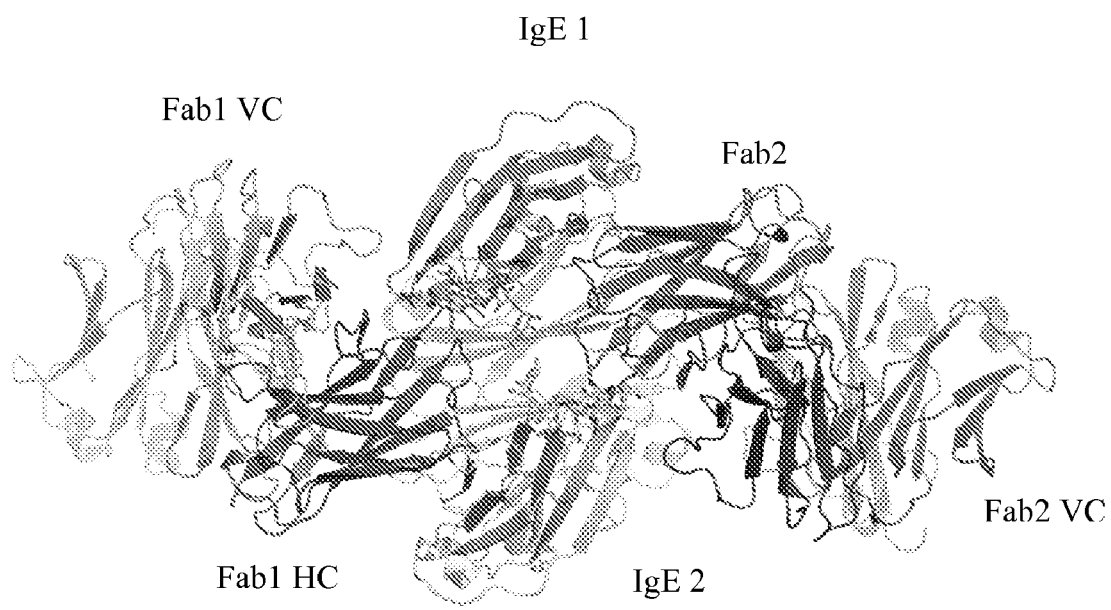

BINDING MEMBERS FOR IGE MOLECULES

This application claims the benefit under 35 U.S.C. §119 (e) of Application No. 60/901,304 filed on 15 Feb. 2007. This invention relates to binding members, especially antibody molecules, for IgE. The binding members are useful for, inter alia, treatment of disorders mediated by IgE including allergies and asthma.

FIELD OF THE INVENTION

IgE is a member of the immunoglobulin family and mediates allergic responses such as asthma, food allergies, type 1 hypersensitivity and sinus inflammation.

IgE is secreted by, and expressed on the surface of, B-cells. Briefly, IgE is anchored in the B-cell membrane by a transmembrane domain that is linked to the mature IgE molecule through a short membrane-binding region. IgE may also be bound via its Fc region to B-cells, monocytes, eosinophils and platelets through a low affinity IgE receptor (FcεRII, also known as CD23). Upon exposure to an allergen, B-cells that produce allergen-specific IgE are clonally amplified. Allergen-specific IgE is then released into the circulation by the B-cells where it is in turn bound by B-cells through the FcεRII, as well as by mast cells and basophils through a high affinity receptor (FcεRI). Such mast cells and basophils are thereby sensitized for allergen. Subsequent exposure to the allergen cross-links the FcεRI on mast cells and basophils thereby activating their release of histamine and other factors responsible for clinical hypersensitivity and anaphylaxis.

Binding members that inhibit binding to and functional activity through FcERI with or without simultaneous inhibition of FcERII are useful for inhibiting IgE-mediated disease conditions, such as allergies and asthma.

It is generally understood that FcεRI and FcεRII bind to recognition site(s) in the IgE constant (Fc) domain. Various studies have been undertaken to identify these recognition sites. For example, peptides corresponding to specific portions of the IgE molecule have been used as either competitive inhibitors of IgE-receptor binding (Burt et al., Eur. J. Immun, 17:437-440 [1987]; Helm et al., Nature, 331:180-183 [1988]; Helm et al., Proc. Natl. Acad. Sci., 86:9465-9469 [1989]; Vercelli et al., Nature, 338:649-651 [1989]; Nio et al., Peptide Chemistry, 203-208 [1990]), or to elicit anti-IgE antibodies that might block IgE-receptor interaction (Burt et al., Molec. Immun. 24:379-389 [1987]; Robertson et al., Molec. Immun., 25:103-113 [1988]; Baniyash et al., Molec. Immun. 25:705-711 [1988]).

More recently, Xolair® (Omalizumab) has been produced and marketed for treating asthma patients. Xolair® is a humanized IgG1k monoclonal antibody that selectively binds to human IgE, thereby reducing the binding of IgE to at least FcεRI on the surface of mast cells and basophils. By reducing surface-bound IgE on FcεRI-bearing cells, Xolair® reduces somewhat the degree of release of mediators of the allergic response. Xolair® is disclosed in International patent application publication numbers: WO 93/04173 and WO 97/04807.

However, other binding members for IgE, such as those with a higher affinity and/or potency than Xolair®, are needed to improve this promising therapeutic strategy.

THE INVENTION

By utilising appropriately designed selection techniques and assays, we have developed binding members which inhibit binding to and functional activity through FcERI (the high-affinity IgE receptor present on mast cells) with or without simultaneous inhibition of FcERII.

A binding member of the invention inhibits binding to and functional activity through FcERI with or without simultaneous inhibition of FcERII. The inhibition of binding may be by direct inhibition, for example, by neutralizing IgE. The binding member of the invention typically neutralizes human IgE with an IC50 of less than about 10 nM as determined by, for example, an RBL-ER51 calcium signalling assay. In certain embodiments, the binding member of the invention neutralizes human IgE with an IC50 of less than about 1 nM, or less than about 0.5 nM, or less than about 0.2 nM as determined by an RBL-ER51 calcium signalling assay, for example.

The binding members of the invention may also bind to and neutralize non-human IgE, meaning IgE orthologs that occur naturally in species other than human.

Binding members of the invention are normally specific for IgE over other immunoglobulins, and thus bind IgE selectively. Such selectivity may be determined or demonstrated, for example, in a standard competition assay.

The binding members are useful for treating and/or preventing disorders that are mediated by IgE, especially allergies and asthma.

The binding members are useful for reducing circulating free IgE in a mammal, and useful for inhibiting allergen-induced mast cell degranulation either in vivo or in vitro.

The binding members are further useful for inhibiting biological responses mediated by IgE bound to FcERI with or without simultaneous inhibition of biological responses mediated by IgE bound to FcERII, either in vivo or in vitro.

The binding members of the invention also have diagnostic utility, such as for detecting the presence or amount of IgE, or the presence or amount of allergen-specific IgE, in a sample of interest, such as a sample from an asthmatic or allergic patient.

Any suitable method may be used to determine the sequence of residues bound by a binding member. For example, a peptide-binding scan may be used, such as a PEPSCAN-based enzyme linked immuno assay (ELISA) as described in detail elsewhere herein. In a peptide-binding scan, such as the kind provided by PEPSCAN Systems, short overlapping peptides derived from the antigen are systematically screened for binding to a binding member. The peptides may be covalently coupled to a support surface to form an array of peptides. Peptides may be in a linear or constrained conformation. A constrained conformation may be produced using peptides having a terminal Cys residue at each end of the peptide sequence. The Cys residues can be covalently coupled directly or indirectly to a support surface such that the peptide is held in a looped conformation. Thus, peptides used in the method may have Cys residues added to each end of a peptide sequence corresponding to a fragment of the antigen. Double looped peptides may also be used, in which a Cys residue is additionally located at or near the middle of the peptide sequence. The Cys residues can be covalently coupled directly or indirectly to a support surface such that the peptides form a double-looped conformation, with one loop on each side of the central Cys residue. Peptides can be synthetically generated, and Cys residues can therefore be engineered at desired locations, despite not occurring naturally in the IgE sequence. Optionally, linear and constrained peptides may both be screened in a peptide-binding assay. A peptide-binding scan may involve identifying (e.g. using ELISA) a set of peptides to which the binding member binds, wherein the peptides have amino acid sequences corresponding to fragments of IgE (e.g. peptides of about 5, 10 or 15 contiguous residues of IgE), and aligning the peptides in order to determine a footprint of residues bound by the binding member, where the footprint comprises residues common to overlapping peptides.

Alternatively or additionally the peptide-binding scan method may involve identifying peptides to which the binding member binds with at least a given signal:noise ratio. Details of a suitable peptide-binding scan method for determining binding are known in the art. Other methods that are well known in the art and that could be used to determine the residues bound by an antibody, and/or to confirm peptide-binding scan results, include site directed mutagenesis, hydrogen deuterium exchange, mass spectrometry, NMR, and X-ray crystallography.

A binding member of the invention may or may not bind and/or neutralise IgE variants. Thus, a binding member of the invention may or may not inhibit binding of IgE variants to FcERI with or without simultaneous inhibition of FcERII.

Linear epitope sequences of IgE, e.g. as isolated peptide fragments or polypeptides comprising them, may be employed to identify, generate, isolate and/or test binding members of the present invention.

As described in more detail below, binding members according to the invention have been shown to neutralise IgE with high potency. Neutralisation means inhibition of a biological activity of IgE. Binding members of the invention may neutralise one or more biological activities of IgE, but typically inhibit IgE binding to FcERI with or without simultaneous inhibition of binding to FcERII.

Neutralisation of IgE binding to FcERI with or without simultaneous inhibition of FcERII may optionally be measured as a function of the biological activity of the receptor, such as allergen-induced mast cell degranulation.

Suitable assays for measuring neutralisation of IgE by binding members of the invention include, for example, ligand receptor biochemical assays and surface plasmon resonance (SPR) (e.g., BIACORE).

Inhibition of biological activity may be partial or total. Binding members may inhibit an IgE biological activity, such as receptor binding or mast cell degranulation, by 100%, or alternatively by: at least 95%, at least 90%, at least 85%, at least 80%, at least 75%, at least 70%, at least 60%, or at least 50% of the activity in absence of the binding member.

The neutralising potency of a binding member is normally expressed as an $IC_{50}$ value, in nM unless otherwise stated. In functional assays, $IC_{50}$ is the concentration of a binding member that reduces a biological response by 50% of its maximum. In ligand-binding studies, $IC_{50}$ is the concentration that reduces receptor binding by 50% of maximal specific binding level. $IC_{50}$ may be calculated by plotting % of maximal biological response as a function of the log of the binding member concentration, and using a software program, such as Prism (GraphPad) to fit a sigmoidal function to the data to generate $IC_{50}$ values. Potency may be determined or measured using one or more assays known to the skilled person and/or as described or referred to herein.

The neutralising potency of a binding member can be expressed as a geomean. Geomean (also known as geometric mean), as used herein means the average of the logarithmic values of a data set, converted back to a base 10 number. This requires there to be at least two measurements, e.g. at least 2, preferably at least 5, more preferably at least 10 replicate. The person skilled in the art will appreciate that the greater the number of replicates the more robust the geomean value will be. The choice of replicate number can be left to the discretion of the person skilled in the art.

Neutralisation of IgE activity by a binding member in an assay described herein, indicates that the binding member binds to and neutralises IgE. Other methods that may be used for determining binding of a binding member to IgE include ELISA, Western blotting, immunoprecipitation, affinity chromatography and biochemical assays.

In another embodiment of the invention there is provided an isolated binding member specific for immunoglobulin E which binding member has an IC50 for the binding of said binding member to immunoglobulin E in serum at least 10 fold lower than Xolair™, or alternatively at least 20 fold lower, at least 50 fold lower, at least 75 folder lower, at least 100 fold lower, at least 125 fold lower, at least 150 fold lower, at least 200 fold lower, at least 300 fold lower, at least 400 fold lower or at least 500 fold lower.

Neutralising potency of a binding member as calculated in an assay using IgE from a first species (e.g. human) may be compared with neutralising potency of the binding member in a similar assay under similar conditions using IgE from a second species (e.g. cynomolgus monkey), in order to assess the extent of cross-reactivity of the binding member for IgE of the two species. Alternatively, cross-reactivity may be assessed in a competition binding assay, as described in more detail elsewhere herein.

A binding member of the invention may have a greater neutralising potency in a human IgE binding or biological assay than in a similar assay with IgE from a species other than human. Thus, neutralising potency of a binding member in an assay with human IgE may be greater than in a similar assay with IgE from a species other than human. Potency in a human IgE binding or biological assay may, for example, be about 5-fold greater than in a similar assay employing IgE of cynomolgus monkey, or in another embodiment, may be about 15 or 20 fold greater. More specifically, potency in the human RBL-ER51 calcium signalling assay may be determined for a concentration of human IgE of 25 ng/ml, and compared to the potency using 100 ng/ml of cynomolgus IgE under otherwise similar conditions. Examples of data obtained in similar RBL-ER51 calcium signalling assays using human IgE and cynomolgus IgE are shown in Table 2b.

A binding member of the invention may have a stronger affinity for human IgE than for IgE of other species. Affinity of a binding member for human IgE may be, for example, about 5 or 10-fold stronger than for cynomolgus monkey IgE, or in another embodiment, may be about 100-fold stronger. Examples of data obtained for both human and cynomolgus monkey IgE are shown in Table 2a and b.

A binding member of the invention may have an IgE-neutralising potency or $IC_{50}$ of about 10 nM or less, with a 25 ng/ml concentration of human IgE in, for example, an RBL-ER51 calcium signalling assay. Alternatively, the $IC_{50}$ is less than about 3 nM. In other embodiments, the $IC_{50}$ is less than about 1 nM, or less than about 0.5 nM, or less than about 0.2 nM.

In another embodiment of the invention there is provided an isolated binding member specific for immunoglobulin E which binding member has an IC50 geomean for inhibition of calcium signalling induced by 25 ng/ml IgE in RBL-ER51 cells of less than 1 nM, or alternatively less than 0.6 nM, less than 0.5 nM, less than 0.4 nM, less than 0.3 nM, less than 0.2 nM or less than 0.1 nM.

Binding kinetics and affinity (expressed as the equilibrium dissociation constant KD) of IgE-binding members for human IgE may be determined, e.g. using surface plasmon resonance (BIACORE). Binding members of the invention normally have an affinity for human IgE (KD) of less than about 10 nM, and in some embodiments have a KD of less than about 5 nM, in other embodiments have a KD of less than 2 nM. Affinity for cynomolgus monkey IgE is normally less than about 20 nM, in some embodiments have a KD of less than about 10 nM.

A number of methodologies are available for the measurement of binding affinity of an antibody to its antigens, one such methodology is KinExA. The Kinetic Exclusion Assay (KinExA) is a general purpose immunoassay platform (basically a flow spectrofluorimeter) that is capable of measuring equilibrium dissociation constants, and association and dissociation rate constants for antigen/antibody interactions. Since KinExA is performed after equilibrium has been obtained, it is an advantageous technique to use for measuring the KD of a multivalent antigen/mAb interaction. The binding of an antibody to an IgE molecule is an example of binding to a multivalent antigen. The use of KinExA is particularly appropriate where a multivalent antigen means that multimers of antibody and antigen are formed comprising more than one antibody and more than one antigen. In such complex interaction models accurate $K_D$ estimation can be difficult. The KinExA methodology can be conducted as described in Drake et al (2004) Analytical Biochemistry 328, 35-43. As measured by the KinExA methodology Antibody 11 has a $K_D$ of 6.3 pM substantially lower than Xolair™ which has a $K_D$ of 353 pM.

In another embodiment of the invention there is provided an isolated binding member specific for immunoglobulin E with a $K_D$ of 300 pM or lower as measured using the KinExA methodology. Alternatively a $K_D$ of 200 pM or lower, 100 pM or lower, 50 pM or lower, 20 pM or lower or 10 pM or lower.

In vivo endogenous IgE may be glycosylated and therefore glycosylated human IgE is a therapeutic target for human therapy. While recombinant human IgE, which may be bacterially-derived and not glycosylated, may be used in assays described herein, binding members of the invention may bind glycosylated human IgE, such as IgE produced by a myeloma cell line such as U266.B1. This represents a significant advantage of binding members of the invention, since glycosylated human IgE is the target antigen for in vivo human applications.

A binding member of the invention may comprise an antibody molecule, preferably a human antibody molecule or a humanized antibody molecule. In one aspect of the invention, the antibody molecule is a monoclonal antibody.

An antigen binding site is generally formed by the variable heavy (VH) and variable light (VL) immunoglobulin domains, with the antigen-binding interface formed by six surface polypeptide loops, termed complimentarity determining regions (CDRs). There are three CDRs in each VH (HCDR1, HCDR2, HCDR3) and in each VL LCDR1, LCDR2, LCDR3), together with framework regions (FRs).

The binding member of the invention normally comprises an antibody VH and/or VL domain. A VH domain of the invention comprises a set of HCDRs, and a VL domain comprises a set of LCDRs. An antibody molecule may comprise an antibody VH domain comprising a VH CDR1, CDR2 and CDR3 and a framework. It may alternatively or also comprise an antibody VL domain comprising a VL CDR1, CDR2 and CDR3 and a framework. Examples of antibody VH domains (SEQ ID NOS:2, 12, 22, 32, 42, 52, 62, 72, 82, 92, 102, 112, 122, 132, 142, 152, 162, 172, 182, 192, 202, 212, 222, 232, 242, 252, 262, 272, 282, 288, 300, and 306) and antibody VL domains (SEQ ID NOS: 318, 320, 322, 324, 326, 328, 330, 332, 334, 336, 338, 340, 342, 344, 346, 348, 350, 352, 354, 356, 358, 360, 362, 364, 366, 368, 370, 372, 374, 376, 378 and 380) and CDRs (SEQ ID NOS:3-5, 8-10, 13-15, 18-20, 23-25, 28-30, 33-35, 38-40, 43-45, 48-50, 53-55, 58-60, 63-65, 68-70, 73-75, 78-80, 83-85, 88-90, 93-95, 98-100, 103-105, 108-110, 113-115, 118-120, 123-125, 128-130, 133-135, 138-140, 143-145, 148-150, 153-155, 158-160, 163-165, 168-170, 173-175, 178-180, 183-185, 188-190, 193-195, 198-200, 203-205, 208-210, 213-215, 218-220, 223-225, 228-230, 233-235, 238-240, 243-245, 248-250, 253-255, 258-260, 263-265, 268-270, 273-275, 278-280, 283-285, 296-298, 289-291, 296-298, 301-303, 307-309, and 314-316) according to the present invention are as listed in the appended sequence listing that forms part of the present disclosure (also see Table 3a). Further CDRs are disclosed below and in Table 1. All VH and VL sequences, CDR sequences, sets of CDRs and sets of HCDRs and sets of LCDRs disclosed herein represent aspects and embodiments of the invention.

As described herein, a "set of CDRs" comprises CDR1, CDR2 and CDR3. Thus, a set of HCDRs refers to HCDR1, HCDR2 and HCDR3, and a set of LCDRs refers to LCDR1, LCDR2 and LCDR3. Unless otherwise stated, a "set of CDRs" includes HCDRs and LCDRs.

Alternatively, a binding member of the invention may comprise an antigen-binding site within a non-antibody molecule, normally provided by one or more CDRs e.g. a set of CDRs in a non-antibody protein scaffold, as discussed further below.

As described herein, a parent antibody molecule was isolated having the set of CDR sequences as shown in Table 1 (see Antibody 1). Through a process of optimisation we generated a panel of antibody clones numbered 2-28, with CDR sequences derived from the parent CDR sequences and having modifications at the positions indicated in Table 1. Thus, for example, it can be seen from Table 1 that Antibody 2 has the parent HCDR1, HCDR2, LCDR1, LCDR2, and LCDR3 sequences, and has a parent HCDR3 sequence in which: Kabat residue 96 is replaced with S, Kabat residue 97 is replaced with L, Kabat residue 99 is replaced with S, and Kabat residue 100 is replaced with A.

Described herein is a binding member comprising the parent set of CDRs as shown in Table 1 (Antibody 1), in which HCDR1 is SEQ ID NO: 3 (Kabat residues 31-35), HCDR2 is SEQ ID NO: 4 (Kabat residues 50-65), HCDR3 is SEQ ID NO: 5 (Kabat residues 95-102), LCDR1 is SEQ ID NO: 8 (Kabat residues 24-34), LCDR2 is SEQ ID NO: 9 (Kabat residues 50-56) and LCDR3 is SEQ ID NO: 10 (Kabat residues 89-97). The binding member according to the invention may also be the parent binding member as shown in Table 1, wherein one or more of the CDRs have one or more amino acid additions, substitutions, deletions, and/or insertions. In some embodiments, the binding member comprises a set of CDRs having from one to ten additions, substitutions, deletions and/or insertions relative to the parent sequences of Antibody 11. In another embodiment one to ten substitutions relative to Antibody 11. In another embodiment form one to eleven additions, substitutions, deletions and/or insertions relative to the parent sequences of Antibody 1. In another embodiment one to ten substitutions relative to Antibody 1.

In certain embodiments the binding member of the invention comprises HCDR1, HCDR2, HCDR3, LCDR1, LCDR2, and LCDR3; wherein the HCDR3 has the amino acid sequence of SEQ ID NO: 5 optionally having from 1 to 5 amino acid additions, substitutions, deletions and/or insertions; and the LCDR3 has the amino acid sequence of SEQ ID NO: 10 optionally having from 1 to 6 amino acid additions, substitutions, deletions and/or insertions. In such embodiments, the HCDR1 may have the amino acid sequence SEQ ID NO: 3; the HCDR2 may have the amino acid sequence SEQ ID NO: 4; the LCDR1 may have the amino acid sequence SEQ ID NO: 8; and the LCDR2 may have the amino acid sequence SEQ ID NO: 9. Alternatively, the HCDR1, the HCDR2, the LCDR1, and the LCDR2 may also collectively have one or more amino acid additions, substitutions, deletions, and/or insertions relative to the parent sequences (Antibody 1), such as from one to ten substitutions.

A binding member of the invention may comprise one or a combination of CDRs as described herein. For example, the binding member of the invention may comprise an HCDR1 having the amino acid sequence of SEQ ID NO: 3; an HCDR2 having the amino acid sequence of SEQ ID NO: 4; an HCDR3 having an amino acid sequence selected from the group consisting of SEQ ID NOS: 5, 15, 25, 65, 75, 85, 95, 145, 155, 175, and 255; an LCDR1 having the amino acid sequence of SEQ ID NO: 8; an LCDR2 having the amino acid sequence SEQ ID NO: 9; and an LCDR3 having an amino acid sequence selected from the group consisting of SEQ ID NOS: 10, 30, 40, 50, 60, 70, 80, 90, 100, 110, 120, 130, 140, 150, 160, 170, 180, 190, 200, 210, 220, 230, 240, 250, 260, 270 and 280.

In certain embodiments, the binding member or VH domain of the invention comprises the parent HCDR3 (SEQ ID NO:5) with one or more of the following substitutions:
Kabat residue 96 replaced by S, M, or T;
Kabat residue 97 replaced by L or G;
Kabat residue 98 replaced by K;
Kabat residue 99 replaced by S, W, A, T, or E;
Kabat residue 100 replaced by A or I.

In some embodiments, a binding member, or a VL domain thereof may comprise the parent LCDR3 (SEQ ID NO 10) with Kabat residue 94 replaced by T, R, D, P, E, N, H, Q, or A.

In certain embodiments, the binding member or VL domain of the invention comprises the parent LCDR3 (SEQ ID NO 10) with one or more of the following substitutions:
Kabat residue 94 replaced by T, R, D, P, E, N, H, Q, or A;
Kabat residue 95 replaced T, K, S, I, G, H, M, F, R, N, K or Q;
Kabat residue 95A replaced by L, H, D, G, R, N, Q, K or E;
Kabat residue 95B replaced by T, H, S, Y, L or N;
Kabat residue 96 replaced by G or A;
Kabat residue 97 replaced by P, S or G.

In one embodiment, the invention is a binding member in which: HCDR1 has amino acid sequence SEQ ID NO: 103, HCDR2 has amino acid sequence SEQ ID NO: 104, HCDR3 has amino acid sequence SEQ ID NO: 105, LCDR1 has amino acid sequence SEQ ID NO: 108, LCDR2 has amino acid sequence SEQ ID NO: 109, and LCDR3 has amino acid sequence SEQ ID NO: 110. For example, see Antibody 11 of Table 1.

Still other embodiments of the invention are binding members, such as antibody molecules, capable of competing with antibodies of the invention such as Antibody 11 of Table 1 for binding to human IgE, said binding members neutralizing human IgE with an IC50 of less than about 1 nM in an assay described herein, or with an IC50 of less than about 0.5 nM. In some embodiments, the IC50 is less than about 0.2 nM.

The invention provides binding members comprising an HCDR1 and/or HCDR2 and/or HCDR3 of any of antibodies 1 to 28 and/or an LCDR1 and/or LCDR2 and/or LCDR3 of any of antibodies 1 to 28, e.g. a set of CDRs of any of antibodies 1 to 28 shown in Table 1. The binding member may comprise a set of VH CDRs of one of these antibodies. Optionally it may also comprise a set of VL CDRs of one of these antibodies, and the VL CDRs may be from the same or a different antibody as the VH CDRs. A VH domain comprising a set of HCDRs of any of antibodies 1 to 28, and/or a VL domain comprising a set of LCDRs of any of antibodies 1 to 28, are also provided by the invention.

Typically, a VH domain is paired with a VL domain to provide an antibody antigen-binding site, although as discussed further below a VH or VL domain alone may be used to bind antigen. The Antibody 1 VH domain (see Table 1) may be paired with the Antibody 1 VL domain, so that an antibody antigen-binding site is formed comprising both the antibody 1 VH and VL domains. Analogous embodiments are provided for the other VH and VL domains disclosed herein. In other embodiments, the Antibody 1 VH is paired with a VL domain other than the Antibody 1 VL. Light-chain promiscuity is well established in the art. Again, analogous embodiments are provided by the invention for the other VH and VL domains disclosed herein. Thus, the VH of the parent or of any of antibodies 2 to 28 may be paired with the VL of the parent or of any of antibodies 2 to 28.

A binding member may comprise a set of H and/or L CDRs of the parent antibody or any of antibodies 2 to 28 with as many as twenty, sixteen, ten, nine or fewer, e.g. one, two, three, four or five, amino acid additions, substitutions, deletions, and/or insertions within the disclosed set of H and/or L CDRs. Alternatively, a binding member may comprise a set of H and/or L CDRs of the parent antibody or any of antibodies 2 to 28 with as many as twenty, sixteen, ten, nine or fewer, e.g. one, two, three, four or five, amino acid substitutions within the disclosed set of H and/or L CDRs. Such modifications may potentially be made at any residue within the set of CDRs. For example, modifications may be made at the positions modified in any of Antibodies 2 to 28, as shown in Table 1. Thus, the one or more modifications, may comprise one or more substitutions at the following residues: Kabat residues 96, 97, 98, 99, and 100 in the HCDRs; and Kabat residues 94, 95, 95A, 95B, 96, and 97 in the LCDRs.

A binding member may comprise an antibody molecule having one or more CDRs, e.g. a set of CDRs, within an antibody framework. For example, one or more CDRs or a set of CDRs of an antibody may be grafted into a framework (e.g. human framework) to provide an antibody molecule. The framework regions may be of human germline gene sequences, or be non-germlined. Thus, the framework may be germlined where one or more residues within the framework are changed to match the residues at the equivalent position in the most similar human germline framework. Thus, a binding member of the invention may be an isolated human antibody molecule having a VH domain comprising a set of HCDRs in a human germline framework, e.g. human germline IgG VH framework. The binding member also has a VL domain comprising a set of LCDRs, e.g. in a human germline IgG VL framework.

VH and/or VL framework residues may be modified as discussed and exemplified herein e.g. using site-directed mutagenesis. A VH or VL domain according to the invention, or a binding member comprising such a VL domain, preferably has the VH and/or VL domain sequence of an antibody of Table 3.

A non-germlined antibody molecule has the same CDRs, but different frameworks, compared to a germlined antibody molecule. Germlined antibodies may be produced by germlining framework regions of the VH and VL domain sequences shown herein for these antibodies.

A binding member of the invention may be one which competes for binding to IgE with any binding member which both binds IgE and comprises a binding member such as VH and/or VL domain, CDR e.g. HCDR3, and/or set of CDRs disclosed herein. Competition between binding members may be assayed easily in vitro, for example using ELISA and/or by tagging a specific reporter molecule to one binding member which can be detected in the presence of one or more other untagged binding members, to enable identification of binding members which bind the same epitope or an overlapping epitope. Such methods are readily known to one of ordinary skill in the art, and are described in more detail herein. Thus, a further aspect of the present invention provides a binding member comprising a human antibody antigen-binding site that competes with an antibody molecule, for example especially an antibody molecule comprising a VH and/or VL domain, CDR e.g. HCDR3 or set of CDRs of the parent antibody or any of antibodies 1 to 28, for binding to human IgE. In one embodiment, the binding member of the invention competes with Antibody 11 of Table 1.

Another embodiment of the invention provides binding members which bind to a specific region of IgE. Binding may be determined for example by detecting or observing specific interactions between the binding member and the residues of IgE, e.g. in a structure of the binding member: IgE complex which may be determined for example using X-ray crystallography. A structure of Antibody 11 bound to human IgE Cε3-Cε4 domains determined using X-ray crystallography provided the opportunity to study two interactions of antibody 11 Fabs with IgE within the crystal. IgE is a bivalent antigen since there are two light chains and two heavy chains. X ray crystallographic studies showed that the Fab bound to an epitope spread across two IgE heavy chains.

The first interaction indicated that the interaction site of Antibody 11 comprises residues Glu390 through to Asn394 inclusive and sugar moieties GlcNAc1 and Man6 of one IgE heavy chain and Leu340, Arg342, Ala428 to Thr434 inclusive, Thr436, Ser437 and Glu472 and sugar moiety Man 5 in the other IgE heavy chain.

In one embodiment of the invention there is provided an isolated binding member specific for immunoglobulin E wherein said binding member binds to an epitope in the immunoglobulin E comprising:
residues Glu390 through to Asn394 inclusive in a first IgE heavy chain and Leu340, Arg342, Ala428 to Thr434 inclusive, Thr436, Ser437 and Glu472 in a second IgE heavy chain; in a further embodiment said epitope further comprising sugar moieties GlcNAc1 and Man6 of a first IgE heavy chain and sugar moiety Man 5 in a second IgE heavy chain.

The second interaction indicated that the interaction site of Antibody 11 comprises residues Glu390, Gln392 to Asn394 inclusive and sugar moieties GlcNAc1 and Man6 in a first IgE heavy chain and Leu340, Arg342, Ala428 to Thr434 inclusive, Thr436, Ser437 and Glu472 in a second IgE heavy chain.

In a further embodiment of the invention there is provided an isolated binding member specific for immunoglobulin E wherein said binding member binds to an epitope in the immunoglobulin E comprising:
residues Glu390, Gln392 to Asn394 inclusive in a first IgE heavy chain and Leu340, Arg342, Ala428 to Thr434 inclusive, Thr436, Ser437 and Glu472 in a second IgE heavy chain; in a further embodiment said epitope further comprising sugar moieties GlcNAc1 and Man6 in a first IgE heavy chain.

In a further embodiment of the invention there is provided an isolated binding member specific for immunoglobulin E wherein said binding member binds to an epitope in the immunoglobulin E comprising:
residues Glu390, Gln392 to Asn393 inclusive in a first IgE heavy chain and Leu340, Arg342, Ala428 to Thr434 inclusive, Thr436, Ser437 and Glu472 in a second IgE heavy chain; in a further embodiment said epitope further comprising sugar moieties GlcNAc1 and Man6 in a first IgE heavy chain.

In a further embodiment of the invention there is provided an isolated binding member specific for immunoglobulin E which binds an epitope which comprises elements from a first IgE heavy chain and elements from a second IgE heavy chain.

In further aspects the present invention provides a binding member comprising a human antibody antigen-binding site which competes with an antibody antigen-binding site for binding to human IgE, wherein the antibody antigen-binding site is composed of a VH domain and a VL domain, and wherein the VH and VL domains comprise a set of CDRs of the parent (Antibody 1), or of any of antibodies 2 to 28, as disclosed herein.

In further aspects, the invention provides an isolated nucleic acid which comprises a sequence encoding a binding member, VH domain and/or VL domain according to the present invention. For example, SEQ ID NOS: 1, 11, 21, 31, 41, 51, 61, 71, 81, 91, 101, 111, 121, 131, 141, 151, 161, 171, 181, 191, 201, 211, 221, 231, 241, 251, 261, 271, 281, 287, 299, and 305 encode exemplary VH domains of the present invention, and SEQ ID NOS: 317, 319, 321, 323, 325, 327, 329, 331, 333, 335, 337, 339, 341, 343, 345, 347, 349, 351, 353, 355, 357, 359, 361, 363, 365, 367, 369, 371, 373, 375, 377 and 379 encode exemplary VL domains of the present invention. The invention also includes methods of preparing a binding member, a VH domain and/or a VL domain of the invention, which comprise expressing said nucleic acid under conditions to bring about production of said binding member, VH domain and/or VL domain, and recovering it by isolating or purifying the binding member.

Another aspect of the present invention provides nucleic acid, generally isolated, encoding a VH CDR or VL CDR sequence disclosed herein.

A further aspect provides a host cell containing or transformed with nucleic acid of the invention.

Further aspects of the present invention provide for compositions containing binding members of the invention, and their use in methods of inhibiting and/or neutralising IgE, including methods of treatment of the human or animal body by therapy.

For example, binding members according to the invention may be used in a method of treatment and/or prevention, or used in a method of diagnosis, of a biological response, disease, disorder, or condition in the human or animal body (e.g. in a human patient), or in vitro.

The method of treatment and/or prevention may comprise administering to said patient a binding member of the invention in an amount sufficient to measurably neutralize IgE. Conditions treatable in accordance with the present invention include any in which IgE plays a role, such as allergies and asthma.

These and other aspects of the invention are described in further detail below.

It is convenient to point out here that "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

IgE is immunoglobulin E. The amino acid sequence of the human IgE constant region is publicly available. In some embodiments IgE may be human or cynomolgus monkey IgE. As described elsewhere herein, IgE may be recombinant, and/or may be either glycosylated or unglycosylated. IgE is expressed naturally in vivo in glycosylated form, e.g. in U266.B1 cells. Glycosylated IgE may also be expressed in recombinant systems.

A binding member generally refers to one member of a pair of molecules that bind one another. The members of a binding pair may be naturally derived or wholly or partially synthetically produced. One member of the pair of molecules has an area on its surface, or a cavity, which binds to and is therefore complementary to a particular spatial and polar organization of the other member of the pair of molecules. Examples of types of binding pairs are antigen-antibody, biotin-avidin, hormone-hormone receptor, receptor-ligand, enzyme-substrate. The present invention is generally concerned with antigen-antibody type reactions.

A binding member normally comprises a molecule having an antigen-binding site. For example, a binding member may be an antibody molecule or a non-antibody protein that comprises an antigen-binding site.

An antigen binding site may be provided by means of arrangement of CDRs on non-antibody protein scaffolds, such as fibronectin or cytochrome B etc. [1, 2, 3], or by randomising or mutating amino acid residues of a loop within a protein scaffold to confer binding specificity for a desired target. Scaffolds for engineering novel binding sites in proteins have been reviewed in detail by Nygren et al. [3]. Protein scaffolds for antibody mimics are disclosed in WO/0034784, which is herein incorporated by reference in its entirety, in which the inventors describe proteins (antibody mimics) that include a fibronectin type III domain having at least one randomised loop. A suitable scaffold into which to graft one or more CDRs, e.g. a set of HCDRs, may be provided by any domain member of the immunoglobulin gene superfamily. The scaffold may be a human or non-human protein. An advantage of a non-antibody protein scaffold is that it may provide an antigen-binding site in a scaffold molecule that is smaller and/or easier to manufacture than at least some antibody molecules. Small size of a binding member may confer useful physiological properties, such as an ability to enter cells, penetrate deep into tissues or reach targets within other structures, or to bind within protein cavities of the target antigen. Use of antigen binding sites in non-antibody protein scaffolds is reviewed in Wess, 2004 [4]. Typical are proteins having a stable backbone and one or more variable loops, in which the amino acid sequence of the loop or loops is specifically or randomly mutated to create an antigen-binding site that binds the target antigen. Such proteins include the IgG-binding domains of protein A from S. aureus, transferrin, tetranectin, fibronectin (e.g. 10th fibronectin type III domain), lipocalins as well as gamma-crystalline and other Affilin™ scaffolds (Scil Proteins). Examples of other approaches include synthetic "Microbodies" based on cyclotides—small proteins having intra-molecular disulphide bonds, Microproteins (Versabodies™, Amunix) and ankyrin repeat proteins (DARPins, Molecular Partners). Such proteins also include small, engineered protein domains such as, for example, immuno-domains (see for example, U.S. Patent Publication Nos. 2003082630 and 2003157561. Immuno-domains contain at least one complementarity determining region (CDR) of an antibody.

In addition to antibody sequences and/or an antigen-binding site, a binding member according to the present invention may comprise other amino acids, e.g. forming a peptide or polypeptide, such as a folded domain, or to impart to the molecule another functional characteristic in addition to ability to bind antigen. Binding members of the invention may carry a detectable label, or may be conjugated to a toxin or a targeting moiety or enzyme (e.g. via a peptidyl bond or linker). For example, a binding member may comprise a catalytic site (e.g. in an enzyme domain) as well as an antigen binding site, wherein the antigen binding site binds to the antigen and thus targets the catalytic site to the antigen. The catalytic site may inhibit biological function of the antigen, e.g. by cleavage.

Although, as noted, CDRs can be carried by non-antibody scaffolds, the structure for carrying a CDR or a set of CDRs of the invention will generally be an antibody heavy or light chain sequence or substantial portion thereof in which the CDR or set of CDRs is located at a location corresponding to the CDR or set of CDRs of naturally occurring VH and VL antibody variable domains encoded by rearranged immunoglobulin genes. The structures and locations of immunoglobulin variable domains may be determined by reference to Kabat, et al., 1987 [5], and updates thereof findable under "Kabat" using any internet search engine).

By CDR region or CDR, it is intended to indicate the hypervariable regions of the heavy and light chains of the immunoglobulin as defined by Kabat et al. 1991 [6], and later editions. An antibody typically contains 3 heavy chain CDRs and 3 light chain CDRs. The term CDR or CDRs is used here in order to indicate, according to the case, one of these regions or several, or even the whole, of these regions which contain the majority of the amino acid residues responsible for the binding by affinity of the antibody for the antigen or the epitope which it recognizes.

Among the six short CDR sequences, the third CDR of the heavy chain (HCDR3) has a greater size variability (greater diversity essentially due to the mechanisms of arrangement of the genes which give rise to it). It may be as short as 2 amino acids although the longest size known is 26. CDR length may also vary according to the length that can be accommodated by the particular underlying framework. Functionally, HCDR3 plays a role in part in the determination of the specificity of the antibody [see references 7, 8, 9, 10, 11, 12, 13, 14]. In another embodiment of the invention there is provided an isolated binding member comprising a HCDR3 sequence selected from Table 3a.

Antibody molecule refers to an immunoglobulin whether natural or partly or wholly synthetically produced. The term also covers any polypeptide or protein comprising an antibody antigen-binding site. It must be understood here that the invention does not relate to the antibodies in natural form, that is to say they are not in their natural environment but have been isolated or obtained by purification from natural sources, or else obtained by genetic recombination, or by chemical synthesis, including modification with unnatural amino acids. Antibody fragments that comprise an antibody antigen-binding site include, but are not limited to, molecules such as Fab, Fab', Fab'-SH, scFv, Fv, dAb and Fd. Various other antibody molecules including one or more antibody antigen-binding sites have been engineered, including for example $Fab_2$, $Fab_3$, diabodies, triabodies, tetrabodies and minibodies. Antibody molecules and methods for their construction and use are described in [15].

It is possible to take monoclonal and other antibodies and use techniques of recombinant DNA technology to produce other antibodies or chimeric molecules that bind the target antigen. Such techniques may involve introducing DNA encoding the immunoglobulin variable region, or the CDRs, of an antibody to the constant regions, or constant regions plus framework regions, of a different immunoglobulin. See, for instance, EP-A-184187, GB 2188638A or EP-A-239400, and a large body of subsequent literature. A hybridoma or other cell producing an antibody may be subject to genetic mutation or other changes, which may or may not alter the binding specificity of antibodies produced.

As antibodies can be modified in a number of ways, the term "antibody molecule" should be construed as covering any binding member or substance having an antibody antigen-binding site with the required specificity and/or binding to antigen. Thus, this term covers antibody fragments and derivatives, including any polypeptide comprising an antibody antigen-binding site, whether natural or wholly or partially synthetic. Chimeric molecules comprising an antibody antigen-binding site, or equivalent, fused to another polypeptide (e.g. derived from another species or belonging to another antibody class or subclass) are therefore included. Cloning and expression of chimeric antibodies are described in EP-A-0120694 and EP-A-0125023, and a large body of subsequent literature.

Further techniques available in the art of antibody engineering have made it possible to isolate human and humanised antibodies. For example, human hybridomas can be made as described by Kontermann & Dubel [16]. Phage display, another established technique for generating binding members has been described in detail in many publications, such as Kontermann & Dubel [16] and WO92/01047 (discussed further below), and U.S. Pat. Nos. 5,969,108, 5,565,332, 5,733,743, 5,858,657, 5,871,907, 5,872,215, 5,885,793, 5,962,255, 6,140,471, 6,172,197, 6,225,447, 6,291,650, 6,492,160 and 6,521,404.

Transgenic mice in which the mouse antibody genes are inactivated and functionally replaced with human antibody genes while leaving intact other components of the mouse immune system, can be used for isolating human antibodies [17]. Humanised antibodies can be produced using techniques known in the art such as those disclosed in for example WO91/09967, U.S. Pat. No. 5,585,089, EP592106, U.S. Pat. No. 5,565,332 and WO93/17105. Further, WO2004/006955 describes methods for humanising antibodies, based on selecting variable region framework sequences from human antibody genes by comparing canonical CDR structure types for CDR sequences of the variable region of a non-human antibody to canonical CDR structure types for corresponding CDRs from a library of human antibody sequences, e.g. germline antibody gene segments. Human antibody variable regions having similar canonical CDR structure types to the non-human CDRs form a subset of member human antibody sequences from which to select human framework sequences. The subset members may be further ranked by amino acid similarity between the human and the non-human CDR sequences. In the method of WO2004/006955, top ranking human sequences are selected to provide the framework sequences for constructing a chimeric antibody that functionally replaces human CDR sequences with the non-human CDR counterparts using the selected subset member human frameworks, thereby providing a humanized antibody of high affinity and low immunogenicity without need for comparing framework sequences between the non-human and human antibodies. Chimeric antibodies made according to the method are also disclosed.

Synthetic antibody molecules may be created by expression from genes generated by means of oligonucleotides synthesized and assembled within suitable expression vectors, for example as described by Knappik et al. [18] or Krebs et al. [19].

It has been shown that fragments of a whole antibody can perform the function of binding antigens. Examples of binding fragments are (i) the Fab fragment consisting of VL, VH, constant light chain domain (CL) and constant heavy chain domain 1 (CH1) domains; (ii) the Fd fragment consisting of the VH and CH1 domains; (iii) the Fv fragment consisting of the VL and VH domains of a single antibody; (iv) the dAb fragment [20, 21, 22], which consists of a VH or a VL domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site [23, 24]; (viii) bispecific single chain Fv dimers (PCT/US92/09965) and (ix) "diabodies", multivalent or multispecific fragments constructed by gene fusion (WO94/13804; [25]). Fv, scFv or diabody molecules may be stabilized by the incorporation of disulphide bridges linking the VH and VL domains [26]. Minibodies comprising a scFv joined to a CH3 domain may also be made [27]. Other examples of binding fragments are Fab', which differs from Fab fragments by the addition of a few residues at the carboxyl terminus of the heavy chain CH1 domain, including one or more cysteines from the antibody hinge region, and Fab'-SH, which is a Fab' fragment in which the cysteine residue(s) of the constant domains bear a free thiol group.

Antibody fragments of the invention can be obtained starting from a parent antibody molecule or any of the antibody molecules 1 to 28, by methods such as digestion by enzymes e.g. pepsin or papain and/or by cleavage of the disulfide bridges by chemical reduction. In another manner, the antibody fragments comprised in the present invention can be obtained by techniques of genetic recombination likewise well known to the person skilled in the art or else by peptide synthesis by means of, for example, automatic peptide synthesizers, such as those supplied by the company Applied Biosystems, etc., or by nucleic acid synthesis and expression.

Functional antibody fragments according to the present invention include any functional fragment whose half-life is increased by a chemical modification, especially by PEGylation, or by incorporation in a liposome.

A dAb (domain antibody) is a small monomeric antigen-binding fragment of an antibody, namely the variable region of an antibody heavy or light chain [22]. VH dAbs occur naturally in camelids (e.g. camel, llama) and may be produced by immunizing a camelid with a target antigen, isolating antigen-specific B cells and directly cloning dAb genes from individual B cells. dAbs are also producible in cell culture. Their small size, good solubility and temperature stability makes them particularly physiologically useful and suitable for selection and affinity maturation. Camelid VH dAbs are being developed for therapeutic use under the name "Nanobodies™". A binding member of the present invention may be a dAb comprising a VH or VL domain substantially as set out herein, or a VH or VL domain comprising a set of CDRs substantially as set out herein.

Bispecific or bifunctional antibodies form a second generation of monoclonal antibodies in which two different variable regions are combined in the same molecule [28]. Their use has been demonstrated both in the diagnostic field and in the therapy field from their capacity to recruit new effector functions or to target several molecules on the surface of tumour cells. Where bispecific antibodies are to be used, these may be conventional bispecific antibodies, which can be manufactured in a variety of ways [29], e.g. prepared chemically or from hybrid hybridomas, or may be any of the bispecific antibody fragments mentioned above. These antibodies can be obtained by chemical methods [30, 31] or somatic methods [32, 33] but likewise and preferentially by genetic engineering techniques which allow the heterodimerization to be forced and thus facilitate the process of purification of the antibody sought [34]. Examples of bispecific antibodies include those of the BiTE™ technology in which the binding domains of two antibodies with different specificity can be used and directly linked via short flexible peptides. This combines two antibodies on a short single polypeptide chain.

Diabodies and scFv can be constructed without an Fc region, using only variable domains, potentially reducing the effects of anti-idiotypic reaction.

Bispecific antibodies can be constructed as entire IgG, as bispecific Fab'2, as Fab'PEG, as diabodies or else as bispecific scFv. Further, two bispecific antibodies can be linked using routine methods known in the art to form tetravalent antibodies.

Bispecific diabodies, as opposed to bispecific whole antibodies, may also be particularly useful because they can be readily constructed and expressed in *E. coli*. Diabodies (and many other polypeptides, such as antibody fragments) of appropriate binding specificities can be readily selected using phage display (WO94/13804) from libraries. If one arm of the diabody is to be kept constant, for instance, with a specificity directed against IgE, then a library can be made where the other arm is varied and an antibody of appropriate specificity selected. Bispecific whole antibodies may be made by alternative engineering methods as described in Ridgeway et al., 1996 [35].

Various methods are available in the art for obtaining antibodies against IgE. The antibodies may be monoclonal antibodies, especially of human, murine, chimeric or humanized origin, which can be obtained according to the standard methods well known to the person skilled in the art.

In general, for the preparation of monoclonal antibodies or their functional fragments, especially of murine origin, it is possible to refer to techniques which are described in particular in the manual "Antibodies" [36] or to the technique of preparation from hybridomas described by Köhler and Milstein [37].

Monoclonal antibodies can be obtained, for example, from an animal cell immunized against IgE, or one of its fragments containing the epitope recognized by said monoclonal antibodies. Suitable fragments and peptides or polypeptides comprising them may be used to immunise animals to generate antibodies against IgE. Said IgE, or one of its fragments, can especially be produced according to the usual working methods, by genetic recombination starting with a nucleic acid sequence contained in the cDNA sequence coding for IgE or fragment thereof, by peptide synthesis starting from a sequence of amino acids comprised in the peptide sequence of the IgE and/or fragment thereof.

The monoclonal antibodies can, for example, be purified on an affinity column on which IgE or one of its fragments containing the epitope recognized by said monoclonal antibodies, has previously been immobilized. More particularly, the monoclonal antibodies can be purified by chromatography on protein A and/or G, followed or not followed by ion-exchange chromatography aimed at eliminating the residual protein contaminants as well as the DNA and the LPS, in itself, followed or not followed by exclusion chromatography on Sepharose gel in order to eliminate the potential aggregates due to the presence of dimers or of other multimers. In one embodiment, the whole of these techniques can be used simultaneously or successively.

An antigen-binding site is the part of a molecule that binds to and is complementary to all or part of the target antigen. In an antibody molecule it is referred to as the antibody antigen-binding site, and comprises the part of the antibody that binds to and is complementary to all or part of the target antigen. Where an antigen is large, an antibody may only bind to a particular part of the antigen, which part is termed an epitope. An antibody antigen-binding site may be provided by one or more antibody variable domains. An antibody antigen-binding site may comprise an antibody light chain variable region (VL) and an antibody heavy chain variable region (VH).

Isolated refers to the state in which binding members of the invention, or nucleic acid encoding such binding members, will generally be in accordance with the present invention. Thus, binding members, VH and/or VL domains, and encoding nucleic acid molecules and vectors according to the present invention may be provided isolated and/or purified, e.g. from their natural environment, in substantially pure or homogeneous form, or, in the case of nucleic acid, free or substantially free of nucleic acid or genes of origin other than the sequence encoding a polypeptide with the required function. Isolated members and isolated nucleic acid will be free or substantially free of material with which they are naturally associated, such as other polypeptides or nucleic acids with which they are found in their natural environment, or the environment in which they are prepared (e.g. cell culture) when such preparation is by recombinant DNA technology practised in vitro or in vivo. Members and nucleic acid may be formulated with diluents or adjuvants and still for practical purposes be isolated—for example the members will normally be mixed with gelatin or other carriers if used to coat microtitre plates for use in immunoassays, or will be mixed with pharmaceutically acceptable carriers or diluents when used in diagnosis or therapy. Binding members may be glycosylated, either naturally or by systems of heterologous eukaryotic cells (e.g. CHO or NS0 (ECACC 85110503) cells, or they may be (for example if produced by expression in a prokaryotic cell) unglycosylated.

Heterogeneous preparations comprising anti-IgE antibody molecules also form part of the invention. For example, such preparations may be mixtures of antibodies with full-length heavy chains and heavy chains lacking the C-terminal lysine, with various degrees of glycosylation and/or with derivatized amino acids, such as cyclization of an N-terminal glutamic acid to form a pyroglutamic acid residue.

As used herein, the phrase "substantially as set out" refers to the characteristic(s) of the relevant CDRs of the VH or VL domain of binding members described herein will be either identical or highly similar to the specified regions of which the sequence is set out herein. As described herein, the phrase "highly similar" with respect to specified region(s) of one or more variable domains, it is contemplated that from 1 to about 6, e.g. from 1 to 5, including 1 to 3, or 1 or 2, or 3 or 4, amino acid substitutions may be made in the CDR and/or VH or VL domain.

DETAILED DESCRIPTION

As noted above, a binding member in accordance with the present invention modulates and may neutralise a biological activity of IgE. As described herein, IgE-binding members of the present invention may be optimised for neutralizing potency. Generally, potency optimisation involves mutating the sequence of a selected binding member (normally the variable domain sequence of an antibody) to generate a library of binding members, which are then assayed for potency and the more potent binding members are selected. Thus selected "potency-optimised" binding members tend to have a higher potency than the binding member from which the library was generated. Nevertheless, high potency binding members may also be obtained without optimisation, for example a high potency binding member may be obtained directly from an initial screen e.g. a biochemical neutralization assay. A "potency optimized" binding member refers to a binding member with an optimized potency of neutralization of a particular activity or downstream function. Assays and potencies are described in more detail elsewhere herein. The present invention provides both potency-optimized and nonoptimized binding members, as well as methods for potency optimization from a selected binding member. The present invention thus allows the skilled person to generate binding members having high potency.

Although potency optimization may be used to generate higher potency binding members from a given binding member, it is also noted that high potency binding members may be obtained even without potency optimization.

In a further aspect, the present invention provides a method of obtaining one or more binding members able to bind the antigen, the method including bringing into contact a library of binding members according to the invention and said antigen, and selecting one or more binding members of the library able to bind said antigen.

The library may be displayed on particles or molecular complexes, e.g. replicable genetic packages, such as yeast, bacterial or bacteriophage (e.g. T7) particles, viruses, cells or covalent, ribosomal or other in vitro display systems, each particle or molecular complex containing nucleic acid encoding the antibody VH variable domain displayed on it, and optionally also a displayed VL domain if present. Phage display is described in WO 92/01047 and e.g. U.S. Pat. Nos. 5,969,108, 5,565,332, 5,733,743, 5,858,657, 5,871,907, 5,872,215, 5,885,793, 5,962,255, 6,140,471, 6,172,197, 6,225,447, 6,291,650, 6,492,160 and 6,521,404, each of which is herein incorporated by reference in their entirety.

Following selection of binding members able to bind the antigen and displayed on bacteriophage or other library particles or molecular complexes, nucleic acid may be taken from a bacteriophage or other particle or molecular complex displaying a selected binding member. Such nucleic acid may be used in subsequent production of a binding member or an antibody VH or VL variable domain by expression from nucleic acid with the sequence of nucleic acid taken from a bacteriophage or other particle or molecular complex displaying a said selected binding member.

An antibody VH variable domain with the amino acid sequence of an antibody VH variable domain of a said selected binding member may be provided in isolated form, as may a binding member comprising such a VH domain.

Ability to bind IgE may be further tested, also ability to compete with e.g. a parent antibody molecule or an antibody molecule 2 to 28 (e.g. in scFv format and/or IgG format, e.g. IgG1) for binding to IgE. Ability to neutralize IgE may be tested, as discussed further elsewhere herein.

A binding member according to the present invention may bind IgE with the affinity of the parent or other antibody molecule, e.g. scFv, or one of antibodies 2 to 28, e.g. IgG1, or with an affinity that is better.

A binding member according to the present invention may neutralise a biological activity of IgE with the potency of the parent or other antibody molecule, one of antibodies 2 to 28 e.g. scFv, or IgG1, or with a potency that is better.

Binding affinity and neutralization potency of different binding members can be compared under appropriate conditions.

Variants of the VH and VL domains and CDRs of the present invention, including those for which amino acid sequences are set out herein, and which can be employed in binding members for IgE can be obtained by means of methods of sequence alteration or mutation and screening for antigen binding members with desired characteristics. Examples of desired characteristics include but are not limited to:

Increased binding affinity for antigen relative to known antibodies which are specific for the antigen Increased neutralization of an antigen activity relative to known antibodies which are specific for the antigen if the activity is known Specified competitive ability with a known antibody or ligand to the antigen at a specific molar ratio
  Ability to immunoprecipitate complex
  Ability to bind to a specified epitope
  Linear epitope, e.g. peptide sequence identified using peptide-binding scan as described herein, e.g. using peptides screened in linear and/or constrained conformation
  Conformational epitope, formed by non-continuous residues Ability to modulate a new biological activity of IgE, or downstream molecule. Such methods are also provided herein.

Variants of antibody molecules disclosed herein may be produced and used in the present invention. Following the lead of computational chemistry in applying multivariate data analysis techniques to the structure/property-activity relationships [38] quantitative activity-property relationships of antibodies can be derived using well-known mathematical techniques, such as statistical regression, pattern recognition and classification [39, 40, 41, 42, 43, 44]. The properties of antibodies can be derived from empirical and theoretical models (for example, analysis of likely contact residues or calculated physicochemical property) of antibody sequence, functional and three-dimensional structures and these properties can be considered singly and in combination.

An antibody antigen-binding site composed of a VH domain and a VL domain is typically formed by six loops of polypeptide: three from the light chain variable domain (VL) and three from the heavy chain variable domain (VH). Analysis of antibodies of known atomic structure has elucidated relationships between the sequence and three-dimensional structure of antibody combining sites [45, 46]. These relationships imply that, except for the third region (loop) in VH domains, binding site loops have one of a small number of main-chain conformations: canonical structures. The canonical structure formed in a particular loop has been shown to be determined by its size and the presence of certain residues at key sites in both the loop and in framework regions [45, 46].

This study of sequence-structure relationship can be used for prediction of those residues in an antibody of known sequence, but of an unknown three-dimensional structure, which are important in maintaining the three-dimensional structure of its CDR loops and hence maintain binding specificity. These predictions can be backed up by comparison of the predictions to the output from lead optimization experiments. In a structural approach, a model can be created of the antibody molecule [47] using any freely available or commercial package, such as WAM [48]. A protein visualisation and analysis software package, such as Insight II (Accelrys, Inc.) or Deep View [49] may then be used to evaluate possible substitutions at each position in the CDR. This information may then be used to make substitutions likely to have a minimal or beneficial effect on activity.

The techniques required to make substitutions within amino acid sequences of CDRs, antibody VH or VL domains and binding members generally are available in the art. Variant sequences may be made, with substitutions that may or may not be predicted to have a minimal or beneficial effect on activity, and tested for ability to bind and/or neutralize IgE and/or for any other desired property.

Variable domain amino acid sequence variants of any of the VH and VL domains whose sequences are specifically disclosed herein may be employed in accordance with the present invention, as discussed.

A further aspect of the invention is an antibody molecule comprising a VH domain that has at least 60, 70, 80, 85, 90, 95, 98 or 99% amino acid sequence identity with a VH domain of any of antibodies 1 to 28 shown in Table 3 and the appended sequence listing, or with an HCDR (e.g., HCDR1, HCDR2, or HCDR3) shown in Table 1. The antibody molecule may optionally also comprise a VL domain that has at least 60, 70, 80, 85, 90, 95, 98 or 99% amino acid sequence identity with a VL domain of any of the antibodies 1 to 28, or with an LCDR (e.g., LCDR1, LCDR2, or LCDR3) shown in Table 1. Algorithms that can be used to calculate % identity of two amino acid sequences include e.g. BLAST [50], FASTA [51], or the Smith-Waterman algorithm [52], e.g. employing default parameters.

Particular variants may include one or more amino acid sequence alterations (addition, deletion, substitution and/or insertion of an amino acid residue). In certain embodiments, the variants have less than about 20 such alterations.

Alterations may be made in one or more framework regions and/or one or more CDRs. The alterations normally do not result in loss of function, so a binding member comprising a thus-altered amino acid sequence may retain an ability to bind and/or neutralize IgE. It may retain the same quantitative binding and/or neutralizing ability as a binding member in which the alteration is not made, e.g. as measured in an assay described herein. The binding member comprising a thus-altered amino acid sequence may have an improved ability to bind and/or neutralize IgE.

Alteration may comprise replacing one or more amino acid residue(s) with a non-naturally occurring or non-standard amino acid, modifying one or more amino acid residue into a non-naturally occurring or non-standard form, or inserting one or more non-naturally occurring or non-standard amino acid into the sequence. Examples of numbers and locations of alterations in sequences of the invention are described elsewhere herein. Naturally occurring amino acids include the 20 "standard" L-amino acids identified as G, A, V, L, I, M, P, F, W, S, T, N, Q, Y, C, K, R, H, D, E by their standard single-letter codes. Non-standard amino acids include any other residue that may be incorporated into a polypeptide backbone or result from modification of an existing amino acid residue. Non-standard amino acids may be naturally occurring or non-naturally occurring. Several naturally occurring non-standard amino acids are known in the art, such as 4-hydroxyproline, 5-hydroxylysine, 3-methylhistidine, N-acetylserine, etc. [53]. Those amino acid residues that are derivatised at their N-alpha position will only be located at the N-terminus of an amino-acid sequence. Normally in the present invention an amino acid is an L-amino acid, but it may be a D-amino acid. Alteration may therefore comprise modifying an L-amino acid into, or replacing it with, a D-amino acid. Methylated, acetylated and/or phosphorylated forms of amino acids are also known, and amino acids in the present invention may be subject to such modification.

Amino acid sequences in antibody domains and binding members of the invention may comprise non-natural or non-standard amino acids described above. Non-standard amino acids (e.g. D-amino acids) may be incorporated into an amino acid sequence during synthesis, or by modification or replacement of the "original" standard amino acids after synthesis of the amino acid sequence.

Use of non-standard and/or non-naturally occurring amino acids increases structural and functional diversity, and can thus increase the potential for achieving desired IgE-binding and neutralizing properties in a binding member of the invention. Additionally, D-amino acids and analogues have been shown to have better pharmacokinetic profiles compared with standard L-amino acids, owing to in vivo degradation of polypeptides having L-amino acids after administration to an animal e.g. a human.

Novel VH or VL regions carrying CDR-derived sequences of the invention may be generated using random mutagenesis of one or more selected VH and/or VL genes to generate mutations within the entire variable domain. Such a technique is described by Gram et al. [54], who used error-prone PCR. In some embodiments one or two amino acid substitutions are made within an entire variable domain or set of CDRs.

Another method that may be used is to direct mutagenesis to CDR regions of VH or VL genes. Such techniques are disclosed by Barbas et al. [55] and Schier et al. [56].

All the above-described techniques are known as such in the art and the skilled person will be able to use such techniques to provide binding members of the invention using routine methodology in the art.

A further aspect of the invention provides a method for obtaining an antibody antigen-binding site for IgE, the method comprising providing by way of addition, deletion, substitution or insertion of one or more amino acids in the amino acid sequence of a VH domain set out herein, optionally combining the VH domain thus provided with one or more VL domains, and testing the VH domain or VH/VL combination or combinations to identify a binding member or an antibody antigen-binding site for IgE and optionally with one or more desired properties, e.g. ability to neutralize IgE activity. Said VL domain may have an amino acid sequence which is substantially as set out herein. An analogous method may be employed in which one or more sequence variants of a VL domain disclosed herein are combined with one or more VH domains.

As noted above, a CDR amino acid sequence substantially as set out herein may be carried as a CDR in a human antibody variable domain or a substantial portion thereof. The HCDR3 sequences substantially as set out herein represent embodiments of the present invention and each of these may be carried as a HCDR3 in a human heavy chain variable domain or a substantial portion thereof.

Variable domains employed in the invention may be obtained or derived from any germline or rearranged human variable domain, or may be a synthetic variable domain based on consensus or actual sequences of known human variable domains. A variable domain can be derived from a non-human antibody. A CDR sequence of the invention (e.g. CDR3) may be introduced into a repertoire of variable domains lacking a CDR (e.g. CDR3), using recombinant DNA technology. For example, Marks et al. [57] describe methods of producing repertoires of antibody variable domains in which consensus primers directed at or adjacent to the 5' end of the variable domain area are used in conjunction with consensus primers to the third framework region of human VH genes to provide a repertoire of VH variable domains lacking a CDR3. Marks et al. further describe how this repertoire may be combined with a CDR3 of a particular antibody. Using analogous techniques, the CDR3-derived sequences of the present invention may be shuffled with repertoires of VH or VL domains lacking a CDR3, and the shuffled complete VH or VL domains combined with a cognate VL or VH domain to provide binding members of the invention. The repertoire may then be displayed in a suitable host system, such as the phage display system of WO92/01047, which is herein incorporated by reference in its entirety, or any of a subsequent large body of literature, including Kay, Winter & McCafferty [58], so that suitable binding members may be selected. A repertoire may consist of from anything from $10^4$ individual members upwards, for example at least $10^5$, at least $10^6$, at least $10^7$, at least $10^8$, at least $10^9$ or at least $10^{10}$ members or more. Other suitable host systems include, but are not limited to yeast display, bacterial display, T7 display, viral display, cell display, ribosome display and covalent display.

A method of preparing a binding member for IgE antigen is provided, which method comprises:

(a) providing a starting repertoire of nucleic acids encoding a VH domain which either include a CDR3 to be replaced or lack a CDR3 encoding region;

(b) combining said repertoire with a donor nucleic acid encoding an amino acid sequence substantially as set out herein for a VH CDR3 such that said donor nucleic acid is inserted into the CDR3 region in the repertoire, so as to provide a product repertoire of nucleic acids encoding a VH domain;

(c) expressing the nucleic acids of said product repertoire;

(d) selecting a binding member for IgE; and (e) recovering said binding member or nucleic acid encoding it.

Again, an analogous method may be employed in which a VL CDR3 of the invention is combined with a repertoire of nucleic acids encoding a VL domain that either include a CDR3 to be replaced or lack a CDR3 encoding region.

Similarly, one or more, or all three CDRs may be grafted into a repertoire of VH or VL domains that are then screened for a binding member or binding members for IgE.

For example, one or more of the parent or antibody 2 to 28 HCDR1, HCDR2 and HCDR3 or the parent or antibody 2 to 28 set of HCDRs may be employed, and/or one or more of the parent or antibody 2 to 28 LCDR1, LCDR2 and LCDR3 or the parent or antibody 2 to 28 set of LCDRs may be employed.

Similarly, other VH and VL domains, sets of CDRs and sets of HCDRs and/or sets of LCDRs disclosed herein may be employed.

A substantial portion of an immunoglobulin variable domain may comprise at least the three CDR regions, together with their intervening framework regions. The portion may also include at least about 50% of either or both of the first and fourth framework regions, the 50% being the C-terminal 50% of the first framework region and the N-terminal 50% of the fourth framework region. Additional residues at the N-terminal or C-terminal end of the substantial part of the variable domain may be those not normally associated with naturally occurring variable domain regions. For example, construction of binding members of the present invention made by recombinant DNA techniques may result in the introduction of N- or C-terminal residues encoded by linkers introduced to facilitate cloning or other manipulation steps. Other manipulation steps include the introduction of linkers to join variable domains of the invention to further protein sequences including antibody constant regions, other variable domains (for example in the production of diabodies) or detectable/functional labels as discussed in more detail elsewhere herein.

Although in some aspects of the invention, binding members comprise a pair of VH and VL domains, single binding domains based on either VH or VL domain sequences form further aspects of the invention. It is known that single immunoglobulin domains, especially VH domains, are capable of binding target antigens in a specific manner. For example, see the discussion of dAbs above.

In the case of either of the single binding domains, these domains may be used to screen for complementary domains capable of forming a two-domain binding member able to bind IgE. This may be achieved by phage display screening methods using the so-called hierarchical dual combinatorial approach as disclosed in WO92/01047, herein incorporated by reference in its entirety, in which an individual colony containing either an H or L chain clone is used to infect a complete library of clones encoding the other chain (L or H) and the resulting two-chain binding member is selected in accordance with phage display techniques, such as those described in that reference. This technique is also disclosed in Marks et al, ibid.

Binding members of the present invention may further comprise antibody constant regions or parts thereof, e.g. human antibody constant regions or parts thereof. For example, a VL domain may be attached at its C-terminal end to antibody light chain constant domains including human Cκ or Cλ chains. Similarly, a binding member based on a VH domain may be attached at its C-terminal end to all or part (e.g. a CH1 domain) of an immunoglobulin heavy chain derived from any antibody isotype, e.g. IgG, IgA, IgE and IgM and any of the isotype sub-classes, particularly IgG1 and IgG2. IgG1 is advantageous due to its ease of manufacture and stability, e.g., half-life. Any synthetic or other constant region variant that has these properties and stabilizes variable regions may also be useful in the present invention.

Binding members of the invention may be labelled with a detectable or functional label. Thus, a binding member or antibody molecule can be present in the form of an immunoconjugate so as to obtain a detectable and/or quantifiable signal. An immunoconjugate may comprise an antibody molecule of the invention conjugated with detectable or functional label. A label can be any molecule that produces or can be induced to produce a signal, including but not limited to fluorescers, radiolabels, enzymes, chemiluminescers or photosensitizers. Thus, binding may be detected and/or measured by detecting fluorescence or luminescence, radioactivity, enzyme activity or light absorbance.

Suitable labels include, by way of illustration and not limitation, enzymes, such as alkaline phosphatase, glucose-6-phosphate dehydrogenase ("G6PDH"), alpha-D-galactosidase, glucose oxydase, glucose amylase, carbonic anhydrase, acetylcholinesterase, lysozyme, malate dehydrogenase and peroxidase e.g. horseradish peroxidase;

dyes;

fluorescent labels or fluorescers, such as fluorescein and its derivatives, fluorochrome, rhodamine compounds and derivatives, GFP (GFP for "Green Fluorescent Protein"), dansyl, umbelliferone, phycoerythrin, phycocyanin, allophycocyanin, o-phthaldehyde, and fluorescamine; fluorophores such as lanthanide cryptates and chelates e.g. Europium etc (Perkin Elmer and C is Biointernational), chemoluminescent labels or chemiluminescers, such as isoluminol, luminol and the dioxetanes;

bio-luminescent labels, such as luciferase and luciferin;

sensitizers;

coenzymes;

enzyme substrates;

radiolabels including but not limited to bromine-77, carbon14, cobalt57, fluorine-8, gallium67, gallium 68, hydrogen3 (tritium), indium111, indium 113m, iodine123m, iodine125, iodine126, iodine131, iodine133, mercury107, mercury203, phosphorous32, rhenium99m, rhenium101, rhenium105, ruthenium95, ruthenium97, ruthenium103, ruthenium105, scandium47, selenium75, sulphur35, technetium99, technetium99m, tellurium121m, tellurium122m, tellurium125m, thulium165, thulium167, thulium168, yttrium199 and other radiolabels mentioned herein;

particles, such as latex or carbon particles; metal sol; crystallite; liposomes; cells, etc., which may be further labelled with a dye, catalyst or other detectable group;

molecules such as biotin, digoxygenin or 5-bromodeoxyuridine;

toxin moieties, such as for example a toxin moiety selected from a group of *Pseudomonas* exotoxin (PE or a cytotoxic fragment or mutant thereof), Diptheria toxin or a cytotoxic fragment or mutant thereof, a botulinum toxin A, B, C, D, E or F, ricin or a cytotoxic fragment thereof e.g. ricin A, abrin or a cytotoxic fragment thereof, saporin or a cytotoxic fragment thereof, pokeweed antiviral toxin or a cytotoxic fragment thereof and bryodin 1 or a cytotoxic fragment thereof.

Suitable enzymes and coenzymes are disclosed in Litman, et al., U.S. Pat. No. 4,275,149, and Boguslaski, et al., U.S. Pat. No. 4,318,980, each of which are herein incorporated by reference in their entireties. Suitable fluorescers and chemiluminescers are disclosed in Litman, et al., U.S. Pat. No. 4,275,149, which is incorporated herein by reference in its entirety. Labels further include chemical moieties, such as biotin that may be detected via binding to a specific cognate detectable moiety, e.g. labelled avidin or streptavidin. Detectable labels may be attached to antibodies of the invention using conventional chemistry known in the art.

Immunoconjugates or their functional fragments can be prepared by methods known to the person skilled in the art. They can be coupled to enzymes or to fluorescent labels directly or by the intermediary of a spacer group or of a linking group, such as a polyaldehyde, like glutaraldehyde, ethylenediaminetetraacetic acid (EDTA), diethylene-triaminepentaacetic acid (DPTA), or in the presence of coupling agents, such as those mentioned above for the therapeutic conjugates. Conjugates containing labels of fluorescein type can be prepared by reaction with an isothiocyanate.

The methods known to the person skilled in the art existing for coupling the therapeutic radioisotopes to the antibodies either directly or via a chelating agent, such as EDTA, DTPA mentioned above can be used for the radioelements which can be used in diagnosis. It is likewise possible to perform labelling with sodium125 by the chloramine T method [59] or else with technetium99m by the technique of Crockford et al., (U.S. Pat. No. 4,424,200, herein incorporated by reference in its entirety) or attached via DTPA as described by Hnatowich (U.S. Pat. No. 4,479,930, herein incorporated by reference in its entirety).

There are numerous methods by which the label can produce a signal detectable by external means, for example, by visual examination, electromagnetic radiation, heat, and chemical reagents. The label can also be bound to another binding member that binds the antibody of the invention, or to a support.

The label can directly produce a signal, and therefore, additional components are not required to produce a signal. Numerous organic molecules, for example fluorescers, are able to absorb ultraviolet and visible light, where the light absorption transfers energy to these molecules and elevates them to an excited energy state. This absorbed energy is then dissipated by emission of light at a second wavelength. This second wavelength emission may also transfer energy to a labelled acceptor molecule, and the resultant energy dissipated from the acceptor molecule by emission of light for example fluorescence resonance energy transfer (FRET). Other labels that directly produce a signal include radioactive isotopes and dyes.

Alternately, the label may need other components to produce a signal, and the signal producing system would then include all the components required to produce a measurable signal, which may include substrates, coenzymes, enhancers, additional enzymes, substances that react with enzymic products, catalysts, activators, cofactors, inhibitors, scavengers, metal ions, and a specific binding substance required for binding of signal generating substances. A detailed discussion of suitable signal producing systems can be found in Ullman, et al. U.S. Pat. No. 5,185,243, which is herein incorporated herein by reference in its entirety.

The present invention provides a method comprising causing or allowing binding of a binding member as provided herein to IgE. As noted, such binding may take place in vivo, e.g. following administration of a binding member or encoding nucleic acid to a human or animal (e.g., a mammal), or it may take place in vitro, for example in ELISA, Western blotting, immunocytochemistry, immunoprecipitation, affinity chromatography, and biochemical or cell-based assays.

Generally, complexes between the binding member of the invention and IgE may be detected by, inter alia, enzyme-linked immunoassay, radioassay, immunoprecipitation, fluorescence immunoassay, chemiluminescent assay, immunoblot assay, lateral flow assay, agglutination assay and particulate-based assay.

The present invention also provides for measuring levels of antigen directly, by employing a binding member according to the invention for example in a biosensor system. For instance, the present invention comprises a method of detecting and/or measuring binding to IgE, comprising, (i) exposing said binding member to IgE and (ii) detecting binding of said binding member to IgE, wherein binding is detected using any method or detectable label described herein. This, and any other binding detection method described herein, may be interpreted directly by the person performing the method, for instance, by visually observing a detectable label. Alternatively, this method, or any other binding detection method described herein, may produce a report in the form of an autoradiograph, a photograph, a computer printout, a flow cytometry report, a graph, a chart, a test tube or container or well containing the result, or any other visual or physical representation of a result of the method.

The amount of binding of binding member to IgE may be determined. Quantitation may be related to the amount of the antigen in a test sample, which may be of diagnostic interest. Screening for IgE binding and/or the quantitation thereof may be useful, for instance, in screening patients for diseases or disorders referred to herein and/or any other disease or disorder involving aberrant IgE production, expression and/or activity.

A diagnostic method of the invention may comprise (i) obtaining a tissue or fluid sample from a subject, (ii) exposing said tissue or fluid sample to one or more binding members of the present invention; and (iii) detecting bound IgE as compared with a control sample, wherein an increase in the amount of IgE binding as compared with the control may indicate an aberrant level of IgE production, expression or activity. Tissue or fluid samples to be tested include blood, serum, urine, biopsy material, tumours, or any tissue suspected of containing aberrant IgE levels. Subjects testing positive for aberrant IgE levels or activity may also benefit from the treatment methods disclosed later herein.

The diagnostic method of the invention may further comprise capturing a complex of the binding member and IgE via an immobilized antigen. For example, an antigen may be immobilized on a lateral strip assay for capturing antigen-specific IgE in a sample of interest.

Those skilled in the art are able to choose a suitable mode of determining binding of the binding member to an antigen according to their preference and general knowledge, in light of the methods disclosed herein.

The reactivities of binding members in a sample may be determined by any appropriate means. Radioimmunoassay (RIA) is one possibility. Radioactive labelled antigen is mixed with unlabelled antigen (the test sample) and allowed to bind to the binding member. Bound antigen is physically separated from unbound antigen and the amount of radioactive antigen bound to the binding member determined. The more antigen there is in the test sample the less radioactive antigen will bind to the binding member. A competitive binding assay may also be used with non-radioactive antigen, using antigen or an analogue linked to a reporter molecule. The reporter molecule may be a fluorochrome, phosphor or laser dye with spectrally isolated absorption or emission characteristics. Suitable fluorochromes include fluorescein, rhodamine, phycoerythrin and Texas Red, and lanthanide chelates or cryptates. Suitable chromogenic dyes include diaminobenzidine.

Other reporters include macromolecular colloidal particles or particulate material, such as latex beads that are colored, magnetic or paramagnetic, and biologically or chemically active agents that can directly or indirectly cause detectable signals to be visually observed, electronically detected or otherwise recorded. These molecules may be enzymes, which catalyze reactions that develop, or change colours or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed.

The signals generated by individual binding member-reporter conjugates may be used to derive quantifiable absolute or relative data of the relevant binding member binding in samples (normal and test).

A kit comprising a binding member according to any aspect or embodiment of the present invention is also provided as an aspect of the present invention. In the kit, the binding member may be labelled to allow its reactivity in a sample to be determined, e.g. as described further below. Further the binding member may or may not be attached to a solid support. Components of a kit are generally sterile and in sealed vials or other containers. Kits may be employed in diagnostic analysis or other methods for which binding members are useful. A kit may contain instructions for use of the components in a method, e.g. a method in accordance with the present invention. Ancillary materials to assist in or to enable performing such a method may be included within a kit of the invention. The ancillary materials include a second, different binding member which binds to the first binding member and is conjugated to a detectable label (e.g., a fluorescent label, radioactive isotope or enzyme). Antibody-based kits may also comprise beads for conducting an immunoprecipitation. Each component of the kits is generally in its own suitable container. Thus, these kits generally comprise distinct containers suitable for each binding member. Further, the kits may comprise instructions for performing the assay and methods for interpreting and analyzing the data resulting from the performance of the assay.

The present invention also provides the use of a binding member as above for measuring antigen levels in a competition assay, that is to say a method of measuring the level of antigen in a sample by employing a binding member as provided by the present invention in a competition assay. This may be where the physical separation of bound from unbound antigen is not required. Linking a reporter molecule to the binding member so that a physical or optical change occurs on binding is one possibility. The reporter molecule may directly or indirectly generate detectable signals, which may be quantifiable. The linkage of reporter molecules may be directly or indirectly, covalently, e.g. via a peptide bond or non-covalently. Linkage via a peptide bond may be as a result of recombinant expression of a gene fusion encoding antibody and reporter molecule.

In various aspects and embodiments, the present invention extends to a binding member that competes for binding to IgE with any binding member defined herein, e.g. the parent antibody or any of antibodies 2 to 28, e.g. in IgG1 format. Competition between binding members may be assayed easily in vitro, for example by tagging a specific reporter molecule to one binding member which can be detected in the presence of other untagged binding member(s), to enable identification of binding members which bind the same epitope or an overlapping epitope. Competition may be determined for example using ELISA in which IgE is immobilized to a plate and a first tagged or labelled binding member along with one or more other untagged or unlabelled binding members is added to the plate. Presence of an untagged binding member that competes with the tagged binding member is observed by a decrease in the signal emitted by the tagged binding member.

For example, the present invention includes a method of identifying an IgE binding compound, comprising (i) immobilizing IgE to a support, (ii) contacting said immobilized IgE simultaneously or in a step-wise manner with at least one tagged or labelled binding member according to the invention and one or more untagged or unlabelled test binding compounds, and (iii) identifying a new IgE binding compound by observing a decrease in the amount of bound tag from the tagged binding member. Such methods can be performed in a high-throughput manner using a multiwell or array format. Such assays may be also be performed in solution. See, for instance, U.S. Pat. No. 5,814,468, which is herein incorporated by reference in its entirety. As described above, detection of binding may be interpreted directly by the person performing the method, for instance, by visually observing a detectable label, or a decrease in the presence thereof. Alternatively, the binding methods of the invention may produce a report in the form of an autoradiograph, a photograph, a computer printout, a flow cytometry report, a graph, a chart, a test tube or container or well containing the result, or any other visual or physical representation of a result of the method.

Competition assays can also be used in epitope mapping. In one instance epitope mapping may be used to identify the epitope bound by an IgE-binding member which optionally may have optimized neutralizing and/or modulating characteristics. Such an epitope can be linear or conformational. A conformational epitope can comprise at least two different fragments of IgE, wherein said fragments are positioned in proximity to each other when IgE is folded in its tertiary or quaternary structure to form a conformational epitope which is recognized by an inhibitor of IgE, such as an IgE-binding member. In testing for competition a peptide fragment of the antigen may be employed, especially a peptide including or consisting essentially of an epitope of interest. A peptide having the epitope sequence plus one or more amino acids at either end may be used. Binding members according to the present invention may be such that their binding for antigen is inhibited by a peptide with or including the sequence given.

The present invention further provides an isolated nucleic acid encoding a binding member of the present invention. Nucleic acid may include DNA and/or RNA. In one, the present invention provides a nucleic acid that codes for a CDR or set of CDRs or VH domain or VL domain or antibody antigen-binding site or antibody molecule, e.g. scFv or IgG1, of the invention as defined above.

The present invention also provides constructs in the form of plasmids, vectors, transcription or expression cassettes which comprise at least one polynucleotide as above.

The present invention also provides a recombinant host cell that comprises one or more constructs as above. A nucleic acid encoding any CDR or set of CDRs or VH domain or VL domain or antibody antigen-binding site or antibody molecule, e.g. scFv or IgG1 as provided, itself forms an aspect of the present invention, as does a method of production of the encoded product, which method comprises expression from encoding nucleic acid therefor. Expression may conveniently be achieved by culturing under appropriate conditions recombinant host cells containing the nucleic acid. Following production by expression a VH or VL domain, or binding member may be isolated and/or purified using any suitable technique, then used as appropriate.

Nucleic acid according to the present invention may comprise DNA or RNA and may be wholly or partially synthetic. Reference to a nucleotide sequence as set out herein encompasses a DNA molecule with the specified sequence, and encompasses a RNA molecule with the specified sequence in which U is substituted for T, unless context requires otherwise.

A yet further aspect provides a method of production of an antibody VH variable domain, the method including causing expression from encoding nucleic acid. Such a method may comprise culturing host cells under conditions for production of said antibody VH variable domain.

Analogous methods for production of VL variable domains and binding members comprising a VH and/or VL domain are provided as further aspects of the present invention.

A method of production may comprise a step of isolation and/or purification of the product. A method of production may comprise formulating the product into a composition including at least one additional component, such as a pharmaceutically acceptable excipient.

Systems for cloning and expression of a polypeptide in a variety of different host cells are well known. Suitable host cells include bacteria, mammalian cells, plant cells, filamentous fungi, yeast and baculovirus systems and transgenic plants and animals. The expression of antibodies and antibody fragments in prokaryotic cells is well established in the art. For a review, see for example Plückthun [60]. A common bacterial host is *E. coli*.

Expression in eukaryotic cells in culture is also available to those skilled in the art as an option for production of a binding member [61, 62, 63]. Mammalian cell lines available in the art for expression of a heterologous polypeptide include Chinese hamster ovary (CHO) cells, HeLa cells, baby hamster kidney cells, NS0 mouse melanoma cells, YB2/0 rat myeloma cells, human embryonic kidney cells, human embryonic retina cells and many others.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids e.g. phagemid, or viral e.g. 'phage, as appropriate [64]. Many known techniques and protocols for manipulation of nucleic acid, for example in preparation of nucleic acid constructs, mutagenesis, sequencing, introduction of DNA into cells and gene expression, and analysis of proteins, are described in detail in Ausubel et al. [65].

A further aspect of the present invention provides a host cell containing nucleic acid as disclosed herein. Such a host cell may be in vitro and may be in culture. Such a host cell may be in vivo. In vivo presence of the host cell may allow intra-cellular expression of the binding members of the present invention as "intrabodies" or intra-cellular antibodies. Intrabodies may be used for gene therapy.

A still further aspect provides a method comprising introducing nucleic acid of the invention into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. Introducing nucleic acid in the host cell, in particular a eukaryotic cell may use a viral or a plasmid based system. The plasmid system may be maintained episomally or may be incorporated into the host cell or into an artificial chromosome. Incorporation may be either by random or targeted integration of one or more copies at single or multiple loci. For bacterial cells, suitable techniques may include calcium chloride transformation, electroporation and transfection using bacteriophage.

The introduction may be followed by causing or allowing expression from the nucleic acid, e.g. by culturing host cells under conditions for expression of the gene. The purification of the expressed product may be achieved by methods known to one of skill in the art.

Nucleic acid of the invention may be integrated into the genome (e.g. chromosome) of the host cell. Integration may be promoted by inclusion of sequences that promote recombination with the genome, in accordance with standard techniques.

The present invention also provides a method that comprises using a construct as stated above in an expression system in order to express a binding member or polypeptide as above.

Binding members of the present invention may be used in methods of diagnosis or treatment in human or animal subjects, especially human. Binding members for IgE may be used to treat disorders characterized by biological effects mediated by IgE, particularly allergies and asthma. For example, binding members of the invention may be used to treat allergic rhinitis, allergic contact dermatitis, atopic dermatitis, anaphylactic reaction, food allergy, urticaria, inflammatory bowel disease, eosinophilic gastroenteritis, drug-induced rash, allergic opthalmopathy, or allergic conjunctivitis.

Binding members for IgE may be used to inhibit allergen-induced mast-cell degranulation in vivo or in vitro, reduce FcεR1-mediated biological responses in vivo or in vitro, as well as to reduce circulating IgE in a human or animal patient.

Accordingly, the invention provides a method for inhibiting allergen-induced mast cell degranulation in a mammal, comprising administering to said mammal a binding member, for examples an antibody, VH domain, or VL domain of the invention, in an amount sufficient to neutralize IgE.

The invention further provides a method for reducing FcεRI-biological responses with or without simultaneous reduction of FcεRII-mediated biological responses, comprising, contacting a cell expressing the FcεRI and/or the FcεRII with a binding member, for examples an antibody, VH domain, or VL domain of the invention, in the presence of IgE.

The invention further provides a method for reducing FcERI-mediated biological responses with or without simultaneous reduction of FcERII-mediated biological responses, comprising, contacting a cell expressing the FcεRI and/or the FcεRII with a binding member, for example an antibody, VH domain, or VL domain of the invention, in the presence of IgE.

When test cells are contacted with the binding member of the invention in vitro, a control cell(s) may also be used for positive controls (e.g., reactions containing no binding member) and/or negative controls (e.g., reactions containing no IgE and/or antigen).

When cells are contacted by the binding member in vivo, for example, by administering the binding member of the invention to a mammal exhibiting FcεRI- and/or FcεRII-mediated biological responses, the binding member of the invention is administered in amounts sufficient to neutralize IgE.

Still further, the invention provides a method for reducing circulating IgE in a mammal, such as a human, comprising administering a binding member, such as an antibody, VH domain, or VL domain of the invention, in an amount sufficient to neutralize and reduce circulating free IgE.

Binding members of the invention may be used in the diagnosis or treatment of diseases or disorders including but not limited to any one or more of the following: allergic rhinitis, allergic contact dermatitis, atopic dermatitis, anaphylactic reaction, food allergy, urticaria, inflammatory bowel disease, eosinophilic gastroenteritis, drug-induced rash, allergic opthalmopathy, rhino-conjunctivitis, allergic conjunctivitis, asthma bronchiale, airway hyperresponsiveness, cosmetic allergy, drug-induced allergy, drug-induced hypersensitivity syndrome, metal allergy, occupational hypersensitivity pneumonitis, chronic hypersensitivity pneumonitis, cold hypersensitivity, helminthic infection induced hypersensitivity, latex allergy and hay fever.

The data presented herein with respect to binding and neutralization of IgE thus indicate that binding members of the invention can be used to treat or prevent such disorders, including the reduction of severity of the disorders. Accordingly, the invention provides a method of treating or reducing the severity of at least one symptom of any of the disorders mentioned herein, comprising administering to a patient in need thereof an effective amount of one or more binding members of the present invention alone or in a combined therapeutic regimen with another appropriate medicament known in the art or described herein such that the severity of at least one symptom of any of the above disorders is reduced.

Binding members of the invention may be used in appropriate animals and in animal models of disease, especially monkeys.

Thus, the binding members of the present invention are useful as therapeutic agents in the treatment of diseases or disorders involving IgE, e.g. IgE production, expression and/or activity, especially aberrant production, expression, or activity. A method of treatment may comprise administering an effective amount of a binding member of the invention to a patient in need thereof, wherein production, expression and/or activity of IgE is thereby decreased. A method of treatment may comprise (i) identifying a patient demonstrating increased IgE levels or activity, for instance using the diagnostic methods described above, and (ii) administering an effective amount of a binding member of the invention to the patient, wherein increased production, expression and/or activity of IgE is decreased. An alternative method of treatment may comprise (i) identifying a patient who has no apparent increase in IgE levels but who is believed to benefit from administration of a binding member of the invention, and (ii) administering an effective amount of a binding member of the invention to the patient. An effective amount according to the invention is an amount that decreases the increased production, expression and/or activity of IgE so as to decrease or lessen the severity of at least one symptom of the particular disease or disorder being treated, but not necessarily cure the disease or disorder.

The invention also provides a method of antagonising at least one effect of IgE comprising contacting with or administering an effective amount of one or more binding members of the present invention such that said at least one effect of IgE is antagonised. Effects of IgE that may be antagonised by the methods of the invention include biological responses mediated by FcεRI and/or FcεRII, and any downstream effects that arise as a consequence of these binding reactions.

Accordingly, further aspects of the invention provide the use of an isolated binding member, such as an antibody, VH domain or VL domain of the invention for the manufacture of a medicament for treating a disorder associated with, or mediated by, IgE as discussed herein. Such use of, or methods of making, a medicament or pharmaceutical composition comprise formulating the binding member with a pharmaceutically acceptable excipient.

A pharmaceutically acceptable excipient may be a compound or a combination of compounds entering into a pharmaceutical composition not provoking secondary reactions and which allows, for example, facilitation of the administration of the active compound(s), an increase in its lifespan and/or in its efficacy in the body, an increase in its solubility in solution or else an improvement in its conservation. These pharmaceutically acceptable vehicles are well known and will be adapted by the person skilled in the art as a function of the nature and of the mode of administration of the active compound(s) chosen.

Binding members of the present invention will usually be administered in the form of a pharmaceutical composition, which may comprise at least one component in addition to the binding member. Thus pharmaceutical compositions according to the present invention, and for use in accordance with the present invention, may comprise, in addition to active ingredient, a pharmaceutically acceptable excipient, carrier, buffer, stabilizer or other materials well known to those skilled in the art. Such materials should be non-toxic and should not interfere with the efficacy of the active ingredient. The precise nature of the carrier or other material will depend on the route of administration, which may be oral, inhaled, intra-tracheal, topical, intra-vesicular or by injection, as discussed below.

Pharmaceutical compositions for oral administration, such as for example single domain antibody molecules (e.g. "Nanobodies™") etc are also envisaged in the present invention. Such oral formulations may be in tablet, capsule, powder, liquid or semi-solid form. A tablet may comprise a solid carrier, such as gelatin or an adjuvant. Liquid pharmaceutical compositions generally comprise a liquid carrier, such as water, petroleum, animal or vegetable oils, mineral oil or synthetic oil. Physiological saline solution, dextrose or other saccharide solution or glycols, such as ethylene glycol, propylene glycol or polyethylene glycol may be included.

For intra-venous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles, such as Sodium Chloride Injection, Ringer's Injection, Lactated Ringer's Injection. Preservatives, stabilizers, buffers, antioxidants and/or other additives may be employed as required including buffers such as phosphate, citrate and other organic acids; antioxidants, such as ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3'-pentanol; and m-cresol); low molecular weight polypeptides; proteins, such as serum albumin, gelatin or immunoglobulins; hydrophilic polymers, such as polyvinylpyrrolidone; amino acids, such as glycine, glutamine, asparagines, histidine, arginine, or lysine; monosaccharides, disaccharides and other carbohydrates including glucose, mannose or dextrins; chelating agents, such as EDTA; sugars, such as sucrose, mannitol, trehalose or sorbitol; salt-forming counter-ions, such as sodium; metal complexes (e.g. Zn-protein complexes); and/or non-ionic surfactants, such as TWEEN™, PLURONICS™ or polyethylene glycol (PEG).

Binding members of the present invention may be formulated in liquid, semi-solid or solid forms depending on the physicochemical properties of the molecule and the route of delivery. Formulations may include excipients, or combinations of excipients, for example: sugars, amino acids and surfactants. Liquid formulations may include a wide range of antibody concentrations and pH. Solid formulations may be produced by lyophilisation, spray drying, or drying by supercritical fluid technology, for example. Formulations of anti-IgE will depend upon the intended route of delivery: for example, formulations for pulmonary delivery may consist of particles with physical properties that ensure penetration into the deep lung upon inhalation; topical formulations (e.g. for treatment of scarring, e.g. dermal scarring) may include viscosity modifying agents, which prolong the time that the drug is resident at the site of action. A binding member may be prepared with a carrier that will protect the binding member against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are known to those skilled in the art [66].

Anti-IgE treatment may be given orally (such as for example single domain antibody molecules (e.g. "Nanobodies™")) by injection (for example, subcutaneously, intra-articular, intra-venously, intra-peritoneal, intra-arterial or intra-muscularly), by inhalation, intra-tracheal, by the intra-vesicular route (instillation into the urinary bladder), or topically (for example intra-ocular, intra-nasal, rectal, into wounds, on skin). The treatment may be administered by pulse infusion, particularly with declining doses of the binding member. The route of administration can be determined by the physicochemical characteristics of the treatment, by special considerations for the disease or by the requirement to optimize efficacy or to minimize side-effects. One particular route of administration is intra-venous. Another route of administering pharmaceutical compositions of the present invention is subcutaneously. It is envisaged that anti-IgE treatment will not be restricted to use in the clinic. Therefore, subcutaneous injection using a needle-free device is also advantageous.

Examples of intravenous formulations include:
Formulation (1) comprises
    An isolated binding member of the invention (optionally 10, 50, 100 or 150 mg/ml of said binding member, for example, an antibody)
    50 mM sodium acetate
    100 mM NaCl
    pH5.5

Formulation (2) comprises
    An isolated binding member of the invention (optionally 10, 50, 100 or 150 mg/ml of said binding member, for example, an antibody)
    20 mM Succinate
    105 mM NaCl
    10 mM Arginine
    pH 6.00

A composition may be administered alone or in combination with other treatments, either simultaneously or sequentially dependent upon the condition to be treated.

A binding member for IgE may be used as part of a combination therapy in conjunction with an additional medicinal component. Combination treatments may be used to provide significant synergistic effects, particularly the combination of an anti-IgE binding member with one or more other drugs. A binding member for IgE may be administered concurrently or sequentially or as a combined preparation with another therapeutic agent or agents, for the treatment of one or more of the conditions listed herein.

A binding member of the invention may be formulated and/or used in combination with other available treatments for asthma and allergic disorders, or other disorders involving IgE mediated effects.

A binding member according to the present invention may be provided in combination or addition with one or more of the following agents:

a cytokine or agonist or antagonist of cytokine function (e.g. an agent which acts on cytokine signalling pathways, such as a modulator of the SOCS system), such as an alpha-, beta- and/or gamma-interferon; insulin-like growth factor type I (IGF-1), its receptors and associated binding proteins; interleukins (IL), e.g. one or more of IL-1 to −33, and/or an interleukin antagonist or inhibitor, such as anakinra; inhibitors of receptors of interleukin family members or inhibitors of specific subunits of such receptors, a tumour necrosis factor alpha (TNF-α) inhibitor, such as an anti-TNF monoclonal antibodies (for example infliximab, adalimumab and/or CDP-870) and/or a TNF receptor antagonist, e.g. an immunoglobulin molecule (such as etanercept) and/or a low-molecular-weight agent, such as pentoxyfylline;

a modulator of B cells, e.g. a monoclonal antibody targeting B-lymphocytes (such as CD20 (rituximab) or MRA-aIL16R) or T-lymphocytes (e.g. CTLA4-Ig, HuMax 1'-15 or Abatacept);

a modulator that inhibits osteoclast activity, for example an antibody to RANKL;

a modulator of chemokine or chemokine receptor function, such as an antagonist of CCR1, CCR2, CCR2A, CCR2B, CCR3, CCR4, CCR5, CCR6, CCR7, CCR8, CCR9, CCR10 and CCR11 (for the C-C family); CXCR1, CXCR2, CXCR3, CXCR4 and CXCR5 and CXCR6 (for the C-X-C family) and $CX_3CR1$ for the $C-X_3-C$ family;

an inhibitor of matrix metalloproteases (MMPs), i.e. one or more of the stromelysins, the collagenases and the gelatinases as well as aggrecanase, especially collagenase-1 (MMP-1), collagenase-2 (MMP-8), collagenase-3 (MMP-13), stromelysin-1 (MMP-3), stromelysin-2 (MMP-10) and/or stromelysin-3 (MMP-11) and/or MMP-9 and/or MMP-12, e.g. an agent such as doxycycline;

a leukotriene biosynthesis inhibitor, 5-lipoxygenase (5-LO) inhibitor or 5-lipoxygenase activating protein (FLAP) antagonist, such as zileuton; ABT-761; fenleuton; tepoxalin; Abbott-79175; Abbott-85761; N-(5-substituted)-thiophene-2-alkylsulfonamides; 2,6-di-tert-butylphenolhydrazones; methoxytetrahydropyrans such as Zeneca ZD-2138; the compound SB-210661; a pyridinyl-substituted 2-cyanonaphthalene compound, such as L-739,010; a 2-cyanoquinoline compound, such as L-746,530; indole and/or a quinoline compound, such as MK-591, MK-886 and/or BAY x 1005;

a receptor antagonist for leukotrienes (LT) B4, LTC4, LTD4, and LTE4, selected from the group consisting of the phenothiazin-3-1s, such as L-651,392; amidino compounds, such as CGS-25019c; benzoxalamines, such as ontazolast; benzenecarboximidamides, such as BIIL 284/260; and compounds, such as zafirlukast, ablukast, montelukast, pranlukast, verlukast (MK-679), RG-12525, Ro-245913, iralukast (CGP 45715A) and BAY x 7195;

a phosphodiesterase (PDE) inhibitor, such as a methylxanthanine, e.g. theophylline and/or aminophylline; and/or a selective PDE isoenzyme inhibitor, e.g. a PDE4 inhibitor and/or inhibitor of the isoform PDE4D and/or an inhibitor of PDE5;

a histamine type 1 receptor antagonist, such as cetirizine, loratadine, desloratadine, fexofenadine, acrivastine, terfenadine, astemizole, azelastine, levocabastine, chlorpheniramine, promethazine, cyclizine, and/or mizolastine (generally applied orally, topically or parenterally);

a proton pump inhibitor (such as omeprazole) or gastroprotective histamine type 2 receptor antagonist;

an antagonist of the histamine type 4 receptor;

an alpha-1/alpha-2 adrenoceptor agonist vasoconstrictor sympathomimetic agent, such as propylhexedrine, phenylephrine, phenylpropanolamine, ephedrine, pseudoephedrine, naphazoline hydrochloride, oxymetazoline hydrochloride, tetrahydrozoline hydrochloride, xylometazoline hydrochloride, tramazoline hydrochloride and ethylnorepinephrine hydrochloride;

an anticholinergic agent, e.g. a muscarinic receptor (M1, M2, and M3) antagonist, such as atropine, hyoscine, glycopyrrrolate, ipratropium bromide, tiotropium bromide, oxitropium bromide, pirenzepine and telenzepine;

a beta-adrenoceptor agonist (including beta receptor subtypes 1-4), such as isoprenaline, salbutamol, formoterol, salmeterol, terbutaline, orciprenaline, bitolterol mesylate and/or pirbuterol, e.g. a chiral enantiomer thereof;

a chromone, e.g. sodium cromoglycate and/or nedocromil sodium;

a glucocorticoid, such as flunisolide, triamcinolone acetonide, beclomethasone dipropionate, budesonide, fluticasone propionate, ciclesonide, and/or mometasone furoate;

an agent that modulate nuclear hormone receptors, such as a PPAR;

an immunoglobulin (Ig) or Ig preparation or an antagonist or antibody modulating Ig function, such as anti-IgE that binds to the same or a different epitope as the binding member of the invention;

other systemic or topically-applied anti-inflammatory agent, e.g. thalidomide or a derivative thereof, a retinoid, dithranol and/or calcipotriol;

combinations of aminosalicylates and sulfapyridine, such as sulfasalazine, mesalazine, balsalazide, and olsalazine; and immunomodulatory agents, such as the thiopurines; and corticosteroids, such as budesonide;

an antibacterial agent, e.g. a penicillin derivative, a tetracycline, a macrolide, a beta-lactam, a fluoroquinolone, metronidazole and/or an inhaled aminoglycoside; and/or an anti-viral agent, e.g. acyclovir, famciclovir, valaciclovir, ganciclovir, cidofovir; amantadine, rimantadine; ribavirin; zanamavir and/or oseltamavir; a protease inhibitor, such as indinavir, nelfinavir, ritonavir and/or saquinavir; a nucleoside reverse transcriptase inhibitor, such as didanosine, lamivudine, stavudine, zalcitabine, zidovudine; a non-nucleoside reverse transcriptase inhibitor, such as nevirapine, efavirenz;

a cardiovascular agent, such as a calcium channel blocker, beta-adrenoceptor blocker, angiotensin-converting enzyme (ACE) inhibitor, angiotensin-2 receptor antagonist; lipid lowering agent, such as a statin and/or fibrate; a modulator of blood cell morphology, such as pentoxyfylline; a thrombolytic and/or an anticoagulant, e.g. a platelet aggregation inhibitor;

a CNS agent, such as an antidepressant (such as sertraline), anti-Parkinsonian drug (such as deprenyl, L-dopa, ropinirole, pramipexole; MAOB inhibitor, such as selegine and rasagiline; comP inhibitor, such as tasmar; A-2 inhibitor, dopamine reuptake inhibitor, NMDA antagonist, nicotine agonist, dopamine agonist and/or inhibitor of neuronal nitric oxide synthase) and an anti-Alzheimer's drug, such as donepezil, rivastigmine, tacrine, COX-2 inhibitor, propentofylline or metrifonate;

an agent for the treatment of acute and chronic pain, e.g. a centrally or peripherally-acting analgesic, such as an opioid analogue or derivative, carbamazepine, phenyloin, sodium valproate, amitryptiline or other antidepressant agent, paracetamol, or non-steroidal anti-inflammatory agent;

a parenterally or topically-applied (including inhaled) local anaesthetic agent, such as lignocaine or an analogue thereof;

an anti-osteoporosis agent, e.g. a hormonal agent, such as raloxifene, or a biphosphonate, such as alendronate;

(i) a tryptase inhibitor; (ii) a platelet activating factor (PAF) antagonist; (iii) an interleukin converting enzyme (ICE) inhibitor; (iv) an IMPDH inhibitor; (v) an adhesion molecule inhibitors including VLA-4 antagonist; (vi) a cathepsin; (vii) a kinase inhibitor, e.g. an inhibitor of tyrosine kinases (such as Btk, Itk, Jak3 MAP examples of inhibitors might include Gefitinib, Imatinib mesylate), a serine/threonine kinase (e.g. an inhibitor of MAP kinase, such as p38, JNK, protein kinases A, B and C and IKK), or a kinase involved in cell cycle regulation (e.g. a cylin dependent kinase); (viii) a glucose-6 phosphate dehydrogenase inhibitor; (ix) a kinin-B$_1$- and/or B$_2$-receptor antagonist; (x) an anti-gout agent, e.g. colchicine; (xi) a xanthine oxidase inhibitor, e.g. allopurinol; (xii) a uricosuric agent, e.g. probenecid, sulfinpyrazone, and/or benzbromarone; (xiii) a growth hormone secretagogue; (xiv) transforming growth factor (TGFβ); (xv) platelet-derived growth factor (PDGF); (xvi) fibroblast growth factor, e.g. basic fibroblast growth factor (bFGF); (xvii) granulocyte macrophage colony stimulating factor (GM-CSF); (xviii) capsaicin cream; (xix) a tachykinin NK$_1$. and/or NK$_3$. receptor antagonist, such as NKP-608C, SB-233412 (talnetant) and/or D-4418; (xx) an elastase inhibitor, e.g. UT-77 and/or ZD-0892; (xxi) a TNF-alpha converting enzyme inhibitor (TACE); (xxii) induced nitric oxide synthase (iNOS) inhibitor or (xxiii) a chemoattractant receptor-homologous molecule expressed on TH2 cells (such as a CRTH2 antagonist); (xxiv) an inhibitor of a P38 (xxv) agent modulating the function of Toll-like receptors (TLR) and (xxvi) an agent modulating the activity of purinergic receptors, such as P2X7; (xxvii) an inhibitor of transcription factor activation, such as NFkB, API, and/or STATS.

An inhibitor may be specific or may be a mixed inhibitor, e.g. an inhibitor targeting more than one of the molecules (e.g. receptors) or molecular classes mentioned above.

The binding member could also be used in association with a chemotherapeutic agent such as a tyrosine kinase inhibitor in co-administration or in the form of an immunoconjugate. Fragments of said antibody could also be use in bispecific antibodies obtained by recombinant mechanisms or biochemical coupling and then associating the specificity of the above described antibody with the specificity of other antibodies able to recognize other molecules involved in the activity for which IgE is associated.

For treatment of an inflammatory disease, e.g. rheumatoid arthritis, osteoarthritis, asthma, allergic rhinitis, chronic obstructive pulmonary disease (COPD), or psoriasis, a binding member of the invention may be combined with one or more agents, such as non-steroidal anti-inflammatory agents (hereinafter NSAIDs) including non-selective cyclo-oxygenase (COX)-1/COX-2 inhibitors whether applied topically or systemically, such as piroxicam, diclofenac, propionic acids, such as naproxen, flurbiprofen, fenoprofen, ketoprofen and ibuprofen, fenamates, such as mefenamic acid, indomethacin, sulindac, azapropazone, pyrazolones, such as phenylbutazone, salicylates, such as aspirin); selective COX-2 inhibitors (such as meloxicam, celecoxib, rofecoxib, valdecoxib, lumarocoxib, parecoxib and etoricoxib); cyclo-oxygenase inhibiting nitric oxide donors (CINODs); glucocorticosteroids (whether administered by topical, oral, intramuscular, intra-venous or intra-articular routes); methotrexate, leflunomide; hydroxychloroquine, d-penicillamine, auranofin or other parenteral or oral gold preparations; analgesics; diacerein; intra-articular therapies, such as hyaluronic acid derivatives; and nutritional supplements, such as glucosamine.

A binding member of the invention and one or more of the above additional medicinal components may be used in the manufacture of a medicament. The medicament may be for separate or combined administration to an individual, and accordingly may comprise the binding member and the additional component as a combined preparation or as separate preparations. Separate preparations may be used to facilitate separate and sequential or simultaneous administration, and allow administration of the components by different routes e.g. oral and parenteral administration.

In accordance with the present invention, compositions provided may be administered to mammals. Administration is normally in a "therapeutically effective amount", this being sufficient to show benefit to a patient. Such benefit may be at least amelioration of at least one symptom. The actual amount administered, and rate and time-course of administration, will depend on the nature and severity of what is being treated, the particular mammal being treated, the clinical condition of the individual patient, the cause of the disorder, the site of delivery of the composition, the type of binding member, the method of administration, the scheduling of administration and other factors known to medical practitioners. Prescription of treatment, e.g. decisions on dosage etc, is within the responsibility of general practitioners and other medical doctors and may depend on the severity of the symptoms and/or progression of a disease being treated. Appropriate doses of antibody are well known in the art [67, 68]. Specific dosages indicated herein or in the Physician's Desk Reference (2003) as appropriate for the type of medicament being administered may be used. A therapeutically effective amount or suitable dose of a binding member of the invention can be determined by comparing its in vitro activity and in vivo activity in an animal model. Methods for extrapolation of effective dosages in mice and other test animals to humans are known. The precise dose will depend upon a number of factors, including whether the antibody is for diagnosis, prevention or for treatment, the size and location of the area to be treated, the precise nature of the antibody (e.g. whole antibody, fragment or diabody) and the nature of any detectable label or other molecule attached to the antibody. A typical antibody dose will be in the range 100 µg to 1 g for systemic applications, and 1 µg to 1 mg for topical applications. An initial higher loading dose, followed by one or more lower doses, may be administered.

Typically, the antibody will be a whole antibody, e.g. the IgG1 isotype, IgG2 isotype, IgG3 isotype or IgG4 isotype. This is a dose for a single treatment of an adult patient, which may be proportionally adjusted for children and infants, and also adjusted for other antibody formats in proportion to molecular weight. Treatments may be repeated at daily, twice-weekly, weekly or monthly intervals, at the discretion of the physician. Treatments may be every two to four weeks for subcutaneous administration and every four to eight weeks for intra-venous administration. Treatment may be periodic, and the period between administrations is about two weeks or more, e.g. about three weeks or more, about four weeks or more, or about once a month. Treatment may be given before, and/or after surgery, and/or may be administered or applied directly at the anatomical site of surgical treatment.

BRIEF DESCRIPTION OF THE TABLES AND FIGURES

Table 1 lists the amino acid sequences of the heavy chain CDRs and the light chain CDRs of each of antibodies 1-28.

Table 2a shows example potencies of clones identified from the targeted mutagenesis libraries when tested in the Receptor-ligand binding HTRF® Assays. Table 2b shows the binding affinity (KD) for exemplary binding members of the invention to human IgE and cynomolgus monkey IgE, using SPR (BIACORE). Table 2b further shows the potency, expressed as IC50, for exemplary binding members of the invention, in an RBL-ER51 calcium signalling assay (at 4 hours with 25 ng/ml human or 100 ng/ml cynomolgus monkey IgE).

Table 3a shows the sequences of exemplary binding members of the invention are shown in the appended sequence listing, in which SEQ ID NOS correspond as shown in Table 3a.

Table 3b shows the VL DNA and VL amino sequences of exemplary binding members of the invention from the provisional application which are shown in the appended sequence listing, in which SEQ ID NOS correspond as shown in Table 3b.

Table 4. Example binding affinity calculation using BIAcore and potency measurements using RBL-ER51 calcium signalling assay for germlined antibodies.

Table 5. shows the direct interactions between IgE Cε3-Cε4 and Antibody 11 Fab in the x-ray crystallographic studies for interaction 1.

Table 6. shows the direct interactions between IgE Cε3-Cε4 and Antibody 11 Fab in the x-ray crystallographic studies for interaction 2.

Table 7. shows Crystal Parameters and X-ray Data-Processing and Refinement Statistics from the x-ray crystallographic studies.

Table 8. shows the summary study design in the safety studies (Example 8).

FIG. 1: relates to Example 2.7 and shows the molar concentration of antibody expressed as a log on the x-axis and the peak height in an RBL-ER51 calcium signalling assay on the y axis. The open squares relate to antibody 11, the crosses an irrelevant IgG1 control antibody and the inverted open triangles a anti-IgE cross-linking antibody (Biosource). Note that the open squares and crosses are superimposed on one another in this figure.

FIG. 2: shows the sequence of Cynomolgus Cε3-4 FLAG His10.

FIGS. 3A-C: show the sequence of variable heavy chain that encodes human anti-oestradiaol scFv (D12_VH) and one of cynomologous IgHE gene haplotype, (cyIgHE TQ).

FIGS. 4A-C: show the sequence of variable heavy chain that encodes human anti-oestradiaol scFv (D12_VH) and one of cynomologous IgHE gene haplotype, cyIgHE ME.

FIGS. 5A and B: show the sequence of the variable light chain of Human anti-eostradiol scFv (D12_VL) and cynomolgus lambda constant region genes cyIGLC 4, Sequence Range: 1 to 708.

FIGS. 6A and B: show the sequence of the variable light chain of Human anti-eostradiol scFv (D12_VL) and cynomolgus lambda constant region genes D12_VL cyIGLC 7.

Figure 7:
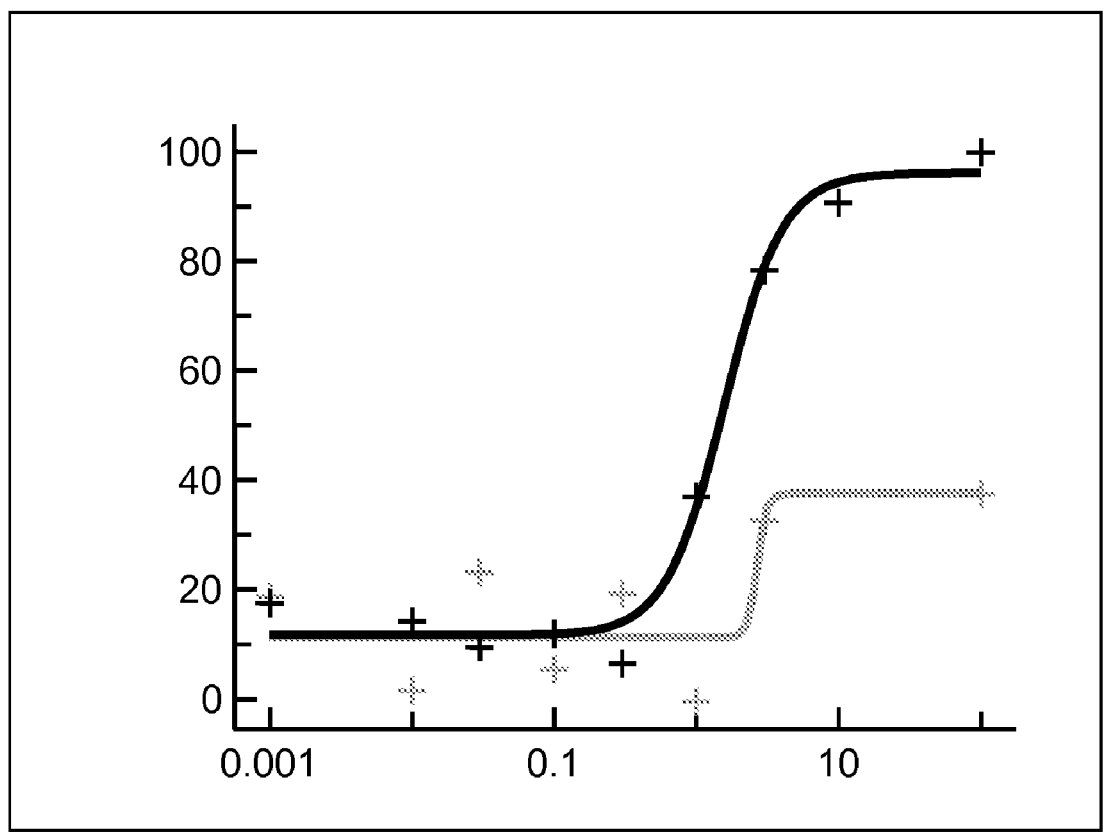

FIG. 7: relates to Example 3 and shows the percentage inhibition of maximum IgE expression in B cells not treated with blocking anti-IgE wherein the x axis is the concentration of Antibody 11 in nM and the y axis is percentage inhibition. The upper graph relates to Antibody 11 and the lower graph the control antibody.

Figure 8:
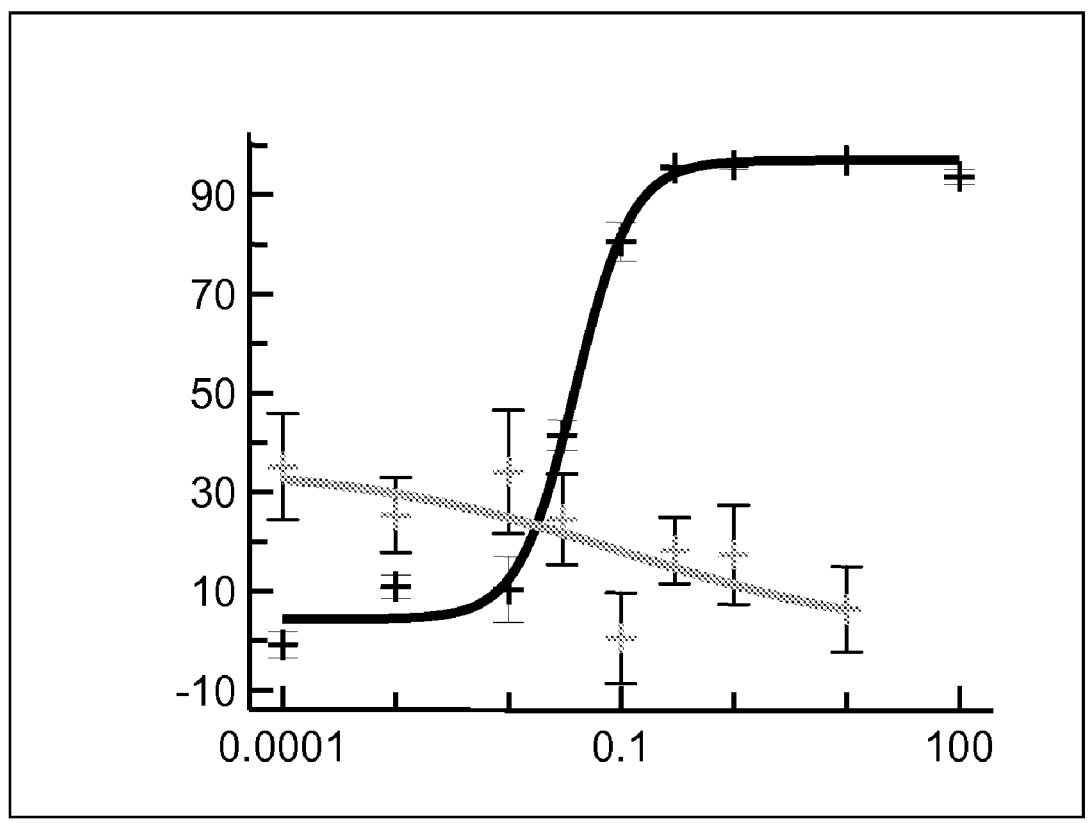

FIG. 8: relates to Example 4 and shows the percentage inhibition of total release of β-hexosaminidase +/−SEM wherein the x axis is the concentration of Antibody 11 in nM and the y axis is percentage inhibition. The upper graph relates to Antibody 11 and the lower graph to the control antibody.

Figure 9:
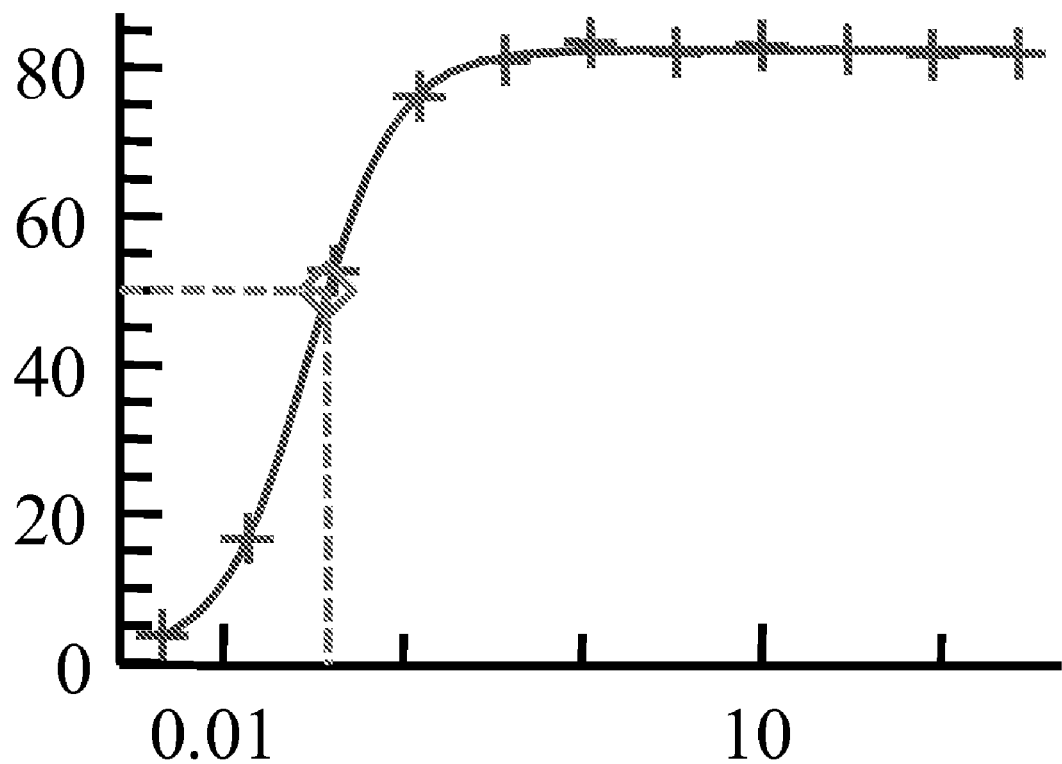

FIG. 9: Relates to Example 5. The figure shows the percentage of bound IgE in human sera with increasing concentrations of the anti-IgE antibody, Antibody 11. The x-axis measures concentration of Antibody 11 in micrograms/ml and the y axis shows amount of bound IgE as a percentage of free IgE analysed and plotted as a function of total IgE.

FIG. 10: Relates to Example 7 and shows
a) A ribbon representation of IgE Cε3-Cε4 dimer, where the two monomers are denoted IgE1 and IgE2 and interacts with two Antibody 11 Fab molecules. Glycosylations at Asn394 are shown as ball-and-stick models; and
b) A 90 degrees rotated view looking down from the top showing that the majority of the interactions to IgE from the Fab fragment is provided by the heavy chain. The figure was generated using the program PyMOL (DeLano Scientific LLC, San Carlos, Calif., U.S.A)

Figure 11:
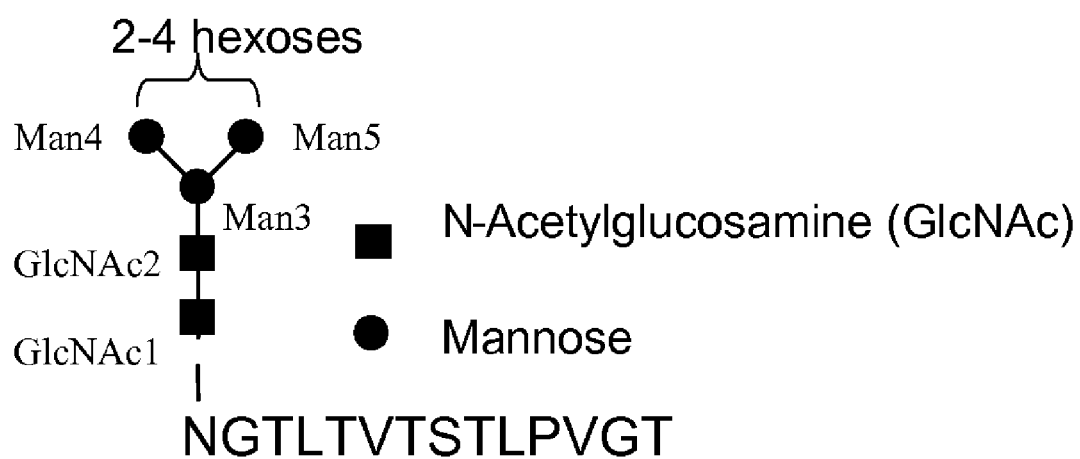

FIG. 11: Relates to Example 7 and shows the glycosylation at position Asn394 of IgE.

Figure 12:
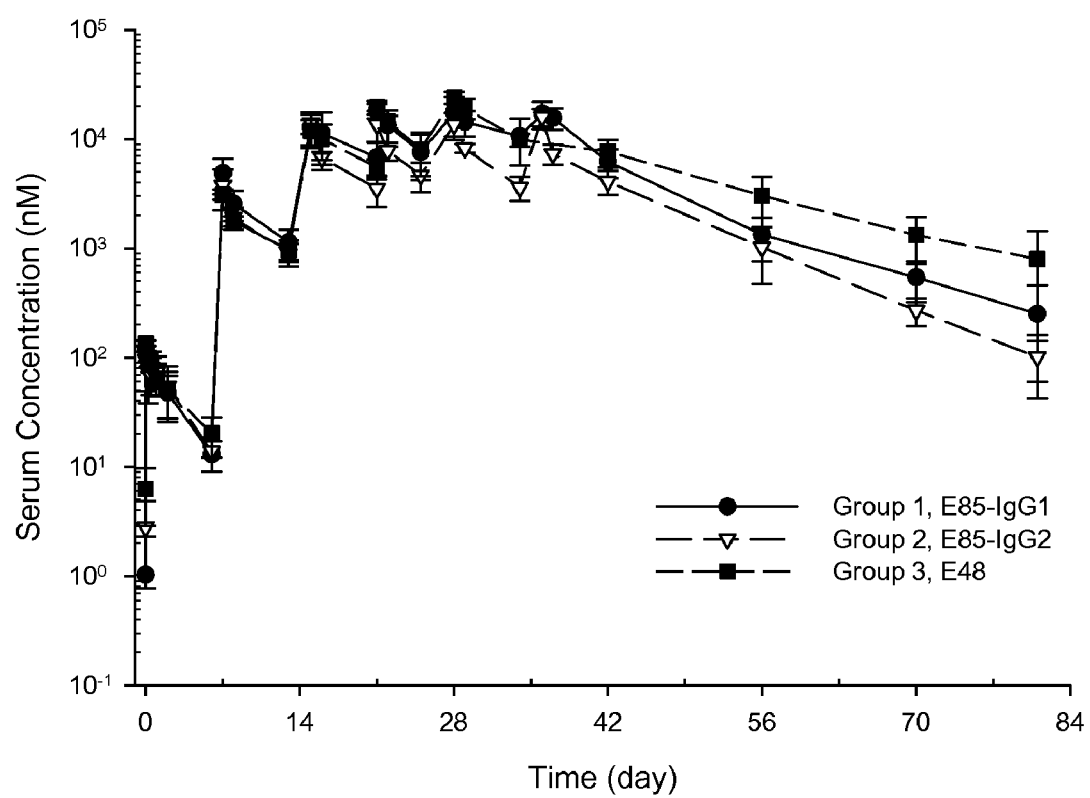

FIG. 12: Relates to Example 8 and shows mean toxicokinetics profiles of Antibody 11 IgG$_1$, Antibody 11 IgG$_2$ and E48 following 1 mg/kg (Day 1), 30 mg/kg (Day 8), and 100 mg/kg (Day 16 and beyond) doses in cynomolgus monkeys. Error bars represent standard deviations. The y-axis is serum concentration of antibody and the x axis is time in days following the first dose. Group 1 (Antibody 11 IgG1) is shown as filled circles, Group 2 (Antibody 11 IgG2) is shown as open triangles and Group 3 (a different anti-IgE molecule E48) is shown as filed squares.

Figure 13:
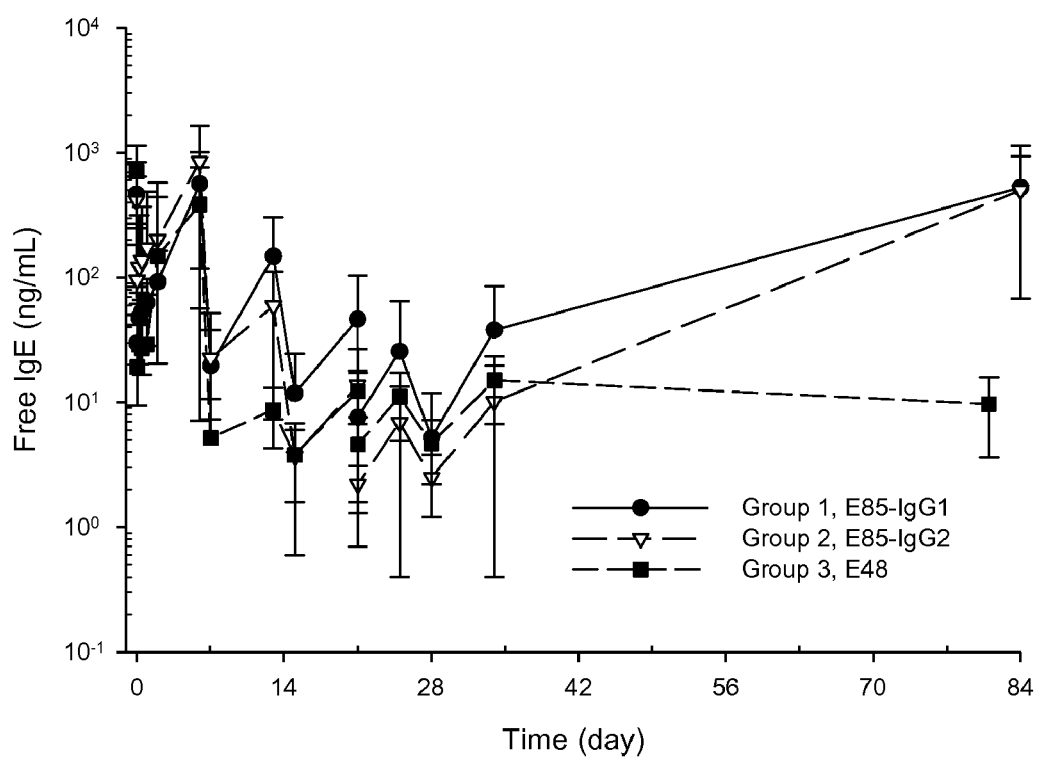

FIG. 13: Relates to Example 8 and shows mean free IgE profiles in cynomolgus monkeys receiving weekly doses of Antibody 11 IgG$_1$, Antibody 11 IgG$_2$ and E48 (1 mg/kg on Day 1, 30 mg/kg on Day 8, and 100 mg/kg on Day 16 and beyond). Error bars are standard deviations. The y-axis is IgE concentration in ng/ml and the x axis is time in days. Group 1 (Antibody 11 IgG1) is shown as filled circles, Group 2 (Antibody 11 IgG2) is shown as open triangles and Group 3 (a different anti-IgE molecule E48) is shown as filed squares.

Figure 14:
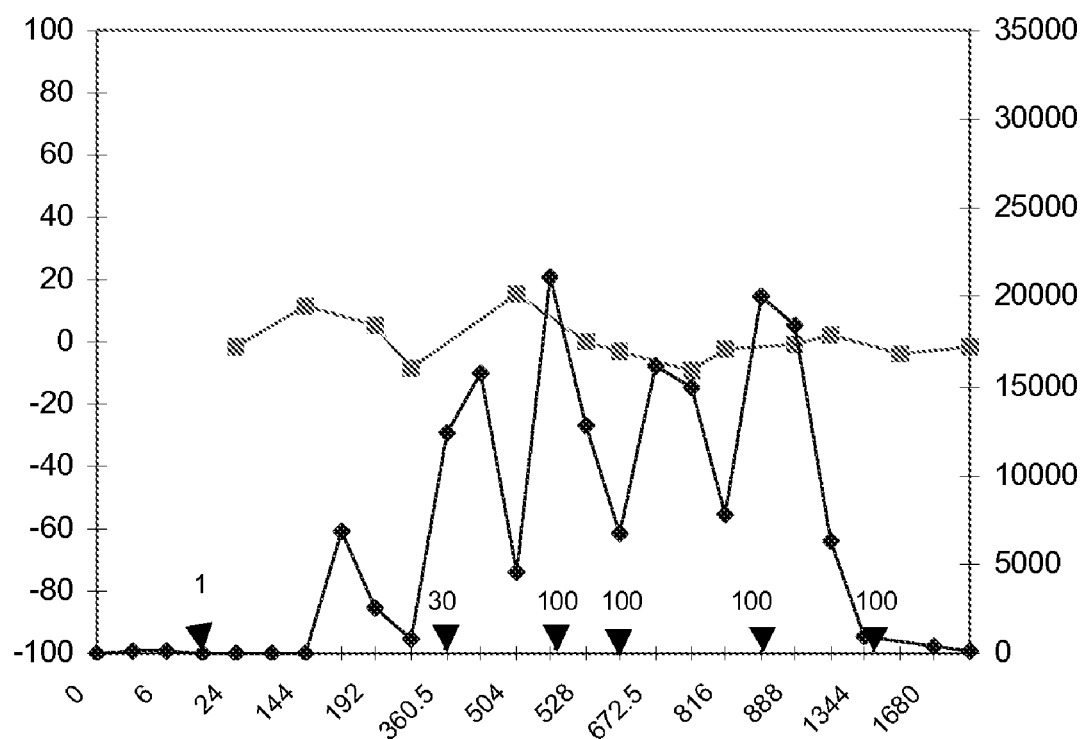

FIG. 14: Relates to Example 8 an shows a plot of platelet numbers (×10^9/L) expressed as a percentage change from the mean of the 2 pre-dose values versus plasma concentration from an animal in Group 1 (Antibody 11-treated). This plot is representative of the other 16 animals across the 3 groups that showed no significant effect on platelets. The x-axis shows time in hours, the left y axis the level of platelets as a percentage change from the mean level pre-treatment and the left y-axis the concentration of anti-IgE antibody in nmol/L. The closed squares show the platelet concentration and the filled diamonds the concentration of anti-IgE antibody. The closed triangles show the dosing of the anti-IgE antibody in mg/kg.

Figure 15:
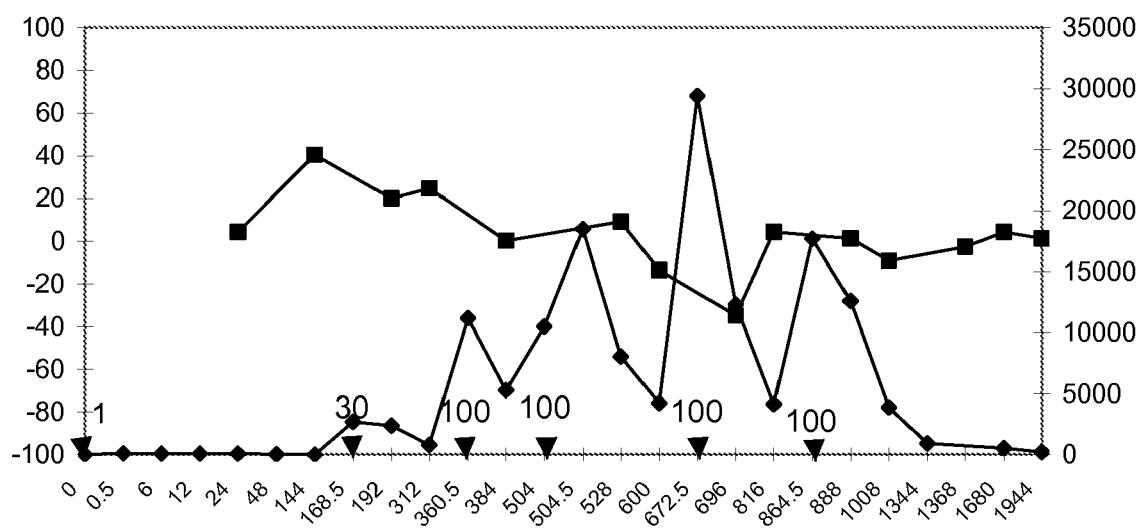

FIG. 15 Relates to Example 8 and shows a plot of platelet numbers (×10$^9$/L) expressed as a percentage change from the mean of the 2 pre-dose values versus plasma concentration from an animal in Group 1 (Antibody 11 IgG1-treated) that showed a transient significant drop (35% below baseline) in platelet numbers on day 29. The x-axis shows time in hours, the left y axis the level of platelets as a percentage change from the mean level pre-treatment and the left y-axis the concentration of anti-IgE antibody in nmol/L. The closed squares show the platelet concentration and the filled diamonds the concentration of anti-IgE antibody. The closed triangles show the dosing of the anti-IgE antibody in mg/kg.

Figure 16:
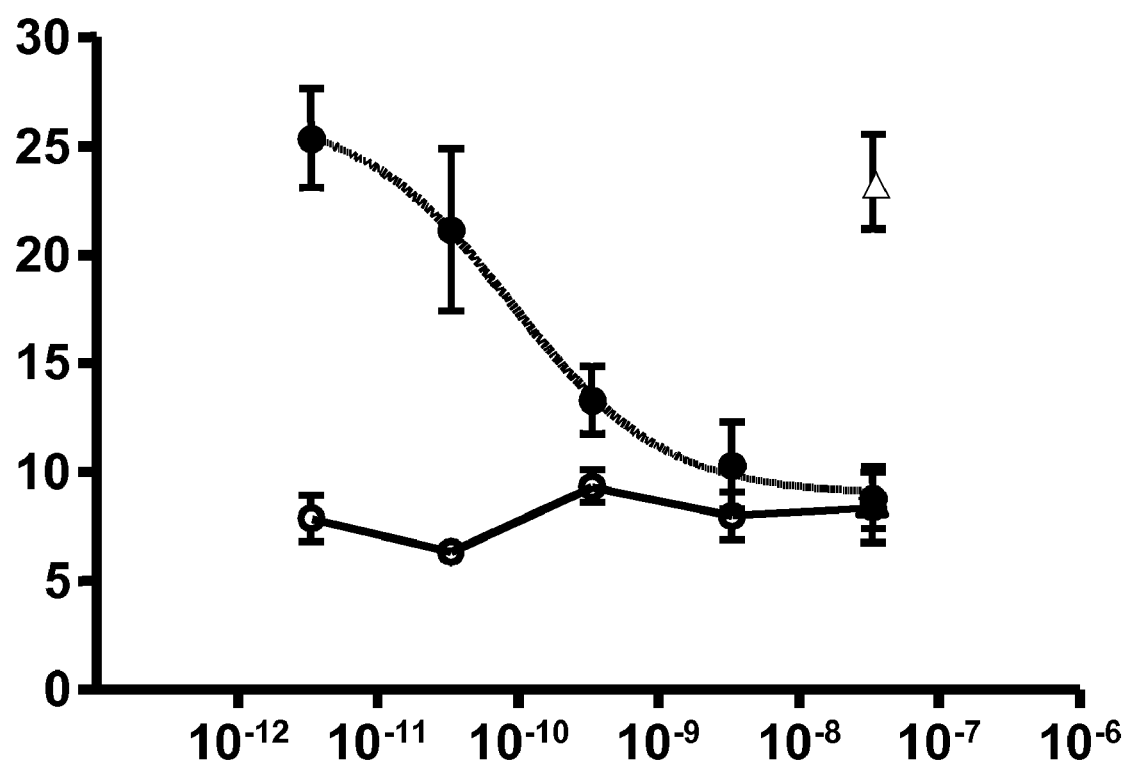

FIG. 16 Relates to Example 9 and shows Antibody 11 inhibition of IgE/FceRI-mediated cytotoxicity. The x axis is molar concentration of Antibody 11 and the y axis is percentage cytotoxicity. In the graph the open triangle and solid circle relate to the Mov18 IgE experiment wherein the open triangle is the isotype control and the solid circle is Antibody 11 and in the graph the bold open triangle (which is hidden under the points at the right hand side of the graph) and open circle related to the NIP IgE control wherein the open bold triangle is the isotype control and the open circle is Antibody 11.

Figure 17:
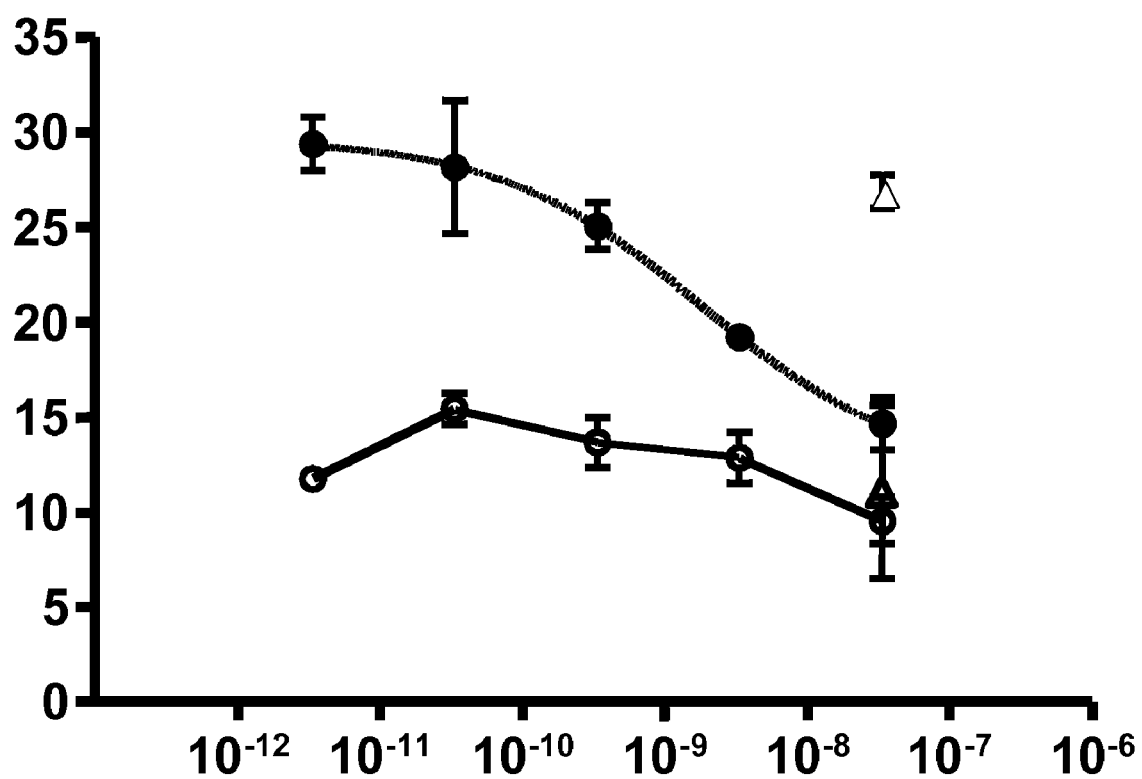

FIG. 17 Relates to Example 9 and shows Antibody 11 inhibition of IgE/CD23-mediated phagocytosis. The x axis is molar concentration of Antibody 11 and the y axis is percentage phagocytosis. In the graph the triangle and solid circle relate to the Mov18 IgE experiment wherein the open triangle is the isotype control and the solid circle is Antibody 11 and in the graph the bold open triangle and open circle related to the NIP IgE control wherein the open bold triangle is the isotype control and the open circle is Antibody 11.

EXAMPLES

Naïve human single chain Fv (scFv) phage display libraries cloned in to a phagemid vector based on the filamentous phage M13 were used for selections [69, 70]).

Anti-IgE specific scFv antibodies are isolated from the phage display libraries using a series of selection cycles on recombinant human IgE.

Selected scFv antibodies are optimized for binding to human IgE and/or for potency, and are reformatted as IgG antibodies.

Sequences

Sequences of exemplary binding members of the invention are shown in the appended sequence listing, in which SEQ ID NOS correspond as shown in Table 3a below wherein:
i) where an antibody number is followed by GL, for example 8GL this refers to the antibody wherein one or more of the residues have been mutated back to the germline configuration, in general where GL is used all non-germline residues which can be mutated back to germline without appreciable loss of activity have been germlined; and
ii) where an antibody number is followed by PGL, for example 11PGL this refers to the antibody wherein one or more of the residues have been mutated back to the germline configuration, in general where PGL is used more residues have been mutated back to germline than GL but resulting in some loss of activity over the non-germlined.

TABLE 3a

| Antibody | SEQ ID No. | Description |
|---|---|---|
| 1 | 1 | VH/DNA |
| 1 | 2 | VH/amino acid |
| 1 | 3 | HCDR1 |
| 1 | 4 | HCDR2 |
| 1 | 5 | HCDR3 |
| 1 | 317 | VL/DNA |
| 1 | 318 | VL/amino acid |
| 1 | 8 | LCDR1 |
| 1 | 9 | LCDR2 |
| 1 | 10 | LCDR3 |
| 2 | 11 | VH/DNA |
| 2 | 12 | VH/amino acid |
| 2 | 13 | HCDR1 |
| 2 | 14 | HCDR2 |
| 2 | 15 | HCDR3 |
| 2 | 319 | VL/DNA |
| 2 | 320 | VL/amino acid |
| 2 | 18 | LCDR1 |
| 2 | 19 | LCDR2 |
| 2 | 20 | LCDR3 |
| 3 | 21 | VH/DNA |
| 3 | 22 | VH/amino acid |
| 3 | 23 | HCDR1 |
| 3 | 24 | HCDR2 |
| 3 | 25 | HCDR3 |
| 3 | 321 | VL/DNA |
| 3 | 322 | VL/amino acid |
| 3 | 28 | LCDR1 |
| 3 | 29 | LCDR2 |
| 3 | 30 | LCDR3 |
| 4 | 31 | VH/DNA |
| 4 | 32 | VH/amino acid |
| 4 | 33 | HCDR1 |
| 4 | 34 | HCDR2 |
| 4 | 35 | HCDR3 |
| 4 | 323 | VL/DNA |
| 4 | 324 | VL/amino acid |
| 4 | 38 | LCDR1 |
| 4 | 39 | LCDR2 |
| 4 | 40 | LCDR3 |
| 5 | 41 | VH/DNA |
| 5 | 42 | VH/amino acid |
| 5 | 43 | HCDR1 |
| 5 | 44 | HCDR2 |
| 5 | 45 | HCDR3 |
| 5 | 325 | VL/DNA |
| 5 | 326 | VL/amino acid |
| 5 | 48 | LCDR1 |
| 5 | 49 | LCDR2 |
| 5 | 50 | LCDR3 |
| 6 | 51 | VH/DNA |
| 6 | 52 | VH/amino acid |
| 6 | 53 | HCDR1 |
| 6 | 54 | HCDR2 |
| 6 | 55 | HCDR3 |
| 6 | 327 | VL/DNA |
| 6 | 328 | VL/amino acid |
| 6 | 58 | LCDR1 |
| 6 | 59 | LCDR2 |
| 6 | 60 | LCDR3 |
| 7 | 61 | VH/DNA |
| 7 | 62 | VH/amino acid |
| 7 | 63 | HCDR1 |
| 7 | 64 | HCDR2 |
| 7 | 65 | HCDR3 |
| 7 | 329 | VL/DNA |
| 7 | 330 | VL/amino acid |
| 7 | 68 | LCDR1 |
| 7 | 69 | LCDR2 |
| 7 | 70 | LCDR3 |
| 8 | 71 | VH/DNA |
| 8 | 72 | VH/amino acid |
| 8 | 73 | HCDR1 |
| 8 | 74 | HCDR2 |
| 8 | 75 | HCDR3 |
| 8 | 331 | VL/DNA |
| 8 | 332 | VL/amino acid |
| 8 | 78 | LCDR1 |
| 8 | 79 | LCDR2 |
| 8 | 80 | LCDR3 |
| 9 | 81 | VH/DNA |
| 9 | 82 | VH/amino acid |
| 9 | 83 | HCDR1 |
| 9 | 84 | HCDR2 |
| 9 | 85 | HCDR3 |
| 9 | 333 | VL/DNA |
| 9 | 334 | VL/amino acid |
| 9 | 88 | LCDR1 |
| 9 | 89 | LCDR2 |
| 9 | 90 | LCDR3 |
| 10 | 91 | VH/DNA |
| 10 | 92 | VH/amino acid |
| 10 | 93 | HCDR1 |
| 10 | 94 | HCDR2 |
| 10 | 95 | HCDR3 |
| 10 | 335 | VL/DNA |
| 10 | 336 | VL/amino acid |
| 10 | 98 | LCDR1 |
| 10 | 99 | LCDR2 |
| 10 | 100 | LCDR3 |
| 11 | 101 | VH/DNA |
| 11 | 102 | VH/amino acid |
| 11 | 103 | HCDR1 |
| 11 | 104 | HCDR2 |
| 11 | 105 | HCDR3 |
| 11 | 337 | VL/DNA |
| 11 | 338 | VL/amino acid |
| 11 | 108 | LCDR1 |
| 11 | 109 | LCDR2 |
| 11 | 110 | LCDR3 |
| 12 | 111 | VH/DNA |
| 12 | 112 | VH/amino acid |
| 12 | 113 | HCDR1 |
| 12 | 114 | HCDR2 |
| 12 | 115 | HCDR3 |
| 12 | 339 | VL/DNA |
| 12 | 340 | VL/amino acid |
| 12 | 118 | LCDR1 |
| 12 | 119 | LCDR2 |
| 12 | 120 | LCDR3 |
| 13 | 121 | VH/DNA |
| 13 | 122 | VH/amino acid |
| 13 | 123 | HCDR1 |
| 13 | 124 | HCDR2 |
| 13 | 125 | HCDR3 |
| 13 | 341 | VL/DNA |
| 13 | 342 | VL/amino acid |
| 13 | 128 | LCDR1 |
| 13 | 129 | LCDR2 |
| 13 | 130 | LCDR3 |
| 14 | 131 | VH/DNA |
| 14 | 132 | VH/amino acid |
| 14 | 133 | HCDR1 |
| 14 | 134 | HCDR2 |
| 14 | 135 | HCDR3 |
| 14 | 343 | VL/DNA |
| 14 | 344 | VL/amino acid |
| 14 | 138 | LCDR1 |
| 14 | 139 | LCDR2 |
| 14 | 140 | LCDR3 |
| 15 | 141 | VH/DNA |
| 15 | 142 | VH/amino acid |
| 15 | 143 | HCDR1 |
| 15 | 144 | HCDR2 |
| 15 | 145 | HCDR3 |
| 15 | 345 | VL/DNA |
| 15 | 346 | VL/amino acid |
| 15 | 148 | LCDR1 |
| 15 | 149 | LCDR2 |
| 15 | 150 | LCDR3 |
| 16 | 151 | VH/DNA |
| 16 | 152 | VH/amino acid |
| 16 | 153 | HCDR1 |
| 16 | 154 | HCDR2 |
| 16 | 155 | HCDR3 |
| 16 | 347 | VL/DNA |

TABLE 3a-continued

| Antibody | SEQ ID No. | Description |
|---|---|---|
| 16 | 348 | VL/amino acid |
| 16 | 158 | LCDR1 |
| 16 | 159 | LCDR2 |
| 16 | 160 | LCDR3 |
| 17 | 161 | VH/DNA |
| 17 | 162 | VH/amino acid |
| 17 | 163 | HCDR1 |
| 17 | 164 | HCDR2 |
| 17 | 165 | HCDR3 |
| 17 | 349 | VL/DNA |
| 17 | 350 | VL/amino acid |
| 17 | 168 | LCDR1 |
| 17 | 169 | LCDR2 |
| 17 | 170 | LCDR3 |
| 18 | 171 | VH/DNA |
| 18 | 172 | VH/amino acid |
| 18 | 173 | HCDR1 |
| 18 | 174 | HCDR2 |
| 18 | 175 | HCDR3 |
| 18 | 351 | VL/DNA |
| 18 | 352 | VL/amino acid |
| 18 | 178 | LCDR1 |
| 18 | 179 | LCDR2 |
| 18 | 180 | LCDR3 |
| 19 | 181 | VH/DNA |
| 19 | 182 | VH/amino acid |
| 19 | 183 | HCDR1 |
| 19 | 184 | HCDR2 |
| 19 | 185 | HCDR3 |
| 19 | 353 | VL/DNA |
| 19 | 354 | VL/amino acid |
| 19 | 188 | LCDR1 |
| 19 | 189 | LCDR2 |
| 19 | 190 | LCDR3 |
| 20 | 191 | VH/DNA |
| 20 | 192 | VH/amino acid |
| 20 | 193 | HCDR1 |
| 20 | 194 | HCDR2 |
| 20 | 195 | HCDR3 |
| 20 | 355 | VL/DNA |
| 20 | 356 | VL/amino acid |
| 20 | 198 | LCDR1 |
| 20 | 199 | LCDR2 |
| 20 | 200 | LCDR3 |
| 21 | 201 | VH/DNA |
| 21 | 202 | VH/amino acid |
| 21 | 203 | HCDR1 |
| 21 | 204 | HCDR2 |
| 21 | 205 | HCDR3 |
| 21 | 357 | VL/DNA |
| 21 | 358 | VL/amino acid |
| 21 | 208 | LCDR1 |
| 21 | 209 | LCDR2 |
| 21 | 210 | LCDR3 |
| 22 | 211 | VH/DNA |
| 22 | 212 | VH/amino acid |
| 22 | 213 | HCDR1 |
| 22 | 214 | HCDR2 |
| 22 | 215 | HCDR3 |
| 22 | 359 | VL/DNA |
| 22 | 360 | VL/amino acid |
| 22 | 218 | LCDR1 |
| 22 | 219 | LCDR2 |
| 22 | 220 | LCDR3 |
| 23 | 221 | VH/DNA |
| 23 | 222 | VH/amino acid |
| 23 | 223 | HCDR1 |
| 23 | 224 | HCDR2 |
| 23 | 225 | HCDR3 |
| 23 | 361 | VL/DNA |
| 23 | 362 | VL/amino acid |
| 23 | 228 | LCDR1 |
| 23 | 229 | LCDR2 |
| 23 | 230 | LCDR3 |
| 24 | 231 | VH/DNA |
| 24 | 232 | VH/amino acid |
| 24 | 233 | HCDR1 |
| 24 | 234 | HCDR2 |
| 24 | 235 | HCDR3 |
| 24 | 363 | VL/DNA |
| 24 | 364 | VL/amino acid |
| 24 | 238 | LCDR1 |
| 24 | 239 | LCDR2 |
| 24 | 240 | LCDR3 |
| 25 | 241 | VH/DNA |
| 25 | 242 | VH/amino acid |
| 25 | 243 | HCDR1 |
| 25 | 244 | HCDR2 |
| 25 | 245 | HCDR3 |
| 25 | 365 | VL/DNA |
| 25 | 366 | VL/amino acid |
| 25 | 248 | LCDR1 |
| 25 | 249 | LCDR2 |
| 25 | 250 | LCDR3 |
| 26 | 251 | VH/DNA |
| 26 | 252 | VH/amino acid |
| 26 | 253 | HCDR1 |
| 26 | 254 | HCDR2 |
| 26 | 255 | HCDR3 |
| 26 | 367 | VL/DNA |
| 26 | 368 | VL/amino acid |
| 26 | 258 | LCDR1 |
| 26 | 259 | LCDR2 |
| 26 | 260 | LCDR3 |
| 27 | 261 | VH/DNA |
| 27 | 262 | VH/amino acid |
| 27 | 263 | HCDR1 |
| 27 | 264 | HCDR2 |
| 27 | 265 | HCDR3 |
| 27 | 369 | VL/DNA |
| 27 | 370 | VL/amino acid |
| 27 | 268 | LCDR1 |
| 27 | 269 | LCDR2 |
| 27 | 270 | LCDR3 |
| 28 | 271 | VH/DNA |
| 28 | 272 | VH/amino acid |
| 28 | 273 | HCDR1 |
| 28 | 274 | HCDR2 |
| 28 | 275 | HCDR3 |
| 28 | 371 | VL/DNA |
| 28 | 372 | VL/amino acid |
| 28 | 278 | LCDR1 |
| 28 | 279 | LCDR2 |
| 28 | 280 | LCDR3 |
| 8GL | 281 | VH/DNA |
| 8GL | 282 | VH/amino acid |
| 8GL | 283 | HCDR1 |
| 8GL | 284 | HCDR2 |
| 8GL | 285 | HCDR3 |
| 8GL | 373 | VL/DNA |
| 8GL | 374 | VL/amino acid |
| 8GL | 296 | LCDR1 |
| 8GL | 297 | LCDR2 |
| 8GL | 298 | LCDR3 |
| 8PGL | 287 | VH/DNA |
| 8PGL | 288 | VH/amino acid |
| 8PGL | 289 | HCDR1 |
| 8PGL | 290 | HCDR2 |
| 8PGL | 291 | HCDR3 |
| 8PGL | 375 | VL/DNA |
| 8PGL | 376 | VL/amino acid |
| 8PGL | 296 | LCDR1 |
| 8PGL | 297 | LCDR2 |
| 8PGL | 298 | LCDR3 |
| 11GL | 299 | VH/DNA |
| 11GL | 300 | VH/amino acid |
| 11GL | 301 | HCDR1 |
| 11GL | 302 | HCDR2 |
| 11GL | 303 | HCDR3 |
| 11GL | 377 | VL/DNA |
| 11GL | 378 | VL/amino acid |
| 11GL | 314 | LCDR1 |
| 11GL | 315 | LCDR2 |
| 11GL | 316 | LCDR3 |
| 11PGL | 305 | VH/DNA |
| 11PGL | 306 | VH/amino acid |

TABLE 3a-continued

| Antibody | SEQ ID No. | Description |
|---|---|---|
| 11PGL | 307 | HCDR1 |
| 11PGL | 308 | HCDR2 |
| 11PGL | 309 | HCDR3 |
| 11PGL | 379 | VL/DNA |
| 11PGL | 380 | VL/amino acid |
| 11PGL | 314 | LCDR1 |
| 11PGL | 315 | LCDR2 |
| 11PGL | 316 | LCDR3 |
|  | 381 | Cynomolgus Ce3-4 FLAG His10 nucleotide |
|  | 382 | Cynomolgus Ce3-4 FLAG His10 protein |
|  | 383 | D12_VHcyIgHE TQ nucleotide |
|  | 384 | D12_VH cyIgHE TQ protein |
|  | 385 | D12_HE cyIgHE ME nucleotide |
|  | 386 | D12_VH cyIgHE ME protein |
|  | 387 | D12_VL cyIgLC 4 nucleotide |
|  | 388 | D12_VL cyIgLC 4 protein |
|  | 389 | D12_VL cyIgLC 7 nucleotide |
|  | 390 | D12_VL cyIgLC 7 protein |
|  | 391 | FceRI_Fc (NSO) nucleotide |
|  | 392 | FceRI_Fc (NSO) protein |

In the sequence listing filed with the provisional application (U.S. provisional application No. 60/901,304) the sequences of the 3' ggt codon, and corresponding Glycine residue, shown in the nucleotide and amino acid sequence for the VL DNA and corresponding VL amino acid were included in the expressed scFv and IgG sequences of this antibody. The C terminal Glycine residue of the sequence corresponds to Kabat residue 108. This terminal glycine is not part of the VL sequence and has been removed from the sequences listed in Table 3a. The sequences for VL DNA and VL amino acid from the provisional application are included with the sequence listing and are listed in Table 3b below. The origin of this residue and its encoding triplet ggt is explained below.

To express the light chain of the IgG, a nucleotide sequence encoding the antibody light chain was provided, comprising a first exon encoding the VL domain, a second exon encoding the CL domain, and an intron separating the first exon and the second exon. Under normal circumstances, the intron is spliced out by cellular mRNA processing machinery, joining the 3' end of the first exon to the 5' end of the second exon. Thus, when DNA having the said nucleotide sequence was expressed as RNA, the first and second exons were spliced together. Translation of the spliced RNA produces a polypeptide comprising the VL domain and CL domain. After splicing, the Gly at Kabat residue 108 is encoded by the last base (g) of the VL domain framework 4 sequence and the first two bases (gt) of the CL domain.

Therefore, the Glycine residue at Kabat residue 108 was included in the sequence listings of the VL sequences in the provisional application but as described above it should not be considered to be the C terminal residue of the VL domain of the antibody molecule and thus has been deleted from sequence listings in Table 3a.

TABLE 3b

| SEQ ID NO | Antibody | Description |
|---|---|---|
| 6 | 1 | VL/DNA |
| 7 | 1 | VL/amino acid |

TABLE 3b-continued

| SEQ ID NO | Antibody | Description |
|---|---|---|
| 16 | 2 | VL/DNA |
| 17 | 2 | VL/amino acid |
| 26 | 3 | VL/DNA |
| 27 | 3 | VL/amino acid |
| 36 | 4 | VL/DNA |
| 37 | 4 | VL/amino acid |
| 46 | 5 | VL/DNA |
| 47 | 5 | VL/amino acid |
| 56 | 6 | VL/DNA |
| 57 | 6 | VL/amino acid |
| 66 | 7 | VL/DNA |
| 67 | 7 | VL/amino acid |
| 76 | 8 | VL/DNA |
| 77 | 8 | VL/amino acid |
| 86 | 9 | VL/DNA |
| 87 | 9 | VL/amino acid |
| 96 | 10 | VL/DNA |
| 97 | 10 | VL/amino acid |
| 106 | 11 | VL/DNA |
| 107 | 11 | VL/amino acid |
| 116 | 12 | VL/DNA |
| 117 | 12 | VL/amino acid |
| 126 | 13 | VL/DNA |
| 127 | 13 | VL/amino acid |
| 136 | 14 | VL/DNA |
| 137 | 14 | VL/amino acid |
| 146 | 15 | VL/DNA |
| 147 | 15 | VL/amino acid |
| 156 | 16 | VL/DNA |
| 157 | 16 | VL/amino acid |
| 166 | 17 | VL/DNA |
| 167 | 17 | VL/amino acid |
| 176 | 18 | VL/DNA |
| 177 | 18 | VL/amino acid |
| 186 | 19 | VL/DNA |
| 187 | 19 | VL/amino acid |
| 196 | 20 | VL/DNA |
| 197 | 20 | VL/amino acid |
| 206 | 21 | VL/DNA |
| 207 | 21 | VL/amino acid |
| 216 | 22 | VL/DNA |
| 217 | 22 | VL/amino acid |
| 226 | 23 | VL/DNA |
| 227 | 23 | VL/amino acid |
| 236 | 24 | VL/DNA |
| 237 | 24 | VL/amino acid |
| 246 | 25 | VL/DNA |
| 247 | 25 | VL/amino acid |
| 256 | 26 | VL/DNA |
| 257 | 26 | VL/amino acid |
| 266 | 27 | VL/DNA |
| 267 | 27 | VL/amino acid |
| 276 | 28 | VL/DNA |
| 277 | 28 | VL/amino acid |
| 294 | 29 (8 GL) | VL/DNA |
| 295 | 29 (8 GL) | VL/amino acid |
| 294 | 30 (8 PGL) | VL/DNA |
| 295 | 30 (8 PGL) | VL/amino acid |
| 312 | 32 (11 GL) | VL/DNA |
| 313 | 32 (11 GL) | VL/amino acid |
| 312 | 33 (11 PGL) | VL/DNA |
| 313 | 33 (11 PGL) | VL/amino acid |

In the sequence listing in the provisional application the sequences listed as Antibodies 29-34 are listed in Table 3a as Antibody 8GL, 8PGL, 11GL and 11PGL. Some of these antibodies shares a common VL domain and as a result some sequences ID Nos in the sequence listing provided in the provisional application are empty. The correct composition of the antibodies is as follows:
Antibody 29 corresponds to 8GL VH domain
Antibody 30 corresponds to 8PGL VH domain
Antibody 31 corresponds to the VL domain shared by 8GL and 8PGL.
Antibody 32 corresponds to 11GL VH domain Antibody 33 corresponds to 11PGL VH domain
Antibody 34 corresponds to the VL domain shared by 11GL and 11PGL.
Sequence ID Nos 286, 292, 293, 304, 310 and 311 are empty. This has been corrected in Table 3a The invention will now be exemplified by the following non-limiting examples:

Example 1

Lead Isolation 1.1 Selections

Naïve human single chain Fv (scFv) phage display libraries cloned in to a phagemid vector based on the filamentous phage M13 were used for selections (Vaughan et al., Nature Biotechnology 14: 309-314 (1996), Hutchings, Antibody Engineering, R. Kontermann and S. Dubel, Editors. 2001, Springer Laboratory Manuals, Berlin. P93). Anti-IgE specific scFv antibodies were isolated from the phage display libraries using a series of selection cycles on either plasma purified human IgEκ (Calbiochem) or plasma purified human IgEλ (Biodesign) essentially as previously described by Vaughan et al (Vaughan et al., Nature Biotechnology 14: 309-314 (1996). In brief, for panning selections, human IgE in PBS (Dulbecco's PBS, pH7.4) was adsorbed onto wells of a Maxisorp microtitre plate (Nunc) overnight at 4° C. Wells were washed with PBS then blocked for 1 h with PBS-Marvel (3% w/v). Purified phage in PBS-Marvel (3% w/v) were added to the wells and allowed to bind coated antigen for 1 h. Unbound phage were removed by a series of wash cycles using PBS-Tween (0.1% v/v) and PBS. Bound phage particles were eluted, infected into bacteria and rescued for the next round of selection (Vaughan et al., Nature Biotechnology 14: 309-314 (1996)). Alternate rounds of selection were performed using the kappa and lambda forms of IgE.

1.2 Inhibition of IgE Binding to FcεRI by Unpurified scFv

A representative number of individual scFv from the second round of selections were grown up in 96-well plates. ScFvs were expressed in the bacterial periplasm and screened for their inhibitory activity in a homogeneous FRET (Fluorescence resonance energy transfer) based human IgE/human FcεRI-binding assay. In this assay, samples competed for binding to human IgE (Calbiochem 401152) labelled with Europium Chelate (Perkin Elmer 1244-302), with human FcεRI-Fc (in house NS0 cell produced). The detailed assay method is provided in the Materials and Methods section.

1.3 Inhibition of IgE Binding to FcεRI by Purified scFv

ScFv which showed a significant inhibitory effect on the IgE:FcεRI interaction as unpurified periplasmic extracts, were subjected to DNA sequencing (Vaughan et al. 1996, Nature Biotechnology 14: 309-314), (Osbourn 1996; Immunotechnology. 2, 181-196). Unique scFvs were expressed again in bacteria and purified by affinity chromatography (as described by Bannister et al (2006) Biotechnology and bioengineering, 94. 931-937). The potencies of these samples were determined by competing a dilution series of the purified preparation against FcεRI (in house NS0 cell produced), for binding to human IgE (Calbiochem 401152) labelled with Europium Chelate (Perkin Elmer 1244-302). Purified scFv preparations e.g Antibody 1 were capable of inhibiting the IgE-FcεRI interaction. Detailed protocols are provided in Materials and Methods section.

1.4 Reformatting of scFv to IgG1

Clones were converted from scFv to IgG format by subcloning the $V_H$ and $V_L$ domains into vectors expressing whole antibody heavy and light chains respectively. The $V_H$ domain was cloned into a vector (pEU15.1 or pEU9.2) containing the human heavy chain constant domains and regulatory elements to express whole IgG1 or IgG2 heavy chain in mammalian cells respectively. Similarly, the $V_L$ domain was cloned into either vector pEU3.4 for the expression of the human kappa light chain or pEU4.4 for the expression of the human lambda light chain constant domains, with regulatory elements to express whole IgG light chain in mammalian cells. Vectors for the expression of heavy chains and light chains were originally described by Persic et al. (Persic, L., et al. (1997) Gene 187, 9-18). Cambridge Antibody Technology vectors have been engineered to include an EBV OriP element which in combination with the EBNA1 protein allows for episomal replication of the plasmid. To obtain IgGs, the heavy and light chain IgG expressing vectors were transfected into EBNA-HEK293 mammalian cells. IgGs were expressed and secreted into the medium. Harvests were pooled and filtered prior to purification. The IgG was purified using Protein A chromatography. Culture supernatants were loaded on a Ceramic Protein A column (BioSepra) and washed with 50 mM Tris-HCl pH 8.0, 250 mM NaCl. Bound IgG was eluted from the column using 0.1 M Sodium Citrate (pH 3.0) and neutralised by the addition of Tris-HCl (pH 9.0). The eluted material was buffer exchanged into PBS using Nap10 columns (Amersham, #17-0854-02) and the concentration of IgG was determined spectrophotometrically using an extinction coefficient based on the amino acid sequence of the IgG (Mach et al Anal. Biochem. 200(1): 20-26, 1992). The purified IgG were analysed for aggregation or degradation using SEC-HPLC and by SDS-PAGE.

1.5 Inhibition of Calcium Signalling in RBL-ER51 Cells by Purified scFv and IgG

The neutralisation potency of purified scFv and IgG preparations against human IgE bioactivity mediated through FcεRI was assessed using an RBL-ER51 calcium-signalling assay. RBL-2H3 cells (a rat basophilic cell line) were stably transfected with the human FcεRI (RBL-ER51 cells). Free IgE in the vicinity of the cells binds to the FcεRI on the cell surface and subsequent cross-linking of receptor-bound IgE leads to a calcium mobilisation that can be detected using a Fluorometric Imaging Plate Reader (FLIPR). A detailed description of the protocol is provided in the Materials and Methods section.

Purified scFv preparations of Antibody 1 were capable of inhibiting the IgE induced calcium signalling of the RBL-ER51 cells at the maximum concentration tested. When tested as a purified IgG, the $IC_{50}$ for Antibody 1 was calculated as being 34 nM.

1.6 Selectivity and Species Cross Reactivity of Antibodies in DELFIA® Epitope Competition Assays The species cross reactivity and selectivity of antibodies to IgE and structurally related molecules; IgA, IgM, IgD and IgG, was established using DELFIA® epitope competition assays. The assay determines relative cross reactivity by measuring inhibition of biotinylated IgE (plasma purified, BIODESIGN International), binding each immobilised anti-IgE antibody.

Titrations of purified IgA, IgM, IgD, and IgG (all Calbiochem) were tested in each assay to establish the specificity profile for each structurally related protein, as measured by IC50 values in the assay.

Titrations of IgE species including cynomolgus IgE Cε3-Cε4 domain (in house HEK-EBNA derived), human IgE Cε3-Cε4 domain (in house HEK-EBNA derived) and human IgE lambda (BIODESIGN International) were tested in each assay to establish the species cross-reactivity of the antibodies. Full-length human IgEλ, along with human and cynomolgus IgE Cε3-Cε4 domains, produced inhibition curves. No inhibition was observed for any of the structurally related proteins. These data demonstrate that Antibody 1 binds to human IgEλ, the Cε3-Cε4 domain of IgE and is cross reactive to cynomolgus IgE. However Antibody 1 does not bind to any of the most related human proteins to IgE. Details of the protocol are provided in the Materials and Methods section.

1.7 Inhibition of IgE Binding to CD23 by Purified IgG

IM9 cells (a human B cell line) were shown to express CD23 but not FcεRI under basal conditions. IgE binds to CD23 on the surface of IM9 cells. CD23-bound IgE can then be bound with anti-IgE-Phycoerythrin (Caltag) and detected by flow cytometry (FACSCalibur, BD Biosciences).

Antibodies were evaluated for inhibition of the IgE/CD23 interaction. A detailed protocol for this procedure is provided in Materials and Methods. In brief, titrations of the test IgG were mixed with IgE prior to incubation with 1M9 cells. Following a 1 hour incubation, cells were washed and bound IgE was detected with anti-IgE-Phycoerythrin (Caltag). Antibody 1 inhibited the IgE/CD23 interaction with an IC50 of 16 nM (n=3).

1.8 Cross-Linking of FcεRI-Bound IgE

Antibodies were evaluated for potential to cross-link FcεRI-bound IgE using an RBL-ER51 calcium-signalling assay. RBL-ER51 cells, described in materials and methods, were loaded with IgE. Antibodies were incubated with the IgE-loaded cells and assessed for their ability to stimulate a calcium response. Antibody 1 was not able to induce a detectable calcium response.

Example 2

Antibody Optimisation 2.1 Optimisation of Parent Clone by Targeted Mutagenesis

Antibody 1 was optimised using a targeted mutagenesis approach with affinity-based phage display selections. For the targeted mutagenesis approach, large scFv phage libraries derived from the lead clone were created by oligonucleotide-directed mutagenesis of the variable heavy ($V_H$) and light ($V_L$) chain complementarity determining regions 3 (CDR3) as described by Clackson and Lowman 2004 (A Practical Approach, 2004. Oxford University Press).

The libraries were subjected to affinity-based phage display selections in order to select variants with higher affinity for IgE. In consequence, these should show an improved inhibitory activity for IgE binding FcεR1. The selections were performed essentially as described previously (Thompson 1996; Journal of Molecular Biology. 256. 77-88). In brief, the scFv phage particles were incubated in solution with biotinylated human IgEλ (U266 derived [Ikeyama et. al. 1986. Molecular Immunology 23 (2); p 159-167] and modified in house). ScFv-phage bound to antigen were then captured on streptavidin-coated paramagnetic beads (Dynabeads® M280) following the manufacturer's recommendations. The selected scFv-phage particles were then rescued as described previously (Vaughan et al., Nature Biotechnology 14: 309-314 (1996)), and the selection process was repeated in the presence of decreasing concentrations of bio-human IgE (250 nM to 25 pM over 5 rounds).

Upon completion of 5 rounds of selection, the VH and VL randomised libraries were recombined to form a single library in which clones contained randomly paired individually randomised VH and VL sequences. Selections were then continued as previously described in the presence of decreasing concentrations of bio-human IgE (100 pM to 1 pM over a further 3 rounds).

2.2 Identification of Improved Clones from the Targeted Mutagenesis Using an Antibody-Ligand Biochemical Assay ScFv from the targeted mutagenesis selection outputs were expressed in bacterial periplasm and screened in an epitope competition HTRF® (Homogeneous Time-Resolved Fluorescence) assay format for inhibition of human IgE (U266-derived [Ikeyama et. al. 1986. Molecular Immunology 23 (2); p 159-167]) labelled with europium cryptate (CIS bio International 62EUSPEA), binding to anti human-IgE (Antibody 1, isolated in example 1). The detailed assay method is provided in the Materials and Methods section. ScFv that showed a significant inhibitory effect were subjected to DNA sequencing and unique scFv were prepared as purified preparations.

2.3 Inhibition of IgE Binding to FcεRI by Purified scFv

Purified scFv were tested in a receptor-ligand binding HTRF® (Homogeneous Time-Resolved Fluorescence) assay format for inhibition of either human IgE (U266-derived [Ikeyama et. al. 1986. Molecular Immunology 23 (2); p 159-167]) or cyno IgE (recombinant, see materials and methods) labelled with europium cryptate (CIS bio International 62EUSPEA), binding to human FcεR1-Fc (in house NS0 cell produced). Example scFv potency data is included in Table 2a TABLE 2a Example potencies of clones identified from the targeted mutagenesis libraries when tested in the Receptor-ligand binding HTRF ® Assays

| Clone (non-germlined) | scFv Geomean (95% CI) $IC_{50}$ (nM) | |
| --- | --- | --- |
| | Human IgE assay | Cynomolgus IgE assay |
| Antibody 1 | 475 (399-565) | Weak/Incomplete |
| Antibody 2 | 28 (n = 1) | 317 (n = 1) |
| Antibody 3 | 5 (n = 1) | 18 (n = 1) |
| Antibody 4 | 2 (0.4-14) | 5 (2-17) |
| Antibody 5 | 3 (0.2-34) | 6 (1-30) |
| Antibody 6 | 3 (n = 2) | 11 (n = 2) |
| Antibody 7 | 9 (n = 1) | 186 (n = 1) |
| Antibody 8 | 5 (2-9) | 12 (8-20) |
| Antibody 9 | 9 (n = 1) | 132 (n = 1) |
| Antibody 10 | 10 (n = 1) | 116 (n = 1) |
| Antibody 11 | 2 (0.5-7) | 7 (3-15) |
| Antibody 12 | 3 (n = 2) | 7 (n = 2) |
| Antibody 13 | 2 (n = 2) | 7 (n = 2) |
| Antibody 14 | 8 (n = 1) | 15 (n = 1) |
| Antibody 15 | 7 (n = 1) | 172 (n = 1) |
| Antibody 16 | 5 (2-11) | 63 (46-87) |
| Antibody 17 | 6 (n = 1) | 109 (n = 1) |
| Antibody 18 | 11 (n = 1) | 110 (n = 1) |
| Antibody 21 | 6 (n = 1) | 65 (n = 1) |
| Antibody 22 | 6 (n = 1) | 68 (n = 1) |
| Antibody 23 | 1 (n = 1) | 6 (n = 1) |
| Antibody 24 | 9 (n = 1) | 111 (n = 1) |
| Antibody 25 | 8 (n = 1) | 86 (n = 1) |
| Antibody 26 | 12 (n = 1) | 121 (n = 1) |
| Antibody 27 | 9 (n = 1) | 117 (n = 1) |
| Antibody 28 | 1 (n = 1) | 7 (n = 1) |

2.4 Inhibition of Calcium Signalling in RBL-ER51 Cells by Purified IgG

After re-formatting as IgG, potencies of optimised clones were determined using a modified RBL-ER51 calcium signalling assay. This assay was adapted from the method used during lead isolation to improve sensitivity for detection of more potent antibodies. A detailed description of the protocol is provided in the Materials and Methods section. $IC_{50}$ potency data against human and cynomolgus IgE are given in Table 2b.

TABLE 2b

Binding affinity Calculation using BIAcore and Potency measurement using RBL-ER51 calcium signalling assay for optimised antibodies.

| Antibody | Biacore KD (nM) (Geomean) | | RBL-ER51 calcium signalling $IC_{50}$ (nM) Geomean (95% CI) | |
|---|---|---|---|---|
| | Human IgE | Cynomolgus IgE | Human IgE | Cynomolgus IgE |
| 4 | 2.1 | 8.0 | 0.088 (0.039-0.199) | 0.151 (0.086-0.265) |
| 5 | 2.4 | 7.9 | 0.091 (0.005-1.79) | 0.181 |
| 6 | 2.1 | 3.7 | 0.096 | 0.168 |
| 8 | 2.6 | 6.3 | 0.112 (0.02-0.62) | 0.188 (0.103-0.340) |
| 11 | 1.6 | 9.3 | 0.069 (0.042-0.12) | 0.153 (0.068-0.34) |
| 12 | 2.3 | 230 | 0.134 | 0.334 |
| 13 | 2.3 | 9.9 | 0.088 (0.038-0.02) | 0.244 (0.134-0.43) |
| 16 | 4.6 | 62 | 0.292 (0.10-0.85) | 4.38 |
| 18 | 8.0 | | 0.532 | 2.97 |
| 19 | 2.5 | 7.9 | 0.095 (0.043-0.21) | 0.111 (0.008-1.55) |
| 20 | 3.3 | 10.5 | 0.191 | 0.31 |
| 21 | | | 0.306 | 3.58 |
| 22 | | | 0.262 | 2.66 |
| 23 | 2.7 | 4.3 | 0.109 | 0.523 |
| 26 | | | 0.398 | 5.1 |
| 28 | 3.2 | 7.2 | 0.099 (0.017-0.586) | 0.253 |

2.5. Germlining

The amino acid sequences of the $V_H$ and $V_L$ domains of the optimised anti-IgE antibodies were aligned to the known human germline sequences in the VBASE database (Tomlinson 1997; Journal of Molecular biology. 224. 487-499), and the closest germline was identified by sequence similarity. For the VH domains of the Antibody 1 lineage this was Vh1 DP-3 (1-f). For the VL domains it was Vλ1 DPL8 (1e).

Without considering the Vernier residues (Foote & Winter 1992), which were left unchanged, there were 10 changes from germline in the frameworks of the VH domain and 2 in the VL domain of Antibody 1. Five of the changes in the VH domain and both the changes in the VL domain were reverted to the closest germline sequence to identically match human antibodies. Changes at Kabat numbers 1, 20, 82a, 83 and 89 of the VH domain were left unchanged to retain potency (Antibody 8 GL and Antibody 11 GL). Germlining of these amino acid residues was carried out using standard site directed mutagenesis techniques with the appropriate mutagenic primers. Germlined IgG were then re-evaluated to confirm there had not been a reduction in affinity or potency. Example affinities and potencies for germlined (GL) antibodies are provided in Table 4.

TABLE 4

Example binding affinity Calculation using BIAcore and Potency measurement using RBL-ER51 calcium signalling assay for germlined antibodies.

| Antibody (germlined) | Biacore KD (nM) (Geomean) Human IgE | RBL-ER51 calcium signalling $IC_{50}$ (nM) Human IgE Geomean (95% CI) |
|---|---|---|
| Antibody 8 GL | 2.5 | 0.085 (0.057-0.13) |
| Antibody 11 GL | 1.5 | 0.084 (0.063-0.11) |

2.6 Inhibition of IgE Binding to CD23 by Purified IgG

Some optimised antibodies were evaluated for inhibition of the IgE/CD23 interaction using the IM9 binding assay as previously described. Antibodies tested in this system were found to inhibit the IgE/CD23 interaction. The $IC_{50}$ values for Antibody 8 and antibody 11 were 16.5 nM and 23 nM respectively.

2.7 Cross-Linking of FcεRI-Bound IgE

Some optimised antibodies were evaluated for potential to cross-link FcεRI-bound IgE using an RBL-ER51 calcium-signalling assay. RBL-ER51 cells, described in materials and methods, were maximally loaded with IgE. Optimised antibodies were incubated with the IgE-loaded cells and assessed for their ability to stimulate a calcium response. No signalling could be detected (FIG. 1).

2.8. Selectivity and Species Cross Reactivity of Optimised Antibodies in DELFIA® Epitope Competition Assays The selectivity and species cross reactivity of the lead antibodies was re-evaluated using the DELFIA® epitope competition assay as previously described (see section 1.6 and Materials and Methods).

Titrations of purified IgA, IgM, IgD, and IgG (all Calbiochem) were tested in each assay to establish the specificity profile for each structurally related protein, as measured by IC50 values in the assay.

Titrations of IgE species including human IgEλ (U266 derived), human IgEκ (Calbiochem), cynomolgus IgE Cε3-Cε4 domain (in house HEK-EBNA derived) and human IgE Cε3-Cε4 domain (in house HEK-EBNA derived) were tested in each assay to establish the species cross-reactivity of the antibodies. Full-length human IgEλ and κ, along with human and cynomolgus IgE Cε3-Cε4 domains, produced inhibition curves. No inhibition was observed for any of the structurally related human proteins (IgA, IgM, IgD and IgG). These data demonstrate that the panel of antibodies tested bind to human IgEλ and κ, the Cε3-Cε4 domain of IgE and are cross reactive to cynomolgus IgE. However the antibodies do not bind to the proteins most related to IgE.

2.9 Binding Affinity Calculation of Affinity Data for Optimised Clones Using BIAcore The binding affinity of purified IgG samples of a representative number of clones to human and cynomolgus IgE was determined by surface plasmon resonance using BIAcore 2000 biosensor (BIAcore AB) essentially as described by Karlsson et al 1991; Journal of Immunological Methods 145 (1-2) 229-240. In brief, Protein G' (Sigma Aldrich, P4689) was covalently coupled to the surface of a CM5 sensor chip using standard amine coupling reagents according to manufacturer's instructions (BIAcore). This protein G' surface was used to capture purified anti-IgE antibodies via the Fc domain to provide a surface density of 50 RU. Human IgEλ or cynomolgus IgE prepared in HBS-EP buffer (BIAcore AB), at a range of concentrations, between 125 nM and 7.6 nM, were passed over the sensor chip surface. The surface was regenerated using 10 mM Glycine, pH 1.75 between each injection of antibody. The resulting sensorgrams were evaluated using BIA evaluation 3.1 software and fitted to a bivalent analyte model, to provide relative binding data.

Example affinities for the IgG tested are shown in Table 2b and Table 4.

Materials and Methods

Example 1 and 2

Inhibition of IgE Binding to FcεRI by Unpurified scFv

Selection outputs were screened in a receptor-ligand binding homogeneous FRET (Fluorescence resonance energy transfer) based assay format for inhibition of human IgE (Calbiochem 401152) labelled with Europium Chelate (Perkin Elmer 1244-302) binding to human FcεRI-Fc (in house NS0 cell produced).

Outputs during lead isolation were screened as undiluted, periplasmic extracts containing unpurified scFv, prepared in: 50 mM MOPS buffer pH7.4, 0.5 mM EDTA and 0.5 M sorbitol.

15 µl of unpurified scFv sample was added to a 384 well assay plate (Perkin Elmer 6006280). This was followed by the addition of 15 µl of 11 nM human FcεRI-Fc (based on a MW of 260 kDa), 15 µl of 40 nM anti human Fc IgG labelled with XL665 (CIS Bio International 61HFCXLA), and then 15 µl of 0.75 nM europium labelled human IgE. Non-specific control binding was defined using 300 nM human IgE (Calbiochem). All dilutions were performed in 50 mM Tris-HCl (pH 7.8) containing 250 mM sodium chloride and 0.05% Tween20 (assay buffer).

Assay plates were then incubated for 1.5 hours at room temperature, prior to reading time resolved fluorescence at 615 nm and 665 nm emission wavelengths sequentially using a VICTOR2 plate reader (Perkin Elmer).

Data was normalised by VICTOR2 software to calculate counts per second (CPS). CPS values were subsequently used to calculate % specific binding as described in equation 1.

$$\% \text{ specific binding} = \frac{(CPS \text{ of sample} - CPS \text{ of non-specific binding control})}{(CPS \text{ of total binding control} - \text{non-specific binding control})} \times 100 \quad \text{Equation 1}$$

Inhibition of IgE Binding to FcεRI by Purified scFv

Purified scFv from positive clones identified from screening were tested in receptor-ligand binding homogeneous FRET (Fluorescence resonance energy transfer) based assay format for inhibition of human IgE (Calbiochem 401152) labelled with Europium Chelate (Perkin Elmer 1244-302), binding to human FcεR1-Fc (in house NS0 cell produced).

A titration of scFv concentrations was used in order to establish the scFv potency as measured by $IC_{50}$ values in the assay. 15 µl of titration of purified scFv sample was added to a 384 well assay plate (Perkin Elmer 6006280). This was followed by the addition of 15 µl of 11 nM human FcεRI-Fc (based on a MW of 260 kDa), 15 µl of 40 nM anti human Fc IgG labelled with XL665 (CIS Bio International 61HFCXLA), and then 15 µl of 0.75 nM europium labelled human IgE. Non-specific control binding was defined using 300 nM human IgE (Calbiochem). All dilutions were performed in 50 mM Tris-HCl (pH 7.8) containing 250 mM sodium chloride and 0.05% Tween20 (assay buffer).

Assay plates were then incubated for 1.5 hours at room temperature, prior to reading time resolved fluorescence at 615 nm and 665 nm emission wavelengths sequentially using a VICTOR2 plate reader (Perkin Elmer).

Data was normalised by VICTOR2 software to calculate counts per second (CPS). CPS values were subsequently used to calculate % specific binding as described in equation 1.

$$\% \text{ specific binding} = \frac{(CPS \text{ of sample} - CPS \text{ of non-specific binding control})}{(CPS \text{ of total binding control} - \text{non-specific binding control})} \times 100 \quad \text{Equation 1}$$

$IC_{50}$ values were determined using GraphPad Prism software by curve fitting using a four-parameter logistic equation (Equation 2).

$$Y = \text{Bottom} + (\text{Top} - \text{Bottom})/(1 + 10^{\wedge}((\text{Log } EC50 - X)^*\text{HillSlope})) \quad \text{Equation 2}$$

X is the logarithm of concentration. Y is specific binding Y starts at Bottom and goes to Top with a sigmoid shape. Inhibition of Calcium Signalling by Purified scFv and IgG in RBL-2H3 Cells Stably Transfected with the Human FcεR1 (RBL-ER51 Cells)

The neutralisation potency of purified scFv and IgG preparations against human IgE bioactivity mediated through FcεRI was assessed using a RBL-ER51 calcium-signalling assay. Human FcεRI was cloned from human peripheral blood lymphocytes into the pcDNA3.1 vector and transfected, using a standard electroporation method, into RBL-2H3 cells (a rat basophilic cell line). Transfected cells were cloned by limiting dilution and analysed for surface FcεRI expression. The resulting RBL-ER51 cells were maintained in media containing G418 (Invitrogen 10131-027) to maintain stable receptor expression. Free IgE in the vicinity of the cells binds to the FcεRI and subsequent cross-linking of receptor-bound IgE leads to a calcium mobilisation that can be detected using a Fluorometric Imaging Plate Reader (FLIPR).

RBL-ER51 cells were seeded at $5 \times 10^4/100$ µl/well in culture media [DMEM (Invitrogen 41966) with 9% v/v FBS Non-Heat Inactivated (Invitrogen 10100-147) and 400 ug/mL G418 (Invitrogen 10131-027)] into 96 well black-walled, flat-bottomed, tissue culture-treated plates (Costar) and incubated at 37° C., 5% $CO_2$ for 18-24 hours. After this time, media was aspirated, leaving cell monolayer intact, and replaced with 100 uL/well of FLUO-4AM loading buffer [DMEM with 0.1% FBS, 20 mM HEPES, 2.5 mM probenicid and 2 ug/mL FLUO-4AM (Teff Labs)] for 1-2 hours at 37° C., 5% $CO_2$. Loading buffer was aspirated and cells washed 3 times with 200 uL/well of PBS. The final wash was aspirated and replaced with 70 uL/well of FLIPR buffer [125 mM $NaCl_2$, 5 nM KCl, 1 mM $MgCl_2$, 1.5 mM $CaCl_2$, 30 mM Hepes, 2.5 mM Probenicid, 5 mM glucose, 0.01% v/v FCS]. Plates were incubated at 37° C., 5% $CO_2$ for 5-45 minutes.

Test solutions of purified scFv or IgG (in duplicate) were diluted to the desired concentration in FLIPR buffer in V-bottom plates (Greiner). An irrelevant antibody not directed at IgE was used as negative control. IgE (Calbiochem or U266-derived [Ikeyama et. al. 1986. Molecular Immunology 23 (2);

p 159-167]) was prepared in FLIPR buffer and mixed with appropriate test antibody to give a final IgE concentration of 3.33 µg/mL in a total volume of 40 µl/well. The concentration of IgE used in the assay was selected as the dose that at final assay concentration gave approximately 80% of maximal calcium response. All samples were incubated for 30 mins at room temperature, prior to transfer of 30 µl of IgE/antibody mixture to the dye-loaded cells prepared above. Assay plates were incubated at 37° C. for 10 minutes to allow free IgE to bind to the RBL-ER51 cells.

To measure calcium mobilisation following addition of cross-linking anti-IgE, the FLIPR (Molecular Devices) was calibrated for suitable exposure according to manufacturers instructions. Anti-IgE (Biosource AHI0501), diluted in FLIPR buffer, was added to the assay plates to a final concentration of 10 ug/mL. Fluorescence of the FLUO-4AM dye was recorded at 1-second intervals for 80 measurements followed by 8-second intervals for 40 measurements. The peak response from each well was exported and data was then analysed using Graphpad Prism software.

Measurement of Anti-IgE Cross-Linking in RBL-ER51 Cells

To measure ability of purified IgGs to cross-link FcεRI-bound IgE, RBL-ER51 cells were prepared and dye-loaded as described in the inhibition assay. Cells were incubated for 10 minutes in 100 uL of 1 ug/mL human IgE (Calbiochem or U266-derived [Ikeyama et. al. 1986. Molecular Immunology 23 (2); p 159-167]), diluted in FLIPR buffer, to allow IgE to bind to FcεRI on the cell surface. The concentration of IgE used in the assay was selected as the dose that gave approximately 80% of maximal calcium response. To measure calcium mobilisation following addition of cross-linking anti-IgE, the FLIPR (Molecular Devices) was calibrated for suitable exposure according to manufacturers instructions. 30 uL of test antibodies, diluted to appropriate concentrations in FLIPR buffer were added to the IgE loaded assay plates. Anti-IgE (Biosource AHI0501) was used as a positive control. Fluorescence of the FLUO-4AM dye (Teff Labs) was recorded at 1-second intervals for 80 measurements followed by 8-second intervals for 40 measurements. The peak response from each well was exported and data was then analysed using Graphpad Prism software.

Selectivity and Species Cross Reactivity of Antibodies in DELFIA® Epitope Competition Assays Purified IgG were adsorbed onto 96-well Maxisorp microtitre plates (Nunc) in PBS at a concentration which gave a significant signal when biotinylated human IgE was added at approximately its estimated KD for that particular IgG. Excess IgG was washed away with PBS-Tween (0.1% v/v) and the wells were blocked with PBS-Marvel (3% w/v) for 1 hour. A dilution series of each of the following competitors was prepared in PBS, starting at a concentration of approximately 1000-fold the KD value of the interaction between biotinylated human IgE and the respective IgG; human IgE lambda (U266 derived [Ikeyama et. al. 1986. Molecular Immunology 23 (2); p 159-167]), human IgE kappa (Calbiochem), human IgE Cε3-Cε4 domain (in house HEK-EBNA derived), cynomolgus IgE Cε3-Cε4 domain (in house HEK-EBNA derived), human IgA, IgM, IgD, and IgD (all Calbiochem). To this series, an equal volume of biotinylated human IgE at a concentration of approximately the KD was added (resulting in a series starting at a ratio of competitor antigen: biotinylated human IgE of approximately 1000:1). These mixtures were then transferred onto the blocked IgG and allowed to equilibrate for 1 hour. Unbound antigen was removed by washing with PBS-Tween (0.1% v/v), while the remaining biotinylated human IgE was detected by streptavidin-Europium3+ conjugate (DELFIA® detection, PerkinElmer). Time-resolved fluorescence was measured at 620 nm on an EnVision plate reader (PerkinElmer). Fluorescence data were analysed using either Graphpad Prism or Microsoft™ Excel software.

Identification of Improved Clones Using an Antibody-Ligand Biochemical Assay

Selection outputs were screened in epitope competition HTRF® (Homogeneous Time-Resolved Fluorescence) assay format for inhibition of cryptate labelled human IgE (U266-derived [Ikeyama et. al. 1986. Molecular Immunology 23 (2); p 159-167]) labelled with europium cryptate (CIS bio International 62EUSPEA), binding to anti human IgE antibody (Antibody 1).

During lead optimisation, selection outputs were screened as undiluted or diluted periplasmic extracts, containing unpurified scFv, prepared in; 50 mM MOPS buffer pH7.4, 0.5 mM EDTA and 0.5 M sorbitol.

4 nM anti human IgE antibody was pre-mixed with 20 nM anti human Fc IgG labelled with XL665 (CIS Bio International 61HFCXLA). 10 µl of unpurified scFv sample was added to a 384 well low volume assay plate (Costar 3676). This was followed by the addition of 5 µl of the anti human IgE antibody anti Fc-XL665 mix, and then 5 µl of a 1/245 dilution of cryptate labelled human IgE (approximately 2.3 nM cryptate labelled human IgE). Non-specific control binding was defined using 300 nM human IgE (U266-derived [Ikeyama et. al. 1986. Molecular Immunology 23 (2); p 159-167]). All dilutions were performed in phosphate buffered saline (PBS) containing 0.4 M potassium fluoride and 0.1% BSA (assay buffer).

Assay plates were then centrifuged at 1000 rpm at room temperature for 1 minute, and incubated for 3 hours at room temperature, prior to reading time resolved fluorescence at 620 nm and 665 nm emission wavelengths using an EnVision plate reader (Perkin Elmer).

Data was analysed by calculating % Delta F values for each sample. Delta F was determined according to equation 1.

$$\% \text{ Delta } F = \frac{(\text{sample 665 nm}/620 \text{ nm ratio value}) - (\text{non-specific control 665 nm}/620 \text{ nm ratio value})}{\text{non-specific control 665 nm}/620 \text{ nm ratio value}} \times 100 \quad \text{Equation 1}$$

% Delta F values were subsequently used to calculate % specific binding as described in equation 2.

$$\% \text{ specific binding} = \frac{\% \text{ Delta } F \text{ of sample}}{\% \text{ Delta } F \text{ of total binding control}} \times 100 \quad \text{Equation 2}$$

Inhibition of IgE Binding to FcεRI by Improved scFv (Purified)

Purified scFv were tested in a receptor-ligand binding HTRF® (Homogeneous Time-Resolved Fluorescence) assay format for inhibition of either human IgE (U266-derived [Ikeyama et. al. 1986. Molecular Immunology 23 (2); p 159-167]) or cyno IgE (recombinant, see materials and methods) labelled with europium cryptate (CIS bio International 62EUSPEA), binding to human FcεR1-Fc (in house NS0 cell produced).

A titration of scFv concentrations was used in order to establish the scFv potency as measured by $IC_{50}$ values in the assay. 1.9 nM human FcεR1-Fc (based on MW of 260 kDa) was pre-mixed with 20 nM anti human Fc IgG labelled with XL665 (CIS Bio International 61HFCXLA). 10 μl of titration of purified scFv sample was added to a 384 well low volume assay plate (Costar 3676). This was followed by the addition of 5 μl of the FcεR1-Fc anti Fc-XL665 mix, and then 5 μl of a 1/197 dilution of cryptate labelled human or cyno IgE (approximately 2.9 nM cryptate labelled human or cyno IgE). Non-specific control binding was defined using 300 nM of human or cynomolgus IgE (in house derived). All dilutions were performed in phosphate buffered saline (PBS) containing 0.4 M potassium fluoride and 0.1% BSA (assay buffer).

Assay plates were then centrifuged at 1000 rpm at room temperature for 1 min, and incubated for 3 h at room temperature, prior to reading time resolved fluorescence at 620 nm and 665 nm emission wavelengths using an EnVision plate reader (Perkin Elmer).

Data was analysed by calculating % Delta F values for each sample. Delta F was determined according to equation 1.

$$\% \text{ Delta } F = \frac{(\text{sample 665 nm}/620\text{ nm ratio value}) - (\text{non-specific control 665 nm}/620\text{ nm ratio value})}{\text{non-specific control 665 nm}/620\text{ nm ratio value}} \times 100 \quad \text{Equation 1}$$

% Delta F values were subsequently used to calculate % specific binding as described in equation 2.

$$\% \text{ specific binding} = \frac{\% \text{ Delta } F \text{ of sample}}{\% \text{ Delta } F \text{ of total binding control}} \times 100 \quad \text{Equation 2}$$

$IC_{50}$ values were determined using GraphPad Prism software by curve fitting using a four-parameter logistic equation (Equation 3).

$$Y = \text{Bottom} + (\text{Top} - \text{Bottom})/(1 + 10^{((\text{Log } EC50 - X) * \text{HillSlope})}) \quad \text{Equation 3}$$

X is the logarithm of concentration. Y is specific binding Y starts at Bottom and goes to Top with a sigmoid shape.

Identification of Improved Clones in the RBL-ER51 Calcium Signalling Assay

The neutralisation potency of purified IgG preparations from improved antibodies was assessed in a modified version of the RBL-ER51 calcium-signalling assay described for lead isolation.

RBL-ER51 cells were seeded at $5 \times 10^4/100$ ul/well in culture media [DMEM (Invitrogen 41966) with 9% v/v FBS Non-Heat Inactivated (Invitrogen 10100-147) and 400 ug/mL G418 (Invitrogen 10131-027)] into 96 well black-walled, flat-bottomed, tissue culture-treated plates (Costar) and incubated at 37° C., 5% $CO_2$ for 18-24 hours. After this time, media was aspirated and replaced with 50 uL/well dilutions of test antibodies (6.67 nM to 1.33 pM) in assay media [DMEM (Invitrogen 41966) with 9% v/v FBS Non-Heat Inactivated (Invitrogen 10100-147), 400 ug/mL G418 (Invitrogen 10131-027) and 1.6% Penicillin/Streptomycin (Invitrogen 15140-122)] followed by addition of IgE [human (U266-derived [Ikeyama et. al. 1986. Molecular Immunology 23 (2); p 159-167]) or cynomolgus (recombinant, see materials and methods)] diluted in assay media to give a final IgE concentration of 25 ng/mL and 100 ng/ml respectively. Assay plates were incubated for 4 hours at 37° C., 5% $CO_2$.

After this time, antibody/IgE mixture was aspirated, leaving cell monolayer intact, and replaced with 100 uL/well of FLUO-4AM loading buffer [DMEM with 0.1% FBS, 20 mM HEPES, 2.5 mM probenicid and 2 ug/mL FLUO-4AM (Invitrogen)] for 1-2 hours at 37° C., 5% $CO_2$. Loading buffer was aspirated and cells washed 3 times with 200 uL/well of PBS. The final wash was aspirated and replaced with 100 uL/well of FLIPR buffer [125 mM $NaCl_2$, 5 nM KCl, 1 mM $MgCl_2$, 1.5 mM $CaCl_2$, 30 mM Hepes, 2.5 mM Probenicid, 5 mM glucose, 0.01% v/v FCS]. Plates were incubated at 37° C., 5% $CO_2$ for 5-45 minutes.

To measure calcium mobilisation following addition of cross-linking anti-IgE, the FLIPR (Molecular Devices) was calibrated for suitable exposure according to manufacturers instructions. Anti-IgE (Biosource AHI0501), diluted in FLIPR buffer, was added to the assay plates to a final concentration of 2.3 ug/mL (to cross-link human IgE) or 20 ug/mL (to cross-link cynomolgus IgE). Fluorescence of the FLUO-4AM dye was recorded at 1-second intervals for 80 measurements followed by 3-second intervals for 40 measurements. The peak response from each well was exported and data was then analysed using Graphpad Prism software.

Measurement of Cross-Linking of FcεRI-Bound IgE by Optimised Antibodies

To measure ability of purified IgGs to cross-link FcεRI-bound IgE, RBL-ER51 cells were prepared as described in the inhibition assay for assessment of improved antibodies. RBL-ER51 cells were seeded at $5 \times 10^4/100$ ul/well in culture media [DMEM (Invitrogen 41966) with 9% v/v FBS Non-Heat Inactivated (Invitrogen 10100-147) and 400 ug/mL G418 (Invitrogen 10131-027)] into 96 well black-walled, flat-bottomed, tissue culture-treated plates (Costar) and incubated at 37° C., 5% $CO_2$ for 18-24 hours. After this time, media was aspirated and replaced with 100 uL/well of human IgE (U266-derived [Ikeyama et. al. 1986. Molecular Immunology 23 (2); p 159-167]) diluted to 1 ug/mL in assay media [DMEM (Invitrogen 41966) with 9% v/v FBS Non-Heat Inactivated (Invitrogen 10100-147), 400 ug/mL G418 (Invitrogen 10131-027) and 1.6% Penicillin/Streptomycin (Invitrogen 15140-122)]. The IgE concentration was chosen to give maximal loading of the RBL-ER51 cells. Assay plates were incubated for 4 hours at 37° C., 5% $CO_2$.

After this time, the IgE solution was aspirated, leaving cell monolayer intact, and replaced with 100 uL/well of FLUO-4AM loading buffer [DMEM with 0.1% FBS, 20 mM HEPES, 2.5 mM probenicid and 2 ug/mL FLUO-4AM (Invitrogen)] for 1-2 hours at 37° C., 5% $CO_2$. Loading buffer was aspirated and cells washed x3 with 200 uL/well of PBS. The final wash was aspirated and replaced with 100 uL/well of FLIPR buffer [125 mM $NaCl_2$, 5 nM KCl, 1 mM $MgCl_2$, 1.5 mM $CaCl_2$, 30 mM Hepes, 2.5 mM Probenicid, 5 mM glucose, 0.01% v/v FCS]. Plates were incubated at 37° C., 5% $CO_2$ for 5-45 minutes.

To measure calcium mobilisation following addition of cross-linking anti-IgE (1.53 uM to 2.33 nM), the FLIPR (Molecular Devices) was calibrated for suitable exposure according to manufacturers instructions. 30 uL of test antibodies, diluted to appropriate concentrations in FLIPR buffer, were added to the assay plates. Anti-IgE (Biosource AHI0501) was used as a positive control. Fluorescence of the FLUO-4AM dye (Invitrogen) was recorded at 1-second intervals for 80 measurements followed by 3-second intervals for 40 measurements. The peak response from each well was exported and data was then analysed using Graphpad Prism software.

Inhibition of IgE Binding to CD23 on IM9 Cells by Purified IgG

Antibodies were evaluated for inhibition of the IgE/CD23 interaction using the IM9 cell binding assay. IM9 cells (a human B cell line) were maintained in culture media [RPMI 1640 glutamax (Invitrogen 61870-010); 9% v/v heat-inactivated FBS (Invitrogen 10100-147)] using standard tissue culture procedures.

To test optimised IgG, the IM9 cells were pre-treated with 25 ng/ml human IL-4 (Peprotech, 200-04) for 3 days at 37° C./5% $CO_2$ in order to up-regulate CD23 expression.

IM9 cells were harvested and resuspended in Flow buffer [PBS with 1% Goat serum (Sigma) and 0.1% BSA fraction V (Sigma) at $1 \times 10^6$ cells/mL. Fc receptor blocking was performed by addition of Fc fragments (TEBU-bio) to a final concentration of 5 ug/mL. This cell suspension was plated at 100 uL/well in U-bottomed polypropylene plates (Greiner) and incubated on ice for 30 minutes.

Antibody dilutions (667 nM to 1 nM) were prepared in U-bottomed polypropylene plates (Greiner) and mixed with IgE (U266-derived [Ikeyama et. al. 1986. Molecular Immunology 23 (2); p 159-167]) to a final IgE concentration of 10 ug/mL for 30 minutes at room temperature. Cell plates were spun at 2000 rpm for 2 minutes and supernatant was aspirated, leaving the cell pellet intact. Cells were resuspended in 100 uL/well antibody/IgE mix and incubated on ice for 1 hour. Cell plates were centrifuged at 200 rpm for 2 minutes and antibody/IgE supernatants were aspirated. Cells were washed by resuspending in 200 uL/well of Flow buffer and centrifuging as above.

IgE bound to the cell surface was detected with anti-IgE-phycoerythin (Caltag) diluted 1/30, v/v, 100 uL/well. Assay plates were incubated on ice for 20 minutes in the dark before centrifuging at 2000 rpm for 2 minutes and washing with $2 \times 200$ uL of Flow buffer as described above. Cells were resuspended in 100 uL Cell Fix (BD biosciences) and analysed using a FACSCalibur (BD Biosciences) to detect FL2 staining.

Data was analysed using CellQuest Software (BD biosciences). FL2 Geomean fluorescence was exported and data was then analysed using Microsoft Excel and Graphpad Prism software.

Generation Human IgE Cε3-4-C-Terminally Tagged with FLAG His10

The fragment of human IgE Cε3-4 was as described previously in Wurzburg et. al. (2000) Structure of the Human IgE-Fc Cε3-C4 Reveals Conformational Flexibility in the Antibody Effector Domains. A cDNA fragment that encompassed nucleotides 2135-2868 (GenBank accession number J00222) was amplified using RT-PCR from total RNA of IL13 stimulated human PBMC. This PCR product was cloned into pCR2.1 TA (Invitrogen).

To allow secretion of the expressed protein and generate a sequence that incorporated an inframe C-terminal FLAG epitope and polyhistidine tag (His10), the IgE Cε3-4 fragment was PCR amplified with primers that incorporated a 5' BssHII site, and 3' FLAG epitope, polyhistidine tag (His10) and XbaI site and subsequent insertion into pEU8.2 vector. The modified pEU8.2 vector contains an EF-1 promoter, the genomic sequence for murine IgG1 leader peptide, oriP origin of replication to allow episomal plasmid replication upon transfection into cell lines expressing the EBNA-1 gene product (such as HEK293-EBNA cells).

Protein was purified from conditioned media using IMAC chromatography followed by Size Exclusion chromatography (SEC).

Generation of Cynomolgus IgE Cε3-4 C-Terminally Tagged with FLAG His10

The cynomolgus IgE constant region was determined by direct sequencing of PCR products amplified from genomic DNA using primers that encompass nucleotides 1174-2989 of the human IgHE (heavy chain of IgE) locus (GenBank Accession J00222).

The exons were identified by homology with the human sequence, and thus it was possible to predict the cDNA sequence for the cynomolgus IgE heavy chain constant region.

A cDNA encoding the sequence for murine IgG1 leader peptide, cynomolgus, Cε3-4 (FIG. 2), and C-terminal FLAG epitope and polyhistidine tag was synthesised (DNA2.0) and cloned into pDONR221 (Invitrogen). Then using LR Gateway® reaction (Invitrogen) the gene of interest was transferred to the expression vector pDEST12.2 (Invitrogen) modified by the insertion of the oriP origin of replication from the pCEP4 vector (Invitrogen) to allow episomal plasmid replication upon transfection into cell lines expressing the EBNA-1 gene product (such as HEK293-EBNA cells).

Protein was purified from conditioned media using IMAC chromatography followed by Size Exclusion chromatography.

Generation Chimaeric D12 Variable Region and Cynomolgus IgE Constant Region

A cDNA encoding the variable heavy chain region that encoded the Human anti-eostradiol scFv (D12_VH) and one of either two different haplotypes cynomolgus IgHE gene (cyIGHE TQ and cyIGHE ME) were synthesised (DNA2.0) and cloned into pDONR221 (Invitrogen). Also a cDNA representing the variable light chain Human anti-eostradiol scFv (D12_VL) and one of either two cynomolgus lambda constant region genes (cyIGLC4 and cyIGLC7) were synthesised (DNA2.0) and cloned into pDONR221 (Invitrogen).

Then using LR Gateway® reaction (Invitrogen) the gene of interest was transferred to the expression vector pDEST12.2 (Invitrogen) modified by the insertion of the oriP origin of replication from the pCEP4 vector (Invitrogen) to allow episomal plasmid replication upon transfection into cell lines expressing the EBNA-1 gene product (such as HEK293-EBNA cells).

Recombinant chimaeric IgE protein representing the variable heavy chain region of the Human anti-eostradiol scFv fused to cynomolgus IgE Cε1-4 (FIGS. 3 and 4), and variable light chain region of the Human anti-eostradiol scFv fused to cynomolgus Lambda constant region (FIGS. 5 and 6), expressed from HEK293 EBNA cells was purified using the method as described in Ikeyam et. al. (1986) Mol Immunol 23 p 159-67.

Human FcεRI-Fc (In House NS0 Cell Produced)

The FcεRI encompassing the nucleotides 67-711 (GenBank Accession number NM_002001) was cloned up stream of the genomic region of the human IgG1 Fc as from pEU1.2 first described in Persic et al. (1997) Gene 187; 9-18. This was cloned into pcDNA3.1 EcoRI-XbaI (SEQ ID NO: 391 and 392). Expression of the recombinant fusion protein FcεRI_Fc was achieved by stable transfection of NS0 cells with the pcDNA3.1 FcεRI_Fc construct. Stable expression was established by selection with G418, isolation of clones via limiting dilution and identification of the clones with the high expression level. The FcεRI_Fc fusion protein was then purified from the conditioned medium using Protein A affinity chromatography, followed by preparative Size Exclusion Chromatography.

Example 3

Human B Cells—Inhibition of Intracellular IgE

Peripheral Blood Mononuclear Cells (PBMC) were isolated from human heparinised whole blood by centrifugation on a Ficoll-Paque gradient (Pharmacia). B cells were subsequently isolated from the PBMC population using positive anti-CD19 selection with magnetic beads (Miltenyi). Both the positive and the negative B cell fractions were collected as the cells were passed over the magnetic column. The cells from the negative B cell fraction containing all PBMC cells except B cells, were treated with Mitomycin C to prevent proliferation. The cells were incubated with 50 µg/mL Mitomycin C for 30 min, then washed with tissue culture media (RPMI 1640 with Glutamax (Gibco)/10% FCS (Gibco)/50 U/mL Penicillin/50 µg/mL Streptomycin (Gibco)) and further incubated with PBS for 70 min before a final wash to ensure all Mitomycin C was removed. To induce the differentiation of the B cells, $4 \times 10^4$ B cells and $9.2 \times 10^5$ cells from the B cell negative fraction were plated in a 96-well plate in tissue culture media supplemented with 3.5 µM beta-mercaptoethanol (Sigma) and 20 µg/mL transferrin (Chemicon), and pre-incubated with anti-IgE monoclonal antibodies or a control antibody at 0.001-100 nM for 30 min before addition of human interleukin-4 (IL-4) at 10 ng/mL. The cells were subsequently incubated in a humidified $CO_2$ incubator for 12-14 days. At day 12-14, the plates were given a brief spin, supernatants collected and the cells stained for intracellular IgE using the following protocol.

The cells were first incubated with PBS with 1% human serum for 10 minutes to block Fc Receptor binding. Cells were then fixed and permeabilised on ice using Cytofix/Cytoperm kit from Becton Dickinson. The cells were then washed before addition of a polyclonal rabbit anti-human IgE-FITC antibody (DAKO) at 1:6 final dilution and a monoclonal mouse anti-human CD19-RPE/Cy5 antibody (DAKO) at 1:10 final dilution. It is important that the cells are thoroughly washed to avoid interference from residual anti-IgE MAb's (monoclonal antibodies). After 30 min incubation the cells were washed and samples were analysed on a FACS Calibur using a HTS 96-well plate loader device. The percentage of cells in the CD19+ population that co-express IgE were then recorded, and the expression of intracellular IgE is presented as % inhibition of maximum IgE expression in cells not treated with blocking anti-IgE monoclonal antibody. Antibody 11 inhibited the induction of IgE positive cells with an IC50 of 1.6 nM (FIG. 7—upper graph). An irrelevant antibody of the same format was used as negative control (CAT-002), and did not inhibit the induction of IgE positive B cells (FIG. 7—lower graph).

Example 4

Mast Cell Line (LAD2)—Inhibition of β-Hexosaminidase Release

LAD2 cells [A. S. Kirshenbaum et al. *Leukemia research* 27 (2003)] were cultured at a cell density of $0.25$-$0.6 \times 10^6$ cells/mL in serum-free media (StemPro-34, Life Technologies) supplemented with StemPro-34 nutrient supplement, 2 mM L-Glutamine and 100 ng/mL recombinant human stem cell factor (rhSCF, R&D).

For the β-hexosaminidase assay, the cells were seeded at a density of $2.5 \times 10^4$ cells/well, and pre-incubated in a 96-well polypropylene plate together with blocking anti-IgE MAb's in a concentration range of 0.0001-100 nM. Cells were incubated at 37° C. for 30 minutes, before IgE at a concentration of 0.15 nM was added, and the cells incubated for an additional 4 hours. After the incubation with IgE, cells were washed with buffer to remove any excess IgE, and subsequently IgE bound to the FcεR's on the LAD2 cells was cross-linked with αIgE (600 µg/mL goat-anti human IgE, Sigma) for 30 minutes at 37° C. The incubation was stopped by cold centrifugation and the cell supernatants collected and transferred to a 96-well plate. β-hexosaminidase content was analysed by using a slightly modified version of the method published by Smith et al [Smith J et al *Biochem. J.* (1997) 323, 321-328]. In brief, 2 mM p-nitrophenyl-N-acetyl-D-glucosaminide in 0.2 M citrate-buffer, pH 4.5 was used as a substrate for the hexosaminidase. The reaction was stopped by addition of 1M Tris-buffer pH 9.0. Optical density was measured spectrophotometrically at 405 nm (minus the values at 570 nm) using a Spectramax reader from Molecular Devices. The effect of the anti-IgE MAb's to inhibit the release of β-hexosaminidase was calculated, and presented as percentage inhibition of total release +/−SEM. Antibody 11 inhibited β-hexosaminidase with an IC50 of 0.04 nM (FIG. 8—upper graph), whereas an irrelevant MAb of the same format (CAT-002) did not inhibit the β-hexosaminidase (FIG. 8—lower graph).

Example 5

Anti-IgE Antibody Binding of IgE in Serum Using ELISA

Assay Description

Serum samples were prepared from blood samples from human donors. 96 well ELISA plates (Nunc Maxisorp, No. 442404) were coated with 150 µl/well of 1 µg/ml FcεRI-Fc-His diluted in PBS, and incubated at 4° C. overnight. After the overnight incubation, the plates were washed three times with PBS containing 0.05% Tween 20 (PBST, Medicago 09-9401-100). To reduce background binding, plates were subsequently incubated with 200 µl/well of block buffer consisting of PBS containing 0.5% BSA, incubated at room temperature for 2 hours, and washed three times with PBST as described above. The samples (human serum or plasma with varied amounts of anti-IgE antibody, Antibody 11) and standards (ImmunoCAP Total IgE (human) calibrator, Phadia, Uppsala) were diluted in PBS containing 0.05% Tween 20, and kept on ice until they were applied to the assay plates in a volume of 150 µl/well. The plates were sealed and samples incubated at room temperature for 2 hours. To remove unbound sample, plates were washed three times with PBST as described. Subsequently, 150 µl/well of rabbit anti-human IgE (D€1, 30-1917-00, 420036-02, 841204, 9911302 from Phadia, Uppsala) at a concentration of 0.25 µg/ml diluted in PBST, was added to detect bound human IgE. The plates were then sealed again, and incubated for 1 hour at room temperature. To remove unbound rabbit anti-human IgE antibodies, plates were washed three times with PBST as described above. A HRP-conjugated secondary antibody (Goat-anti-rabbit IgG, HRP conjugated. Pierce. 0.8 mg/ml) was used to detect the rabbit anti-human IgE. The conjugate was diluted 1:25000 in PBST, 150 µl added per well, the plates sealed, and incubated for 1 hour at room temperature. The plates were then washed three times with PBST as described. TMB-substrate solution (DAKO Substrate-Chromogen, No. S1599), 150 µl/well, was then added to each well and the plates incubated for 10 minutes at room temperature. The reaction was stopped by adding 150 μl/well of Stop solution (2M $H_2SO_4$) and the 450 nm absorbance read on a Tecan SAFIRE instrument.

Since the measurement of IC50 is dependent on the concentration of ligand (i.e. IgE) in an assay, in the present assay the $IC_{50}$ will vary depending on the amount of IgE ligand present in the human serum sample. In a representative experiment Antibody 11 had an $IC_{50}$ of 202 pM [FIG. 9). In the same experiment Xolair™ had an $IC_{50}$ of 57 nM.

Example 6

Measurement of Complex Formation Between IgE and Purified IgG

Characterisation of the immune complexes formed between purified human IgE and purified anti-IgE IgG (antibody 11) was performed by high-performance size exclusion liquid chromatography. In addition, on line multi-angle light scattering (MALS) was used to estimate complex size. Complexes were formed by incubating IgE and IgG together at three different molar ratios (3:1, 1:1 and 1:3 respectively) in Dulbecco's PBS at 18° C. for one hour. For the 1:1 molar ratio, the concentration of each protein was 2.5 μM. The higher ratios were achieved by increasing the concentration of the relevant protein to 7.5 μM. These samples were analysed on two Bio-Sep-SEC-S 4000 columns (300×7.8 mm) arranged in tandem. The columns were equilibrated and samples analysed in Dulbecco's PBS at a flow rate of 1 ml/min on an Agilent HP1100 HPLC system. Peaks were detected at 220 and 280 nm using a diode array detector and the eluate was also directed through a Wyatt Technologies DAWN EOS (MALS) and Optilab rEX (refractive index) detectors.

Chromatography of the 1:1 molar ratio sample gave a doublet of peaks (detected by UV absorbance) which were not completely resolved and corresponded to retention times of 13.88 minutes and 14.9 minutes. These retention times indicate the formation of non-covalent complexes of IgE with IgG. MALS analysis gave molecular masses of 1,085 kDa (13.88 min peak) and 702 kDa (14.9 min peak). These masses are consistent with complexes corresponding to a heterotetramer (predicted mass 674 kDa, 2IgE:2IgG) and a heterohexamer (predicted mass 1010 kDa, 3IgE:3IgG). Chromatographic and MALS analysis of both the 3:1 and 1:3 (IgE:IgG) molar ratio samples gives a similar profile to the 1:1 sample with peaks corresponding to heterotetramer and heterohexamer detectable by UV absorbance. Additional peaks were detected corresponding to the excess IgE or IgG in the samples.

Example 7

Determination of the Epitope Bound by Germlined Antibody 11

Use of X-ray crystallography to determine the precise 3-dimensional structure of proteins at atomic resolution is well known to those in the art and has been used to visualise in detail the parts of proteins that interact with antibodies (Padavattan et al, 2007; Karpusas et el., 2001). This is the most definitive epitope mapping technique, but requires considerable effort and relies on being able to obtain crystals of sufficient quality, which in turn depends on purity and quality of protein sample and expertise in being able to find the appropriate crystallisation conditions. Once crystals of the protein-antibody complex are obtained, they are irradiated with X-rays to give a diffraction pattern, which depends on the exact atomic distribution. The diffraction pattern can be analysed by crystallographers to determine the three dimensional positional coordinates of the atoms in the structure. This allows a detailed inspection of the interaction sites between protein and antibody.

7.1 X-Ray Crystal Structure Determination of the IgE Cε3-Cε4 Antibody Complex

IgE domain Cε2-Cε3 was cloned and expressed and purified for the purpose of structure determination. Similarly a Fab fragment was prepared by digestion and purification of the full Antibody 11 developed to bind to IgE. The complex was formed by mixing and purified by size exclusion chromatography to remove non-complexed IgE domains and Fab molecules.

Crystals of the IgE Cε3-Cε4/Fab complex were obtained that belong to the trigonal space group $P3_221$. They were analysed at the European Synchrotron Radiation Facility (ESRF) in Grenoble, France. Complete diffraction data to 2.85 Å resolution were obtained. The structure could be solved by Molecular Replacement (Rossman, 1972) using the variable and constant part of a Fab fragment as separate search models, thereby orienting and positioning the Fab fragments in the crystallographic asymmetric unit. In total, three Fab fragments were identified in the asymmetric unit. Subsequently three IgE Cε3-Cε4 molecules could be placed in the asymmetric unit. Each IgE dimer binds two Fab molecules and thus, in total the asymmetric unit comprises one and a half complete IgE/Fab complexes.

7.1.1 Overall Description of the IgE Cε3-Cε4/Antibody 11 Fab Complex

The crystal structure shows that each IgE Cε3-Cε4 dimer, is bound in a symmetric or near symmetric fashion to two Fab fragments (FIG. 10). Since the asymmetric unit of the crystal comprises one and a half IgE/Fab complexes, the incomplete complex forms a dimer with a symmetry related partner in the neighbouring asymmetric unit, via a two-fold axis.

Both molecules of the IgE dimer, denoted IgE1 and IgE2, interacts with the Fab fragment of Antibody 11. The majority of the interactions are provided by the Fab Heavy chain, which interacts with both IgE1 and IgE2 whereas the Light chain is only observed to interact with IgE1. The epitope of the antigen is situated mainly in domain Cε3, with contribution from one amino acid located close to the hinge in domain Cε4.

The three interaction sites between the IgE Cε3-Cε4 and the Fab in the asymmetric unit of the crystal are very similar. However, after refinement it was clear that one of the Fab molecules is considerable less ordered than the other two Fab molecules. This is commonly seen in crystal structures and is explained by the fact that the particular region is flexible and adopts different orientations throughout the crystal such that the electron density is less well defined. This Fab molecule and the interaction it makes with the IgE Cε3-Cε4 molecule were therefore not considered in the analysis.

IgE is known to be glyscosylated in the Fc region at residue Asn394 (Wurzburg et al). Characterization of the Fc glycosylation, performed by mass spectrometry analysis after trypsin digestion, showed three different glycan variants bound to Asn394, consisting of the core structure $Man_3GlcNAc_2$ with the extension of 2, 3 or 4 hexoses, probably all mannoses (FIG. 11). Indeed from residue Asn394 in all three IgE Cε3 domains an extended electron density protrudes into the cavity between the two IgE molecules in the dimer. The electron density suggests a high-mannose-type structure, with two N-acetyl-glucosamine (GlcNAc) and three or four mannose units visible in each chain, consistent with the mass spectrometry analysis. Only one of the hexoses outside the core structure, Man6 which is coupled to Man4, is visible in the electron density indicating that the remaining 1-3 hexoses are flexible.

7.1.2 Describing the Epitope and Paratope

This crystal structure allows the epitope interactions between IgE Cε3-Cε4 and Fab to be examined in atomic detail. There are two independent IgE/Fab interactions in the solved structure, excluding the third Fab molecule due to its badly defined electron density map, which will be described. They are very similar indicated by an root-mean-square deviation between the two equivalent Fab Variable chain fragments of 0.31 Å calculated using Cε positions (superpose, CCP4 1994) and between the equivalent IgE monomers of 0.82 and 0.96 Å respectively. Despite this high similarity the two interactions will be described separately and will be denoted IgE/Fab1 and IgE/Fab2. Details of the interactions are captured in Table 5 and Table 6, where the residue number contains a chain indicator (HC: Fab Heavy chain, LC: Fab Light chain, IgE1, IgE2). The numbering of the amino-acid residues of Antibody 11 is according to the Kabat system (Kabat et al 1991). The distances were obtained using the CCP4 program CONTACT (CCP4, 1994).

Both interactions involve the complementarity determining regions (CDRs) from both the Heavy and the Light chain of the antibody fragment, residues from the framework (the region outside the CDRs of the Fab) and amino acid residues from both monomers in the IgE Cε3-Cε4 monomer. The antibody Light chain interacts with IgE1 in the IgE Cε3-Cε4 dimer, while the Heavy chain interacts with both monomers. The majority of the contacts are, however, between the Heavy chain and monomer IgE2 of the antigen. The two interactions are described in detail below.

7.1.3 Detailed Description of the Interaction Between Fab1 and IgE, Interaction 1

The interaction site defining the epitope of IgE Cε3-Cε4 covers an area of 1100 Å$^2$ (calculated using the program areaimol, see reference CCP4, 1994) and is made up by amino acid residues Glu390 through to Asn394 inclusive of IgE1 and Leu340, Arg342, Ala428 to Thr434 inclusive, Thr436, Ser437 and Glu472 in IgE2 of the antigen. In addition the sugar moieties GlcNAc1 and Man6 in IgE1 and Man5 in IgE are in contact with the Fab molecules. Amino acid residues from the Heavy chain interacting with the antigen, including the sugar moieties, are from CDR1: Tyr32, from CDR2: Asp53 and Asn54, from CDR3: Val95, Met96, Ile100, Gly100b, Gly100c, Asp101 and Tyr102 and from the framework: Glu1, Lys23, Thr30, Ala71 to Arg77 inclusive and Tyr79. Residues contributing from the Fab Light chain are Asp50 and Ser56 from CDR2 and Leu 46 and Tyr49 from the framework. The interaction include 19 hydrogen bonds in addition to non-polar van der Waals contacts.

7.1.4 Detailed Description of the Interaction Between Fab1 and IgE, Interaction 2

The interaction site defining the epitope of IgE Cε3-Cε4 covers an area of 1165 Å$^2$ (calculated using the program areaimol, see reference CCP4, 1994) and is made up by amino acid residues Glu390, Gln392 to Asn394 inclusive of IgE1 and Leu340, Arg342, Ala428 to Thr434 inclusive, Thr436, Ser437 and Glu472 in IgE2 of the antigen. In addition the sugar moieties GlcNAc1 and Man6 in IgE1 are in contact with the Fab Heavy chain. Amino acid residues from the Heavy chain interacting with the antigen, including the sugar moieties, are from CDR1: Tyr32, from CDR2: Pro52a, Asp53 and Asn54, from CDR3: Val95, Met96, Ile100, Gly100b, Gly100c, Asp101 and Tyr102 and from the framework: Glu1, Lys19, Lys23, Thr30, Ala71 to Ser75 inclusive, Arg77 and Tyr79. Residues contributing from the Fab Light chain are Ser56 from CDR2 and Tyr49 from the framework. The interaction include 19 hydrogen bonds in addition to non-polar van der Waals contacts.

TABLE 5

Direct interactions between IgE Cε3-Cε4 and Antibody 11 Fab, interaction 1

| Chain Fab | Residue Fab | Monomer IgE | Residue IgE | Distance (Å) |
|---|---|---|---|---|
| Hydrogen bonds | | | | |
| HC | Tyr 32 OH | IgE1 | GlcNAc 1 O7 | 2.58 |
| HC | Met 96 O | IgE1 | Asn 394 ND2 | 3.08 |
| HC | Gly 100b O | IgE1 | Arg 393 NH1 | 2.60 |
| HC | Gly 100c O | IgE1 | Arg 393 NE | 2.80 |
| HC | Tyr 102 OH | IgE1 | GlcNAc 1O6 | 3.08 |
| HC | Asp 53 O | IgE2 | Met 430 N | 2.83 |
| HC | Asp 53 O | IgE2 | Arg 431 NH1 | 2.67 |
| HC | Asp 53 OD1 | IgE2 | Arg 431 NH1 | 2.77 |
| HC | Asp 53 OD1 | IgE2 | Arg 431 NH2 | 2.60 |
| HC | Ala 71 O | IgE2 | Ser 432 OG | 2.64 |
| HC | Asp 72 OD2 | IgE2 | Arg 342 NH1 | 3.06 |
| HC | Asp 72 OD2 | IgE2 | Thr 434 N | 3.02 |
| HC | Asp 72 OD2 | IgE2 | Thr 434 O | 2.97 |
| HC | Thr 73 OG1 | IgE2 | Ser 432 N | 2.79 |
| HC | Thr 73 OG1 | IgE2 | Ser 432 O | 3.05 |
| HC | Ser 74 N | IgE2 | Ser 432 O | 3.08 |
| HC | Ser 74 OG | IgE2 | Arg 342 NH1 | 3.10 |
| HC | Ser 74 OG | IgE2 | Thr 433 OG1 | 2.87 |
| HC | Arg 77 NH1 | IgE2 | Glu 472 OE2 | 2.56 |
| Non-polar contacts < 4 Å | | | | |
| LC | Leu 46 | IgE1 | Arg 393 | 3.79 |
| LC | Tyr 49 | IgE1 | Gln 392 | 3.85 |
| LC | Tyr 49 | IgE1 | Arg 393 | 3.66 |
| LC | Asp 50 | IgE1 | Arg 393 | 3.71 |
| LC | Ser 56 | IgE1 | Glu 390 | 3.47 |
| LC | Ser 56 | IgE1 | Lys 391 | 3.87 |
| HC | Glu 1 | IgE1 | Man 6 | 3.40 |
| HC | Val 95 | IgE1 | Arg 393 | 3.49 |
| HC | Ile 100 | IgE1 | Arg 393 | 3.55 |
| HC | Asp 101 | IgE1 | Arg 393 | 3.50 |
| HC | Met 96 | IgE1 | GlcNAc 1 | 3.67 |
| HC | Lys 23 | IgE2 | Glu 472 | 3.43 |
| HC | Thr 30 | IgE2 | Arg 431 | 3.80 |
| HC | Asp 53 | IgE2 | Leu 429 | 3.34 |
| HC | Asn 54 | IgE2 | Ala 428 | 3.45 |
| HC | Asp 72 | IgE2 | Ser 432 | 3.22 |
| HC | Asp 72 | IgE2 | Thr 433 | 3.53 |
| HC | Thr 73 | IgE2 | Met 430 | 3.98 |
| HC | Thr 73 | IgE2 | Arg 431 | 3.22 |
| HC | Ser 74 | IgE2 | Leu 340 | 3.33 |
| HC | Ser 75 | IgE2 | Arg 342 | 3.32 |
| HC | Asp 76 | IgE2 | Man 5 | 3.27 |
| HC | Arg 77 | IgE2 | Thr 436 | 3.84 |
| HC | Tyr 79 | IgE2 | Thr 436 | 3.43 |
| HC | Tyr 79 | IgE2 | Ser 437 | 3.27 |

The distance cut-off used for hydrogen bonds is 3.2 Å, for non-polar interactions 4.0 Å

TABLE 6

Direct interactions between IgE Cε3-Cε4 and Antibody 11 Fab, Interaction 2

| Chain Fab | Redidue Fab | Monomer IgE | Residue IgE | Distance (Å) |
|---|---|---|---|---|
| Hydrogen bonds | | | | |
| LC | Ser 56 OG | IgE1 | Glu 390 OE1 | 2.44 |
| LC | Ser 56 OG | IgE1 | Glu 390 OE2 | 2.99 |
| HC | Tyr 32 OH | IgE1 | GlcNAc 1O7 | 2.41 |
| HC | Gly 100b O | IgE1 | Arg 393 NH2 | 2.58 |
| HC | Gly 100c O | IgE1 | Arg 393 NE | 3.01 |

TABLE 6-continued

Direct interactions between IgE Cε3-Cε4 and Antibody 11 Fab, Interaction 2

| Chain Fab | Redidue Fab | Monomer IgE | Residue IgE | Distance (Å) |
|---|---|---|---|---|
| HC | Tyr 102 OH | IgE1 | GlcNAc 1 O6 | 2.73 |
| HC | Asp 53 O | IgE2 | Met 430 N | 2.74 |
| HC | Asp 53 O | IgE2 | Arg 431 NH1 | 2.62 |
| HC | Asp 53 OD1 | IgE2 | Arg 431 NH1 | 2.88 |
| HC | Asp 53 OD1 | IgE2 | Arg 431 NH2 | 2.65 |
| HC | Ala 71 O | IgE2 | Ser 432 OG | 2.87 |
| HC | Asp 72 OD1 | IgE2 | Ser 432 O | 3.13 |
| HC | Asp 72 OD2 | IgE2 | Arg 342 NH1 | 3.17 |
| HC | Asp 72 OD2 | IgE2 | Thr 434 O | 3.11 |
| HC | Thr 73 OG1 | IgE2 | Ser 432 N | 2.94 |
| HC | Ser 74 N | IgE2 | Ser 432 O | 3.17 |
| HC | Ser 74 OG | IgE2 | Arg 342 NH1 | 3.00 |
| HC | Ser 74 OG | IgE2 | Thr 433 OG1 | 2.77 |
| HC | Tyr 79 OH | IgE2 | Ser 437 N | 3.09 |
| Non-polar contacts < 4 Å | | | | |
| LC | Tyr 49 | IgE1 | Gln 392 | 3.76 |
| LC | Tyr 49 | IgE1 | Arg 393 | 3.63 |
| LC | Ser 56 | IgE1 | Gln 392 | 3.89 |
| HC | Glu 1 | IgE1 | Man 6 | 3.25 |
| HC | Val 95 | IgE1 | Arg 393 | 3.48 |
| HC | Met 96 | IgE1 | GlcNAc 1 | 3.68 |
| HC | Met 96 | IgE1 | Asn 394 | 3.31 |
| HC | Ile 100 | IgE1 | Arg 393 | 3.44 |
| HC | Asp 101 | IgE1 | Arg 393 | 3.81 |
| HC | Lys 19 | IgE2 | Ser 437 | 3.53 |
| HC | Lys 23 | IgE2 | Glu 472 | 3.70 |
| HC | Thr 30 | IgE2 | Arg 431 | 3.88 |
| HC | Pro 52a | IgE2 | Met 430 | 3.95 |
| HC | Asp 53 | IgE2 | Leu 429 | 3.51 |
| HC | Asn 54 | IgE2 | Met 430 | 3.90 |
| HC | Asn 54 | IgE2 | Ala 428 | 3.47 |
| HC | Asp 72 | IgE2 | Thr 433 | 3.61 |
| HC | Thr 73 | IgE2 | Arg 431 | 3.26 |
| HC | Ser 74 | IgE2 | Leu 340 | 3.30 |
| HC | Ser 75 | IgE2 | Arg 342 | 3.55 |
| HC | Arg 77 | IgE2 | Thr 436 | 3.88 |
| HC | Arg 77 | IgE2 | Glu 472 | 3.27 |
| HC | Tyr 79 | IgE2 | Thr 436 | 3.37 |

The distance cut-off used for hydrogen bonds is 3.2 Å, for non-polar interactions 4.0 Å

Material and Methods for Experiment 7

Over Expression of IgE Cε3-Cε4

Cell Lines and Culture Medium.

In this work the original adherent cell line HEK293-EBNA (Invitrogen, Stockholm, Sweden) stably expressing the Epstein Barr virus Nuclear Antigen-1 gene were used. Cells were adapted to suspension growth before transferred into DHI medium by stepwise medium replacement (Davies et al. 2005). The DHI medium used deviated from the original description slightly by being CA2+-free. After adaptation a working cell bank was made and both cell lines were grown routinely in CA2+-free-DHI medium supplemented with 4 mM Glutamine, 2% v/v ultra-low IgG foetal bovine serum, 250 μg/ml G418 (all from Invitrogen, Stockholm, Sweden) and 0.1% w/v Pluronic F68 (Sigma-Aldrich, Stockholm, Sweden) to a maximum of 20 passages.

Transfection Procedure

The 1 mg/ml stock solution of linear 25 kDa polyethylenimin (Polysciences Europe, Eppenheim, Germany) was prepared in water, pH adjusted to 7.0, sterile filtered and stored in small aliquots at −80° C. until use. The transfection cocktail was prepared shortly before transfection in non-supplemented DHI media in a volume equivalent to one-tenth of the transfection volume. For preparing the transfection cocktail the DHI media was divided into two halves. 0.8 μg DNA per ml transfection volume was added to one half of the DHI medium and into the other half 2 μg PEI per ml transfection volume was added. After shaking the two solutions briefly and incubating them for 5 minutes the DNA solution was slowly added to the PEI solution. The transfection cocktail was incubated for 20-30 minutes at room temperature before addition to the Wave bioreactor (Wave Biotech AG, Tagelswangen, Switzerland). Four hours post transfection the culture was fed to the final production volume with supplemented DHI medium and HypPep 1510 (Kerry Bio-Sciences, Almere, the Netherlands) to a final concentration of 0.3% (w/v).

Seeding Cultures

For expansion of the seeding culture the cells were grown in plastic shake bottles at 37° C. in 5% $CO_2$ atmosphere placed in an orbital shaker incubator (Infors AG, Bottmingen, Switzerland). The cells were routinely passaged twice a week reaching approximately $2 \times 10^6$ cells/ml before splitting. Cell density and viability were assessed using a Cedex automatic cell counter (Innovatis AG, Bielefeld, Germany). For Wave cultures the cells were split to $1 \times 10^6$ cells/ml one day before transfection to ensure that they were in logarithmic growth phase at the start of the experiment. Wave cultures were inoculated directly from shakers. All seeding cultures were concentrated by centrifugation and resuspended in fresh culture medium before addition to the bioreactors.

Wave Cultures

Expression was performed in Wave bioreactors (Wave Biotech AG, Tagelswangen, Switzerland) at a working volume of 10 L. The wave bioreactors were seeded to $1 \times 10^6$ cells/ml in 4.5 L supplemented DHI medium. After a 2 hours adaptation phase the culture was transfected with 0.5 L transfection cocktail. Four hours post transfection the culture was fed to 10 L total volume with supplemented DHI medium and HyPep 1510 to a final concentration of 0.3% (w/v). Samples were taken daily to determine cell density, viability and protein concentration.

Expression Vector

The vector expressing the human IgE Cε3-Cε4, with C-terminal Flag tag and 10-histidine tag, was derived from a vector described by Persic et al. (1997). The system is under the control of the EF1-a promotor.

Purification of IgE Cε3-Cε4

20 L of cell supernatant were concentrated five times and diafiltered to 2×PBS (308 mM NaCl, 20 mM phosphate, pH 7.4) with a 10 kDa molecular weight cut-off cross-flow membrane (Pellicon 2, Millipore). The medium was batch bound with 30 mL NiSepharose (GE Healthcare) for two hours at 4° C., washed with five volumes 2×PBS and packed into an XK26 column. The column was then washed with five column volumes 40 mM imidazole in 2×PBS to wash away contaminating proteins. IgE was finally eluted with 400 mM imidazole in 2×PBS. The pool contained IgE with high purity and was concentrated about four times (to ~5 mg/mL) before it was run over a Superdex 200 50/60 SEC-column (1200 mL, GE Healthcare) with 2×PBS used as running buffer. Some larger proteins were separated out and IgE was found in the main peak. Only the main peak fractions were pooled because of contamination in the other two fractions. This step increased the purity of the sample to 99%. The total amount produced was 42 mg and the purified IgE had a concentration of 2 mg/mL.

Analysis of Glycosylation of IgE Cε3-Cε4

In-Solution Digestion with Trypsin

Human IgE minimal domain, IgE Cε3-Cε4, 2 mg/ml, in 2×PBS (composition 308 mM NaCl, 20 mM phosphate, pH 7.4) was mixed with 100 µl trypsin 0.02 mg/ml in 25 mM $NH_4HCO_3$. Digestion proceeded overnight in 37° C. and was stopped with 2 µl formic acid (67%) in $H_2O$.

Nano-LC MS/MS:

Analysis was performed on a 20 cm×50 µm i.d. fused silica column packed with ReproSil-Pur $C_{18}$-AQ 3 µm porous particles, connected to an LTQ-Orbitrap mass spectrometer (Thermo). 8 µl sample injection was made (Agilent autosampler) and the peptides were trapped on a precolumn, 4.5 cm×100 µm i.d., before separation. After 5 minutes linear run with 0.1% formic acid, the gradient was 10-50% acetonitril during 5-30 min (Agilent), 200 nl/min, and the eluent was electrosprayed from the emitter tip. The instrument was operated in data-dependent mode to switch between Orbitrap (FT-MS) survey scan and ion trap (IT-MS/MS) of the three most abundant multiply protonated ions.

Static Electrospray MS/MS:

To verify the charge state of the glycopeptide fragments, selected precursors were analyzed with ESI needle at 1.6 kV, fragmented and detected in the Orbitrap opposed to the linear ion trap in the nano-LC analysis.

Glycopeptide Data Analysis:

the calculated $MH^+$ masses of possible glycopeptides were examined for the presence of glycosylation by use of the GlycoMod tool (http:expasy.org/tools/glycomod) (Cooper et al 2001). The protein sequence and a mass tolerance of 10 ppm was entered. All suggested glycopeptides were checked for the presence of glycan containing fragments.

Production of Antibody 11 Fab.

IgG Purification

Antibody 11 was purified from CHO-EBNA transient material using MabSelect SuRe (GE Healthcare) protein A chromatography media. The protein A eluate was buffer exchanged into PBS, pH7.2 using PD-10 columns (GE Healthcare) then 0.22 µm filtered using a Millex-GP syringe tip filter (Millipore).

Fab Digest and Purification

A digest buffer of 30 mM DL-cysteine hydrochloride dissolved in GIBCO PBS (Invitrogen) was prepared. Papain from papaya latex (Sigma) was reconstituted in digest buffer to give a 10 mg/mL solution and kept at room temperature for a minimum of 30 minutes before use. Cysteine was added to Antibody 11 IgG to give a 30 mM solution and papain was added at a ratio of 1 mg papain to 100 mg IgG. The digest was terminated after 90 minutes by the addition of 0.5M iodoacetamide (Sigma) to give 50 mM iodoacetamide in the final digest mixture. The Fab was purified from the digest mixture using MabSelect SuRe (GE Healthcare) protein A chromatography media in a non-binding mode. The Fab fraction from the MabSelect SuRe step was buffer exchanged into 50 mM sodium acetate/100 mM NaCl, pH5.5 using PD-10 columns (GE Healthcare) and then concentrated to 10 mg/mL using Amicon Ultra-15 5 kDa MWCO centrifugal filter devices (Millipore). The final product was further purified using a Mustang Q acrodisc (Pall) and then 0.22 µm filtered using a Millex-GP syringe tip filter (Millipore).

Generation of the IgE Cε3-Cε4 Antibody 11 Fab Complex.

A solution containing 2 mg/mL of IgE Cε3-Cε4 in buffer 308 mM NaCl and 20 mM phosphate, pH 7.4, was mixed with a solution containing 10.6 mg/mL of Antibody 11 Fab in 50 mM sodium acetate, 100 mM NaCl, pH5.5 at a stoichiometric ratio of 1 to 1.1 of IgE Fcε3-4 homodimer and Antibody 11 Fab heterodimer respectively. The mix was left in ice over night followed by gel filtration on a HiLoad Superdex200 16/60 column (GE Healthcare) equilibrated in 20 mM Tris HCl pH 7.6 and 0.15 M NaCl. The main peak containing the complex was collected and concentrated to 10.4 mg/mL before used in crystallisation experiments.

Crystallisation of the IgE Cε3-Cε4 Antibody 11 Fab Complex.

Crystallisations were carried out according to the method of sitting drop vapour diffusion. The drops contained an equal volume of protein and reservoir solution (150+150 mL) and were set up in a Crystal Quick 96 well plate (Greiner Bio-one) with reservoir volumes of 80 uL. The complex crystals grew in drops with a reservoir solution of 100 mM $MgCl_2$, 100 mM sodium citrate pH 5.0 and 15% PEG 4000 over a period of 2-3 weeks at 4° C. The crystals were harvested into a cryoprotectant solution (100 mM $MgCl_2$, 100 mM sodium citrate pH 5.0 and 15% PEG 4000 made 20% glycerol by addition of 100% glycerol) and cooled rapidly in liquid nitrogen.

Data Collection and Structure Solution of the IgE Cε3-Cε4 Antibody 11 Fab Complex.

Diffraction data were collected from single crystals at the European Synchrotron Radiation Facility (ESRF) in Grenoble, France at beam line ID-29. An initial dataset (data set 1, table 7) was recorded to 3 Å resolution and later a higher resolution data set was collected to 2.85 Å resolution, both of which belong to space group $P3_221$. The data was processed with autoPROC (Global Phasing Limited GPhL, Cambridge, UK). Statistics from the data processing is presented in table 7. The asymmetric unit contains three Fab molecules and three molecules of IgE Cε3-Cε4 corresponding to a solvent content of 54%. The structure was solved by the method of molecular replacement using the program PHASER (Read 2001, Storoni et al 2004, McCoy et al 2005). Initial models for the Fab fragment and the IgE Fc domain was generated from the previously reported structures 1AQK (Faber et al 1998) and 1FP5 (Wurzburg et al 2000).

Use of the entire Fab as the search model failed, due to variations of angles in the hinge region between the variable domain and the constant domains. Instead two separate search models consisting of the variable domains and constant domains respectively were prepared and identified in the initial run of PHASER(Read 2001, Storoni et al 2004, McCoy et al 2005). These were later joined to complete Fab fragments. In total two Fab fragments and one variable domain was identified in this fashion. Subsequent runs of molecular replacement located three IgE Cε3-Cε4 molecules, of which one had to be trimmed back to comprise only domain 4. At this stage better quality data had been collected (dataset 2, table 7) and this model was refine against the new data using the program autoBUSTER (Global Phasing Limited GPhL, Cambridge, UK). Subsequently the amino acids of the Fab molecules were manually altered to the correct sequence of Antibody 11 using the graphical program COOT (Emsley & Cowtan 2004). After a second round of restrained maximum-likelihood refinement using isotropic B factors refinement in Refmac (CCP4 1994) the remaining domains of the last Fab and IgE molecules were manually fitted into the electron density. Two additional features of elongated electron density was observed protruding from amino acid residue Asn394 into the cavity between the IgE molecules. This was interpreted as glycosylations and therefore two N-acetyl-glucosamine and three to four mannose units were added to the IgE models. Further rounds of refinement included manual rebuilding of loop regions in COOT (Emsley & Cowtan 2004) intervened by refinement in either autoBUSTER (Global Phasing Limited GPhL, Cambridge, UK) or Refmac5 (Murshudov et al 1997) applying TLS for individual domains and non-crystallographic symmetry (NCS) restrains for the IgE molecules. In total 213 waters were built in using the water picking option in Refmac5 (Murshudov et al 1997) followed by manual inspection. In the final refinement round the NCS restraints were released resulting in a final model with R=20.0% and Rfree=27.0%.

TABLE 7

Crystal Parameters and X-ray Data-Processing and Refinement Statistics

|  |  | Data set 1 | Data set 2 |
|---|---|---|---|
| Space group |  | P3$_2$21 | P3$_2$21 |
| Wavelength (Å) |  | 0.976 | 0.976 |
| Cell constants | a (Å) | 140.62 | 141.562 |
|  | b (Å) | 140.62 | 141.562 |
|  | c (Å) | 244.65 | 245.562 |
| Resolution range (Å) |  | 2.93-35.16 | 2.85-109.11 |
| Resolution highest shell (Å) |  | 2.93-3.01 | 2.85-2.92 |
| Completeness overall (%) |  | 99.9 | 100.0 |
| Completeness highest shell (%) |  | 100.0 | 100.0 |
| Reflections, unique |  | 60601 | 66338 |
| Multiplicity |  | 6.6 | 10.7 |
| Multiplicity highest shell |  | 6.8 | 11.0 |
| Rmerge$_{overall}$ (%)[1] |  | 0.133 | 0.099 |
| Rmerge highest shell (%) |  | 0.914 | 0.75 |
| Mean(I)/sd(I) |  | 13.1 | 20.2 |
| Mean(I)/sd(I) highest shell |  | 2.0 | 3.4 |
| Rvalue$_{overall}$ (%)[2] |  | N/A | 20.0 |
| Rvalue$_{free}$ (%) |  | N/A | 27.0 |

[1] $R_{merge} = [(\Sigma_i|I_i - <I>|)/\Sigma_i I_i]$
[2] $R_{value} = \Sigma_{hkl}||F_{obs}| - |F_{calc}||/\Sigma_{hkl}|F_{obs}|$
$R_{free}$ is the cross-validation R factor computed for the test set of 5% of unique reflections References Cited in Example 7

Davies A. Greene A. Lullau E. Abbott W M. Optimisation and evaluation of a high-throughput mammalian protein expression system. *Protein Expression & Purification*. 42(1):111-21. (2005)

CCP4 (Collaborative Computational Project, Number 4) (1994) The CCP4 suite: programs for protein crystallography. *Acta Crystallogr* D 50: 760-763

Cooper C. A., Gasteiger E., Packer N.

GlycoMod—A software Tool for Determining Glycosylation Compositions from Mass Spectrometric Data *Proteomics* 1:340-349 (2001).

Emsley, P. & Cowtan, K. Coot: model-building tools for molecular graphics. *Acta Crystallogr* D60: 2126-2132 (2004)

Faber, C., Shan, L., Fan, Z., Guddat, L. W., Furebring, C., Ohlin, M., Borrebaeck, C. A., Edmundson, A. B. Three-dimensional structure of a human Fab with high affinity for tetanus toxoid. *Immunotechnology* 3: 253-270 (1998)

Kabat, E. A., Wu, T. T., Perry, H., Gottesman, K. and Foeller, C. (1991) *Sequences of Proteins of Immunological Interest*, Fifth Edition. NIH Publication No. 91-3242.

Karpusas, M., Lucci, J., Ferrant, J., Benjamin, C., Taylor, F. R., Strauch, K., Garber, E., Hsu, Y. M. (2001) Structure of CD40 ligand in complex with the Fab fragment of a neutralizing humanized antibody. *Structure* 9, 321, (2001)

Leslie A. (1991) Macromolecular data processing. In Moras, D., Podjarny, A. D. and Thierry, J. C. (eds), Crystallographic Computing V. Oxford University Press, Oxford, UK, pp. 27-38

McCoy, A. J., Grosse-Kunstleve, R. W., Storoni, L. C. & Read, R. J. Likelihood-enhanced fast translation functions. *Acta Cryst* D61, 458-464 (2005)

Murshudov, G. N., Vagin, A. A., and Dodson, E. J. (1997) Refinement of Macromolecular structures by the maximum-likelihood method, *Acta Crystallogr* D53: 240-255

Padavattan, S., Schirmer, T., Schmidt, M., Akdis, C., Valenta, R., Mittermann, I., Soldatova, L., Slater, J., Mueller, U. & Markovic-Housley, Z. Identification of a B-cell Epitope of Hyaluronidase, a Major Bee Venom Allergen, from its Crystal Structure in Complex with a Specific Fab. *J Mol Biol* 368, 742-752. (2007)

Persic L. Roberts A. Wilton J. Cattaneo A. Bradbury A. Hoogenboom H R. An integrated vector system for the eukaryotic expression of antibodies or their fragments after selection from phage display libraries. *Gene*. 187(1):9-18. (1997)

Read, R. J. Pushing the boundaries of molecular replacement with maximum likelihood. *Acta Cryst*. D57, 1373-1382 (2001)

Rossmann, M. G. (edt): "The Molecular Replacement Method" Gordon & Breach, New York (1972)

Storoni, L. C., McCoy, A. J. & Read, R. J. Likelihood-enhanced fast rotation functions. *Acta Cryst* D60, 432-438 (2004)

Wurzburg, B. A., Garman, S. C. and Jerdetzky, H. S. Structure of the human IgE-Fc C epsilon 3-C epsilon 4 reveals conformational flexibility in the antibody effector domains. *Immunity*, 13, 375-385 (2000).

Example 8

Assessment of the General Safety and Capacity of Germlined Anti-IgE mAbs to Induce Decreases in Platelet Numbers in Juvenile Cynomolgus Monkeys An investigative (non-GLP compliant) study was performed in juvenile cynomolgus monkeys to assess the general safety and relative abilities of antibodies of the invention anti-IgE mAbs Antibody 11 IgG$_1$ Antibody 11 IgG$_2$ and another anti-IgE antibody E48 to cause decreases in numbers of blood platelets.

The objectives of the study were 1) to determine the general safety and relative abilities of the three candidate anti-IgE mAbs to induce a reduction in platelet counts/TCP and associated effects in juvenile cynomolgus monkeys 2) to determine preliminary pharmacokinetic parameters for the mAbs in monkeys 3) to assess the capacity of the three candidate mAbs to cause a reduction in free IgE and determine the (PK/PD) relationship between mAb concentration and free IgE levels Materials and Methods for Example 8

Eighteen purpose-bred cynomolgus monkeys (*Macaca fascicularis*) were obtained from Bioculture, Mauritius. The animals were between 63 to 67 weeks old at the start of dosing. Monkeys were pre-selected (from a larger pool of 100 animals) to have high IgE levels (U/ml) which were normalised across 3 groups each containing 3 male and 3 female monkeys and receiving either Antibody 11 IgG$_1$ (Group 1), Antibody 11 IgG$_2$ (Group 2) or E48 (Group 3). Each of the 3 mAbs were formulated in 50 mM sodium acetate, 100 mM NaCl, pH5.5 and adminstered to animals in a dose volume of 2 mL/kg by slow intravenous injection (using a motorised syringe/infusion pump) at a rate of 1 mL/min. The animals were dosed once weekly (for 5 weeks/5 doses) with rising dose levels of 1 mg/kg, 30 mg/kg and 100 mg/kg (×3) on Days 1, 8, 16, 22 and 29 (Table 8). Additional doses of Antibody 11 IgG$_1$ and Antibody 11 IgG$_2$ were administered to Groups 1 and 2 respectively on Day 37. The 2 highest dose levels were predicted to achieve serum concentrations that have previously shown to result in thrombocytopenia (TCP) with Xolair in juvenile cynomolgus monkeys. The low dose was expected to allow a determination of the ability of the mAbs to effect a reduction in free IgE levels

TABLE 8

Summary Study Design

| Group | Description | Dose level (mg/kg/day) on Day: | | | | | | Number of Animals | |
|---|---|---|---|---|---|---|---|---|---|
| | | 1 | 8 | 16 | 22 | 29 | 37 | Male | Female |
| 1 | Ab 11 IgG$_1$ | 1 | 30 | 100 | 100 | 100 | 100 | 3 | 3 |
| 2 | Ab 11 IgG$_2$ | 1 | 30 | 100 | 100 | 100 | 100 | 3 | 3 |
| 3 | E48 | 1 | 30 | 100 | 100 | 100 | — | 3 | 3 |

(Ab 11 = Antibody 11)

Animals were observed for 8 weeks post the Day 28 dose and examined for recovery from any toxicological effects.

All animals were observed daily for signs of ill health or overt toxicity and body weights and food consumption recorded. In addition, each animal was given a detailed physical examination daily during dosing periods and at least once weekly during non-dosing periods. All animals were also observed prior to each dose and at 0.5, 2, 6, 24, 48 and 168 hours post dose.

Blood samples for analysis of standard haematology parameters (including platelet counts; collected in EDTA) and coagulation parameters (collected in trisodium citrate) were taken from the femoral vein/artery twice pre-treatment (Weeks −2 and −1). Further samples for platelet counts and standard haematology were collected at 24 hours and 144 hours after each dosing occasion (Days 2, 7, 9, 14, 17, 22, 23, 26, 30 and 35; samples from Groups 1 and 2 only on Days 38 and 43) and every 2 weeks during the 8-week recovery period (Days 43, 57, 71 and 82). Samples for coagulation were collected at 144 hours after each dosing occasion (Days 7, 14, 22, 26 and 35) and at the end of the recovery period (Day 82). Samples for coagulation were also collected on Day 57. Blood samples for complement activation (C3a, C3b and BB fragments) were taken once pre-treatment (Week −1) and approximately 24 hours following completion of the treatment period (Day 30)

Serum samples for TK analysis were collected from all groups on day Day 1 at pre-dose, 0.5, 6, 12, 24, 48, 144 hours post-dose, on Days 8, 16, 22 and 29 at 0.5, 24 and 144 hours post-dose, on Day 29 (Groups 3 & 4 only) at 336, 672, 1008, 1272 hours post-dose, on day 37 (Groups 1 & 2 only) at 0.5, 24, 144, 480, 816, 1080 hours post-dose. Samples were analysed for mAb using a generic sandwich immunoassay (using biotinylated human IgE for mAb and Alexa-647 labelled murine anti-human IgG detection reagent) and the Gyrolab Bioaffy platform (incorporating streptavidin bead columns). Further serum samples for IgE analysis were collected on Day 1 at pre-dose, 0.5, 6, 12, 24, 48, 144 hours post-dose, on Days 8, 16, 22 and 29 at 0.5, 144 hours post-dose and at the end of the study (Day 82) at 1272 hours (Groups 3 & 4) or 1080 hours (Groups 1 & 2) post-final dose. Samples were analysed for free IgE by immunoassay using the ImmunoCap system (Phadia AB, Uppsala, Sweden) with human IgG-Fcε-RIa for free IgE capture and Rabbit anti-human IgE (PCS-conjugate) for detection.

On termination of the animals on Day 85, a full macroscopic examination was performed under the general supervision of a pathologist and all lesions were recorded. Absolute organs weights and organ:body weight raions were determined. Tissues from a range of organs were collected and stored frozen but no microscopic examination was performed (except for macroscopic abnormalities or an unscheduled death, see below)

Results for Example 8

General Safety Observations

All 3 mAbs were generally well-tolerated with no clinical signs of ill-health throughout the study with the exception of a single animal receiving Antibody 11 that was sent to necropsy ahead of schedule due to deteriorating clinical condition and reduced bodyweight. Since this animal deteriorated well into the recovery period and there were no findings noted during the pathology or haematology review of these animals, the observed effects are not believed to be mAb-related. Incidences of soft or liquid faeces were noted across all groups, however since these findings were not dose-related, were not seen in all animals or at all timepoints within the same animal and were seen as frequently during the dosing and recovery periods, they are unlikely to be mAb-related. Mean body weights and mean body weight gains showed some individual variation in animals within each group throughout the study. However all animals gained weight as expected over the treatment period. (with the exception of the 1 animal discussed above) and there was no clear differences between the groups. No clear treatment-related effects on absolute or relative organ weights were noted in any group. In gross pathology and microscopic pathology examinations, no findings were noted in the limited range of tissues examined that would suggest an effect of mAb treatment.

Toxicokinetics (TK) and IgE Levels

No gender difference in TK was observed in this study. In general the exposure was similar for these 3 mAbs, and appeared linear with dose in the 1-100 mg/kg dose range. The mean TK profiles of Antibody 11 IgG$_1$, Antibody 11 IgG$_2$ and E48 are shown in FIG. 12. No apparent IgE-sink effect on TK was observed, even at the lowest dose level. The TK of these 3 antibodies appeared typical for an human IgG in cynomolgus monkeys.

The mean maximum observed concentration (Cmax) following the last 100 mg/kg dose was 18700, 15900 and 24000 nM for Antibody 11 IgG$_1$, Antibody 11 IgG$_2$ and E48, respectively. The mean terminal TK half-life following the last 100 mg/kg dose was approximately 10-13 days. There was no evidence of reduced TK exposure due to the potential development of primate anti-human antibodies in these animals.

The mean free IgE profiles following weekly dosing of Antibody 11 IgG$_1$, Antibody 11 IgG$_2$ and E48 at various dose levels in cynomolgus monkeys are shown in FIG. 13. The average baseline IgE before the animals received the first dose was 514, 414 and 690 ng/mL for Antibody 11 IgG$_1$, Antibody 11 IgG$_2$ and E48 groups, respectively. On Day 1, 1 mg/kg dose induced a 75-80% reduction in free IgE at 1 hour after the dose. Due to the low exposure after the 1 mg/kg dose, free IgE returned to baseline level within 1 week. Higher doses resulted in consistent suppression of free IgE during the treatment period. Free IgE returned to baseline for the 2 Antibody 11 groups at the end of the study, while the free IgE in the E48 group remained suppressed.

Effects on Platelets

None of the 3 mAbs (Antibody 11 IgG$_1$, Antibody 11 IgG$_2$ nor E48) induced a significant decrease in platelet counts at any timepoint in any animal with the exception of a single animal receiving Antibody 11 IgG$_1$ that had a reduction in platelets (34.9%) at a single timepoint on day 29 (24 hours following the third 100 mg/kg dose on day 28). A 4 th dose of Antibody 11 IgG$_1$ and Antibody 11 IgG$_2$ on day 37 did not induce any further platelet reduction in this or any animal within these 2 groups.

FIG. 14 shows a plot of platelet numbers ($\times 10^9$/L) expressed as a percentage change from the mean of the 2 pre-dose values versus plasma concentration from an animal in Group 1 (Antibody 11 IgG1-treated). This plot is representative of the other 16 animals across the 3 groups that showed no significant effect on platelets [Change for Antibody 11 animal]. FIG. 15 shows the same plot for the animal in Group 1 (Antibody 11 IgG$_1$-treated) that showed a transient significant drop (35% below baseline) in platelet numbers on day 29.

Interestingly, the Antibody 11 IgG$_1$-treated monkey that showed a transient drop in platelet numbers after dosing on day 29 had the highest Cmax value (29400 nmol/L) (but not exposure) at this time. The plasma levels subsequently dropped sharply and the platelet counts returned to pre-dose values. This hints to the possibility that a higher threshold of plasma concentration might be required to evoke decreases in platelet numbers. However a single E48-treated animal reached similar levels (28500 nm/L) with no corresponding platelet effects (FIG. 14). Other Haematological Effects.

With the exception of platelet counts (see below), no consistent effects of mAb treatment were noted on the majority of haematological parameters (haemoglobin concentration, packed cell volume, mean cell volume, mean cell haemoglobin concentration, red cell distribution width, platelet crit, platelet distribution width, red blood cell count, mean cell haemoglobin, haemoglobin distribution width, mean platelet volume, reticulocyte count, total and differential white cell count) and blood coagulation parameters (prothrombin time, activated partial thromboplastin time). An increase in the numbers of reticulocytes was observed in all groups however the changes were not dose/exposure-related, were not consistent within a group (animals within a group had higher, lower or unchanged levels from pre-dose values) or within an animal (values within animals rose and fell between time-points independent of exposure) and, in the absence of a parallel control group, the relationship to mAb treatment cannot be fully determined at this time. Any such changes had generally reversed at the end of the recovery period. No significant treatment-related effects on complement activation (C5a, C3a or BB fragments) were noted.

Discussion and Conclusions

This study has shown that anti-IgE mAbs Antibody 11 IgG$_1$, Antibody 11 IgG$_2$ and E48 were well-tolerated when administered at high repeated dose levels (up to 100 mg/kg) to juvenile cynomolgus monkeys with no significant adverse toxicological effects. Only 1 animal out of 18 monkeys showed a significant drop in platelet numbers at a single timepoint after dosing with 100 mg/kg Antibody 11 IgG$_1$ when plasma concentrations of mAb reached almost 30000 nmol/L. The plasma Cmax concentrations reached with all 3 mAbs in this study are expected to be far in excess of those that will be achieved in the clinic (e.g. 200 nmol/L).

Example 9

Functional Inhibition of IgE Effects on FcεRI and CD23

The ability of the optimised Antibody 11 to inhibit functionally the interaction of IgE with FcεRI and CD23 was evaluated in an IgE-mediated cell killing assay adapted from Bracher et al (Journal Immunol. Methods 2007 323:160-171). U937 cells pre-treated with IL-4 were shown to express both FcεRI and CD23. When co-cultured with the ovarian tumour cells IGROV1 in the presence of IgE specific to an antigen expressed on IGROV1 cells, the U937 cells were able to kill the tumour cells. The killing was mediated both by cytotoxicity and phagocytosis mechanisms which were shown to be triggered through the interaction of IgE with FcεRI and CD23 respectively on the U937 effector cells.

Antibody 11 and an isotype control were evaluated in this assay for inhibition of IgE-mediated killing through either FcεRI or CD23. A detailed protocol for this procedure is provided in Materials and Methods. In brief, titrations of the test IgG were mixed with a target specific (MOv18) or irrelevant (NIP) IgE prior to incubation with IL-4-stimulated U937 effector cells and labelled-IGROV1 target cells. Following a 2.5 hours incubation, the cells were washed, stained with an anti-CD89-phycoerythrin antibody (BD Biosciences) and propidium iodide (Molecular Probes). After washing, the cell fluorescence was analysed using a FACSCalibur flow cytometer (BD Biosciences). The fluorescent dyes above were used to differentiate live cells from cells killed by cytotoxicity and cells killed by phagocytosis. Conversely to the isotype control antibody, Antibody 11 was able to inhibit both the IgE/FcεRI-mediated cytotoxicity (FIG. 16) and the IgE/CD23-mediated phagocytosis (FIG. 17).

Materials and Method

Example 9

Antibodies were evaluated for inhibition of IgE-mediated IGROV1 tumour cell killing by the U937 cells. IGROV1 cells (a human ovarian carcinoma cell line) and U937 cells (a human myelomonocytic cell line) were maintained in culture medium [RPMI1640, 10% v/v FCS, 2 mM glutamine, 5000 U/ml penicillin, 100 ug/ml streptomycin (all from Invitrogen)] using standard tissue culture procedures. The MOv18 IgE directed against FBP (folate binding protein) expressed on the IGROV1 cells was used as a tumour specific antibody. The NIP (hapten 4-hydroxy-3-nitro-phenacetyl)-specific IgE was used as a control irrelevant antibody. The MOv18 and NIP antibodies were prepared as described in Gould et al, (1999) Eur. J. Immunol. 29:3527-3537.

U937 cells were pre-treated for 4 days prior to the killing experiment with 10 ng/ml recombinant human IL-4 (R&D Systems) in order to up-regulate the expression of CD23. The day before the killing experiment, the IGROV1 target cells were labelled with the fluorescent dye CFSE (Carboxy-fluorescein diacetate succinimidyl ester, Molecular Probes). Briefly, the cells were trypsinised (Trypsin/EDTA, Gibco), washed in culture medium and resuspended in PBS at $50 \times 10^6$ cells/ml. The cells were then incubated at 37° C. for 10 minutes with CFSE at 0.01 mM. After the labelling, the cells were washed once in ice-cold culture medium and then incubated overnight at 37° C., 5% $CO_2$.

To evaluate the inhibitory effect of Antibody 11, antibody dilutions were prepared in 12×75 mm tubes (Falcon, BD Biosciences) and 2 ug of MOv1 or NIP IgE were added given a final volume of 80 ul. This mixture was incubated without cells for 30 minutes. IL-4-stimulated U937 cells were washed once in medium and resuspended at $1.33 \times 10^6$ cells/ml. CFSE-labelled IGROV1 cells were trypsinised, washed once in medium and resuspended at $4 \times 10^5$ cells/ml. The cells were added to the tubes containing the antibodies (120 ul for the U937 cells and 200 ul for the IGROV1 cells), mixed and incubated for 2.5 hours at 37° C., 5% $CO_2$. The cells were then washed in ice-cold FACS buffer (calcium/magnesium-free PBS, 5% normal goat serum) and incubated for 25 minutes with an anti-CD89-phycoerythrin antibody (BD Biosciences, 10 ug/ml) to label the U937 effector cells. The cells were washed once more in ice-cold FACS buffer and dead cells were stained by adding 0.25 ug/ml propidium iodide (Molecular Probes). After 15 minutes at 4° C., the cells were washed in ice-cold FACS buffer, resuspended in 250 ul ice-cold FACS buffer and the fluorescence was analysed using a FACSCalibur flow cytometer (BD Biosciences) according to manufacturer instructions. Cells with the relevant single staining were used to adjust the voltage and compensation of the detection channels (FL1, FL2 and FL3).

The combination of fluorescent dyes used in this assay allowed for the gating of different cell populations [live effector cells (phycoerythrin positive), phagocytosed IGROV1 tumour cells (phycoerythrin and CFSE positive), live tumour cells (CFSE positive), dead tumour cells (CFSE and propidium iodide positive), dead effector cells (phycoerythrin and propidium iodide positive)]. These gates were used to calculate the percentage of target cells killed by FcεRI-mediated cytotoxicity (equation 1) and by CD23-mediated phagocytosis (equation 2).

$$\% \text{ cytotoxicity} = \{[(R1SL \text{ control} - R1) + R3]/R1SL\} \times 100 \quad \text{Equation 1}$$

Where:
R1=total number of CFSE positive tumour cells
R3=number of killed but intact tumour cells (no fragmentation or phagocytosis)
R1SL control=Average R1 of 3 control samples of effector and target cells without antibody (R1 Spontaneous Loss control).

$$\% \text{ phagocytosis} = (R2/R1SL \text{ control}) \times 100 \quad \text{Equation 2}$$

Where:
R2=number of tumour cells phagocytosed by effector cells
R1SL control=Average R1 of 3 control samples of effector and target cells without antibody (R1 Spontaneous Loss control).

REFERENCES

All references cited anywhere in this specification, including those cited anywhere above, are incorporated herein by reference in their entirety and for all purposes.
1 Haan & Maggos (2004) BioCentury, 12(5): A1-A6
2 Koide et al. (1998) Journal of Molecular Biology, 284: 1141-1151.
3 Nygren et al. (1997) Current Opinion in Structural Biology, 7: 463-469
4 Wess, L. In: BioCentury, The Bernstein Report on BioBusiness, 12(42), A1-A7, 2004
5 Kabat, E. A. et al, Sequences of Proteins of Immunological Interest. 4th Edition. US Department of Health and Human Services. 1987
6 Kabat, E. A. et al. (1991) Sequences of Proteins of Immunological Interest, 5th Edition. US Department of Health and Human Services, Public Service, NIH, Washington
7 Segal et al., PNAS, 71:4298-4302, 1974
8 Amit et al., Science, 233:747-753, 1986
9 Chothia et al., J. Mol. Biol., 196:901-917, 1987
10 Chothia et al., Nature, 342:877-883, 1989
11 Caton et al., J. Immunol., 144:1965-1968, 1990
12 Sharon et al., PNAS, 87:4814-4817, 1990
13 Sharon et al., J. Immunol., 144:4863-4869, 1990
14 Kabat et al., J. Immunol., 147:1709-1719, 1991
15 Holliger & Hudson, Nature Biotechnology 23(9):1126-1136 2005
16 Kontermann, R & Dubel, S, Antibody Engineering, Springer-Verlag New York, LLC; 2001, ISBN: 3540413545
17 Mendez, M. et al. (1997) Nature Genet, 15(2): 146-156
18 Knappik et al. J. Mol. Biol. (2000) 296, 57-86
19 Krebs et al. Journal of Immunological Methods 254 2001 67-84
20 Ward, E. S. et al., Nature 341, 544-546 (1989)
21 McCafferty et al (1990) Nature, 348, 552-554
22 Holt et al (2003) Trends in Biotechnology 21, 484-490
23 Bird et al, Science, 242, 423-426, 1988
24 Huston et al, PNAS USA, 85, 5879-5883, 1988
25 Holliger, P. et al, Proc. Natl. Acad. Sci. USA 90 6444-6448, 1993
26 Reiter, Y. et al, Nature Biotech, 14, 1239-1245, 1996
27 Hu, S. et al, Cancer Res., 56, 3055-3061, 1996
28 Holliger and Bohlen 1999 Cancer and metastasis rev. 18: 411-419
29 Holliger, P. and Winter G. Current Opinion Biotechnol 4, 446-449 1993
30 Glennie M J et al., 1987 J. Immunol. 139, 2367-2375
31 Repp R. et al., 1995 J. Hemat. 377-382
32 Staerz U. D. and Bevan M. J. 1986 PNAS 83
33 Suresh M. R. et al., 1986 Method Enzymol. 121: 210-228
34 Merchand et al., 1998 Nature Biotech. 16:677-681
35 Ridgeway, J. B. B. et al, Protein Eng., 9, 616-621, 1996
36 Harlow and Lane, Antibodies: A Laboratory Manual, Cold Spring Harbor Laboratory, Cold Spring Harbor N.Y., pp. 726, 1988
37 Köhler and Milstein, Nature, 256:495-497, 1975
38 Wold, et al. Multivariate data analysis in chemistry. Chemometrics—Mathematics and Statistics in Chemistry (Ed.: B. Kowalski), D. Reidel Publishing Company, Dordrecht, Holland, 1984 (ISBN 90-277-1846-6)
39 Norman et al. Applied Regression Analysis. Wiley-Interscience; 3rd edition (April 1998) ISBN: 0471170828
40 Kandel, Abraham & Backer, Eric. Computer-Assisted Reasoning in Cluster Analysis. Prentice Hall PTR, (May 11, 1995), ISBN: 0133418847
41 Krzanowski, Wojtek. Principles of Multivariate Analysis: A User's Perspective (Oxford Statistical Science Series, No 22 (Paper)). Oxford University Press; (December 2000), ISBN: 0198507089
42 Witten, Ian H. & Frank, Eibe. Data Mining: Practical Machine Learning Tools and Techniques with Java Implementations. Morgan Kaufmann; (Oct. 11, 1999), ISBN: 1558605525
43 Denison David G. T. (Editor), Christopher C. Holmes, Bani K. Mallick, Adrian F. M. Smith. Bayesian Methods for Nonlinear Classification and Regression (Wiley Series in Probability and Statistics). John Wiley & Sons; (July 2002), ISBN: 0471490369

44 Ghose, Arup K. & Viswanadhan, Vellarkad N. Combinatorial Library Design and Evaluation Principles, Software, Tools, and Applications in Drug Discovery. ISBN: 0-8247-0487-8
45 Chothia C. et al. Journal Molecular Biology (1992) 227, 799-817
46 Al-Lazikani, et al Journal Molecular Biology (1997) 273 (4), 927-948
47 Chothia, et al. Science, 223, 755-758 (1986)
48 Whitelegg, N. R. u. and Rees, A. R (2000). Prot. Eng., 12, 815-824
49 Guex, N. and Peitsch, M. C. Electrophoresis (1997) 18, 2714-2723
50 Altschul et al. (1990) J. Mol. Biol. 215: 405-410
51 Pearson and Lipman (1988) PNAS USA 85: 2444-2448
52 Smith and Waterman (1981) J. Mol Biol. 147: 195-197
53 Voet & Voet, *Biochemistry*, 2nd Edition, (Wiley) 1995.
54 Gram et al., 1992, *Proc. Natl. Acad. Sci., USA,* 89:3576-3580
55 Barbas et al., 1994, *Proc. Natl. Acad. Sci., USA,* 91:3809-3813
56 Schier et al., 1996, *J. Mol. Biol.* 263:551-567
57 Marks et al *Bio/Technology,* 1992, 10:779-783
58 Kay, B. K., Winter, J., and McCafferty, J. (1996) Phage Display of Peptides and Proteins: A Laboratory Manual, San Diego: Academic Press
59 Hunter W. M. and Greenwood F. C. (1962) Nature 194:495
60 Plückthun, A. Bio/Technology 9: 545-551 (1991)
61 Chadd H E and Chamow S M (2001) Current Opinion in Biotechnology 12: 188-194
62 Andersen D C and Krummen L (2002) Current Opinion in Biotechnology 13: 117
63 Larrick J W and Thomas D W (2001) Current Opinion in Biotechnology 12:411-418
64 Sambrook and Russell, *Molecular Cloning: a Laboratory Manual:* 3rd edition, 2001, Cold Spring Harbor Laboratory Press
65 Ausubel et al. eds., *Short Protocols in Molecular Biology: A Compendium of Methods from Current Protocols in Molecular Biology,* John Wiley & Sons, 4$^{th}$ edition 1999
66 Robinson, J. R. ed., Sustained and Controlled Release Drug Delivery Systems, Marcel Dekker, Inc., New York, 1978
67 Ledermann J. A. et al. (1991) Int. J. Cancer 47: 659-664
68 Bagshawe K. D. et al. (1991) Antibody, Immunoconjugates and Radiopharmaceuticals 4: 915-922
69 Vaughan, T. J., et al. (1996). *Nature Biotechnology* 14, 309-314.
70 Hutchings, C. Generation of Naïve Human Antibody Libraries, in Antibody Engineering, R. Kontermann and S. Dubel, Editors. 2001, Springer Laboratory Manuals, Berlin. p. 93

TABLE 1

| Kabat numbering | HCDR1 | | | | | HCDR2 | | | | | | | | | | | | | | |
|---|---|---|---|---|---|---|---|---|---|---|---|---|---|---|---|---|---|---|---|---|
| | 31 | 32 | 33 | 34 | 35 | 50 | 51 | 52 | 52A | 53 | 54 | 55 | 56 | 57 | 58 | 59 | 60 | 61 | 62 | 63 | 64 | 65 |
| Antibody 11 | D | Y | N | I | Y | L | I | D | P | D | N | G | E | T | F | Y | A | E | K | F | Q | G |
| Antibody 19 | | | | | | | | | | | | | | | | | | | | | | |
| Antibody 5 | | | | | | | | | | | | | | | | | | | | | | |
| Antibody 20 | | | | | | | | | | | | | | | | | | | | | | |
| Antibody 28 | | | | | | | | | | | | | | | | | | | | | | |
| Antibody 13 | | | | | | | | | | | | | | | | | | | | | | |
| Antibody 8 | | | | | | | | | | | | | | | | | | | | | | |
| Antibody 4 | | | | | | | | | | | | | | | | | | | | | | |
| Antibody 12 | | | | | | | | | | | | | | | | | | | | | | |
| Antibody 14 | | | | | | | | | | | | | | | | | | | | | | |
| Antibody 23 | | | | | | | | | | | | | | | | | | | | | | |
| Antibody 6 | | | | | | | | | | | | | | | | | | | | | | |
| Antibody 3 | | | | | | | | | | | | | | | | | | | | | | |
| Antibody 27 | | | | | | | | | | | | | | | | | | | | | | |
| Antibody 11 GL | | | | | | | | | | | | | | | | | | | | | | |
| Antibody 9 | | | | | | | | | | | | | | | | | | | | | | |
| Antibody 17 | | | | | | | | | | | | | | | | | | | | | | |
| Antibody 25 | | | | | | | | | | | | | | | | | | | | | | |
| Antibody 21 | | | | | | | | | | | | | | | | | | | | | | |
| Antibody 7 | | | | | | | | | | | | | | | | | | | | | | |
| Antibody 18 | | | | | | | | | | | | | | | | | | | | | | |
| Antibody 11 PGL | | | | | | | | | | | | | | | | | | | | | | |
| Antibody 22 | | | | | | | | | | | | | | | | | | | | | | |
| Antibody 16 | | | | | | | | | | | | | | | | | | | | | | |
| Antibody 26 | | | | | | | | | | | | | | | | | | | | | | |
| Antibody 2 | | | | | | | | | | | | | | | | | | | | | | |
| Antibody 10 | | | | | | | | | | | | | | | | | | | | | | |
| Antibody 1 | | | | | | | | | | | | | | | | | | | | | | |
| Antibody 8 GL | | | | | | | | | | | | | | | | | | | | | | |
| Antibody 24 | | | | | | | | | | | | | | | | | | | | | | |
| Antibody 15 | | | | | | | | | | | | | | | | | | | | | | |
| Antibody 8 PGL | | | | | | | | | | | | | | | | | | | | | | |

| Kabat numbering | HCDR3 | | | | | | | | | | | |
|---|---|---|---|---|---|---|---|---|---|---|---|---|
| | 95 | 96 | 97 | 98 | 99 | 100 | 100A | 100B | 100C | 100D | 101 | 102 |
| Antibody 11 | V | M | G | K | W | I | K | G | G | Y | D | Y |
| Antibody 19 | | | | | | | | | | | | |
| Antibody 5 | | | | | | | | | | | | |
| Antibody 20 | | | | | | | | | | | | |
| Antibody 28 | | | | | | | | | | | | |
| Antibody 13 | | | | | | | | | | | | |

TABLE 1-continued

| | | | | | |
|---|---|---|---|---|---|
| Antibody 8 | L | | R | | |
| Antibody 4 | | | | | |
| Antibody 12 | | | | | |
| Antibody 14 | | | | | |
| Antibody 23 | | | | | |
| Antibody 6 | | | | | |
| Antibody 3 | | | | | |
| Antibody 27 | | S | L | | E | A |
| Antibody 11 GL | | | | | | |
| Antibody 9 | | T | L | R | S | A |
| Antibody 17 | | T | L | | S | A |
| Antibody 25 | | T | L | | S | A |
| Antibody 21 | | T | L | | S | A |
| Antibody 7 | | T | L | | S | A |
| Antibody 18 | L | L | R | | S | A |
| Antibody 11 PGL | | | | | | |
| Antibody 22 | | T | L | | S | A |
| Antibody 16 | | S | L | | S | A |
| Antibody 26 | | S | L | | E | A |
| Antibody 2 | | S | L | R | S | A |
| Antibody 10 | | S | L | R | A | A |
| Antibody 1 | | L | H | R | R | L |
| Antibody 8 GL | L | | R | | | |
| Antibody 24 | | T | L | | T | A |
| Antibody 15 | | T | L | | T | A |
| Antibody 8 PGL | L | | R | | | |

| Kabat | LCDR1 | | | | | | | | | | | | LCDR2 | | | | | | |
|---|---|---|---|---|---|---|---|---|---|---|---|---|---|---|---|---|---|---|---|
| numbering | 24 | 25 | 26 | 27 | 27A | 27B | 27C | 28 | 29 | 30 | 31 | 32 | 33 | 34 | 50 | 51 | 52 | 53 | 54 | 55 | 56 |
| Antibody 11 | T | G | S | S | S | N | I | G | A | G | Y | D | V | H | D | N | F | N | R | P | S |
| Antibody 19 | | | | | | | | | | | | | | | | | | | | | |
| Antibody 5 | | | | | | | | | | | | | | | | | | | | | |
| Antibody 20 | | | | | | | | | | | | | | | | | | | | | |
| Antibody 28 | | | | | | | | | | | | | | | | | | | | | |
| Antibody 13 | | | | | | | | | | | | | | | | | | | | | |
| Antibody 8 | | | | | | | | | | | | | | | | | | | | | |
| Antibody 12 | | | | | | | | | | | | | | | | | | | | | |
| Antibody 4 | | | | | | | | | | | | | | | | | | | | | |
| Antibody 14 | | | | | | | | | | | | | | | | | | | | | |
| Antibody 23 | | | | | | | | | | | | | | | | | | | | | |
| Antibody 6 | | | | | | | | | | | | | | | | | | | | | |
| Antibody 3 | | | | | | | | | | | | | | | | | | | | | |
| Antibody 27 | | | | | | | | | | | | | | | | | | | | | |
| Antibody 11 GL | | | | | | | | | | | | | | | | | | | | | |
| Antibody 9 | | | | | | | | | | | | | | | | | | | | | |
| Antibody 17 | | | | | | | | | | | | | | | | | | | | | |
| Antibody 25 | | | | | | | | | | | | | | | | | | | | | |
| Antibody 21 | | | | | | | | | | | | | | | | | | | | | |
| Antibody 7 | | | | | | | | | | | | | | | | | | | | | |
| Antibody 18 | | | | | | | | | | | | | | | | | | | | | |
| Antibody 11 PGL | | | | | | | | | | | | | | | | | | | | | |
| Antibody 22 | | | | | | | | | | | | | | | | | | | | | |
| Antibody 16 | | | | | | | | | | | | | | | | | | | | | |
| Antibody 26 | | | | | | | | | | | | | | | | | | | | | |
| Antibody 2 | | | | | | | | | | | | | | | | | | | | | |
| Antibody 10 | | | | | | | | | | | | | | | | | | | | | |
| Antibody 1 | | | | | | | | | | | | | | | | | | | | | |
| Antibody 8 GL | | | | | | | | | | | | | | | | | | | | | |
| Antibody 24 | | | | | | | | | | | | | | | | | | | | | |
| Antibody 15 | | | | | | | | | | | | | | | | | | | | | |
| Antibody 8 PGL | | | | | | | | | | | | | | | | | | | | | |

| Kabat | LCDR3 | | | | | | | | | | |
|---|---|---|---|---|---|---|---|---|---|---|---|
| numbering | 89 | 90 | 91 | 92 | 93 | 94 | 95 | 95A | 95B | 96 | 97 |
| Antibody 11 | Q | S | Y | D | S | P | T | L | T | S | P |
| Antibody 19 | | | | | | T | L | S | H | | |
| Antibody 5 | | | | | | T | K | H | | | |
| Antibody 20 | | | | | | S | | S | S | | |
| Antibody 28 | | | | | | S | S | | H | | |
| Antibody 13 | | | | | | N | I | | Y | | |
| Antibody 8 | | | | | | | | H | | | |
| Antibody 12 | | | | | | S | I | D | H | | |
| Antibody 4 | | | | | | R | G | G | H | | |
| Antibody 14 | | | | | | H | H | R | H | | |
| Antibody 23 | | | | | | H | H | | Y | | S |
| Antibody 6 | | | | | | T | M | R | H | G | |

TABLE 1-continued

|  |  |  |  |  |  |  |
|---|---|---|---|---|---|---|
| Antibody 3 |  | T | F | N | H | A |
| Antibody 27 |  |  |  | Q |  |  |
| Antibody 11 GL |  |  |  |  |  |  |
| Antibody 9 |  |  | S | S |  |  |
| Antibody 17 |  | Q | S | S |  |  |
| Antibody 25 |  | N | H | K |  |  |
| Antibody 21 |  | S | S | Q | L |  |
| Antibody 7 |  | D | R | R | N |  |
| Antibody 18 |  | H | L | Q | L |  |
| Antibody 11 PGL |  |  |  |  |  |  |
| Antibody 22 |  | S | G | G | Y | A |
| Antibody 16 |  | R | H | H | H | A |
| Antibody 26 |  | A | S | R | H | A |
| Antibody 2 |  | S | L | S | G |  | L |
| Antibody 10 |  | E | Q | E | L | A |
| Antibody 1 |  | S | L | S | G |  | L |
| Antibody 8 GL |  |  |  | H |  |  |
| Antibody 24 |  | R | N | G | Y | G | G |
| Antibody 15 |  | H | K | G | Y | G | G |
| Antibody 8 PGL |  |  |  | H |  |  |

We claim:

1. An isolated antibody molecule specific for human immunoglobulin E, the antibody molecule comprising a set of CDRs: HCDR1, HCDR2, HCDR3, LCDR1, LCDR2 and LCDR3 in which:
   HCDR1 comprises the amino acid sequence of SEQ. ID. NO: 103;
   HCDR2 comprises the amino acid sequence of SEQ. ID. NO: 104;
   HCDR3 comprises the amino acid sequence of SEQ. ID. NO: 105; wherein SEQ. ID. NO: 105 may comprise one or more of the following substitutions:
   M at position 2 is substituted for L, S, or T;
   G at position 3 is substituted for L or H;
   K at position 4 is substituted for R;
   W at position 5 is substituted for D, S, A, R, or T; and
   I at position 6 is substituted for A or L;
   LCDR1 comprises the amino acid sequence of SEQ. ID. NO: 108;
   LCDR2 comprises the amino acid sequence of SEQ. ID. NO: 109;
   LCDR3 comprises the amino acid sequence of SEQ. ID. NO: 110, wherein SEQ. ID. NO: 110 may comprise one or more of the following substitutions:
   P at position 6 is substituted for T, S, N, S, R, H, Q, D, A, or E;
   T at position 7 is substituted for L, K, S, I, G, H, M, F, R, Q, or N,
   L at position is 8 substituted for S, H, D, G, R, N, or G;
   T at position 9 is substituted for H, S, Y, H, L, N, or G;
   S at position 10 is substituted for G or A, and
   P at position 11 is substituted for S, L, or G.

2. An isolated antibody molecule specific for human immunoglobulin E according to claim 1 wherein the amino acid substitutions in SEQ. ID NOs: 105 and 110 comprise 6 or fewer amino acid substitutions.

3. An isolated antibody molecule according to claim 1 wherein the set of CDRs comprises:
   HCDR1 comprises the amino acid sequence of SEQ. ID. NO: 103;
   HCDR2 comprises the amino acid sequence of SEQ. ID. NO: 104;
   HCDR3 comprises the amino acid sequence of SEQ. ID. NO: 105;
   LCDR1 comprises the amino acid sequence of SEQ. ID. NO: 108;
   LCDR2 comprises the amino acid sequence of SEQ. ID. NO: 109;
   LCDR3 comprises the amino acid sequence of SEQ. ID. NO: 110.

4. An isolated antibody molecule specific for immunoglobulin E wherein said antibody molecule binds to an epitope in immunoglobulin E comprising:
   residues Glu390 to Asn394 inclusive in a first IgE heavy chain and Leu340, Arg342, Ala428 to Thr434 inclusive, Thr436, Ser437 and Glu472 in a second IgE heavy chain.

5. An isolated antibody molecule specific for immunoglobulin E according to claim 4 wherein the epitope further comprises sugar moieties GlcNAcl and Man6 in a first IgE heavy chain and sugar moiety Man 5 in a second IgE heavy chain.

6. An isolated antibody molecule specific for immunoglobulin E wherein said antibody molecule binds to an epitope in immunoglobulin E comprising:
   residues Glu390, Gln392 to Asn394 inclusive in a first IgE heavy chain and Leu340, Arg342, Ala428 to Thr434 inclusive, Thr436, Ser437 and Glu472 in a second IgE heavy chain.

7. An isolated antibody molecule specific for immunoglobulin E according to claim 6 wherein the epitope further comprises sugar moieties GlcNAcl and Man6 in a first IgE heavy chain.

8. The antibody molecule according to claim 1 wherein the antibody molecule is a monoclonal antibody.

9. A pharmaceutical composition comprising an antibody molecule according to claim 1 and a pharmaceutically acceptable excipient.

10. A pharmaceutical composition according to claim 9 comprising: an isolated antibody molecule according to claim 1.

11. The antibody molecule according to claim 3 wherein the antibody molecule is a monoclonal antibody.

12. A pharmaceutical composition comprising an antibody molecule according to claim 3 and a pharmaceutically acceptable excipient.

13. The antibody molecule according to claim 11, wherein the antibody molecule comprises an amino acid sequence chosen from the amino acid sequence of SEQ ID NO: 300, SEQ ID NO: 306, SEQ ID NO: 338, and SEQ ID NO: 378.

* * * * *

UNITED STATES PATENT AND TRADEMARK OFFICE
CERTIFICATE OF CORRECTION

Page 1 of 1

PATENT NO. : 7,959,917 B2
APPLICATION NO. : 12/032061
DATED : June 14, 2011
INVENTOR(S) : Duncan Cochrane It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 399 days.

Signed and Sealed this
Sixth Day of March, 2012

David J. Kappos
*Director of the United States Patent and Trademark Office*

SEQUENCE LISTING

<160> NUMBER OF SEQ ID NOS: 392

<210> SEQ ID NO 1
<211> LENGTH: 363
<212> TYPE: DNA
<213> ORGANISM: Homo sapiens
<220> FEATURE:
<223> OTHER INFORMATION: Antibody 1

<400> SEQUENCE: 1
caggtccagc tggtgcagtc tggggctgag gtgaagaaac ctggggccac agtgaaactc      60
tcctgcaagg tttatggata cattttcacc gactacaaca tttactgggt gcgccaggcc     120
cctggaaaag ggcttgagtg gatgggactt attgatcctg acaatggtga gacattttac     180
gcagagaagt tccagggcag agccaccatg accgcggaca cgtcttcaga cagagcctac     240
atggaattga ccagcctgac ctttgaggac acggccactt attattgtgc aacagtctta     300
catcggagac ttaaggggg ctatgactac tggggccggg gcaccctggt caccgtctcg     360
agt     363

<210> SEQ ID NO 2
<211> LENGTH: 121
<212> TYPE: PRT
<213> ORGANISM: Homo sapiens
<220> FEATURE:
<223> OTHER INFORMATION: Antibody 1

<400> SEQUENCE: 2

Gln Val Gln Leu Val Gln Ser Gly Ala Glu Val Lys Lys Pro Gly Ala
1               5                   10                  15

Thr Val Lys Leu Ser Cys Lys Val Tyr Gly Tyr Ile Phe Thr Asp Tyr
            20                  25                  30

Asn Ile Tyr Trp Val Arg Gln Ala Pro Gly Lys Gly Leu Glu Trp Met
        35                  40                  45

Gly Leu Ile Asp Pro Asp Asn Gly Glu Thr Phe Tyr Ala Glu Lys Phe
    50                  55                  60

Gln Gly Arg Ala Thr Met Thr Ala Asp Thr Ser Ser Asp Arg Ala Tyr
65                  70                  75                  80

Met Glu Leu Thr Ser Leu Thr Phe Glu Asp Thr Ala Thr Tyr Tyr Cys

```
                85                  90                  95
Ala Thr Val Leu His Arg Arg Leu Lys Gly Gly Tyr Asp Tyr Trp Gly
            100                 105                 110

Arg Gly Thr Leu Val Thr Val Ser Ser
        115                 120
```

<210> SEQ ID NO 3
<211> LENGTH: 5
<212> TYPE: PRT
<213> ORGANISM: Homo sapiens
<220> FEATURE:
<223> OTHER INFORMATION: Antibody 1

<400> SEQUENCE: 3

```
Asp Tyr Asn Ile Tyr
1               5
```

<210> SEQ ID NO 4
<211> LENGTH: 17
<212> TYPE: PRT
<213> ORGANISM: Homo sapiens
<220> FEATURE:
<223> OTHER INFORMATION: Antibody 1

<400> SEQUENCE: 4

```
Leu Ile Asp Pro Asp Asn Gly Glu Thr Phe Tyr Ala Glu Lys Phe Gln
1               5                   10                  15

Gly
```

<210> SEQ ID NO 5
<211> LENGTH: 12
<212> TYPE: PRT
<213> ORGANISM: Homo sapiens
<220> FEATURE:
<223> OTHER INFORMATION: Antibody 1

<400> SEQUENCE: 5

```
Val Leu His Arg Arg Leu Lys Gly Gly Tyr Asp Tyr
1               5                   10
```

<210> SEQ ID NO 6
<211> LENGTH: 336
<212> TYPE: DNA
<213> ORGANISM: Homo sapiens
<220> FEATURE:
<223> OTHER INFORMATION: Antibody 1

<400> SEQUENCE: 6

```
cagtctgtgc tgacgcagcc gccctcagtg tctggggccc cagggcagag ggtcaccatc    60
tcctgcactg ggagcagctc caacatcggg gcaggttatg atgtacactg gtatcagcaa   120
cttccaggaa cagcccccaa actcctcatc tatgataatt caatcggccc tcaggggtc    180 cctgaccgat tctctggctc caagtctggc acctcagcct ccctggccat cattgggctc    240
cagactgaag atgaggctga ttattattgc cagtcctatg acagcagcct gagtggttcc    300
ctcttcggaa ccgggaccaa gctgaccgtc ctaggt                              336
```

<210> SEQ ID NO 7
<211> LENGTH: 112
<212> TYPE: PRT
<213> ORGANISM: Homo sapiens
<220> FEATURE:
<223> OTHER INFORMATION: Antibody 1

<400> SEQUENCE: 7

```
Gln Ser Val Leu Thr Gln Pro Pro Ser Val Ser Gly Ala Pro Gly Gln
  1               5                  10                  15

Arg Val Thr Ile Ser Cys Thr Gly Ser Ser Asn Ile Gly Ala Gly
             20                  25                  30

Tyr Asp Val His Trp Tyr Gln Gln Leu Pro Gly Thr Ala Pro Lys Leu
             35                  40                  45

Leu Ile Tyr Asp Asn Phe Asn Arg Pro Ser Gly Val Pro Asp Arg Phe
 50                  55                  60

Ser Gly Ser Lys Ser Gly Thr Ser Ala Ser Leu Ala Ile Ile Gly Leu
 65                  70                  75                  80

Gln Thr Glu Asp Glu Ala Asp Tyr Tyr Cys Gln Ser Tyr Asp Ser Ser
                 85                  90                  95

Leu Ser Gly Ser Leu Phe Gly Thr Gly Thr Lys Leu Thr Val Leu Gly
            100                 105                 110

<210> SEQ ID NO 8
<211> LENGTH: 14
<212> TYPE: PRT
<213> ORGANISM: Homo sapiens
<220> FEATURE:
<223> OTHER INFORMATION: Antibody 1

<400> SEQUENCE: 8

Thr Gly Ser Ser Ser Asn Ile Gly Ala Gly Tyr Asp Val His
  1               5                  10

<210> SEQ ID NO 9
<211> LENGTH: 7
<212> TYPE: PRT
<213> ORGANISM: Homo sapiens
<220> FEATURE:
<223> OTHER INFORMATION: Antibody 1

<400> SEQUENCE: 9

Asp Asn Phe Asn Arg Pro Ser
  1               5

<210> SEQ ID NO 10
<211> LENGTH: 11
<212> TYPE: PRT
<213> ORGANISM: Homo sapiens
<220> FEATURE:
<223> OTHER INFORMATION: Antibody 1

<400> SEQUENCE: 10

Gln Ser Tyr Asp Ser Ser Leu Ser Gly Ser Leu
  1               5                  10

<210> SEQ ID NO 11
<211> LENGTH: 363
<212> TYPE: DNA
<213> ORGANISM: Homo sapiens
<220> FEATURE:
<223> OTHER INFORMATION: Antibody 2

<400> SEQUENCE: 11
caggtccagc tggtgcagtc tggggctgag gtgaagaaac ctggggccac agtgaaactc      60
tcctgcaagg tttatggata cattttcacc gactacaaca tttactgggt gcgccaggcc    120
cctggaaaag gcttgagtg gatgggactt attgatcctg acaatggtga cattttac       180 gcagagaagt tccagggcag agccaccatg accgcggaca cgtcttcaga cagagcctac    240
atggaattga ccagcctgac ctttgaggac acggccactt attattgtgc aacagtgagc    300
```

```
ctccggagcg cgaaggggg ctatgactac tggggccggg gcaccctggt caccgtctcg    360
agt                                                                  363
```

<210> SEQ ID NO 12
<211> LENGTH: 121
<212> TYPE: PRT
<213> ORGANISM: Homo sapiens
<220> FEATURE:
<223> OTHER INFORMATION: Antibody 2

<400> SEQUENCE: 12

```
Gln Val Gln Leu Val Gln Ser Gly Ala Glu Val Lys Lys Pro Gly Ala
1               5                   10                  15

Thr Val Lys Leu Ser Cys Lys Val Tyr Gly Tyr Ile Phe Thr Asp Tyr
            20                  25                  30

Asn Ile Tyr Trp Val Arg Gln Ala Pro Gly Lys Gly Leu Glu Trp Met
        35                  40                  45

Gly Leu Ile Asp Pro Asp Asn Gly Glu Thr Phe Tyr Ala Glu Lys Phe
    50                  55                  60

Gln Gly Arg Ala Thr Met Thr Ala Asp Thr Ser Ser Asp Arg Ala Tyr
65                  70                  75                  80

Met Glu Leu Thr Ser Leu Thr Phe Glu Asp Thr Ala Thr Tyr Tyr Cys
                85                  90                  95

Ala Thr Val Ser Leu Arg Ser Ala Lys Gly Gly Tyr Asp Tyr Trp Gly
            100                 105                 110

Arg Gly Thr Leu Val Thr Val Ser Ser
        115                 120
```

<210> SEQ ID NO 13
<211> LENGTH: 5
<212> TYPE: PRT
<213> ORGANISM: Homo sapiens
<220> FEATURE:
<223> OTHER INFORMATION: Antibody 2

<400> SEQUENCE: 13

```
Asp Tyr Asn Ile Tyr
1               5
```

<210> SEQ ID NO 14
<211> LENGTH: 17
<212> TYPE: PRT
<213> ORGANISM: Homo sapiens
<220> FEATURE:
<223> OTHER INFORMATION: Antibody 2

<400> SEQUENCE: 14

```
Leu Ile Asp Pro Asp Asn Gly Glu Thr Phe Tyr Ala Glu Lys Phe Gln
1               5                   10                  15

Gly
```

<210> SEQ ID NO 15
<211> LENGTH: 12
<212> TYPE: PRT
<213> ORGANISM: Homo sapiens
<220> FEATURE:
<223> OTHER INFORMATION: Antibody 2

<400> SEQUENCE: 15

```
Val Ser Leu Arg Ser Ala Lys Gly Gly Tyr Asp Tyr
1               5                   10
```

-continued

```
<210> SEQ ID NO 16
<211> LENGTH: 336
<212> TYPE: DNA
<213> ORGANISM: Homo sapiens
<220> FEATURE:
<223> OTHER INFORMATION: Antibody 2

<400> SEQUENCE: 16
cagtctgtgc tgacgcagcc gccctcagtg tctggggccc cagggcagag ggtcaccatc      60
tcctgcactg ggagcagctc caacatcggg gcaggttatg atgtacactg gtatcagcaa     120
cttccaggaa cagcccccaa actcctcatc tatgataatt tcaatcggcc ctcagggggtc    180 cctgaccgat tctctggctc caagtctggc acctcagcct ccctggccat cattgggctc     240
cagactgaag atgaggctga ttattattgc cagtcctatg acagcagcct gagtggttcc     300
ctcttcggaa ccgggaccaa gctgaccgtc ctaggt                                336

<210> SEQ ID NO 17
<211> LENGTH: 112
<212> TYPE: PRT
<213> ORGANISM: Homo sapiens
<220> FEATURE:
<223> OTHER INFORMATION: Antibody 2

<400> SEQUENCE: 17

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Asp Asn Phe Asn Arg Pro Ser Gly Val Pro Asp Arg Phe
    50                  55                  60

Ser Gly Ser Lys Ser Gly Thr Ser Ala Ser Leu Ala Ile Ile Gly Leu
65                  70                  75                  80

Gln Thr Glu Asp Glu Ala Asp Tyr Tyr Cys Gln Ser Tyr Asp Ser Ser
                85                  90                  95

Leu Ser Gly Ser Leu Phe Gly Thr Gly Thr Lys Leu Thr Val Leu Gly
            100                 105                 110

<210> SEQ ID NO 18
<211> LENGTH: 14
<212> TYPE: PRT
<213> ORGANISM: Homo sapiens
<220> FEATURE:
<223> OTHER INFORMATION: Antibody 2

<400> SEQUENCE: 18

Thr Gly Ser Ser Ser Asn Ile Gly Ala Gly Tyr Asp Val His
1               5                   10

<210> SEQ ID NO 19
<211> LENGTH: 7
<212> TYPE: PRT
<213> ORGANISM: Homo sapiens
<220> FEATURE:
<223> OTHER INFORMATION: Antibody 2

<400> SEQUENCE: 19

Asp Asn Phe Asn Arg Pro Ser
1               5
```

```
<210> SEQ ID NO 20
<211> LENGTH: 11
<212> TYPE: PRT
<213> ORGANISM: Homo sapiens
<220> FEATURE:
<223> OTHER INFORMATION: Antibody 2

<400> SEQUENCE: 20

Gln Ser Tyr Asp Ser Ser Leu Ser Gly Ser Leu
1               5                   10

<210> SEQ ID NO 21
<211> LENGTH: 363
<212> TYPE: DNA
<213> ORGANISM: Homo sapiens
<220> FEATURE:
<223> OTHER INFORMATION: Antibody 3

<400> SEQUENCE: 21
caggtccagc tggtgcagtc tggggctgag gtgaagaaac ctggggccac agtgaaactc      60
tcctgcaagg tttatggata catttcacc gactacaaca tttactgggt gcgccaggcc     120
cctggaaaag gcttgagtg gatgggactt attgatcctg acaatggtga gacattttac     180
gcagagaagt tccagggcag agccaccatg accgcggaca cgtcttcaga cagagcctac     240
atggaattga ccagcctgac ctttgaggac acggccactt attattgtgc aacagtgatg     300
gggaagtgga tcaaggggg ctatgactac tggggccggg gcaccctggt caccgtctcg     360
agt                                                                   363

<210> SEQ ID NO 22
<211> LENGTH: 121
<212> TYPE: PRT
<213> ORGANISM: Homo sapiens
<220> FEATURE:
<223> OTHER INFORMATION: Antibody 3

<400> SEQUENCE: 22

Gln Val Gln Leu Val Gln Ser Gly Ala Glu Val Lys Lys Pro Gly Ala
1               5                   10                  15

Thr Val Lys Leu Ser Cys Lys Val Tyr Gly Tyr Ile Phe Thr Asp Tyr
                20                  25                  30

Asn Ile Tyr Trp Val Arg Gln Ala Pro Gly Lys Gly Leu Glu Trp Met
            35                  40                  45

Gly Leu Ile Asp Pro Asp Asn Gly Glu Thr Phe Tyr Ala Glu Lys Phe
        50                  55                  60

Gln Gly Arg Ala Thr Met Thr Ala Asp Thr Ser Ser Asp Arg Ala Tyr
65                  70                  75                  80

Met Glu Leu Thr Ser Leu Thr Phe Glu Asp Thr Ala Thr Tyr Tyr Cys
                85                  90                  95

Ala Thr Val Met Gly Lys Trp Ile Lys Gly Gly Tyr Asp Tyr Trp Gly
                100                 105                 110

Arg Gly Thr Leu Val Thr Val Ser Ser
            115                 120

<210> SEQ ID NO 23
<211> LENGTH: 5
<212> TYPE: PRT
<213> ORGANISM: Homo sapiens
<220> FEATURE:
<223> OTHER INFORMATION: Antibody 3

<400> SEQUENCE: 23
```

```
Asp Tyr Asn Ile Tyr
1               5
```

<210> SEQ ID NO 24
<211> LENGTH: 17
<212> TYPE: PRT
<213> ORGANISM: Homo sapiens
<220> FEATURE:
<223> OTHER INFORMATION: Antibody 3

<400> SEQUENCE: 24

```
Leu Ile Asp Pro Asp Asn Gly Glu Thr Phe Tyr Ala Glu Lys Phe Gln
1               5                   10                  15

Gly
```

<210> SEQ ID NO 25
<211> LENGTH: 12
<212> TYPE: PRT
<213> ORGANISM: Homo sapiens
<220> FEATURE:
<223> OTHER INFORMATION: Antibody 3

<400> SEQUENCE: 25

```
Val Met Gly Lys Trp Ile Lys Gly Gly Tyr Asp Tyr
1               5                   10
```

<210> SEQ ID NO 26
<211> LENGTH: 336
<212> TYPE: DNA
<213> ORGANISM: Homo sapiens
<220> FEATURE:
<223> OTHER INFORMATION: Antibody 3

<400> SEQUENCE: 26

```
cagtctgtgc tgacgcagcc gccctcagtg tctggggccc cagggcagag ggtcaccatc      60
tcctgcactg ggagcagctc aacatcggg gcaggttatg atgtacactg gtatcagcaa      120
cttccaggaa cagcccccaa actcctcatc tatgataatt tcaatcggcc ctcagggggtc    180 cctgaccgat tctctggctc caagtctggc acctcagcct ccctggccat cattgggctc    240
cagactgaag atgaggctga ttattattgc cagtcctatg acagcacgtt caaccacgcc    300
cccttcggaa ccgggaccaa gctgaccgtc ctaggt                               336
```

<210> SEQ ID NO 27
<211> LENGTH: 112
<212> TYPE: PRT
<213> ORGANISM: Homo sapiens
<220> FEATURE:
<223> OTHER INFORMATION: Antibody 3

<400> SEQUENCE: 27

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
                20                  25                  30

Tyr Asp Val His Trp Tyr Gln Gln Leu Pro Gly Thr Ala Pro Lys Leu
            35                  40                  45

Leu Ile Tyr Asp Asn Phe Asn Arg Pro Ser Gly Val Pro Asp Arg Phe
        50                  55                  60

Ser Gly Ser Lys Ser Gly Thr Ser Ala Ser Leu Ala Ile Ile Gly Leu
65                  70                  75                  80

Gln Thr Glu Asp Glu Ala Asp Tyr Tyr Cys Ser Tyr Asp Ser Thr
                85                  90                  95
```

Phe Asn His Ala Pro Phe Gly Thr Gly Thr Lys Leu Thr Val Leu Gly
            100                 105                 110

<210> SEQ ID NO 28
<211> LENGTH: 14
<212> TYPE: PRT
<213> ORGANISM: Homo sapiens
<220> FEATURE:
<223> OTHER INFORMATION: Antibody 3

<400> SEQUENCE: 28

Thr Gly Ser Ser Ser Asn Ile Gly Ala Gly Tyr Asp Val His
1               5                   10

<210> SEQ ID NO 29
<211> LENGTH: 7
<212> TYPE: PRT
<213> ORGANISM: Homo sapiens
<220> FEATURE:
<223> OTHER INFORMATION: Antibody 3

<400> SEQUENCE: 29

Asp Asn Phe Asn Arg Pro Ser
1               5

<210> SEQ ID NO 30
<211> LENGTH: 11
<212> TYPE: PRT
<213> ORGANISM: Homo sapiens
<220> FEATURE:
<223> OTHER INFORMATION: Antibody 3

<400> SEQUENCE: 30

Gln Ser Tyr Asp Ser Thr Phe Asn His Ala Pro
1               5                   10

<210> SEQ ID NO 31
<211> LENGTH: 363
<212> TYPE: DNA
<213> ORGANISM: Homo sapiens
<220> FEATURE:
<223> OTHER INFORMATION: Antibody 4

<400> SEQUENCE: 31
caggtccagc tggtgcagtc tggggctgag gtgaagaaac ctggggccac agtgaaactc      60
tcctgcaagg tttatggata cattttcacc gactacaaca tttactgggt gcgccaggcc     120
cctggaaaag ggcttgagtg gatgggactt attgatcctg acaatggtga acatttttac    180
gcagagaagt tccagggcag agccaccatg accgcggaca cgtcttcaga cagagcctac     240
atggaattga ccagcctgac ctttgaggac acggccactt attattgtgc aacagtgatg     300
gggaagtgga tcaaggggggg ctatgactac tggggccggg gcaccctggt caccgtctcg    360
agt                                                                   363

<210> SEQ ID NO 32
<211> LENGTH: 121
<212> TYPE: PRT
<213> ORGANISM: Homo sapiens
<220> FEATURE:
<223> OTHER INFORMATION: Antibody 4

<400> SEQUENCE: 32

Gln Val Gln Leu Val Gln Ser Gly Ala Glu Val Lys Lys Pro Gly Ala
1               5                   10                  15

-continued

```
Thr Val Lys Leu Ser Cys Lys Val Tyr Gly Tyr Ile Phe Thr Asp Tyr
         20                  25                  30

Asn Ile Tyr Trp Val Arg Gln Ala Pro Gly Lys Gly Leu Glu Trp Met
         35                  40                  45

Gly Leu Ile Asp Pro Asp Asn Gly Glu Thr Phe Tyr Ala Glu Lys Phe
 50                  55                  60

Gln Gly Arg Ala Thr Met Thr Ala Asp Thr Ser Ser Asp Arg Ala Tyr
 65                  70                  75                  80

Met Glu Leu Thr Ser Leu Thr Phe Glu Asp Thr Ala Thr Tyr Tyr Cys
                 85                  90                  95

Ala Thr Val Met Gly Lys Trp Ile Lys Gly Gly Tyr Asp Tyr Trp Gly
             100                 105                 110

Arg Gly Thr Leu Val Thr Val Ser Ser
         115                 120
```

<210> SEQ ID NO 33
<211> LENGTH: 5
<212> TYPE: PRT
<213> ORGANISM: Homo sapiens
<220> FEATURE:
<223> OTHER INFORMATION: Antibody 4

<400> SEQUENCE: 33

```
Asp Tyr Asn Ile Tyr
 1               5
```

<210> SEQ ID NO 34
<211> LENGTH: 17
<212> TYPE: PRT
<213> ORGANISM: Homo sapiens
<220> FEATURE:
<223> OTHER INFORMATION: Antibody 4

<400> SEQUENCE: 34

```
Leu Ile Asp Pro Asp Asn Gly Glu Thr Phe Tyr Ala Glu Lys Phe Gln
 1               5                  10                  15

Gly
```

<210> SEQ ID NO 35
<211> LENGTH: 12
<212> TYPE: PRT
<213> ORGANISM: Homo sapiens
<220> FEATURE:
<223> OTHER INFORMATION: Antibody 4

<400> SEQUENCE: 35

```
Val Met Gly Lys Trp Ile Lys Gly Gly Tyr Asp Tyr
 1               5                  10
```

<210> SEQ ID NO 36
<211> LENGTH: 336
<212> TYPE: DNA
<213> ORGANISM: Homo sapiens
<220> FEATURE:
<223> OTHER INFORMATION: Antibody 4

<400> SEQUENCE: 36

```
cagtctgtgc tgacgcagcc gccctcagtg tctggggccc cagggcagag ggtcaccatc      60
tcctgcactg ggagcagctc caacatcggg gcaggttatg atgtacactg gtatcagcaa     120
cttccaggaa cagcccccaa actcctcatc tatgataatt caatcggcc ctcaggggtc     180 cctgaccgat tctctggctc caagtctggc acctcagcct ccctggccat cattgggctc     240
```

```
cagactgaag atgaggctga ttattattgc cagtcctatg acagccgggg cggccactcc    300
ccgttcggaa ccgggaccaa gctgaccgtc ctaggt                              336
```

<210> SEQ ID NO 37
<211> LENGTH: 112
<212> TYPE: PRT
<213> ORGANISM: Homo sapiens
<220> FEATURE:
<223> OTHER INFORMATION: Antibody 4

<400> SEQUENCE: 37

```
Gln Ser Val Leu Thr Gln Pro Pro Ser Val Ser Gly Ala Pro Gly Gln
 1               5                  10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Asp Asn Phe Asn Arg Pro Ser Gly Val Pro Asp Arg Phe
    50                  55                  60

Ser Gly Ser Lys Ser Gly Thr Ser Ala Ser Leu Ala Ile Ile Gly Leu
65                  70                  75                  80

Gln Thr Glu Asp Glu Ala Asp Tyr Tyr Cys Gln Ser Tyr Asp Ser Arg
                85                  90                  95

Gly Gly His Ser Pro Phe Gly Thr Gly Thr Lys Leu Thr Val Leu Gly
            100                 105                 110
```

<210> SEQ ID NO 38
<211> LENGTH: 14
<212> TYPE: PRT
<213> ORGANISM: Homo sapiens
<220> FEATURE:
<223> OTHER INFORMATION: Antibody 4

<400> SEQUENCE: 38

```
Thr Gly Ser Ser Ser Asn Ile Gly Ala Gly Tyr Asp Val His
 1               5                  10
```

<210> SEQ ID NO 39
<211> LENGTH: 7
<212> TYPE: PRT
<213> ORGANISM: Homo sapiens
<220> FEATURE:
<223> OTHER INFORMATION: Antibody 4

<400> SEQUENCE: 39

```
Asp Asn Phe Asn Arg Pro Ser
 1               5
```

<210> SEQ ID NO 40
<211> LENGTH: 11
<212> TYPE: PRT
<213> ORGANISM: Homo sapiens
<220> FEATURE:
<223> OTHER INFORMATION: Antibody 4

<400> SEQUENCE: 40

```
Gln Ser Tyr Asp Ser Arg Gly Gly His Ser Pro
 1               5                  10
```

<210> SEQ ID NO 41
<211> LENGTH: 363
<212> TYPE: DNA
<213> ORGANISM: Homo sapiens
<220> FEATURE:

<223> OTHER INFORMATION: Antibody 5

<400> SEQUENCE: 41

```
caggtccagc tggtgcagtc tggggctgag gtgaagaaac ctggggccac agtgaaactc      60
tcctgcaagg tttatggata cattttcacc gactacaaca tttactgggt gcgccaggcc     120
cctggaaaag gccttgagtg gatgggactt attgatcctg acaatggtga acattttac      180
gcagagaagt tccagggcag agccaccatg accgcggaca cgtcttcaga cagagcctac     240
atggaattga ccagcctgac ctttgaggac acggccactt attattgtgc aacagtgatg     300
gggaagtgga tcaagggggg ctatgactac tggggccggg gcaccctggt caccgtctcg     360
agt                                                                   363
```

<210> SEQ ID NO 42
<211> LENGTH: 121
<212> TYPE: PRT
<213> ORGANISM: Homo sapiens
<220> FEATURE:
<223> OTHER INFORMATION: Antibody 5

<400> SEQUENCE: 42

Gln Val Gln Leu Val Gln Ser Gly Ala Glu Val Lys Lys Pro Gly Ala
1               5                   10                  15

Thr Val Lys Leu Ser Cys Lys Val Tyr Gly Tyr Ile Phe Thr Asp Tyr
            20                  25                  30

Asn Ile Tyr Trp Val Arg Gln Ala Pro Gly Lys Gly Leu Glu Trp Met
        35                  40                  45

Gly Leu Ile Asp Pro Asp Asn Gly Glu Thr Phe Tyr Ala Glu Lys Phe
    50                  55                  60

Gln Gly Arg Ala Thr Met Thr Ala Asp Thr Ser Ser Asp Arg Ala Tyr
65                  70                  75                  80

Met Glu Leu Thr Ser Leu Thr Phe Glu Asp Thr Ala Thr Tyr Tyr Cys
                85                  90                  95

Ala Thr Val Met Gly Lys Trp Ile Lys Gly Gly Tyr Asp Tyr Trp Gly
            100                 105                 110

Arg Gly Thr Leu Val Thr Val Ser Ser
        115                 120

<210> SEQ ID NO 43
<211> LENGTH: 5
<212> TYPE: PRT
<213> ORGANISM: Homo sapiens
<220> FEATURE:
<223> OTHER INFORMATION: Antibody 5

<400> SEQUENCE: 43

Asp Tyr Asn Ile Tyr
1               5

<210> SEQ ID NO 44
<211> LENGTH: 17
<212> TYPE: PRT
<213> ORGANISM: Homo sapiens
<220> FEATURE:
<223> OTHER INFORMATION: Antibody 5

<400> SEQUENCE: 44

Leu Ile Asp Pro Asp Asn Gly Glu Thr Phe Tyr Ala Glu Lys Phe Gln
1               5                   10                  15

Gly

```
<210> SEQ ID NO 45
<211> LENGTH: 12
<212> TYPE: PRT
<213> ORGANISM: Homo sapiens
<220> FEATURE:
<223> OTHER INFORMATION: Antibody 5

<400> SEQUENCE: 45

Val Met Gly Lys Trp Ile Lys Gly Gly Tyr Asp Tyr
1               5                   10

<210> SEQ ID NO 46
<211> LENGTH: 336
<212> TYPE: DNA
<213> ORGANISM: Homo sapiens
<220> FEATURE:
<223> OTHER INFORMATION: Antibody 5

<400> SEQUENCE: 46
cagtctgtgc tgacgcagcc gccctcagtg tctggggccc cagggcagag ggtcaccatc      60
tcctgcactg ggagcagctc aacatcgggg gcaggttatg atgtacactg gtatcagcaa     120
cttccaggaa cagcccccaa actcctcatc tatgataatt tcaatcggcc ctcaggggtc     180
cctgaccgat tctctggctc caagtctggc acctcagcct ccctggccat cattgggctc     240
cagactgaag atgaggctga ttattattgc cagtcctatg acagcaccaa gcacacctcc     300
cccttcggaa ccgggaccaa gctgaccgtc ctaggt                               336

<210> SEQ ID NO 47
<211> LENGTH: 112
<212> TYPE: PRT
<213> ORGANISM: Homo sapiens
<220> FEATURE:
<223> OTHER INFORMATION: Antibody 5

<400> SEQUENCE: 47

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Asp Asn Phe Asn Arg Pro Ser Gly Val Pro Asp Arg Phe
    50                  55                  60

Ser Gly Ser Lys Ser Gly Thr Ser Ala Ser Leu Ala Ile Ile Gly Leu
65                  70                  75                  80

Gln Thr Glu Asp Glu Ala Asp Tyr Tyr Cys Gln Ser Tyr Asp Ser Thr
                85                  90                  95

Lys His Thr Ser Pro Phe Gly Thr Gly Thr Lys Leu Thr Val Leu Gly
            100                 105                 110

<210> SEQ ID NO 48
<211> LENGTH: 14
<212> TYPE: PRT
<213> ORGANISM: Homo sapiens
<220> FEATURE:
<223> OTHER INFORMATION: Antibody 5

<400> SEQUENCE: 48

Thr Gly Ser Ser Ser Asn Ile Gly Ala Gly Tyr Asp Val His
1               5                   10
```

<210> SEQ ID NO 49
<211> LENGTH: 7
<212> TYPE: PRT
<213> ORGANISM: Homo sapiens
<220> FEATURE:
<223> OTHER INFORMATION: Antibody 5

<400> SEQUENCE: 49

Asp Asn Phe Asn Arg Pro Ser
1               5

<210> SEQ ID NO 50
<211> LENGTH: 11
<212> TYPE: PRT
<213> ORGANISM: Homo sapiens
<220> FEATURE:
<223> OTHER INFORMATION: Antibody 5

<400> SEQUENCE: 50

Gln Ser Tyr Asp Ser Thr Lys His Thr Ser Pro
1               5                   10

<210> SEQ ID NO 51
<211> LENGTH: 363
<212> TYPE: DNA
<213> ORGANISM: Homo sapiens
<220> FEATURE:
<223> OTHER INFORMATION: Antibody 6

<400> SEQUENCE: 51

```
caggtccagc tggtgcagtc tggggctgag gtgaagaaac ctggggccac agtgaaactc      60
tcctgcaagg tttatggata cattttcacc gactacaaca tttactgggt gcgccaggcc     120
cctggaaaag gcttgagtg gatgggactt attgatcctg acaatggtga gacattttac     180
gcagagaagt tccagggcag agccaccatg accgcgagca cgtcttcaga cagagcctac     240
atggaattga ccagcctgac ctttgaggac acggccactt attattgtgc aacagtgatg     300
gggaagtgga tcaagggggg ctatgactac tggggccggg gcaccctggt caccgtctcg     360
agt                                                                    363
```

<210> SEQ ID NO 52
<211> LENGTH: 121
<212> TYPE: PRT
<213> ORGANISM: Homo sapiens
<220> FEATURE:
<223> OTHER INFORMATION: Antibody 6

<400> SEQUENCE: 52

Gln Val Gln Leu Val Gln Ser Gly Ala Glu Val Lys Lys Pro Gly Ala
1               5                   10                  15

Thr Val Lys Leu Ser Cys Lys Val Tyr Gly Tyr Ile Phe Thr Asp Tyr
            20                  25                  30

Asn Ile Tyr Trp Val Arg Gln Ala Pro Gly Lys Gly Leu Glu Trp Met
        35                  40                  45

Gly Leu Ile Asp Pro Asp Asn Gly Glu Thr Phe Tyr Ala Glu Lys Phe
    50                  55                  60

Gln Gly Arg Ala Thr Met Thr Ala Asp Thr Ser Ser Asp Arg Ala Tyr
65                  70                  75                  80

Met Glu Leu Thr Ser Leu Thr Phe Glu Asp Thr Ala Thr Tyr Tyr Cys
                85                  90                  95

Ala Thr Val Met Gly Lys Trp Ile Lys Gly Gly Tyr Asp Tyr Trp Gly
            100                 105                 110

```
Arg Gly Thr Leu Val Thr Val Ser Ser
        115                 120
```

<210> SEQ ID NO 53
<211> LENGTH: 5
<212> TYPE: PRT
<213> ORGANISM: Homo sapiens
<220> FEATURE:
<223> OTHER INFORMATION: Antibody 6

<400> SEQUENCE: 53

```
Asp Tyr Asn Ile Tyr
1               5
```

<210> SEQ ID NO 54
<211> LENGTH: 17
<212> TYPE: PRT
<213> ORGANISM: Homo sapiens
<220> FEATURE:
<223> OTHER INFORMATION: Antibody 6

<400> SEQUENCE: 54

```
Leu Ile Asp Pro Asp Asn Gly Glu Thr Phe Tyr Ala Glu Lys Phe Gln
1               5                   10                  15

Gly
```

<210> SEQ ID NO 55
<211> LENGTH: 12
<212> TYPE: PRT
<213> ORGANISM: Homo sapiens
<220> FEATURE:
<223> OTHER INFORMATION: Antibody 6

<400> SEQUENCE: 55

```
Val Met Gly Lys Trp Ile Lys Gly Gly Tyr Asp Tyr
1               5                   10
```

<210> SEQ ID NO 56
<211> LENGTH: 336
<212> TYPE: DNA
<213> ORGANISM: Homo sapiens
<220> FEATURE:
<223> OTHER INFORMATION: Antibody 6

<400> SEQUENCE: 56

```
cagtctgtgc tgacgcagcc gccctcagtg tctggggccc cagggcagag ggtcaccatc    60
tcctgcactg ggagcagctc caacatcggg gcaggttatg atgtacactg gtatcagcaa   120
cttccaggaa cagcccccaa actcctcatc tatgataatt caatcggcc ctcaggggtc    180 cctgaccgat tctctggctc caagtctggc acctcagcct ccctggccat cattgggctc   240
cagactgaag atgaggctga ttattattgc cagtcctatg acagcaccat gaggcacggg   300
ccgttcggaa ccgggaccaa gctgaccgtc ctaggt                            336
```

<210> SEQ ID NO 57
<211> LENGTH: 112
<212> TYPE: PRT
<213> ORGANISM: Homo sapiens
<220> FEATURE:
<223> OTHER INFORMATION: Antibody 6

<400> SEQUENCE: 57

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
```

```
                20                  25                  30
Tyr Asp Val His Trp Tyr Gln Gln Leu Pro Gly Thr Ala Pro Lys Leu
            35                  40                  45

Leu Ile Tyr Asp Asn Phe Asn Arg Pro Ser Gly Val Pro Asp Arg Phe
        50                  55                  60

Ser Gly Ser Lys Ser Gly Thr Ser Ala Ser Leu Ala Ile Ile Gly Leu
65                  70                  75                  80

Gln Thr Glu Asp Glu Ala Asp Tyr Tyr Cys Gln Ser Tyr Asp Ser Thr
                85                  90                  95

Met Arg His Gly Pro Phe Gly Thr Gly Thr Lys Leu Thr Val Leu Gly
            100                 105                 110
```

<210> SEQ ID NO 58
<211> LENGTH: 14
<212> TYPE: PRT
<213> ORGANISM: Homo sapiens
<220> FEATURE:
<223> OTHER INFORMATION: Antibody 6

<400> SEQUENCE: 58

```
Thr Gly Ser Ser Ser Asn Ile Gly Ala Gly Tyr Asp Val His
1               5                   10
```

<210> SEQ ID NO 59
<211> LENGTH: 7
<212> TYPE: PRT
<213> ORGANISM: Homo sapiens
<220> FEATURE:
<223> OTHER INFORMATION: Antibody 6

<400> SEQUENCE: 59

```
Asp Asn Phe Asn Arg Pro Ser
1               5
```

<210> SEQ ID NO 60
<211> LENGTH: 11
<212> TYPE: PRT
<213> ORGANISM: Homo sapiens
<220> FEATURE:
<223> OTHER INFORMATION: Antibody 6

<400> SEQUENCE: 60

```
Gln Ser Tyr Asp Ser Thr Met Arg His Gly Pro
1               5                   10
```

<210> SEQ ID NO 61
<211> LENGTH: 363
<212> TYPE: DNA
<213> ORGANISM: Homo sapiens
<220> FEATURE:
<223> OTHER INFORMATION: Antibody 7

<400> SEQUENCE: 61

```
caggtccagc tggtgcagtc tggggctgag gtgaagaaac ctggggccac agtgaaactc      60
tcctgcaagg tttatggata cattttcacc gactacaaca tttactgggt gcgccaggcc     120
cctggaaaag ggcttgagtg gatgggactt attgatcctg acaatggtga gacattttac     180
gcagagaagt tccagggcag agccaccatg accgcggaca cgtcttcaga cagagcctac     240
atggaattga ccagcctgac ctttgaggac acggccactt attattgtgc aacagtgacg     300
ctgaagagcg cgaagggggg ctatgactac tggggccggg gcaccctggt caccgtctcg     360
agt                                                                    363
```

```
<210> SEQ ID NO 62
<211> LENGTH: 121
<212> TYPE: PRT
<213> ORGANISM: Homo sapiens
<220> FEATURE:
<223> OTHER INFORMATION: Antibody 7

<400> SEQUENCE: 62

Gln Val Gln Leu Val Gln Ser Gly Ala Glu Val Lys Lys Pro Gly Ala
1               5                   10                  15

Thr Val Lys Leu Ser Cys Lys Val Tyr Gly Tyr Ile Phe Thr Asp Tyr
            20                  25                  30

Asn Ile Tyr Trp Val Arg Gln Ala Pro Gly Lys Gly Leu Glu Trp Met
        35                  40                  45

Gly Leu Ile Asp Pro Asp Asn Gly Glu Thr Phe Tyr Ala Glu Lys Phe
    50                  55                  60

Gln Gly Arg Ala Thr Met Thr Ala Asp Thr Ser Asp Arg Ala Tyr
65                  70                  75                  80

Met Glu Leu Thr Ser Leu Thr Phe Glu Asp Thr Ala Thr Tyr Tyr Cys
                85                  90                  95

Ala Thr Val Thr Leu Lys Ser Ala Lys Gly Gly Tyr Asp Tyr Trp Gly
            100                 105                 110

Arg Gly Thr Leu Val Thr Val Ser Ser
        115                 120

<210> SEQ ID NO 63
<211> LENGTH: 5
<212> TYPE: PRT
<213> ORGANISM: Homo sapiens
<220> FEATURE:
<223> OTHER INFORMATION: Antibody 7

<400> SEQUENCE: 63

Asp Tyr Asn Ile Tyr
1               5

<210> SEQ ID NO 64
<211> LENGTH: 17
<212> TYPE: PRT
<213> ORGANISM: Homo sapiens
<220> FEATURE:
<223> OTHER INFORMATION: Antibody 7

<400> SEQUENCE: 64

Leu Ile Asp Pro Asp Asn Gly Glu Thr Phe Tyr Ala Glu Lys Phe Gln
1               5                   10                  15

Gly

<210> SEQ ID NO 65
<211> LENGTH: 12
<212> TYPE: PRT
<213> ORGANISM: Homo sapiens
<220> FEATURE:
<223> OTHER INFORMATION: Antibody 7

<400> SEQUENCE: 65

Val Thr Leu Lys Ser Ala Lys Gly Gly Tyr Asp Tyr
1               5                   10

<210> SEQ ID NO 66
<211> LENGTH: 336
<212> TYPE: DNA
<213> ORGANISM: Homo sapiens
```

```
<220> FEATURE:
<223> OTHER INFORMATION: Antibody 7

<400> SEQUENCE: 66
cagtctgtgc tgacgcagcc gcccctcagtg tctggggccc cagggcagag ggtcaccatc      60
tcctgcactg ggagcagctc caacatcggg gcaggttatg atgtacactg gtatcagcaa     120
cttccaggaa cagcccccaa actcctcatc tatgataatt tcaatcggcc ctcaggggtc     180
cctgaccgat tctctggctc caagtctggc acctcagcct ccctggccat cattgggctc     240
cagactgaag atgaggctga ttattattgc cagtcctatg acagcgacag gaggaactcc     300
ccgttcggaa ccgggaccaa gctgaccgtc ctaggt                                336

<210> SEQ ID NO 67
<211> LENGTH: 112
<212> TYPE: PRT
<213> ORGANISM: Homo sapiens
<220> FEATURE:
<223> OTHER INFORMATION: Antibody 7

<400> SEQUENCE: 67

Gln Ser Val Leu Thr Gln Pro Pro Ser Val Ser Gly Ala Pro Gly Gln
 1               5                  10                  15

Arg Val Thr Ile Ser Cys Thr Gly Ser Ser Asn Ile Gly Ala Gly
                20                  25                  30

Tyr Asp Val His Trp Tyr Gln Gln Leu Pro Gly Thr Ala Pro Lys Leu
            35                  40                  45

Leu Ile Tyr Asp Asn Phe Asn Arg Pro Ser Gly Val Pro Asp Arg Phe
        50                  55                  60

Ser Gly Ser Lys Ser Gly Thr Ser Ala Ser Leu Ala Ile Ile Gly Leu
65                  70                  75                  80

Gln Thr Glu Asp Glu Ala Asp Tyr Tyr Cys Gln Ser Tyr Asp Ser Asp
                85                  90                  95

Arg Arg Asn Ser Pro Phe Gly Thr Gly Thr Lys Leu Thr Val Leu Gly
            100                 105                 110

<210> SEQ ID NO 68
<211> LENGTH: 14
<212> TYPE: PRT
<213> ORGANISM: Homo sapiens
<220> FEATURE:
<223> OTHER INFORMATION: Antibody 7

<400> SEQUENCE: 68

Thr Gly Ser Ser Ser Asn Ile Gly Ala Gly Tyr Asp Val His
 1               5                  10

<210> SEQ ID NO 69
<211> LENGTH: 7
<212> TYPE: PRT
<213> ORGANISM: Homo sapiens
<220> FEATURE:
<223> OTHER INFORMATION: Antibody 7

<400> SEQUENCE: 69

Asp Asn Phe Asn Arg Pro Ser
 1               5

<210> SEQ ID NO 70
<211> LENGTH: 11
<212> TYPE: PRT
<213> ORGANISM: Homo sapiens
<220> FEATURE:
```

<223> OTHER INFORMATION: Antibody 7

<400> SEQUENCE: 70

Gln Ser Tyr Asp Ser Asp Arg Arg Asn Ser Pro
1               5                   10

<210> SEQ ID NO 71
<211> LENGTH: 363
<212> TYPE: DNA
<213> ORGANISM: Homo sapiens
<220> FEATURE:
<223> OTHER INFORMATION: Antibody 8

<400> SEQUENCE: 71
caggtccagc tggtgcagtc tggggctgag gtgaagaaac ctggggccac agtgaaactc    60
tcctgcaagg tttatggata cattttcacc gactacaaca tttactgggt gcgccaggcc   120
cctggaaaag ggcttgagtg gatgggactt attgatcctg acaatggtga gacattttac   180
gcagagaagt tccagggcag agccaccatg accgcggaca cgtcttcaga cagagcctac   240
atggaattga ccagcctgac ctttgaggac acggccactt attattgtgc aacagtcctg   300
ggccggtgga tcaagggggg ctatgactac tggggccggg gcaccctggt caccgtctcg   360
agt                                                                 363

<210> SEQ ID NO 72
<211> LENGTH: 121
<212> TYPE: PRT
<213> ORGANISM: Homo sapiens
<220> FEATURE:
<223> OTHER INFORMATION: Antibody 8

<400> SEQUENCE: 72

Gln Val Gln Leu Val Gln Ser Gly Ala Glu Val Lys Lys Pro Gly Ala
1               5                   10                  15

Thr Val Lys Leu Ser Cys Lys Val Tyr Gly Tyr Ile Phe Thr Asp Tyr
                20                  25                  30

Asn Ile Tyr Trp Val Arg Gln Ala Pro Gly Lys Gly Leu Glu Trp Met
            35                  40                  45

Gly Leu Ile Asp Pro Asp Asn Gly Glu Thr Phe Tyr Ala Glu Lys Phe
        50                  55                  60

Gln Gly Arg Ala Thr Met Thr Ala Asp Thr Ser Ser Asp Arg Ala Tyr
65                  70                  75                  80

Met Glu Leu Thr Ser Leu Thr Phe Glu Asp Thr Ala Thr Tyr Tyr Cys
                85                  90                  95

Ala Thr Val Leu Gly Arg Trp Ile Lys Gly Gly Tyr Asp Tyr Trp Gly
            100                 105                 110

Arg Gly Thr Leu Val Thr Val Ser Ser
        115                 120

<210> SEQ ID NO 73
<211> LENGTH: 5
<212> TYPE: PRT
<213> ORGANISM: Homo sapiens
<220> FEATURE:
<223> OTHER INFORMATION: Antibody 8

<400> SEQUENCE: 73

Asp Tyr Asn Ile Tyr
1               5

<210> SEQ ID NO 74

```
<211> LENGTH: 17
<212> TYPE: PRT
<213> ORGANISM: Homo sapiens
<220> FEATURE:
<223> OTHER INFORMATION: Antibody 8

<400> SEQUENCE: 74

Leu Ile Asp Pro Asp Asn Gly Glu Thr Phe Tyr Ala Glu Lys Phe Gln
1               5                   10                  15
Gly

<210> SEQ ID NO 75
<211> LENGTH: 12
<212> TYPE: PRT
<213> ORGANISM: Homo sapiens
<220> FEATURE:
<223> OTHER INFORMATION: Antibody 8

<400> SEQUENCE: 75

Val Leu Gly Arg Trp Ile Lys Gly Gly Tyr Asp Tyr
1               5                   10

<210> SEQ ID NO 76
<211> LENGTH: 336
<212> TYPE: DNA
<213> ORGANISM: Homo sapiens
<220> FEATURE:
<223> OTHER INFORMATION: Antibody 8

<400> SEQUENCE: 76
cagtctgtgc tgacgcagcc gccctcagtg tctggggccc cagggcagag ggtcaccatc      60
tcctgcactg ggagcagctc caacatcggg gcaggttatg atgtacactg gtatcagcaa     120
cttccaggaa cagcccccaa actcctcatc tatgataatt tcaatcggcc ctcagggatc     180
cctgaccgat tctctggctc caagtctggc acctcagcct ccctggccat cattgggctc     240
cagactgaag atgaggctga ttattattgc cagtcctatg acagccccac ccacacctcc     300
cccttcggaa ccgggaccaa gctgaccgtc ctaggt                              336

<210> SEQ ID NO 77
<211> LENGTH: 112
<212> TYPE: PRT
<213> ORGANISM: Homo sapiens
<220> FEATURE:
<223> OTHER INFORMATION: Antibody 8

<400> SEQUENCE: 77

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Asp Asn Phe Asn Arg Pro Ser Gly Val Pro Asp Arg Phe
    50                  55                  60

Ser Gly Ser Lys Ser Gly Thr Ser Ala Ser Leu Ala Ile Ile Gly Leu
65                  70                  75                  80

Gln Thr Glu Asp Glu Ala Asp Tyr Tyr Cys Gln Ser Tyr Asp Ser Pro
                85                  90                  95

Thr His Thr Ser Pro Phe Gly Thr Gly Thr Lys Leu Thr Val Leu Gly
            100                 105                 110
```

```
<210> SEQ ID NO 78
<211> LENGTH: 14
<212> TYPE: PRT
<213> ORGANISM: Homo sapiens
<220> FEATURE:
<223> OTHER INFORMATION: Antibody 8

<400> SEQUENCE: 78

Thr Gly Ser Ser Ser Asn Ile Gly Ala Gly Tyr Asp Val His
1               5                   10

<210> SEQ ID NO 79
<211> LENGTH: 7
<212> TYPE: PRT
<213> ORGANISM: Homo sapiens
<220> FEATURE:
<223> OTHER INFORMATION: Antibody 8

<400> SEQUENCE: 79

Asp Asn Phe Asn Arg Pro Ser
1               5

<210> SEQ ID NO 80
<211> LENGTH: 11
<212> TYPE: PRT
<213> ORGANISM: Homo sapiens
<220> FEATURE:
<223> OTHER INFORMATION: Antibody 8

<400> SEQUENCE: 80

Gln Ser Tyr Asp Ser Pro Thr His Thr Ser Pro
1               5                   10

<210> SEQ ID NO 81
<211> LENGTH: 363
<212> TYPE: DNA
<213> ORGANISM: Homo sapiens
<220> FEATURE:
<223> OTHER INFORMATION: Antibody 9

<400> SEQUENCE: 81
caggtccagc tggtgcagtc tggggctgag gtgaagaaac ctggggccac agtgaaactc      60
tcctgcaagg tttatggata cattttcacc gactacaaca tttactgggt gcgccaggcc     120
cctggaaaag gcttgagtg gatgggactt attgatcctg acaatggtga gacattttac      180
gcagagaagt tccagggcag agccaccatg accgcggaca cgtcttcaga cagagcctac     240
atggaattga ccagcctgac ctttgaggac acggccactt attattgtgc aacagtgacg     300
ctgaggagcg cgaagggggg ctatgactac tggggccggg gcaccctggt caccgtctcg     360
agt                                                                    363

<210> SEQ ID NO 82
<211> LENGTH: 121
<212> TYPE: PRT
<213> ORGANISM: Homo sapiens
<220> FEATURE:
<223> OTHER INFORMATION: Antibody 9

<400> SEQUENCE: 82

Gln Val Gln Leu Val Gln Ser Gly Ala Glu Val Lys Lys Pro Gly Ala
1               5                   10                  15

Thr Val Lys Leu Ser Cys Lys Val Tyr Gly Tyr Ile Phe Thr Asp Tyr
            20                  25                  30

Asn Ile Tyr Trp Val Arg Gln Ala Pro Gly Lys Gly Leu Glu Trp Met
        35                  40                  45
```

Gly Leu Ile Asp Pro Asp Asn Gly Glu Thr Phe Tyr Ala Glu Lys Phe
    50                  55                  60

Gln Gly Arg Ala Thr Met Thr Ala Asp Thr Ser Ser Asp Arg Ala Tyr
 65                  70                  75                  80

Met Glu Leu Thr Ser Leu Thr Phe Glu Asp Thr Ala Thr Tyr Tyr Cys
                 85                  90                  95

Ala Thr Val Thr Leu Arg Ser Ala Lys Gly Gly Tyr Asp Tyr Trp Gly
            100                 105                 110

Arg Gly Thr Leu Val Thr Val Ser Ser
         115                 120

<210> SEQ ID NO 83
<211> LENGTH: 5
<212> TYPE: PRT
<213> ORGANISM: Homo sapiens
<220> FEATURE:
<223> OTHER INFORMATION: Antibody 9

<400> SEQUENCE: 83

Asp Tyr Asn Ile Tyr
1               5

<210> SEQ ID NO 84
<211> LENGTH: 17
<212> TYPE: PRT
<213> ORGANISM: Homo sapiens
<220> FEATURE:
<223> OTHER INFORMATION: Antibody 9

<400> SEQUENCE: 84

Leu Ile Asp Pro Asp Asn Gly Glu Thr Phe Tyr Ala Glu Lys Phe Gln
1               5                   10                  15

Gly

<210> SEQ ID NO 85
<211> LENGTH: 12
<212> TYPE: PRT
<213> ORGANISM: Homo sapiens
<220> FEATURE:
<223> OTHER INFORMATION: Antibody 9

<400> SEQUENCE: 85

Val Thr Leu Arg Ser Ala Lys Gly Gly Tyr Asp Tyr
1               5                   10

<210> SEQ ID NO 86
<211> LENGTH: 336
<212> TYPE: DNA
<213> ORGANISM: Homo sapiens
<220> FEATURE:
<223> OTHER INFORMATION: Antibody 9

<400> SEQUENCE: 86
cagtctgtgc tgacgcagcc gccctcagtg tctggggccc cagggcagag ggtcaccatc      60
tcctgcactg ggagcagctc caacatcggg gcaggttatg atgtacactg gtatcagcaa     120
cttccaggaa cagcccccaa actcctcatc tatgataatt caatcggcc ctcaggggtc     180 cctgaccgat tctctggctc caagtctggc acctcagcct ccctggccat cattgggctc     240
cagactgaag atgaggctga ttattattgc cagtcctatg acagcccctc ctccaccctcc     300 ccccttcggaa ccgggaccaa gctgaccgtc ctaggt                              336

<210> SEQ ID NO 87
<211> LENGTH: 112
<212> TYPE: PRT
<213> ORGANISM: Homo sapiens
<220> FEATURE:
<223> OTHER INFORMATION: Antibody 9

<400> SEQUENCE: 87

Gln Ser Val Leu Thr Gln Pro Pro Ser Val Gly Ala Pro Gly Gln
1               5                   10                  15

Arg Val Thr Ile Ser Cys Thr Gly Ser Ser Asn Ile Gly Ala Gly
                20                  25                  30

Tyr Asp Val His Trp Tyr Gln Gln Leu Pro Gly Thr Ala Pro Lys Leu
            35                  40                  45

Leu Ile Tyr Asp Asn Phe Asn Arg Pro Ser Gly Val Pro Asp Arg Phe
    50                  55                  60

Ser Gly Ser Lys Ser Gly Thr Ser Ala Ser Leu Ala Ile Ile Gly Leu
65                  70                  75                  80

Gln Thr Glu Asp Glu Ala Asp Tyr Tyr Cys Gln Ser Tyr Asp Ser Pro
                85                  90                  95

Ser Ser Thr Ser Pro Phe Gly Thr Gly Thr Lys Leu Thr Val Leu Gly
            100                 105                 110

<210> SEQ ID NO 88
<211> LENGTH: 14
<212> TYPE: PRT
<213> ORGANISM: Homo sapiens
<220> FEATURE:
<223> OTHER INFORMATION: Antibody 9

<400> SEQUENCE: 88

Thr Gly Ser Ser Ser Asn Ile Gly Ala Gly Tyr Asp Val His
1               5                   10

<210> SEQ ID NO 89
<211> LENGTH: 7
<212> TYPE: PRT
<213> ORGANISM: Homo sapiens
<220> FEATURE:
<223> OTHER INFORMATION: Antibody 9

<400> SEQUENCE: 89

Asp Asn Phe Asn Arg Pro Ser
1               5

<210> SEQ ID NO 90
<211> LENGTH: 11
<212> TYPE: PRT
<213> ORGANISM: Homo sapiens
<220> FEATURE:
<223> OTHER INFORMATION: Antibody 9

<400> SEQUENCE: 90

Gln Ser Tyr Asp Ser Pro Ser Ser Thr Ser Pro
1               5                   10

<210> SEQ ID NO 91
<211> LENGTH: 363
<212> TYPE: DNA
<213> ORGANISM: Homo sapiens
<220> FEATURE:
<223> OTHER INFORMATION: Antibody 10

<400> SEQUENCE: 91
caggtccagc tggtgcagtc tggggctgag gtgaagaaac ctggggccac agtgaaactc      60

```
tcctgcaagg tttatggata cattttcacc gactacaaca tttactgggt gcgccaggcc      120
cctggaaaag ggcttgagtg gatgggactt attgatcctg acaatggtga gacattttac      180
gcagagaagt tccagggcag agccaccatg accgcggaca cgtcttcaga cagagcctac      240
atggaattga ccagcctgac ctttgaggac acggccactt attattgtgc aacagtctcg      300
ctccgggccg ccaagggggg ctatgactac tggggccggg caccctggt caccgtctcg       360 agt                                                                    363
```

```
<210> SEQ ID NO 92
<211> LENGTH: 121
<212> TYPE: PRT
<213> ORGANISM: Homo sapiens
<220> FEATURE:
<223> OTHER INFORMATION: Antibody 10

<400> SEQUENCE: 92

Gln Val Gln Leu Val Gln Ser Gly Ala Glu Val Lys Lys Pro Gly Ala
1               5                   10                  15

Thr Val Lys Leu Ser Cys Lys Val Tyr Gly Tyr Ile Phe Thr Asp Tyr
            20                  25                  30

Asn Ile Tyr Trp Val Arg Gln Ala Pro Gly Lys Gly Leu Glu Trp Met
        35                  40                  45

Gly Leu Ile Asp Pro Asp Asn Gly Glu Thr Phe Tyr Ala Glu Lys Phe
    50                  55                  60

Gln Gly Arg Ala Thr Met Thr Ala Asp Thr Ser Ser Asp Arg Ala Tyr
65                  70                  75                  80

Met Glu Leu Thr Ser Leu Thr Phe Glu Asp Thr Ala Thr Tyr Tyr Cys
                85                  90                  95

Ala Thr Val Ser Leu Arg Ala Ala Lys Gly Gly Tyr Asp Tyr Trp Gly
            100                 105                 110

Arg Gly Thr Leu Val Thr Val Ser Ser
        115                 120
```

```
<210> SEQ ID NO 93
<211> LENGTH: 5
<212> TYPE: PRT
<213> ORGANISM: Homo sapiens
<220> FEATURE:
<223> OTHER INFORMATION: Antibody 10

<400> SEQUENCE: 93

Asp Tyr Asn Ile Tyr
1               5
```

```
<210> SEQ ID NO 94
<211> LENGTH: 17
<212> TYPE: PRT
<213> ORGANISM: Homo sapiens
<220> FEATURE:
<223> OTHER INFORMATION: Antibody 10

<400> SEQUENCE: 94

Leu Ile Asp Pro Asp Asn Gly Glu Thr Phe Tyr Ala Glu Lys Phe Gln
1               5                   10                  15

Gly
```

```
<210> SEQ ID NO 95
<211> LENGTH: 12
<212> TYPE: PRT
<213> ORGANISM: Homo sapiens
```

```
<220> FEATURE:
<223> OTHER INFORMATION: Antibody 10

<400> SEQUENCE: 95

Val Ser Leu Arg Ala Ala Lys Gly Gly Tyr Asp Tyr
1               5                   10

<210> SEQ ID NO 96
<211> LENGTH: 336
<212> TYPE: DNA
<213> ORGANISM: Homo sapiens
<220> FEATURE:
<223> OTHER INFORMATION: Antibody 10

<400> SEQUENCE: 96
cagtctgtgc tgacgcagcc gccctcagtg tctggggccc cagggcagag ggtcaccatc      60
tcctgcactg ggagcagctc caacatcggg gcaggttatg atgtacactg gtatcagcaa     120
cttccaggaa cagcccccaa actcctcatc tatgataatt tcaatcggcc ctcagggtc      180 cctgaccgat tctctggctc caagtctggc acctcagcct ccctggccat cattgggctc     240
cagactgaag atgaggctga ttattattgc cagtcctatg acagcgagca ggagttggcg     300
ccgttcggaa ccgggaccaa gctgaccgtc ctaggt                               336

<210> SEQ ID NO 97
<211> LENGTH: 112
<212> TYPE: PRT
<213> ORGANISM: Homo sapiens
<220> FEATURE:
<223> OTHER INFORMATION: Antibody 10

<400> SEQUENCE: 97

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
                20                  25                  30

Tyr Asp Val His Trp Tyr Gln Gln Leu Pro Gly Thr Ala Pro Lys Leu
            35                  40                  45

Leu Ile Tyr Asp Asn Phe Asn Arg Pro Ser Gly Val Pro Asp Arg Phe
        50                  55                  60

Ser Gly Ser Lys Ser Gly Thr Ser Ala Ser Leu Ala Ile Ile Gly Leu
65                  70                  75                  80

Gln Thr Glu Asp Glu Ala Asp Tyr Tyr Cys Gln Ser Tyr Asp Ser Glu
                85                  90                  95

Gln Glu Leu Ala Pro Phe Gly Thr Gly Thr Lys Leu Thr Val Leu Gly
            100                 105                 110

<210> SEQ ID NO 98
<211> LENGTH: 14
<212> TYPE: PRT
<213> ORGANISM: Homo sapiens
<220> FEATURE:
<223> OTHER INFORMATION: Antibody 10

<400> SEQUENCE: 98

Thr Gly Ser Ser Ser Asn Ile Gly Ala Gly Tyr Asp Val His
1               5                   10

<210> SEQ ID NO 99
<211> LENGTH: 7
<212> TYPE: PRT
<213> ORGANISM: Homo sapiens
<220> FEATURE:
```

<223> OTHER INFORMATION: Antibody 10

<400> SEQUENCE: 99

Asp Asn Phe Asn Arg Pro Ser
1               5

<210> SEQ ID NO 100
<211> LENGTH: 11
<212> TYPE: PRT
<213> ORGANISM: Homo sapiens
<220> FEATURE:
<223> OTHER INFORMATION: Antibody 10

<400> SEQUENCE: 100

Gln Ser Tyr Asp Ser Glu Gln Glu Leu Ala Pro
1               5                   10

<210> SEQ ID NO 101
<211> LENGTH: 363
<212> TYPE: DNA
<213> ORGANISM: Homo sapiens
<220> FEATURE:
<223> OTHER INFORMATION: Antibody 11

<400> SEQUENCE: 101

```
caggtccagc tggtgcagtc tgggctgag gtgaagaaac ctggggccac agtgaaactc      60
tcctgcaagg tttatggata cattttcacc gactacaaca tttactgggt gcgccaggcc     120
cctggaaaag ggcttgagtg gatgggactt attgatcctg acaatggtga gacattttac     180
gcagagaagt tccagggcag agccaccatg accgcggaca cgtcttcaga cagagcctac     240
atggaattga ccagcctgac ctttgaggac acggccactt attattgtgc aacagtgatg     300
gggaagtgga tcaaggggg ctatgactac tggggccggg gcaccctggt caccgtctcg     360
agt                                                                   363
```

<210> SEQ ID NO 102
<211> LENGTH: 121
<212> TYPE: PRT
<213> ORGANISM: Homo sapiens
<220> FEATURE:
<223> OTHER INFORMATION: Antibody 11

<400> SEQUENCE: 102

Gln Val Gln Leu Val Gln Ser Gly Ala Glu Val Lys Lys Pro Gly Ala
1               5                   10                  15

Thr Val Lys Leu Ser Cys Lys Val Tyr Gly Tyr Ile Phe Thr Asp Tyr
                20                  25                  30

Asn Ile Tyr Trp Val Arg Gln Ala Pro Gly Lys Gly Leu Glu Trp Met
            35                  40                  45

Gly Leu Ile Asp Pro Asp Asn Gly Glu Thr Phe Tyr Ala Glu Lys Phe
        50                  55                  60

Gln Gly Arg Ala Thr Met Thr Ala Asp Thr Ser Ser Asp Arg Ala Tyr
65                  70                  75                  80

Met Glu Leu Thr Ser Leu Thr Phe Glu Asp Thr Ala Thr Tyr Tyr Cys
                85                  90                  95

Ala Thr Val Met Gly Lys Trp Ile Lys Gly Gly Tyr Asp Tyr Trp Gly
                100                 105                 110

Arg Gly Thr Leu Val Thr Val Ser Ser
            115                 120

<210> SEQ ID NO 103

<211> LENGTH: 5
<212> TYPE: PRT
<213> ORGANISM: Homo sapiens
<220> FEATURE:
<223> OTHER INFORMATION: Antibody 11

<400> SEQUENCE: 103

Asp Tyr Asn Ile Tyr
1               5

<210> SEQ ID NO 104
<211> LENGTH: 17
<212> TYPE: PRT
<213> ORGANISM: Homo sapiens
<220> FEATURE:
<223> OTHER INFORMATION: Antibody 11

<400> SEQUENCE: 104

Leu Ile Asp Pro Asp Asn Gly Glu Thr Phe Tyr Ala Glu Lys Phe Gln
1               5                   10                  15

Gly

<210> SEQ ID NO 105
<211> LENGTH: 12
<212> TYPE: PRT
<213> ORGANISM: Homo sapiens
<220> FEATURE:
<223> OTHER INFORMATION: Antibody 11

<400> SEQUENCE: 105

Val Met Gly Lys Trp Ile Lys Gly Gly Tyr Asp Tyr
1               5                   10

<210> SEQ ID NO 106
<211> LENGTH: 336
<212> TYPE: DNA
<213> ORGANISM: Homo sapiens
<220> FEATURE:
<223> OTHER INFORMATION: Antibody 11

<400> SEQUENCE: 106
cagtctgtgc tgacgcagcc gccctcagtg tctggggccc cagggcagag ggtcaccatc      60
tcctgcactg ggagcagctc caacatcggg gcaggttatg atgtacactg gtatcagcaa     120
cttccaggaa cagcccccaa actcctcatc tatgataatt caatcggcc ctcagggtc      180 cctgaccgat tctctggctc caagtctggc acctcagcct ccctggccat cattgggctc     240
cagactgaag atgaggctga ttattattgc cagtcctatg acagcccac cctcacctcc     300 cccttcggaa ccgggaccaa gctgaccgtc ctaggt                               336

<210> SEQ ID NO 107
<211> LENGTH: 112
<212> TYPE: PRT
<213> ORGANISM: Homo sapiens
<220> FEATURE:
<223> OTHER INFORMATION: Antibody 11

<400> SEQUENCE: 107

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
                20                  25                  30

Tyr Asp Val His Trp Tyr Gln Gln Leu Pro Gly Thr Ala Pro Lys Leu
            35                  40                  45

```
Leu Ile Tyr Asp Asn Phe Asn Arg Pro Ser Gly Val Pro Asp Arg Phe
        50                  55                  60

Ser Gly Ser Lys Ser Gly Thr Ser Ala Ser Leu Ala Ile Ile Gly Leu
 65                  70                  75                  80

Gln Thr Glu Asp Glu Ala Asp Tyr Tyr Cys Gln Ser Tyr Asp Ser Pro
                 85                  90                  95

Thr Leu Thr Ser Pro Phe Gly Thr Gly Thr Lys Leu Thr Val Leu Gly
            100                 105                 110

<210> SEQ ID NO 108
<211> LENGTH: 14
<212> TYPE: PRT
<213> ORGANISM: Homo sapiens
<220> FEATURE:
<223> OTHER INFORMATION: Antibody 11

<400> SEQUENCE: 108

Thr Gly Ser Ser Ser Asn Ile Gly Ala Gly Tyr Asp Val His
 1               5                  10

<210> SEQ ID NO 109
<211> LENGTH: 7
<212> TYPE: PRT
<213> ORGANISM: Homo sapiens
<220> FEATURE:
<223> OTHER INFORMATION: Antibody 11

<400> SEQUENCE: 109

Asp Asn Phe Asn Arg Pro Ser
 1               5

<210> SEQ ID NO 110
<211> LENGTH: 11
<212> TYPE: PRT
<213> ORGANISM: Homo sapiens
<220> FEATURE:
<223> OTHER INFORMATION: Antibody 11

<400> SEQUENCE: 110

Gln Ser Tyr Asp Ser Pro Thr Leu Thr Ser Pro
 1               5                  10

<210> SEQ ID NO 111
<211> LENGTH: 363
<212> TYPE: DNA
<213> ORGANISM: Homo sapiens
<220> FEATURE:
<223> OTHER INFORMATION: Antibody 12

<400> SEQUENCE: 111
caggtccagc tggtgcagtc tggggctgag gtgaagaaac ctggggccac agtgaaactc      60
tcctgcaagg tttatggata cattttcacc gactacaaca tttactgggt gcgccaggcc     120
cctggaaaag ggcttgagtg gatgggactt attgatcctg acaatggtga acatttttac     180
gcagagaagt tccagggcag agccaccatg accgcggaca cgtcttcaga cagagcctac     240
atggaattga ccagcctgac ctttgaggac acggccactt attattgtgc aacagtgatg     300
gggaagtgga tcaaggggggg ctatgactac tggggccggg gcaccctggt caccgtctcg     360
agt                                                                   363

<210> SEQ ID NO 112
<211> LENGTH: 121
<212> TYPE: PRT
<213> ORGANISM: Homo sapiens
```

```
<220> FEATURE:
<223> OTHER INFORMATION: Antibody 12

<400> SEQUENCE: 112

Gln Val Gln Leu Val Gln Ser Gly Ala Glu Val Lys Lys Pro Gly Ala
1               5                   10                  15

Thr Val Lys Leu Ser Cys Lys Val Tyr Gly Tyr Ile Phe Thr Asp Tyr
            20                  25                  30

Asn Ile Tyr Trp Val Arg Gln Ala Pro Gly Lys Gly Leu Glu Trp Met
        35                  40                  45

Gly Leu Ile Asp Pro Asp Asn Gly Glu Thr Phe Tyr Ala Glu Lys Phe
    50                  55                  60

Gln Gly Arg Ala Thr Met Thr Ala Asp Thr Ser Ser Asp Arg Ala Tyr
65                  70                  75                  80

Met Glu Leu Thr Ser Leu Thr Phe Glu Asp Thr Ala Thr Tyr Tyr Cys
                85                  90                  95

Ala Thr Val Met Gly Lys Trp Ile Lys Gly Gly Tyr Asp Tyr Trp Gly
            100                 105                 110

Arg Gly Thr Leu Val Thr Val Ser Ser
        115                 120

<210> SEQ ID NO 113
<211> LENGTH: 5
<212> TYPE: PRT
<213> ORGANISM: Homo sapiens
<220> FEATURE:
<223> OTHER INFORMATION: Antibody 12

<400> SEQUENCE: 113

Asp Tyr Asn Ile Tyr
1               5

<210> SEQ ID NO 114
<211> LENGTH: 17
<212> TYPE: PRT
<213> ORGANISM: Homo sapiens
<220> FEATURE:
<223> OTHER INFORMATION: Antibody 12

<400> SEQUENCE: 114

Leu Ile Asp Pro Asp Asn Gly Glu Thr Phe Tyr Ala Glu Lys Phe Gln
1               5                   10                  15

Gly

<210> SEQ ID NO 115
<211> LENGTH: 12
<212> TYPE: PRT
<213> ORGANISM: Homo sapiens
<220> FEATURE:
<223> OTHER INFORMATION: Antibody 12

<400> SEQUENCE: 115

Val Met Gly Lys Trp Ile Lys Gly Gly Tyr Asp Tyr
1               5                   10

<210> SEQ ID NO 116
<211> LENGTH: 336
<212> TYPE: DNA
<213> ORGANISM: Homo sapiens
<220> FEATURE:
<223> OTHER INFORMATION: Antibody 12

<400> SEQUENCE: 116
```

```
cagtctgtgc tgacgcagcc gccctcagtg tctggggccc cagggcagag ggtcaccatc        60
tcctgcactg ggagcagctc caacatcggg gcaggttatg atgtacactg gtatcagcaa       120
cttccaggaa cagcccccaa actcctcatc tatgataatt tcaatcggcc ctcaggggtc       180
cctgaccgat tctctggctc caagtctggc acctcagcct ccctggccat cattgggctc       240
cagactgaag atgaggctga ttattattgc cagtcctatg acagctccat cgaccactcc       300
cccttcggaa ccgggaccaa gctgaccgtc ctaggt                                 336
```

<210> SEQ ID NO 117
<211> LENGTH: 112
<212> TYPE: PRT
<213> ORGANISM: Homo sapiens
<220> FEATURE:
<223> OTHER INFORMATION: Antibody 12

<400> SEQUENCE: 117

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Asp Asn Phe Asn Arg Pro Ser Gly Val Pro Asp Arg Phe
    50                  55                  60

Ser Gly Ser Lys Ser Gly Thr Ser Ala Ser Leu Ala Ile Ile Gly Leu
65                  70                  75                  80

Gln Thr Glu Asp Glu Ala Asp Tyr Tyr Cys Gln Ser Tyr Asp Ser Ser
                85                  90                  95

Ile Asp His Ser Pro Phe Gly Thr Gly Thr Lys Leu Thr Val Leu Gly
            100                 105                 110
```

<210> SEQ ID NO 118
<211> LENGTH: 14
<212> TYPE: PRT
<213> ORGANISM: Homo sapiens
<220> FEATURE:
<223> OTHER INFORMATION: Antibody 12

<400> SEQUENCE: 118

```
Thr Gly Ser Ser Ser Asn Ile Gly Ala Gly Tyr Asp Val His
1               5                   10
```

<210> SEQ ID NO 119
<211> LENGTH: 7
<212> TYPE: PRT
<213> ORGANISM: Homo sapiens
<220> FEATURE:
<223> OTHER INFORMATION: Antibody 12

<400> SEQUENCE: 119

```
Asp Asn Phe Asn Arg Pro Ser
1               5
```

<210> SEQ ID NO 120
<211> LENGTH: 11
<212> TYPE: PRT
<213> ORGANISM: Homo sapiens
<220> FEATURE:
<223> OTHER INFORMATION: Antibody 12

<400> SEQUENCE: 120

```
Gln Ser Tyr Asp Ser Ser Ile Asp His Ser Pro
```

<210> SEQ ID NO 121
<211> LENGTH: 363
<212> TYPE: DNA
<213> ORGANISM: Homo sapiens
<220> FEATURE:
<223> OTHER INFORMATION: Antibody 13

<400> SEQUENCE: 121

```
caggtccagc tggtgcagtc tggggctgag gtgaagaaac ctggggccac agtgaaactc      60
tcctgcaagg tttatggata cattttcacc gactacaaca tttactgggt gcgccaggcc     120
cctggaaaag ggcttgagtg gatgggactt attgatcctg acaatggtga gacattttac     180
gcagagaagt tccagggcag agccaccatg accgcggaca cgtcttcaga cagagcctac     240
atggaattga ccagcctgac ctttgaggac acggccactt attattgtgc aacagtgatg     300
gggaagtgga tcaagggggg ctatgactac tggggccggg gcaccctggt caccgtctcg     360
agt                                                                    363
```

<210> SEQ ID NO 122
<211> LENGTH: 121
<212> TYPE: PRT
<213> ORGANISM: Homo sapiens
<220> FEATURE:
<223> OTHER INFORMATION: Antibody 13

<400> SEQUENCE: 122

Gln Val Gln Leu Val Gln Ser Gly Ala Glu Val Lys Lys Pro Gly Ala
1               5                   10                  15

Thr Val Lys Leu Ser Cys Lys Val Tyr Gly Tyr Ile Phe Thr Asp Tyr
            20                  25                  30

Asn Ile Tyr Trp Val Arg Gln Ala Pro Gly Lys Gly Leu Glu Trp Met
        35                  40                  45

Gly Leu Ile Asp Pro Asp Asn Gly Glu Thr Phe Tyr Ala Glu Lys Phe
    50                  55                  60

Gln Gly Arg Ala Thr Met Thr Ala Asp Thr Ser Ser Asp Arg Ala Tyr
65                  70                  75                  80

Met Glu Leu Thr Ser Leu Thr Phe Glu Asp Thr Ala Thr Tyr Tyr Cys
                85                  90                  95

Ala Thr Val Met Gly Lys Trp Ile Lys Gly Gly Tyr Asp Tyr Trp Gly
            100                 105                 110

Arg Gly Thr Leu Val Thr Val Ser Ser
        115                 120

<210> SEQ ID NO 123
<211> LENGTH: 5
<212> TYPE: PRT
<213> ORGANISM: Homo sapiens
<220> FEATURE:
<223> OTHER INFORMATION: Antibody 13

<400> SEQUENCE: 123

Asp Tyr Asn Ile Tyr
1               5

<210> SEQ ID NO 124
<211> LENGTH: 17
<212> TYPE: PRT
<213> ORGANISM: Homo sapiens
<220> FEATURE:
<223> OTHER INFORMATION: Antibody 13

<400> SEQUENCE: 124

Leu Ile Asp Pro Asp Asn Gly Glu Thr Phe Tyr Ala Glu Lys Phe Gln
1               5                   10                  15

Gly

<210> SEQ ID NO 125
<211> LENGTH: 12
<212> TYPE: PRT
<213> ORGANISM: Homo sapiens
<220> FEATURE:
<223> OTHER INFORMATION: Antibody 13

<400> SEQUENCE: 125

Val Met Gly Lys Trp Ile Lys Gly Gly Tyr Asp Tyr
1               5                   10

<210> SEQ ID NO 126
<211> LENGTH: 336
<212> TYPE: DNA
<213> ORGANISM: Homo sapiens
<220> FEATURE:
<223> OTHER INFORMATION: Antibody 13

<400> SEQUENCE: 126
cagtctgtgc tgacgcagcc gccctcagtg tctggggccc cagggcagag ggtcaccatc      60
tcctgcactg ggagcagctc aacatcgggg gcaggttatg atgtacactg gtatcagcaa     120
cttccaggaa cagcccccaa actcctcatc tatgataatt tcaatcggcc ctcaggggtc     180
cctgaccgat tctctggctc caagtctggc acctcagcct ccctggccat cattgggctc     240
cagactgaag atgaggctga ttattattgc cagtcctatg acagcaacat cttgtactcc     300
cccttcggaa ccgggaccaa gctgaccgtc ctaggt                              336

<210> SEQ ID NO 127
<211> LENGTH: 112
<212> TYPE: PRT
<213> ORGANISM: Homo sapiens
<220> FEATURE:
<223> OTHER INFORMATION: Antibody 13

<400> SEQUENCE: 127

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
                20                  25                  30

Tyr Asp Val His Trp Tyr Gln Gln Leu Pro Gly Thr Ala Pro Lys Leu
            35                  40                  45

Leu Ile Tyr Asp Asn Phe Asn Arg Pro Ser Gly Val Pro Asp Arg Phe
        50                  55                  60

Ser Gly Ser Lys Ser Gly Thr Ser Ala Ser Leu Ala Ile Ile Gly Leu
65                  70                  75                  80

Gln Thr Glu Asp Glu Ala Asp Tyr Tyr Cys Gln Ser Tyr Asp Ser Asn
                85                  90                  95

Ile Leu Tyr Ser Pro Phe Gly Thr Gly Thr Lys Leu Thr Val Leu Gly
            100                 105                 110

<210> SEQ ID NO 128
<211> LENGTH: 14
<212> TYPE: PRT
<213> ORGANISM: Homo sapiens
<220> FEATURE:

<223> OTHER INFORMATION: Antibody 13

<400> SEQUENCE: 128

Thr Gly Ser Ser Ser Asn Ile Gly Ala Gly Tyr Asp Val His
1               5                   10

<210> SEQ ID NO 129
<211> LENGTH: 7
<212> TYPE: PRT
<213> ORGANISM: Homo sapiens
<220> FEATURE:
<223> OTHER INFORMATION: Antibody 13

<400> SEQUENCE: 129

Asp Asn Phe Asn Arg Pro Ser
1               5

<210> SEQ ID NO 130
<211> LENGTH: 11
<212> TYPE: PRT
<213> ORGANISM: Homo sapiens
<220> FEATURE:
<223> OTHER INFORMATION: Antibody 13

<400> SEQUENCE: 130

Gln Ser Tyr Asp Ser Asn Ile Leu Tyr Ser Pro
1               5                   10

<210> SEQ ID NO 131
<211> LENGTH: 363
<212> TYPE: DNA
<213> ORGANISM: Homo sapiens
<220> FEATURE:
<223> OTHER INFORMATION: Antibody 14

<400> SEQUENCE: 131
caggtccagc tggtgcagtc tggggctgag gtgaagaaac ctggggccac agtgaaactc      60
tcctgcaagg tttatggata catttttcacc gactacaaca tttactgggt gcgccaggcc     120
cctggaaaag gcttgagtg gatgggactt attgatcctg acaatggtga gacattttac     180
gcagagaagt tccagggcag agccaccatg accgcggaca cgtcttcaga cagagcctac     240
atggaattga ccagcctgac ctttgaggac acggccactt attattgtgc aacagtgatg     300
gggaagtgga tcaaggggggg ctatgactac tggggccggg gcaccctggt caccgtctcg     360
agt                                                                    363

<210> SEQ ID NO 132
<211> LENGTH: 121
<212> TYPE: PRT
<213> ORGANISM: Homo sapiens
<220> FEATURE:
<223> OTHER INFORMATION: Antibody 14

<400> SEQUENCE: 132

Gln Val Gln Leu Val Gln Ser Gly Ala Glu Val Lys Lys Pro Gly Ala
1               5                   10                  15

Thr Val Lys Leu Ser Cys Lys Val Tyr Gly Tyr Ile Phe Thr Asp Tyr
                20                  25                  30

Asn Ile Tyr Trp Val Arg Gln Ala Pro Gly Lys Gly Leu Glu Trp Met
            35                  40                  45

Gly Leu Ile Asp Pro Asp Asn Gly Glu Thr Phe Tyr Ala Glu Lys Phe
        50                  55                  60

Gln Gly Arg Ala Thr Met Thr Ala Asp Thr Ser Ser Asp Arg Ala Tyr

```
                65                  70                  75                  80
Met Glu Leu Thr Ser Leu Thr Phe Glu Asp Thr Ala Thr Tyr Tyr Cys
                        85                  90                  95
Ala Thr Val Met Gly Lys Trp Ile Lys Gly Gly Tyr Asp Tyr Trp Gly
                    100                 105                 110
Arg Gly Thr Leu Val Thr Val Ser Ser
            115                 120

<210> SEQ ID NO 133
<211> LENGTH: 5
<212> TYPE: PRT
<213> ORGANISM: Homo sapiens
<220> FEATURE:
<223> OTHER INFORMATION: Antibody 14

<400> SEQUENCE: 133

Asp Tyr Asn Ile Tyr
1               5

<210> SEQ ID NO 134
<211> LENGTH: 17
<212> TYPE: PRT
<213> ORGANISM: Homo sapiens
<220> FEATURE:
<223> OTHER INFORMATION: Antibody 14

<400> SEQUENCE: 134

Leu Ile Asp Pro Asp Asn Gly Glu Thr Phe Tyr Ala Glu Lys Phe Gln
1               5                   10                  15
Gly

<210> SEQ ID NO 135
<211> LENGTH: 12
<212> TYPE: PRT
<213> ORGANISM: Homo sapiens
<220> FEATURE:
<223> OTHER INFORMATION: Antibody 14

<400> SEQUENCE: 135

Val Met Gly Lys Trp Ile Lys Gly Gly Tyr Asp Tyr
1               5                   10

<210> SEQ ID NO 136
<211> LENGTH: 336
<212> TYPE: DNA
<213> ORGANISM: Homo sapiens
<220> FEATURE:
<223> OTHER INFORMATION: Antibody 14

<400> SEQUENCE: 136
cagtctgtgc tgacgcagcc gccctcagtg tctggggccc cagggcagag ggtcaccatc      60
tcctgcactg ggagcagctc caacatcggg gcaggttatg atgtacactg gtatcagcaa     120
cttccaggaa cagcccccaa actcctcatc tatgataatt caatcggcc ctcaggggtc      180 cctgaccgat tctctggctc caagtctggc acctcagcct ccctggccat cattgggctc     240
cagactgaag atgaggctga ttattattgc cagtcctatg acagccacca ccgccactcc     300
cccttcggaa ccgggaccaa gctgaccgtc ctaggt                              336

<210> SEQ ID NO 137
<211> LENGTH: 112
<212> TYPE: PRT
<213> ORGANISM: Homo sapiens
<220> FEATURE:
```

<223> OTHER INFORMATION: Antibody 14

<400> SEQUENCE: 137

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Asp Asn Phe Asn Arg Pro Ser Gly Val Pro Asp Arg Phe
    50                  55                  60

Ser Gly Ser Lys Ser Gly Thr Ser Ala Ser Leu Ala Ile Ile Gly Leu
65                  70                  75                  80

Gln Thr Glu Asp Glu Ala Asp Tyr Tyr Cys Gln Ser Tyr Asp Ser His
                85                  90                  95

His Arg His Ser Pro Phe Gly Thr Gly Thr Lys Leu Thr Val Leu Gly
            100                 105                 110

<210> SEQ ID NO 138
<211> LENGTH: 14
<212> TYPE: PRT
<213> ORGANISM: Homo sapiens
<220> FEATURE:
<223> OTHER INFORMATION: Antibody 14

<400> SEQUENCE: 138

Thr Gly Ser Ser Asn Ile Gly Ala Gly Tyr Asp Val His
1               5                   10

<210> SEQ ID NO 139
<211> LENGTH: 7
<212> TYPE: PRT
<213> ORGANISM: Homo sapiens
<220> FEATURE:
<223> OTHER INFORMATION: Antibody 14

<400> SEQUENCE: 139

Asp Asn Phe Asn Arg Pro Ser
1               5

<210> SEQ ID NO 140
<211> LENGTH: 11
<212> TYPE: PRT
<213> ORGANISM: Homo sapiens
<220> FEATURE:
<223> OTHER INFORMATION: Antibody 14

<400> SEQUENCE: 140

Gln Ser Tyr Asp Ser His His Arg His Ser Pro
1               5                   10

<210> SEQ ID NO 141
<211> LENGTH: 363
<212> TYPE: DNA
<213> ORGANISM: Homo sapiens
<220> FEATURE:
<223> OTHER INFORMATION: Antibody 15

<400> SEQUENCE: 141
caggtccagc tggtgcagtc tggggctgag gtgaagaagc ctggggccac agtgaaactc      60
tcctgcaagg tttatggata cattttcacc gactacaaca tttactgggt gcgccaggcc     120
cctggaaaag ggcttgagtg gatgggactt attgatcctg acaatggtga gacattttac     180

```
gcagagaagt tccagggcag agccaccatg accgcggaca cgtcttcaga cagagcctac    240
atggaattga ccagcctgac ctttgaggac acggccactt attattgtgc aacagtgacc    300
ttgaagaccg cgaaggggggg ctatgactac tggggccggg gcaccctggt caccgtctcg    360
agt                                                                  363
```

```
<210> SEQ ID NO 142
<211> LENGTH: 121
<212> TYPE: PRT
<213> ORGANISM: Homo sapiens
<220> FEATURE:
<223> OTHER INFORMATION: Antibody 15

<400> SEQUENCE: 142
```

Gln Val Gln Leu Val Gln Ser Gly Ala Glu Val Lys Lys Pro Gly Ala
1               5                   10                  15

Thr Val Lys Leu Ser Cys Lys Val Tyr Gly Tyr Ile Phe Thr Asp Tyr
            20                  25                  30

Asn Ile Tyr Trp Val Arg Gln Ala Pro Gly Lys Gly Leu Glu Trp Met
        35                  40                  45

Gly Leu Ile Asp Pro Asp Asn Gly Glu Thr Phe Tyr Ala Glu Lys Phe
    50                  55                  60

Gln Gly Arg Ala Thr Met Thr Ala Asp Thr Ser Ser Asp Arg Ala Tyr
65                  70                  75                  80

Met Glu Leu Thr Ser Leu Thr Phe Glu Asp Thr Ala Thr Tyr Tyr Cys
                85                  90                  95

Ala Thr Val Thr Leu Lys Thr Ala Lys Gly Gly Tyr Asp Tyr Trp Gly
            100                 105                 110

Arg Gly Thr Leu Val Thr Val Ser Ser
        115                 120

```
<210> SEQ ID NO 143
<211> LENGTH: 5
<212> TYPE: PRT
<213> ORGANISM: Homo sapiens
<220> FEATURE:
<223> OTHER INFORMATION: Antibody 15

<400> SEQUENCE: 143
```

Asp Tyr Asn Ile Tyr
1               5

```
<210> SEQ ID NO 144
<211> LENGTH: 17
<212> TYPE: PRT
<213> ORGANISM: Homo sapiens
<220> FEATURE:
<223> OTHER INFORMATION: Antibody 15

<400> SEQUENCE: 144
```

Leu Ile Asp Pro Asp Asn Gly Glu Thr Phe Tyr Ala Glu Lys Phe Gln
1               5                   10                  15

Gly

```
<210> SEQ ID NO 145
<211> LENGTH: 12
<212> TYPE: PRT
<213> ORGANISM: Homo sapiens
<220> FEATURE:
<223> OTHER INFORMATION: Antibody 15

<400> SEQUENCE: 145
```

Val Thr Leu Lys Thr Ala Lys Gly Gly Tyr Asp Tyr
1               5                   10

<210> SEQ ID NO 146
<211> LENGTH: 336
<212> TYPE: DNA
<213> ORGANISM: Homo sapiens
<220> FEATURE:
<223> OTHER INFORMATION: Antibody 15

<400> SEQUENCE: 146
cagtctgtgc tgacgcagcc gccctcagtg tctggggccc cagggcagag ggtcaccatc      60
tcctgcactg ggagcagctc caacatcggg gcaggttatg atgtacactg gtatcagcaa     120
cttccaggaa cagcccccaa actcctcatc tatgataatt tcaatcgccc ctcaggggtc     180
cctgaccgat tctctggctc caagtctggc acctcagcct ccctggccat cattgggctc     240
cagactgaag atgaggctga ttattattgc cagtcctatg acagccacaa ggggtacggg     300
gggttcggaa ccgggaccaa gctgaccgtc ctaggt                               336

<210> SEQ ID NO 147
<211> LENGTH: 112
<212> TYPE: PRT
<213> ORGANISM: Homo sapiens
<220> FEATURE:
<223> OTHER INFORMATION: Antibody 15

<400> SEQUENCE: 147

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Asp Asn Phe Asn Arg Pro Ser Gly Val Pro Asp Arg Phe
    50                  55                  60

Ser Gly Ser Lys Ser Gly Thr Ser Ala Ser Leu Ala Ile Ile Gly Leu
65                  70                  75                  80

Gln Thr Glu Asp Glu Ala Asp Tyr Tyr Cys Gln Ser Tyr Asp Ser His
                85                  90                  95

Lys Gly Tyr Gly Gly Phe Gly Thr Gly Thr Lys Leu Thr Val Leu Gly
            100                 105                 110

<210> SEQ ID NO 148
<211> LENGTH: 14
<212> TYPE: PRT
<213> ORGANISM: Homo sapiens
<220> FEATURE:
<223> OTHER INFORMATION: Antibody 15

<400> SEQUENCE: 148

Thr Gly Ser Ser Ser Asn Ile Gly Ala Gly Tyr Asp Val His
1               5                   10

<210> SEQ ID NO 149
<211> LENGTH: 7
<212> TYPE: PRT
<213> ORGANISM: Homo sapiens
<220> FEATURE:
<223> OTHER INFORMATION: Antibody 15

<400> SEQUENCE: 149

Asp Asn Phe Asn Arg Pro Ser
1               5

<210> SEQ ID NO 150
<211> LENGTH: 11
<212> TYPE: PRT
<213> ORGANISM: Homo sapiens
<220> FEATURE:
<223> OTHER INFORMATION: Antibody 15

<400> SEQUENCE: 150

Gln Ser Tyr Asp Ser His Lys Gly Tyr Gly Gly
1               5                   10

<210> SEQ ID NO 151
<211> LENGTH: 363
<212> TYPE: DNA
<213> ORGANISM: Homo sapiens
<220> FEATURE:
<223> OTHER INFORMATION: Antibody 16

<400> SEQUENCE: 151
caggtccagc tggtgcagtc tggggctgag gtgaagaaac ctggggccac agtgaaactc     60
tcctgcaagg tttatggata cattttcacc gactacaaca tttactgggt gcgccaggcc    120
cctggaaaag gcttgagtg gatgggactt attgatcctg acaatggtga cattttac       180 gcagagaagt tccagggcag agccaccatg accgcggaca cgtcttcaga cagagcctac    240
atggaattga ccagcctgac ctttgaggac acggccactt attattgtgc aacagtgagc    300
ctcaagagcg cgaaggggg ctatgactac tggggccggg gcaccctggt caccgtctcg    360
agt                                                                  363

<210> SEQ ID NO 152
<211> LENGTH: 121
<212> TYPE: PRT
<213> ORGANISM: Homo sapiens
<220> FEATURE:
<223> OTHER INFORMATION: Antibody 16

<400> SEQUENCE: 152

Gln Val Gln Leu Val Gln Ser Gly Ala Glu Val Lys Lys Pro Gly Ala
1               5                   10                  15

Thr Val Lys Leu Ser Cys Lys Val Tyr Gly Tyr Ile Phe Thr Asp Tyr
                20                  25                  30

Asn Ile Tyr Trp Val Arg Gln Ala Pro Gly Lys Gly Leu Glu Trp Met
            35                  40                  45

Gly Leu Ile Asp Pro Asp Asn Gly Glu Thr Phe Tyr Ala Glu Lys Phe
        50                  55                  60

Gln Gly Arg Ala Thr Met Thr Ala Asp Thr Ser Ser Asp Arg Ala Tyr
65                  70                  75                  80

Met Glu Leu Thr Ser Leu Thr Phe Glu Asp Thr Ala Thr Tyr Tyr Cys
                85                  90                  95

Ala Thr Val Ser Leu Lys Ser Ala Lys Gly Gly Tyr Asp Tyr Trp Gly
                100                 105                 110

Arg Gly Thr Leu Val Thr Val Ser Ser
            115                 120

<210> SEQ ID NO 153
<211> LENGTH: 5
<212> TYPE: PRT
<213> ORGANISM: Homo sapiens
<220> FEATURE:
<223> OTHER INFORMATION: Antibody 16

-continued

```
<400> SEQUENCE: 153

Asp Tyr Asn Ile Tyr
1               5

<210> SEQ ID NO 154
<211> LENGTH: 17
<212> TYPE: PRT
<213> ORGANISM: Homo sapiens
<220> FEATURE:
<223> OTHER INFORMATION: Antibody 16

<400> SEQUENCE: 154

Leu Ile Asp Pro Asp Asn Gly Glu Thr Phe Tyr Ala Glu Lys Phe Gln
1               5                   10                  15

Gly

<210> SEQ ID NO 155
<211> LENGTH: 12
<212> TYPE: PRT
<213> ORGANISM: Homo sapiens
<220> FEATURE:
<223> OTHER INFORMATION: Antibody 16

<400> SEQUENCE: 155

Val Ser Leu Lys Ser Ala Lys Gly Gly Tyr Asp Tyr
1               5                   10

<210> SEQ ID NO 156
<211> LENGTH: 336
<212> TYPE: DNA
<213> ORGANISM: Homo sapiens
<220> FEATURE:
<223> OTHER INFORMATION: Antibody 16

<400> SEQUENCE: 156
cagtctgtgc tgacgcagcc gccctcagtg tctggggccc cagggcagag ggtcaccatc        60
tcctgcactg ggagcagctc caacatcggg gcaggttatg atgtacactg gtatcagcaa       120
cttccaggaa cagcccccaa actcctcatc tatgataatt tcaatcggcc ctcaggggtc       180
cctgaccgat tctctggctc caagtctggc acctcagcct ccctggccat cattgggctc       240
cagactgaag atgaggctga ttattattgc cagtcctatg acagccgcca ccaccacgcg       300
ccgttcggaa ccgggaccaa gctgaccgtc ctaggt                                 336

<210> SEQ ID NO 157
<211> LENGTH: 112
<212> TYPE: PRT
<213> ORGANISM: Homo sapiens
<220> FEATURE:
<223> OTHER INFORMATION: Antibody 16

<400> SEQUENCE: 157

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Asp Asn Phe Asn Arg Pro Ser Gly Val Pro Asp Arg Phe
    50                  55                  60

Ser Gly Ser Lys Ser Gly Thr Ser Ala Ser Leu Ala Ile Ile Gly Leu
65                  70                  75                  80
```

Gln Thr Glu Asp Glu Ala Asp Tyr Tyr Cys Gln Ser Tyr Asp Ser Arg
            85                  90                  95

His His His Ala Pro Phe Gly Thr Gly Thr Lys Leu Thr Val Leu Gly
            100                 105                 110

<210> SEQ ID NO 158
<211> LENGTH: 14
<212> TYPE: PRT
<213> ORGANISM: Homo sapiens
<220> FEATURE:
<223> OTHER INFORMATION: Antibody 16

<400> SEQUENCE: 158

Thr Gly Ser Ser Ser Asn Ile Gly Ala Gly Tyr Asp Val His
1               5                   10

<210> SEQ ID NO 159
<211> LENGTH: 7
<212> TYPE: PRT
<213> ORGANISM: Homo sapiens
<220> FEATURE:
<223> OTHER INFORMATION: Antibody 16

<400> SEQUENCE: 159

Asp Asn Phe Asn Arg Pro Ser
1               5

<210> SEQ ID NO 160
<211> LENGTH: 11
<212> TYPE: PRT
<213> ORGANISM: Homo sapiens
<220> FEATURE:
<223> OTHER INFORMATION: Antibody 16

<400> SEQUENCE: 160

Gln Ser Tyr Asp Ser Arg His His His Ala Pro
1               5                   10

<210> SEQ ID NO 161
<211> LENGTH: 363
<212> TYPE: DNA
<213> ORGANISM: Homo sapiens
<220> FEATURE:
<223> OTHER INFORMATION: Antibody 17

<400> SEQUENCE: 161
caggtccagc tggtgcagtc tggggctgag gtgaagaaac ctggggccac agtgaaactc      60
tcctgcaagg tttatggata cattttcacc gactacaaca tttactgggt gcgccaggcc    120
cctggaaaag gcttgagtg gatgggactt attgatcctg acaatggtga gacattttac    180
gcagagaagt tccagggcag agccaccatg accgcggaca cgtcttcaga cagagcctac    240
atggaattga ccagcctgac ctttgaggac acgccactt attattgtgc aacagtcacg    300
ttgaagagcg cgaaggggg ctatgactac tggggccggg gcaccctggt caccgtctcg    360
agt                                                                  363

<210> SEQ ID NO 162
<211> LENGTH: 121
<212> TYPE: PRT
<213> ORGANISM: Homo sapiens
<220> FEATURE:
<223> OTHER INFORMATION: Antibody 17

<400> SEQUENCE: 162

```
Gln Val Gln Leu Val Gln Ser Gly Ala Glu Val Lys Pro Gly Ala
1               5                   10                  15

Thr Val Lys Leu Ser Cys Lys Val Gly Tyr Ile Phe Thr Asp Tyr
            20                  25                  30

Asn Ile Tyr Trp Val Arg Gln Ala Pro Gly Lys Gly Leu Glu Trp Met
        35                  40                  45

Gly Leu Ile Asp Pro Asp Asn Gly Glu Thr Phe Tyr Ala Glu Lys Phe
    50                  55                  60

Gln Gly Arg Ala Thr Met Thr Ala Asp Thr Ser Ser Asp Arg Ala Tyr
65                  70                  75                  80

Met Glu Leu Thr Ser Leu Thr Phe Glu Asp Thr Ala Tyr Tyr Cys
                85                  90                  95

Ala Thr Val Thr Leu Lys Ser Ala Lys Gly Gly Tyr Asp Tyr Trp Gly
            100                 105                 110

Arg Gly Thr Leu Val Thr Val Ser Ser
        115                 120

<210> SEQ ID NO 163
<211> LENGTH: 5
<212> TYPE: PRT
<213> ORGANISM: Homo sapiens
<220> FEATURE:
<223> OTHER INFORMATION: Antibody 17

<400> SEQUENCE: 163

Asp Tyr Asn Ile Tyr
1               5

<210> SEQ ID NO 164
<211> LENGTH: 17
<212> TYPE: PRT
<213> ORGANISM: Homo sapiens
<220> FEATURE:
<223> OTHER INFORMATION: Antibody 17

<400> SEQUENCE: 164

Leu Ile Asp Pro Asp Asn Gly Glu Thr Phe Tyr Ala Glu Lys Phe Gln
1               5                   10                  15

Gly

<210> SEQ ID NO 165
<211> LENGTH: 12
<212> TYPE: PRT
<213> ORGANISM: Homo sapiens
<220> FEATURE:
<223> OTHER INFORMATION: Antibody 17

<400> SEQUENCE: 165

Val Thr Leu Lys Ser Ala Lys Gly Gly Tyr Asp Tyr
1               5                   10

<210> SEQ ID NO 166
<211> LENGTH: 336
<212> TYPE: DNA
<213> ORGANISM: Homo sapiens
<220> FEATURE:
<223> OTHER INFORMATION: Antibody 17

<400> SEQUENCE: 166
cagtctgtgc tgacgcagcc gccctcagtg tctggggccc cagggcagag ggtcaccatc      60
tcctgcactg ggagcagctc caacatcggg gcaggttatg atgtacactg gtatcagcaa     120
cttccaggaa cagccccaa actcctcatc tatgataatt caatcggcc ctcagggggtc     180
```

```
cctgaccgat tctctggctc caagtctggc acctcagcct ccctggccat cattgggctc    240
cagactgaag atgaggctga ttattattgc cagtcctatg acagccagag ctccacctcc    300
cccttcggaa ccgggaccaa gctgaccgtc ctaggt                              336
```

<210> SEQ ID NO 167
<211> LENGTH: 112
<212> TYPE: PRT
<213> ORGANISM: Homo sapiens
<220> FEATURE:
<223> OTHER INFORMATION: Antibody 17

<400> SEQUENCE: 167

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
                20                  25                  30

Tyr Asp Val His Trp Tyr Gln Gln Leu Pro Gly Thr Ala Pro Lys Leu
            35                  40                  45

Leu Ile Tyr Asp Asn Phe Asn Arg Pro Ser Gly Val Pro Asp Arg Phe
        50                  55                  60

Ser Gly Ser Lys Ser Gly Thr Ser Ala Ser Leu Ala Ile Ile Gly Leu
65                  70                  75                  80

Gln Thr Glu Asp Glu Ala Asp Tyr Tyr Cys Gln Ser Tyr Asp Ser Gln
                85                  90                  95

Ser Ser Thr Ser Pro Phe Gly Thr Gly Thr Lys Leu Thr Val Leu Gly
            100                 105                 110
```

<210> SEQ ID NO 168
<211> LENGTH: 14
<212> TYPE: PRT
<213> ORGANISM: Homo sapiens
<220> FEATURE:
<223> OTHER INFORMATION: Antibody 17

<400> SEQUENCE: 168

```
Thr Gly Ser Ser Ser Asn Ile Gly Ala Gly Tyr Asp Val His
1               5                   10
```

<210> SEQ ID NO 169
<211> LENGTH: 7
<212> TYPE: PRT
<213> ORGANISM: Homo sapiens
<220> FEATURE:
<223> OTHER INFORMATION: Antibody 17

<400> SEQUENCE: 169

```
Asp Asn Phe Asn Arg Pro Ser
1               5
```

<210> SEQ ID NO 170
<211> LENGTH: 11
<212> TYPE: PRT
<213> ORGANISM: Homo sapiens
<220> FEATURE:
<223> OTHER INFORMATION: Antibody 17

<400> SEQUENCE: 170

```
Gln Ser Tyr Asp Ser Gln Ser Ser Thr Ser Pro
1               5                   10
```

<210> SEQ ID NO 171
<211> LENGTH: 363

```
<212> TYPE: DNA
<213> ORGANISM: Homo sapiens
<220> FEATURE:
<223> OTHER INFORMATION: Antibody 18

<400> SEQUENCE: 171
caggtccagc tggtgcagtc tggggctgag gtgaagaaac ctggggccac agtgaaactc      60
tcctgcaagg tttatggata cattttcacc gactacaaca tttactgggt gcgccaggcc     120
cctggaaaag ggcttgagtg gatgggactt attgatcctg acaatggtga acatttttac     180
gcagagaagt tccagggcag agccaccatg accgcggaca cgtcttcaga cagagcctac     240
atggaattga ccagcctgac ctttgaggac acggccactt attattgtgc aacagtgctc     300
ctgcgcagcg cgaaggggg ctatgactac tggggccggg gcaccctggt caccgtctcg      360
agt                                                                   363

<210> SEQ ID NO 172
<211> LENGTH: 121
<212> TYPE: PRT
<213> ORGANISM: Homo sapiens
<220> FEATURE:
<223> OTHER INFORMATION: Antibody 18

<400> SEQUENCE: 172

Gln Val Gln Leu Val Gln Ser Gly Ala Glu Val Lys Lys Pro Gly Ala
1               5                   10                  15

Thr Val Lys Leu Ser Cys Lys Val Tyr Gly Tyr Ile Phe Thr Asp Tyr
            20                  25                  30

Asn Ile Tyr Trp Val Arg Gln Ala Pro Gly Lys Gly Leu Glu Trp Met
        35                  40                  45

Gly Leu Ile Asp Pro Asp Asn Gly Glu Thr Phe Tyr Ala Glu Lys Phe
    50                  55                  60

Gln Gly Arg Ala Thr Met Thr Ala Asp Thr Ser Ser Asp Arg Ala Tyr
65                  70                  75                  80

Met Glu Leu Thr Ser Leu Thr Phe Glu Asp Thr Ala Thr Tyr Tyr Cys
                85                  90                  95

Ala Thr Val Leu Leu Arg Ser Ala Lys Gly Gly Tyr Asp Tyr Trp Gly
            100                 105                 110

Arg Gly Thr Leu Val Thr Val Ser Ser
        115                 120

<210> SEQ ID NO 173
<211> LENGTH: 5
<212> TYPE: PRT
<213> ORGANISM: Homo sapiens
<220> FEATURE:
<223> OTHER INFORMATION: Antibody 18

<400> SEQUENCE: 173

Asp Tyr Asn Ile Tyr
1               5

<210> SEQ ID NO 174
<211> LENGTH: 17
<212> TYPE: PRT
<213> ORGANISM: Homo sapiens
<220> FEATURE:
<223> OTHER INFORMATION: Antibody 18

<400> SEQUENCE: 174

Leu Ile Asp Pro Asp Asn Gly Glu Thr Phe Tyr Ala Glu Lys Phe Gln
1               5                   10                  15
```

Gly

<210> SEQ ID NO 175
<211> LENGTH: 12
<212> TYPE: PRT
<213> ORGANISM: Homo sapiens
<220> FEATURE:
<223> OTHER INFORMATION: Antibody 18

<400> SEQUENCE: 175

Val Leu Leu Arg Ser Ala Lys Gly Gly Tyr Asp Tyr
1               5                   10

<210> SEQ ID NO 176
<211> LENGTH: 336
<212> TYPE: DNA
<213> ORGANISM: Homo sapiens
<220> FEATURE:
<223> OTHER INFORMATION: Antibody 18

<400> SEQUENCE: 176
cagtctgtgc tgacgcagcc gccctcagtg tctggggccc cagggcagag ggtcaccatc        60
tcctgcactg ggagcagctc caacatcggg gcaggttatg atgtacactg gtatcagcaa       120
cttccaggaa cagccccaaa actcctcatc tatgataatt tcaatcggcc ctcaggggtc       180
cctgaccgat tctctggctc caagtctggc acctcagcct ccctggccat cattgggctc       240
cagactgaag atgaggctga ttattattgc cagtcctatg acagccacct ccagttgagc       300
ccgttcggaa ccgggaccaa gctgaccgtc ctaggt                                  336

<210> SEQ ID NO 177
<211> LENGTH: 112
<212> TYPE: PRT
<213> ORGANISM: Homo sapiens
<220> FEATURE:
<223> OTHER INFORMATION: Antibody 18

<400> SEQUENCE: 177

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Asp Asn Phe Asn Arg Pro Ser Gly Val Pro Asp Arg Phe
    50                  55                  60

Ser Gly Ser Lys Ser Gly Thr Ser Ala Ser Leu Ala Ile Ile Gly Leu
65                  70                  75                  80

Gln Thr Glu Asp Glu Ala Asp Tyr Tyr Cys Gln Ser Tyr Asp Ser His
                85                  90                  95

Leu Gln Leu Ser Pro Phe Gly Thr Gly Thr Lys Leu Thr Val Leu Gly
            100                 105                 110

<210> SEQ ID NO 178
<211> LENGTH: 14
<212> TYPE: PRT
<213> ORGANISM: Homo sapiens
<220> FEATURE:
<223> OTHER INFORMATION: Antibody 18

<400> SEQUENCE: 178

Thr Gly Ser Ser Ser Asn Ile Gly Ala Gly Tyr Asp Val His

<210> SEQ ID NO 179
<211> LENGTH: 7
<212> TYPE: PRT
<213> ORGANISM: Homo sapiens
<220> FEATURE:
<223> OTHER INFORMATION: Antibody 18

<400> SEQUENCE: 179

Asp Asn Phe Asn Arg Pro Ser
1               5

<210> SEQ ID NO 180
<211> LENGTH: 11
<212> TYPE: PRT
<213> ORGANISM: Homo sapiens
<220> FEATURE:
<223> OTHER INFORMATION: Antibody 18

<400> SEQUENCE: 180

Gln Ser Tyr Asp Ser His Leu Gln Leu Ser Pro
1               5                   10

<210> SEQ ID NO 181
<211> LENGTH: 363
<212> TYPE: DNA
<213> ORGANISM: Homo sapiens
<220> FEATURE:
<223> OTHER INFORMATION: Antibody 19

<400> SEQUENCE: 181
caggtccagc tggtgcagtc tggggctgag gtgaagaaac ctggggccac agtgaaactc      60
tcctgcaagg tttatggata catttttcacc gactacaaca tttactgggt gcgccaggcc     120
cctggaaaag ggcttgagtg gatgggactt attgatcctg acaatggtga gacattttac     180
gcagagaagt tccagggcag agccaccatg accgcggaca cgtcttcaga cagagcctac     240
atggaattga ccagcctgac ctttgaggac acggccactt attattgtgc aacagtgatg     300
gggaagtgga tcaaggggggg ctatgactac tggggccggg gcaccctggt caccgtctcg     360
agt                                                                    363

<210> SEQ ID NO 182
<211> LENGTH: 121
<212> TYPE: PRT
<213> ORGANISM: Homo sapiens
<220> FEATURE:
<223> OTHER INFORMATION: Antibody 19

<400> SEQUENCE: 182

Gln Val Gln Leu Val Gln Ser Gly Ala Glu Val Lys Lys Pro Gly Ala
1               5                   10                  15

Thr Val Lys Leu Ser Cys Lys Val Tyr Gly Tyr Ile Phe Thr Asp Tyr
            20                  25                  30

Asn Ile Tyr Trp Val Arg Gln Ala Pro Gly Lys Gly Leu Glu Trp Met
        35                  40                  45

Gly Leu Ile Asp Pro Asp Asn Gly Glu Thr Phe Tyr Ala Glu Lys Phe
    50                  55                  60

Gln Gly Arg Ala Thr Met Thr Ala Asp Thr Ser Ser Asp Arg Ala Tyr
65                  70                  75                  80

Met Glu Leu Thr Ser Leu Thr Phe Glu Asp Thr Ala Thr Tyr Tyr Cys
                85                  90                  95

Ala Thr Val Met Gly Lys Trp Ile Lys Gly Gly Tyr Asp Tyr Trp Gly
            100                 105                 110

Arg Gly Thr Leu Val Thr Val Ser Ser
        115                 120

<210> SEQ ID NO 183
<211> LENGTH: 5
<212> TYPE: PRT
<213> ORGANISM: Homo sapiens
<220> FEATURE:
<223> OTHER INFORMATION: Antibody 19

<400> SEQUENCE: 183

Asp Tyr Asn Ile Tyr
1               5

<210> SEQ ID NO 184
<211> LENGTH: 17
<212> TYPE: PRT
<213> ORGANISM: Homo sapiens
<220> FEATURE:
<223> OTHER INFORMATION: Antibody 19

<400> SEQUENCE: 184

Leu Ile Asp Pro Asp Asn Gly Glu Thr Phe Tyr Ala Glu Lys Phe Gln
1               5                   10                  15

Gly

<210> SEQ ID NO 185
<211> LENGTH: 12
<212> TYPE: PRT
<213> ORGANISM: Homo sapiens
<220> FEATURE:
<223> OTHER INFORMATION: Antibody 19

<400> SEQUENCE: 185

Val Met Gly Lys Trp Ile Lys Gly Gly Tyr Asp Tyr
1               5                   10

<210> SEQ ID NO 186
<211> LENGTH: 336
<212> TYPE: DNA
<213> ORGANISM: Homo sapiens
<220> FEATURE:
<223> OTHER INFORMATION: Antibody 19

<400> SEQUENCE: 186
cagtctgtgc tgacgcagcc gccctcagtg tctggggccc cagggcagag ggtcaccatc      60
tcctgcactg ggagcagctc caacatcggg gcaggttatg atgtacactg gtatcagcaa     120
cttccaggaa cagcccccaa actcctcatc tatgataatt caatcggcc ctcagggtc      180 cctgaccgat tctctggctc caagtctggc acctcagcct ccctggccat cattgggctc     240
cagactgaag atgaggctga ttattattgc cagtcctatg acagcacgtt gtcccactcc     300
cccttcggaa ccgggaccaa gctgaccgtc ctaggt                               336

<210> SEQ ID NO 187
<211> LENGTH: 112
<212> TYPE: PRT
<213> ORGANISM: Homo sapiens
<220> FEATURE:
<223> OTHER INFORMATION: Antibody 19

<400> SEQUENCE: 187

Gln Ser Val Leu Thr Gln Pro Pro Ser Val Ser Gly Ala Pro Gly Gln

```
                1               5                  10                 15
Arg Val Thr Ile Ser Cys Thr Gly Ser Ser Asn Ile Gly Ala Gly
                    20                  25                  30

Tyr Asp Val His Trp Tyr Gln Gln Leu Pro Gly Thr Ala Pro Lys Leu
            35                  40                  45

Leu Ile Tyr Asp Asn Phe Asn Arg Pro Ser Gly Val Pro Asp Arg Phe
        50                  55                  60

Ser Gly Ser Lys Ser Gly Thr Ser Ala Ser Leu Ala Ile Ile Gly Leu
65                  70                  75                  80

Gln Thr Glu Asp Glu Ala Asp Tyr Tyr Cys Gln Ser Tyr Asp Ser Thr
                85                  90                  95

Leu Ser His Ser Pro Phe Gly Thr Gly Thr Lys Leu Thr Val Leu Gly
            100                 105                 110
```

<210> SEQ ID NO 188
<211> LENGTH: 14
<212> TYPE: PRT
<213> ORGANISM: Homo sapiens
<220> FEATURE:
<223> OTHER INFORMATION: Antibody 19

<400> SEQUENCE: 188

```
Thr Gly Ser Ser Asn Ile Gly Ala Gly Tyr Asp Val His
1               5                   10
```

<210> SEQ ID NO 189
<211> LENGTH: 7
<212> TYPE: PRT
<213> ORGANISM: Homo sapiens
<220> FEATURE:
<223> OTHER INFORMATION: Antibody 19

<400> SEQUENCE: 189

```
Asp Asn Phe Asn Arg Pro Ser
1               5
```

<210> SEQ ID NO 190
<211> LENGTH: 11
<212> TYPE: PRT
<213> ORGANISM: Homo sapiens
<220> FEATURE:
<223> OTHER INFORMATION: Antibody 19

<400> SEQUENCE: 190

```
Gln Ser Tyr Asp Ser Thr Leu Ser His Ser Pro
1               5                   10
```

<210> SEQ ID NO 191
<211> LENGTH: 363
<212> TYPE: DNA
<213> ORGANISM: Homo sapiens
<220> FEATURE:
<223> OTHER INFORMATION: Antibody 20

<400> SEQUENCE: 191

```
caggtccagc tggtgcagtc tggggctgag gtgaagaaac ctggggccac agtgaaactc      60
tcctgcaagg tttatggata cattttcacc gactacaaca tttactgggt gcgccaggcc     120
cctggaaaag ggcttgagtg gatgggactt attgatcctg acaatggtga cattttttac     180
gcagagaagt tccagggcag agccaccatg accgcggaca cgtcttcaga cagagcctac     240
atggaattga ccagcctgac ctttgaggac acggccactt attattgtgc aacagtgatg     300
gggaagtgga tcaagggggg ctatgactac tggggccggg gcaccctggt caccgtctcg     360
``` agt                                                                                           363

<210> SEQ ID NO 192
<211> LENGTH: 121
<212> TYPE: PRT
<213> ORGANISM: Homo sapiens
<220> FEATURE:
<223> OTHER INFORMATION: Antibody 20

<400> SEQUENCE: 192

Gln Val Gln Leu Val Gln Ser Gly Ala Glu Val Lys Lys Pro Gly Ala
1               5                   10                  15

Thr Val Lys Leu Ser Cys Lys Val Tyr Gly Tyr Ile Phe Thr Asp Tyr
            20                  25                  30

Asn Ile Tyr Trp Val Arg Gln Ala Pro Gly Lys Gly Leu Glu Trp Met
        35                  40                  45

Gly Leu Ile Asp Pro Asp Asn Gly Glu Thr Phe Tyr Ala Glu Lys Phe
    50                  55                  60

Gln Gly Arg Ala Thr Met Thr Ala Asp Thr Ser Ser Asp Arg Ala Tyr
65                  70                  75                  80

Met Glu Leu Thr Ser Leu Thr Phe Glu Asp Thr Ala Tyr Tyr Cys
                85                  90                  95

Ala Thr Val Met Gly Lys Trp Ile Lys Gly Gly Tyr Asp Tyr Trp Gly
            100                 105                 110

Arg Gly Thr Leu Val Thr Val Ser Ser
        115                 120

<210> SEQ ID NO 193
<211> LENGTH: 5
<212> TYPE: PRT
<213> ORGANISM: Homo sapiens
<220> FEATURE:
<223> OTHER INFORMATION: Antibody 20

<400> SEQUENCE: 193

Asp Tyr Asn Ile Tyr
1               5

<210> SEQ ID NO 194
<211> LENGTH: 17
<212> TYPE: PRT
<213> ORGANISM: Homo sapiens
<220> FEATURE:
<223> OTHER INFORMATION: Antibody 20

<400> SEQUENCE: 194

Leu Ile Asp Pro Asp Asn Gly Glu Thr Phe Tyr Ala Glu Lys Phe Gln
1               5                   10                  15

Gly

<210> SEQ ID NO 195
<211> LENGTH: 12
<212> TYPE: PRT
<213> ORGANISM: Homo sapiens
<220> FEATURE:
<223> OTHER INFORMATION: Antibody 20

<400> SEQUENCE: 195

Val Met Gly Lys Trp Ile Lys Gly Gly Tyr Asp Tyr
1               5                   10

<210> SEQ ID NO 196

<211> LENGTH: 336
<212> TYPE: DNA
<213> ORGANISM: Homo sapiens
<220> FEATURE:
<223> OTHER INFORMATION: Antibody 20

<400> SEQUENCE: 196

```
cagtctgtgc tgacgcagcc gccctcagtg tctggggccc cagggcagag ggtcaccatc    60
tcctgcactg ggagcagctc caacatcggg gcaggttatg atgtacactg gtatcagcaa   120
cttccaggaa cagcccccaa actcctcatc tatgataatt tcaatcggcc ctcaggggtc   180
cctgaccgat tctctggctc caagtctggc acctcagcct ccctggccat cattgggctc   240
cagactgaag atgaggctga ttattattgc cagtcctatg acagctccac gtcctcctcc   300
cccttcggaa ccgggaccaa gctgaccgtc ctaggt                             336
```

<210> SEQ ID NO 197
<211> LENGTH: 112
<212> TYPE: PRT
<213> ORGANISM: Homo sapiens
<220> FEATURE:
<223> OTHER INFORMATION: Antibody 20

<400> SEQUENCE: 197

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Asp Asn Phe Asn Arg Pro Ser Gly Val Pro Asp Arg Phe
    50                  55                  60

Ser Gly Ser Lys Ser Gly Thr Ser Ala Ser Leu Ala Ile Ile Gly Leu
65                  70                  75                  80

Gln Thr Glu Asp Glu Ala Asp Tyr Tyr Cys Gln Ser Tyr Asp Ser Ser
                85                  90                  95

Thr Ser Ser Pro Phe Gly Thr Gly Thr Lys Leu Thr Val Leu Gly
            100                 105                 110

<210> SEQ ID NO 198
<211> LENGTH: 14
<212> TYPE: PRT
<213> ORGANISM: Homo sapiens
<220> FEATURE:
<223> OTHER INFORMATION: Antibody 20

<400> SEQUENCE: 198

Thr Gly Ser Ser Ser Asn Ile Gly Ala Gly Tyr Asp Val His
1               5                   10

<210> SEQ ID NO 199
<211> LENGTH: 7
<212> TYPE: PRT
<213> ORGANISM: Homo sapiens
<220> FEATURE:
<223> OTHER INFORMATION: Antibody 20

<400> SEQUENCE: 199

Asp Asn Phe Asn Arg Pro Ser
1               5

<210> SEQ ID NO 200
<211> LENGTH: 11

```
<212> TYPE: PRT
<213> ORGANISM: Homo sapiens
<220> FEATURE:
<223> OTHER INFORMATION: Antibody 20

<400> SEQUENCE: 200

Gln Ser Tyr Asp Ser Ser Thr Ser Ser Ser Pro
1               5                   10

<210> SEQ ID NO 201
<211> LENGTH: 363
<212> TYPE: DNA
<213> ORGANISM: Homo sapiens
<220> FEATURE:
<223> OTHER INFORMATION: Antibody 21

<400> SEQUENCE: 201
caggtccagc tggtgcagtc tggggctgag gtgaagaaac ctggggccac agtgaaactc     60
tcctgcaagg tttatggata cattttcacc gactacaaca tttactgggt gcgccaggcc    120
cctggaaaag gcttgagtg gatgggactt attgatcctg acaatggtga acatttttac    180
gcagagaagt tccagggcag agccaccatg accgcggaca cgtcttcaga cagagcctac    240
atggaattga ccagcctgac ctttgaggac acggccactt attattgtgc aacagtcacg    300
ttgaagagcg cgaaggggg ctatgactac tggggccggg gcaccctggt caccgtctcg    360
agt                                                                 363

<210> SEQ ID NO 202
<211> LENGTH: 121
<212> TYPE: PRT
<213> ORGANISM: Homo sapiens
<220> FEATURE:
<223> OTHER INFORMATION: Antibody 21

<400> SEQUENCE: 202

Gln Val Gln Leu Val Gln Ser Gly Ala Glu Val Lys Lys Pro Gly Ala
1               5                   10                  15

Thr Val Lys Leu Ser Cys Lys Val Tyr Gly Tyr Ile Phe Thr Asp Tyr
            20                  25                  30

Asn Ile Tyr Trp Val Arg Gln Ala Pro Gly Lys Gly Leu Glu Trp Met
        35                  40                  45

Gly Leu Ile Asp Pro Asp Asn Gly Glu Thr Phe Tyr Ala Glu Lys Phe
    50                  55                  60

Gln Gly Arg Ala Thr Met Thr Ala Asp Thr Ser Ser Asp Arg Ala Tyr
65                  70                  75                  80

Met Glu Leu Thr Ser Leu Thr Phe Glu Asp Thr Ala Thr Tyr Tyr Cys
                85                  90                  95

Ala Thr Val Thr Leu Lys Ser Ala Lys Gly Gly Tyr Asp Tyr Trp Gly
            100                 105                 110

Arg Gly Thr Leu Val Thr Val Ser Ser
        115                 120

<210> SEQ ID NO 203
<211> LENGTH: 5
<212> TYPE: PRT
<213> ORGANISM: Homo sapiens
<220> FEATURE:
<223> OTHER INFORMATION: Antibody 21

<400> SEQUENCE: 203

Asp Tyr Asn Ile Tyr
1               5
```

-continued

```
<210> SEQ ID NO 204
<211> LENGTH: 17
<212> TYPE: PRT
<213> ORGANISM: Homo sapiens
<220> FEATURE:
<223> OTHER INFORMATION: Antibody 21

<400> SEQUENCE: 204

Leu Ile Asp Pro Asp Asn Gly Glu Thr Phe Tyr Ala Glu Lys Phe Gln
1               5                   10                  15

Gly

<210> SEQ ID NO 205
<211> LENGTH: 12
<212> TYPE: PRT
<213> ORGANISM: Homo sapiens
<220> FEATURE:
<223> OTHER INFORMATION: Antibody 21

<400> SEQUENCE: 205

Val Thr Leu Lys Ser Ala Lys Gly Gly Tyr Asp Tyr
1               5                   10

<210> SEQ ID NO 206
<211> LENGTH: 336
<212> TYPE: DNA
<213> ORGANISM: Homo sapiens
<220> FEATURE:
<223> OTHER INFORMATION: Antibody 21

<400> SEQUENCE: 206
cagtctgtgc tgacgcagcc gccctcagtg tctggggccc cagggcagag ggtcaccatc        60
tcctgcactg ggagcagctc aacatcgggg gcaggttatg atgtacactg gtatcagcaa       120
cttccaggaa cagcccccaa actcctcatc tatgataatt tcaatcggcc ctcaggggtc       180
cctgaccgat tctctggctc caagtctggc acctcagcct ccctggccat cattggactc       240
cagactgaag atgaggctga ttattattgc cagtcctatg acagctcgtc gcagttgagc       300
ccgttcggaa ccgggaccaa gctgaccgtc ctaggt                                 336

<210> SEQ ID NO 207
<211> LENGTH: 112
<212> TYPE: PRT
<213> ORGANISM: Homo sapiens
<220> FEATURE:
<223> OTHER INFORMATION: Antibody 21

<400> SEQUENCE: 207

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Asp Asn Phe Asn Arg Pro Ser Gly Val Pro Asp Arg Phe
    50                  55                  60

Ser Gly Ser Lys Ser Gly Thr Ser Ala Ser Leu Ala Ile Ile Gly Leu
65                  70                  75                  80

Gln Thr Glu Asp Glu Ala Asp Tyr Tyr Cys Gln Ser Tyr Asp Ser Ser
                85                  90                  95

Ser Gln Leu Ser Pro Phe Gly Thr Gly Thr Lys Leu Thr Val Leu Gly
```

<210> SEQ ID NO 208
<211> LENGTH: 14
<212> TYPE: PRT
<213> ORGANISM: Homo sapiens
<220> FEATURE:
<223> OTHER INFORMATION: Antibody 21

<400> SEQUENCE: 208

Thr Gly Ser Ser Ser Asn Ile Gly Ala Gly Tyr Asp Val His
1               5                   10

<210> SEQ ID NO 209
<211> LENGTH: 7
<212> TYPE: PRT
<213> ORGANISM: Homo sapiens
<220> FEATURE:
<223> OTHER INFORMATION: Antibody 21

<400> SEQUENCE: 209

Asp Asn Phe Asn Arg Pro Ser
1               5

<210> SEQ ID NO 210
<211> LENGTH: 11
<212> TYPE: PRT
<213> ORGANISM: Homo sapiens
<220> FEATURE:
<223> OTHER INFORMATION: Antibody 21

<400> SEQUENCE: 210

Gln Ser Tyr Asp Ser Ser Ser Gln Leu Ser Pro
1               5                   10

<210> SEQ ID NO 211
<211> LENGTH: 363
<212> TYPE: DNA
<213> ORGANISM: Homo sapiens
<220> FEATURE:
<223> OTHER INFORMATION: Antibody 22

<400> SEQUENCE: 211
caggtccagc tggtgcagtc tggggctgag gtgaagaaac ctggggccac agtgaaactc      60
tcctgcaagg tttatggata cattttcacc gactacaaca tttactgggt gcgccaggcc    120
cctggaaaag ggcttgagtg gatgggactt attgatcctg acaatggtga gacattttac    180
gcagagaagt tccagggcag agccaccatg accgcggaca cgtcttcaga cagagcctac    240
atggaattga ccagcctgac ctttgaggac acggccactt attattgtgc aacagtcacg    300
ttgaagagcg cgaaggggggg ctatgactac tggggccggg gcaccctggt caccgtctcg    360
agt                                                                  363

<210> SEQ ID NO 212
<211> LENGTH: 121
<212> TYPE: PRT
<213> ORGANISM: Homo sapiens
<220> FEATURE:
<223> OTHER INFORMATION: Antibody 22

<400> SEQUENCE: 212

Gln Val Gln Leu Val Gln Ser Gly Ala Glu Val Lys Lys Pro Gly Ala
1               5                   10                  15

Thr Val Lys Leu Ser Cys Lys Val Tyr Gly Tyr Ile Phe Thr Asp Tyr
                20                  25                  30

```
Asn Ile Tyr Trp Val Arg Gln Ala Pro Gly Lys Gly Leu Glu Trp Met
        35                  40                  45

Gly Leu Ile Asp Pro Asp Asn Gly Glu Thr Phe Tyr Ala Glu Lys Phe
 50                  55                  60

Gln Gly Arg Ala Thr Met Thr Ala Asp Thr Ser Ser Asp Arg Ala Tyr
 65                  70                  75                  80

Met Glu Leu Thr Ser Leu Thr Phe Glu Asp Thr Ala Thr Tyr Tyr Cys
                 85                  90                  95

Ala Thr Val Thr Leu Lys Ser Ala Lys Gly Gly Tyr Asp Tyr Trp Gly
            100                 105                 110

Arg Gly Thr Leu Val Thr Val Ser Ser
            115                 120

<210> SEQ ID NO 213
<211> LENGTH: 5
<212> TYPE: PRT
<213> ORGANISM: Homo sapiens
<220> FEATURE:
<223> OTHER INFORMATION: Antibody 22

<400> SEQUENCE: 213

Asp Tyr Asn Ile Tyr
 1               5

<210> SEQ ID NO 214
<211> LENGTH: 17
<212> TYPE: PRT
<213> ORGANISM: Homo sapiens
<220> FEATURE:
<223> OTHER INFORMATION: Antibody 22

<400> SEQUENCE: 214

Leu Ile Asp Pro Asp Asn Gly Glu Thr Phe Tyr Ala Glu Lys Phe Gln
 1               5                  10                  15

Gly

<210> SEQ ID NO 215
<211> LENGTH: 12
<212> TYPE: PRT
<213> ORGANISM: Homo sapiens
<220> FEATURE:
<223> OTHER INFORMATION: Antibody 22

<400> SEQUENCE: 215

Val Thr Leu Lys Ser Ala Lys Gly Gly Tyr Asp Tyr
 1               5                  10

<210> SEQ ID NO 216
<211> LENGTH: 336
<212> TYPE: DNA
<213> ORGANISM: Homo sapiens
<220> FEATURE:
<223> OTHER INFORMATION: Antibody 22

<400> SEQUENCE: 216
cagtctgtgc tgacgcagcc gccctcagtg tctggggccc cagggcagag ggtcaccatc     60
tcctgcactg ggagcagctc aacatcggg gcaggttatg atgtacactg gtatcagcaa    120
cttccaggaa cagcccccaa actcctcatc tatgataatt caatcggcc ctcaggggtc    180 cctgaccgat tctctggctc caagtctggc acctcagcct ccctggccat cattgggctc    240
cagactgaag atgaggctga ttattattgc cagtcctatg acagcagcgg ggggtacgcg    300
```
ccgttcggaa ccgggaccaa gctgaccgtc ctaggt 336

<210> SEQ ID NO 217
<211> LENGTH: 112
<212> TYPE: PRT
<213> ORGANISM: Homo sapiens
<220> FEATURE:
<223> OTHER INFORMATION: Antibody 22

<400> SEQUENCE: 217

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Asp Asn Phe Asn Arg Pro Ser Gly Val Pro Asp Arg Phe
    50                  55                  60

Ser Gly Ser Lys Ser Gly Thr Ser Ala Ser Leu Ala Ile Ile Gly Leu
65                  70                  75                  80

Gln Thr Glu Asp Glu Ala Asp Tyr Tyr Cys Gln Ser Tyr Asp Ser Ser
                85                  90                  95

Gly Gly Tyr Ala Pro Phe Gly Thr Gly Thr Lys Leu Thr Val Leu Gly
            100                 105                 110

<210> SEQ ID NO 218
<211> LENGTH: 14
<212> TYPE: PRT
<213> ORGANISM: Homo sapiens
<220> FEATURE:
<223> OTHER INFORMATION: Antibody 22

<400> SEQUENCE: 218

Thr Gly Ser Ser Ser Asn Ile Gly Ala Gly Tyr Asp Val His
1               5                   10

<210> SEQ ID NO 219
<211> LENGTH: 7
<212> TYPE: PRT
<213> ORGANISM: Homo sapiens
<220> FEATURE:
<223> OTHER INFORMATION: Antibody 22

<400> SEQUENCE: 219

Asp Asn Phe Asn Arg Pro Ser
1               5

<210> SEQ ID NO 220
<211> LENGTH: 11
<212> TYPE: PRT
<213> ORGANISM: Homo sapiens
<220> FEATURE:
<223> OTHER INFORMATION: Antibody 22

<400> SEQUENCE: 220

Gln Ser Tyr Asp Ser Ser Gly Gly Tyr Ala Pro
1               5                   10

<210> SEQ ID NO 221
<211> LENGTH: 363
<212> TYPE: DNA
<213> ORGANISM: Homo sapiens
<220> FEATURE:
<223> OTHER INFORMATION: Antibody 23

-continued

<400> SEQUENCE: 221

```
caggtccagc tggtgcagtc tggggctgag gtgaagaaac ctggggccac agtgaaactc    60
tcctgcaagg tttatggata cattttcacc gactacaaca tttactgggt gcgccaggcc   120
cctggaaaag gcttgagtg gatgggactt attgatcctg acaatggtga gacattttac   180
gcagagaagt tccagggcag agccaccatg accgcggaca cgtcttcaga cagagcctac   240
atggaattga ccagcctgac ctttgaggac acggccactt attattgtgc aacagtgatg   300
gggaagtgga tcaaggggggg ctatgactac tggggccggg gcaccctggt caccgtctcg   360
agt                                                                 363
```

<210> SEQ ID NO 222
<211> LENGTH: 121
<212> TYPE: PRT
<213> ORGANISM: Homo sapiens
<220> FEATURE:
<223> OTHER INFORMATION: Antibody 23

<400> SEQUENCE: 222

```
Gln Val Gln Leu Val Gln Ser Gly Ala Glu Val Lys Lys Pro Gly Ala
1               5                   10                  15
Thr Val Lys Leu Ser Cys Lys Val Tyr Gly Tyr Ile Phe Thr Asp Tyr
            20                  25                  30
Asn Ile Tyr Trp Val Arg Gln Ala Pro Gly Lys Gly Leu Glu Trp Met
        35                  40                  45
Gly Leu Ile Asp Pro Asp Asn Gly Glu Thr Phe Tyr Ala Glu Lys Phe
    50                  55                  60
Gln Gly Arg Ala Thr Met Thr Ala Asp Thr Ser Ser Asp Arg Ala Tyr
65                  70                  75                  80
Met Glu Leu Thr Ser Leu Thr Phe Glu Asp Thr Ala Thr Tyr Tyr Cys
                85                  90                  95
Ala Thr Val Met Gly Lys Trp Ile Lys Gly Gly Tyr Asp Tyr Trp Gly
            100                 105                 110
Arg Gly Thr Leu Val Thr Val Ser Ser
        115                 120
```

<210> SEQ ID NO 223
<211> LENGTH: 5
<212> TYPE: PRT
<213> ORGANISM: Homo sapiens
<220> FEATURE:
<223> OTHER INFORMATION: Antibody 23

<400> SEQUENCE: 223

```
Asp Tyr Asn Ile Tyr
1               5
```

<210> SEQ ID NO 224
<211> LENGTH: 17
<212> TYPE: PRT
<213> ORGANISM: Homo sapiens
<220> FEATURE:
<223> OTHER INFORMATION: Antibody 23

<400> SEQUENCE: 224

```
Leu Ile Asp Pro Asp Asn Gly Glu Thr Phe Tyr Ala Glu Lys Phe Gln
1               5                   10                  15
Gly
```

<210> SEQ ID NO 225

<211> LENGTH: 12
<212> TYPE: PRT
<213> ORGANISM: Homo sapiens
<220> FEATURE:
<223> OTHER INFORMATION: Antibody 23

<400> SEQUENCE: 225

Val Met Gly Lys Trp Ile Lys Gly Gly Tyr Asp Tyr
1               5                   10

<210> SEQ ID NO 226
<211> LENGTH: 336
<212> TYPE: DNA
<213> ORGANISM: Homo sapiens
<220> FEATURE:
<223> OTHER INFORMATION: Antibody 23

<400> SEQUENCE: 226
cagtctgtgc tgacgcagcc gccctcagtg tctggggccc cagggcagag ggtcaccatc      60
tcctgcactg ggagcagctc caacatcggg gcaggttatg atgtacactg gtatcagcaa     120
cttccaggaa cagcccccaa actcctcatc tatgataatt tcaatcggcc ctcaggggtc     180
cctgaccgat tctctggctc caagtctggc acctcagcct ccctggccat cattgggctc     240
cagactgaag atgaggctga ttattattgc cagtcctatg acagccacca cctctactcc     300
tccttcggaa ccgggaccaa gctgaccgtc ctaggt                               336

<210> SEQ ID NO 227
<211> LENGTH: 112
<212> TYPE: PRT
<213> ORGANISM: Homo sapiens
<220> FEATURE:
<223> OTHER INFORMATION: Antibody 23

<400> SEQUENCE: 227

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Asp Asn Phe Asn Arg Pro Ser Gly Val Pro Asp Arg Phe
    50                  55                  60

Ser Gly Ser Lys Ser Gly Thr Ser Ala Ser Leu Ala Ile Ile Gly Leu
65                  70                  75                  80

Gln Thr Glu Asp Glu Ala Asp Tyr Tyr Cys Gln Ser Tyr Asp Ser His
                85                  90                  95

His Leu Tyr Ser Ser Phe Gly Thr Gly Thr Lys Leu Thr Val Leu Gly
            100                 105                 110

<210> SEQ ID NO 228
<211> LENGTH: 14
<212> TYPE: PRT
<213> ORGANISM: Homo sapiens
<220> FEATURE:
<223> OTHER INFORMATION: Antibody 23

<400> SEQUENCE: 228

Thr Gly Ser Ser Ser Asn Ile Gly Ala Gly Tyr Asp Val His
1               5                   10

<210> SEQ ID NO 229
<211> LENGTH: 7

```
<212> TYPE: PRT
<213> ORGANISM: Homo sapiens
<220> FEATURE:
<223> OTHER INFORMATION: Antibody 23

<400> SEQUENCE: 229

Asp Asn Phe Asn Arg Pro Ser
 1               5

<210> SEQ ID NO 230
<211> LENGTH: 11
<212> TYPE: PRT
<213> ORGANISM: Homo sapiens
<220> FEATURE:
<223> OTHER INFORMATION: Antibody 23

<400> SEQUENCE: 230

Gln Ser Tyr Asp Ser His His Leu Tyr Ser Ser
 1               5                   10

<210> SEQ ID NO 231
<211> LENGTH: 363
<212> TYPE: DNA
<213> ORGANISM: Homo sapiens
<220> FEATURE:
<223> OTHER INFORMATION: Antibody 24

<400> SEQUENCE: 231
caggtccagc tggtgcagtc tggggctgag gtgaagaaac ctggggccac agtgaaactc      60
tcctgcaagg tttatggata cattttcacc gactacaaca tttactgggt gcgccaggcc     120
cctggaaaag ggcttgagtg gatgggactt attgatcctg acaatggtga acatttttac     180
gcagagaagt tccagggcag agccaccatg accgcggaca cgtcttcaga cagagcctac     240
atggaattga ccagcctgac ctttgaggac acggccactt attattgtgc aacagtgacc     300
ttgaagaccg cgaagggggg ctatgactac tggggccggg gcaccctggt caccgtctcg     360
agt                                                                   363

<210> SEQ ID NO 232
<211> LENGTH: 121
<212> TYPE: PRT
<213> ORGANISM: Homo sapiens
<220> FEATURE:
<223> OTHER INFORMATION: Antibody 24

<400> SEQUENCE: 232

Gln Val Gln Leu Val Gln Ser Gly Ala Glu Val Lys Lys Pro Gly Ala
 1               5                  10                  15

Thr Val Lys Leu Ser Cys Lys Val Tyr Gly Tyr Ile Phe Thr Asp Tyr
                20                  25                  30

Asn Ile Tyr Trp Val Arg Gln Ala Pro Gly Lys Gly Leu Glu Trp Met
            35                  40                  45

Gly Leu Ile Asp Pro Asp Asn Gly Glu Thr Phe Tyr Ala Glu Lys Phe
        50                  55                  60

Gln Gly Arg Ala Thr Met Thr Ala Asp Thr Ser Ser Asp Arg Ala Tyr
 65                  70                  75                  80

Met Glu Leu Thr Ser Leu Thr Phe Glu Asp Thr Ala Thr Tyr Tyr Cys
                85                  90                  95

Ala Thr Val Thr Leu Lys Thr Ala Lys Gly Gly Tyr Asp Tyr Trp Gly
               100                 105                 110

Arg Gly Thr Leu Val Thr Val Ser Ser
           115                 120
```

<210> SEQ ID NO 233
<211> LENGTH: 5
<212> TYPE: PRT
<213> ORGANISM: Homo sapiens
<220> FEATURE:
<223> OTHER INFORMATION: Antibody 24

<400> SEQUENCE: 233

Asp Tyr Asn Ile Tyr
1               5

<210> SEQ ID NO 234
<211> LENGTH: 17
<212> TYPE: PRT
<213> ORGANISM: Homo sapiens
<220> FEATURE:
<223> OTHER INFORMATION: Antibody 24

<400> SEQUENCE: 234

Leu Ile Asp Pro Asp Asn Gly Glu Thr Phe Tyr Ala Glu Lys Phe Gln
1               5                   10                  15

Gly

<210> SEQ ID NO 235
<211> LENGTH: 12
<212> TYPE: PRT
<213> ORGANISM: Homo sapiens
<220> FEATURE:
<223> OTHER INFORMATION: Antibody 24

<400> SEQUENCE: 235

Val Thr Leu Lys Thr Ala Lys Gly Gly Tyr Asp Tyr
1               5                   10

<210> SEQ ID NO 236
<211> LENGTH: 336
<212> TYPE: DNA
<213> ORGANISM: Homo sapiens
<220> FEATURE:
<223> OTHER INFORMATION: Antibody 24

<400> SEQUENCE: 236
cagtctgtgc tgacgcagcc gccctcagtg tctggggccc cagggcagag ggtcaccatc      60
tcctgcactg ggagcagctc aacatcgggg gcaggttatg atgtacactg gtatcagcaa     120
cttccaggaa cagcccccaa actcctcatc tatgataatt caatcggcc ctcaggggtc     180 cctgaccgat tctctggctc caagtctggc acctcagcct ccctggccat cattgggctc     240
cagactgaag atgaggctga ttattattgc cagtcctatg acagcaggaa cggctacggc     300
gggttcggaa ccgggaccaa gctgaccgtc ctaggt                               336

<210> SEQ ID NO 237
<211> LENGTH: 112
<212> TYPE: PRT
<213> ORGANISM: Homo sapiens
<220> FEATURE:
<223> OTHER INFORMATION: Antibody 24

<400> SEQUENCE: 237

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
            35                  40                  45

Leu Ile Tyr Asp Asn Phe Asn Arg Pro Ser Gly Val Pro Asp Arg Phe
 50                  55                  60

Ser Gly Ser Lys Ser Gly Thr Ser Ala Ser Leu Ala Ile Ile Gly Leu
 65                  70                  75                  80

Gln Thr Glu Asp Glu Ala Asp Tyr Tyr Cys Gln Ser Tyr Asp Ser Arg
                 85                  90                  95

Asn Gly Tyr Gly Gly Phe Gly Thr Gly Thr Lys Leu Thr Val Leu Gly
            100                 105                 110

<210> SEQ ID NO 238
<211> LENGTH: 14
<212> TYPE: PRT
<213> ORGANISM: Homo sapiens
<220> FEATURE:
<223> OTHER INFORMATION: Antibody 24

<400> SEQUENCE: 238

Thr Gly Ser Ser Ser Asn Ile Gly Ala Gly Tyr Asp Val His
1               5                   10

<210> SEQ ID NO 239
<211> LENGTH: 7
<212> TYPE: PRT
<213> ORGANISM: Homo sapiens
<220> FEATURE:
<223> OTHER INFORMATION: Antibody 24

<400> SEQUENCE: 239

Asp Asn Phe Asn Arg Pro Ser
1               5

<210> SEQ ID NO 240
<211> LENGTH: 11
<212> TYPE: PRT
<213> ORGANISM: Homo sapiens
<220> FEATURE:
<223> OTHER INFORMATION: Antibody 24

<400> SEQUENCE: 240

Gln Ser Tyr Asp Ser Arg Asn Gly Tyr Gly Gly
1               5                   10

<210> SEQ ID NO 241
<211> LENGTH: 363
<212> TYPE: DNA
<213> ORGANISM: Homo sapiens
<220> FEATURE:
<223> OTHER INFORMATION: Antibody 25

<400> SEQUENCE: 241
caggtccagc tggtgcagtc tggggctgag gtgaagaaac ctggggccac agtgaaactc      60
tcctgcaagg tttatggata catttcacc gactacaaca tttactgggt gcgccaggcc     120
cctggaaaag ggcttgagtg gatgggactt attgatcctg acaatggtga gacattttac     180
gcagagaagt tccagggcag agccaccatg accgcggaca cgtcttcaga cagagcctac     240
atggaattga ccagcctgac ctttgaggac acggccactt attattgtgc aacagtcacg     300
ttgaagagcg cgaagggggg ctatgactac tggggccggg gcaccctggt caccgtctcg     360
agt                                                                  363

<210> SEQ ID NO 242

<211> LENGTH: 121
<212> TYPE: PRT
<213> ORGANISM: Homo sapiens
<220> FEATURE:
<223> OTHER INFORMATION: Antibody 25

<400> SEQUENCE: 242

Gln Val Gln Leu Val Gln Ser Gly Ala Glu Val Lys Lys Pro Gly Ala
1               5                   10                  15
Thr Val Lys Leu Ser Cys Lys Val Tyr Gly Tyr Ile Phe Thr Asp Tyr
            20                  25                  30
Asn Ile Tyr Trp Val Arg Gln Ala Pro Gly Lys Gly Leu Glu Trp Met
        35                  40                  45
Gly Leu Ile Asp Pro Asp Asn Gly Glu Thr Phe Tyr Ala Glu Lys Phe
    50                  55                  60
Gln Gly Arg Ala Thr Met Thr Ala Asp Thr Ser Asp Arg Ala Tyr
65                  70                  75                  80
Met Glu Leu Thr Ser Leu Thr Phe Glu Asp Thr Ala Thr Tyr Tyr Cys
                85                  90                  95
Ala Thr Val Thr Leu Lys Ser Ala Lys Gly Gly Tyr Asp Tyr Trp Gly
            100                 105                 110
Arg Gly Thr Leu Val Thr Val Ser Ser
        115                 120

<210> SEQ ID NO 243
<211> LENGTH: 5
<212> TYPE: PRT
<213> ORGANISM: Homo sapiens
<220> FEATURE:
<223> OTHER INFORMATION: Antibody 25

<400> SEQUENCE: 243

Asp Tyr Asn Ile Tyr
1               5

<210> SEQ ID NO 244
<211> LENGTH: 17
<212> TYPE: PRT
<213> ORGANISM: Homo sapiens
<220> FEATURE:
<223> OTHER INFORMATION: Antibody 25

<400> SEQUENCE: 244

Leu Ile Asp Pro Asp Asn Gly Glu Thr Phe Tyr Ala Glu Lys Phe Gln
1               5                   10                  15
Gly

<210> SEQ ID NO 245
<211> LENGTH: 12
<212> TYPE: PRT
<213> ORGANISM: Homo sapiens
<220> FEATURE:
<223> OTHER INFORMATION: Antibody 25

<400> SEQUENCE: 245

Val Thr Leu Lys Ser Ala Lys Gly Gly Tyr Asp Tyr
1               5                   10

<210> SEQ ID NO 246
<211> LENGTH: 336
<212> TYPE: DNA
<213> ORGANISM: Homo sapiens
<220> FEATURE:
<223> OTHER INFORMATION: Antibody 25

<400> SEQUENCE: 246

```
cagtctgtgc tgacgcagcc gccctcagtg tctggggccc cagggcagag ggtcaccatc    60
tcctgcactg ggagcagctc caacatcggg gcaggttatg atgtacactg gtatcagcaa   120
cttccaggaa cagcccccaa actcctcatc tatgataatt tcaatcggcc ctcagggtc    180
cctgaccgat tctctggctc caagtctggc acctcagcct ccctggccat cattgggctc   240
cagactgaag atgaggctga ttattattgc cagtcctatg acagcaacca caagacctcc   300
cccttcggaa ccgggaccaa gctgaccgtc ctaggt                             336
```

<210> SEQ ID NO 247
<211> LENGTH: 112
<212> TYPE: PRT
<213> ORGANISM: Homo sapiens
<220> FEATURE:
<223> OTHER INFORMATION: Antibody 25

<400> SEQUENCE: 247

```
Gln Ser Val Leu Thr Gln Pro Pro Ser Val Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Asp Asn Phe Asn Arg Pro Ser Gly Val Pro Asp Arg Phe
    50                  55                  60

Ser Gly Ser Lys Ser Gly Thr Ser Ala Ser Leu Ala Ile Ile Gly Leu
65                  70                  75                  80

Gln Thr Glu Asp Glu Ala Asp Tyr Tyr Cys Gln Ser Tyr Asp Ser Asn
                85                  90                  95

His Lys Thr Ser Pro Phe Gly Thr Gly Thr Lys Leu Thr Val Leu Gly
            100                 105                 110
```

<210> SEQ ID NO 248
<211> LENGTH: 14
<212> TYPE: PRT
<213> ORGANISM: Homo sapiens
<220> FEATURE:
<223> OTHER INFORMATION: Antibody 25

<400> SEQUENCE: 248

```
Thr Gly Ser Ser Ser Asn Ile Gly Ala Gly Tyr Asp Val His
1               5                   10
```

<210> SEQ ID NO 249
<211> LENGTH: 7
<212> TYPE: PRT
<213> ORGANISM: Homo sapiens
<220> FEATURE:
<223> OTHER INFORMATION: Antibody 25

<400> SEQUENCE: 249

```
Asp Asn Phe Asn Arg Pro Ser
1               5
```

<210> SEQ ID NO 250
<211> LENGTH: 11
<212> TYPE: PRT
<213> ORGANISM: Homo sapiens
<220> FEATURE:
<223> OTHER INFORMATION: Antibody 25

<400> SEQUENCE: 250

Gln Ser Tyr Asp Ser Asn His Lys Thr Ser Pro
1               5                   10

<210> SEQ ID NO 251
<211> LENGTH: 363
<212> TYPE: DNA
<213> ORGANISM: Homo sapiens
<220> FEATURE:
<223> OTHER INFORMATION: Antibody 26

<400> SEQUENCE: 251
caggtccagc tggtgcagtc tggggctgag gtgaagaaac ctggggccac agtgaaactc      60
tcctgcaagg tttatggata cattttcacc gactacaaca tttactgggt gcgccaggcc     120
cctggaaaag gcttgagtg gatgggactt attgatcctg acaatggtga gacattttac      180
gcagagaagt tccagggcag agccaccatg accgcggaca cgtcttcaga cagagcctac     240
atggaattga ccagcctgac ctttgaggac acggccactt attattgtgc aacagtgagc     300
ctgaaggagg ccaaggggg ctatgactac tggggccggg gcaccctggt caccgtctcg      360
agt                                                                    363

<210> SEQ ID NO 252
<211> LENGTH: 121
<212> TYPE: PRT
<213> ORGANISM: Homo sapiens
<220> FEATURE:
<223> OTHER INFORMATION: Antibody 26

<400> SEQUENCE: 252

Gln Val Gln Leu Val Gln Ser Gly Ala Glu Val Lys Lys Pro Gly Ala
1               5                   10                  15

Thr Val Lys Leu Ser Cys Lys Val Tyr Gly Tyr Ile Phe Thr Asp Tyr
                20                  25                  30

Asn Ile Tyr Trp Val Arg Gln Ala Pro Gly Lys Gly Leu Glu Trp Met
            35                  40                  45

Gly Leu Ile Asp Pro Asp Asn Gly Glu Thr Phe Tyr Ala Glu Lys Phe
        50                  55                  60

Gln Gly Arg Ala Thr Met Thr Ala Asp Thr Ser Ser Asp Arg Ala Tyr
65                  70                  75                  80

Met Glu Leu Thr Ser Leu Thr Phe Glu Asp Thr Ala Thr Tyr Tyr Cys
                85                  90                  95

Ala Thr Val Ser Leu Lys Glu Ala Lys Gly Gly Tyr Asp Tyr Trp Gly
                100                 105                 110

Arg Gly Thr Leu Val Thr Val Ser Ser
        115                 120

<210> SEQ ID NO 253
<211> LENGTH: 5
<212> TYPE: PRT
<213> ORGANISM: Homo sapiens
<220> FEATURE:
<223> OTHER INFORMATION: Antibody 26

<400> SEQUENCE: 253

Asp Tyr Asn Ile Tyr
1               5

<210> SEQ ID NO 254
<211> LENGTH: 17
<212> TYPE: PRT

<213> ORGANISM: Homo sapiens
<220> FEATURE:
<223> OTHER INFORMATION: Antibody 26

<400> SEQUENCE: 254

Leu Ile Asp Pro Asp Asn Gly Glu Thr Phe Tyr Ala Glu Lys Phe Gln
1               5                   10                  15

Gly

<210> SEQ ID NO 255
<211> LENGTH: 12
<212> TYPE: PRT
<213> ORGANISM: Homo sapiens
<220> FEATURE:
<223> OTHER INFORMATION: Antibody 26

<400> SEQUENCE: 255

Val Ser Leu Lys Glu Ala Lys Gly Gly Tyr Asp Tyr
1               5                   10

<210> SEQ ID NO 256
<211> LENGTH: 336
<212> TYPE: DNA
<213> ORGANISM: Homo sapiens
<220> FEATURE:
<223> OTHER INFORMATION: Antibody 26

<400> SEQUENCE: 256
cagtctgtgc tgacgcagcc gccctcagtg tctggggccc cagggcagag ggtcaccatc      60
tcctgcactg ggagcagctc caacatcggg gcaggttatg atgtacactg gtatcagcaa     120
cttccaggaa cagcccccaa actcctcatc tatgataatt tcaatcggcc ctcaggggtc     180
cctgaccgat tctctggctc caagtctggc acctcagcct ccctggccat cattgggctc     240
cagactgaag atgaggctga ttattattgc cagtcctatg acagcgcctc ccgccacgcc     300
cccttcggaa ccgggaccaa gctgaccgtc ctaggt                               336

<210> SEQ ID NO 257
<211> LENGTH: 112
<212> TYPE: PRT
<213> ORGANISM: Homo sapiens
<220> FEATURE:
<223> OTHER INFORMATION: Antibody 26

<400> SEQUENCE: 257

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
                20                  25                  30

Tyr Asp Val His Trp Tyr Gln Gln Leu Pro Gly Thr Ala Pro Lys Leu
            35                  40                  45

Leu Ile Tyr Asp Asn Phe Asn Arg Pro Ser Gly Val Pro Asp Arg Phe
        50                  55                  60

Ser Gly Ser Lys Ser Gly Thr Ser Ala Ser Leu Ala Ile Ile Gly Leu
65                  70                  75                  80

Gln Thr Glu Asp Glu Ala Asp Tyr Tyr Cys Gln Ser Tyr Asp Ser Ala
                85                  90                  95

Ser Arg His Ala Pro Phe Gly Thr Gly Thr Lys Leu Thr Val Leu Gly
            100                 105                 110

<210> SEQ ID NO 258
<211> LENGTH: 14

```
<212> TYPE: PRT
<213> ORGANISM: Homo sapiens
<220> FEATURE:
<223> OTHER INFORMATION: Antibody 26

<400> SEQUENCE: 258

Thr Gly Ser Ser Ser Asn Ile Gly Ala Gly Tyr Asp Val His
1               5                   10

<210> SEQ ID NO 259
<211> LENGTH: 7
<212> TYPE: PRT
<213> ORGANISM: Homo sapiens
<220> FEATURE:
<223> OTHER INFORMATION: Antibody 26

<400> SEQUENCE: 259

Asp Asn Phe Asn Arg Pro Ser
1               5

<210> SEQ ID NO 260
<211> LENGTH: 11
<212> TYPE: PRT
<213> ORGANISM: Homo sapiens
<220> FEATURE:
<223> OTHER INFORMATION: Antibody 26

<400> SEQUENCE: 260

Gln Ser Tyr Asp Ser Ala Ser Arg His Ala Pro
1               5                   10

<210> SEQ ID NO 261
<211> LENGTH: 363
<212> TYPE: DNA
<213> ORGANISM: Homo sapiens
<220> FEATURE:
<223> OTHER INFORMATION: Antibody 27

<400> SEQUENCE: 261
caggtccagc tggtgcagtc tggggctgag gtgaagaaac ctggggccac agtgaaactc      60
tcctgcaagg tttatggata catttttcacc gactacaaca tttactgggt gcgccaggcc    120
cctggaaaag ggcttgagtg gatgggactt attgatcctg acaatggtga gacattttac    180
gcagagaagt tccagggcag agccaccatg accgcggaca cgtcttcaga cagagcctac    240
atggaattga ccagcctgac ctttgaggac acggccactt attattgtgc aacagtgagc    300
ctgaaggagg ccaagggggg ctatgactac tggggccggg gcaccctggt caccgtctcg    360
agt                                                                  363

<210> SEQ ID NO 262
<211> LENGTH: 121
<212> TYPE: PRT
<213> ORGANISM: Homo sapiens
<220> FEATURE:
<223> OTHER INFORMATION: Antibody 27

<400> SEQUENCE: 262

Gln Val Gln Leu Val Gln Ser Gly Ala Glu Val Lys Lys Pro Gly Ala
1               5                   10                  15

Thr Val Lys Leu Ser Cys Lys Val Tyr Gly Tyr Ile Phe Thr Asp Tyr
                20                  25                  30

Asn Ile Tyr Trp Val Arg Gln Ala Pro Gly Lys Gly Leu Glu Trp Met
            35                  40                  45

Gly Leu Ile Asp Pro Asp Asn Gly Glu Thr Phe Tyr Ala Glu Lys Phe
```

```
                  50                  55                  60
Gln Gly Arg Ala Thr Met Thr Ala Asp Thr Ser Ser Asp Arg Ala Tyr
 65                  70                  75                  80

Met Glu Leu Thr Ser Leu Thr Phe Glu Asp Thr Ala Thr Tyr Tyr Cys
                     85                  90                  95

Ala Thr Val Ser Leu Lys Glu Ala Lys Gly Gly Tyr Asp Tyr Trp Gly
                    100                 105                 110

Arg Gly Thr Leu Val Thr Val Ser Ser
                115                 120

<210> SEQ ID NO 263
<211> LENGTH: 5
<212> TYPE: PRT
<213> ORGANISM: Homo sapiens
<220> FEATURE:
<223> OTHER INFORMATION: Antibody 27

<400> SEQUENCE: 263

Asp Tyr Asn Ile Tyr
1               5

<210> SEQ ID NO 264
<211> LENGTH: 17
<212> TYPE: PRT
<213> ORGANISM: Homo sapiens
<220> FEATURE:
<223> OTHER INFORMATION: Antibody 27

<400> SEQUENCE: 264

Leu Ile Asp Pro Asp Asn Gly Glu Thr Phe Tyr Ala Glu Lys Phe Gln
1               5                   10                  15

Gly

<210> SEQ ID NO 265
<211> LENGTH: 12
<212> TYPE: PRT
<213> ORGANISM: Homo sapiens
<220> FEATURE:
<223> OTHER INFORMATION: Antibody 27

<400> SEQUENCE: 265

Val Ser Leu Lys Glu Ala Lys Gly Gly Tyr Asp Tyr
1               5                   10

<210> SEQ ID NO 266
<211> LENGTH: 336
<212> TYPE: DNA
<213> ORGANISM: Homo sapiens
<220> FEATURE:
<223> OTHER INFORMATION: Antibody 27

<400> SEQUENCE: 266
cagtctgtgc tgacgcagcc gccctcagtg tctggggccc cagggcagag ggtcaccatc      60
tcctgcactg ggagcagctc caacatcggg gcaggttatg atgtacactg gtatcagcaa     120
cttccaggaa cagcccccaa actcctcatc tatgataatt caatcggcc ctcagggggtc     180 cctgaccgat tctctggctc caagtctggc acctcagcct ccctggccat cattgggctc     240
cagactgaag atgaggctga ttattattgc cagtcctatg acagccccac ccagacctcc     300
cccttcggaa ccgggaccaa gctgaccgtc ctaggt                               336

<210> SEQ ID NO 267
<211> LENGTH: 112
```

```
<212> TYPE: PRT
<213> ORGANISM: Homo sapiens
<220> FEATURE:
<223> OTHER INFORMATION: Antibody 27

<400> SEQUENCE: 267

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Asp Asn Phe Asn Arg Pro Ser Gly Val Pro Asp Arg Phe
    50                  55                  60

Ser Gly Ser Lys Ser Gly Thr Ser Ala Ser Leu Ala Ile Ile Gly Leu
65              70                  75                  80

Gln Thr Glu Asp Glu Ala Asp Tyr Tyr Cys Gln Ser Tyr Asp Ser Pro
                85                  90                  95

Thr Gln Thr Ser Pro Phe Gly Thr Gly Thr Lys Leu Thr Val Leu Gly
            100                 105                 110

<210> SEQ ID NO 268
<211> LENGTH: 14
<212> TYPE: PRT
<213> ORGANISM: Homo sapiens
<220> FEATURE:
<223> OTHER INFORMATION: Antibody 27

<400> SEQUENCE: 268

Thr Gly Ser Ser Ser Asn Ile Gly Ala Gly Tyr Asp Val His
1               5                   10

<210> SEQ ID NO 269
<211> LENGTH: 7
<212> TYPE: PRT
<213> ORGANISM: Homo sapiens
<220> FEATURE:
<223> OTHER INFORMATION: Antibody 27

<400> SEQUENCE: 269

Asp Asn Phe Asn Arg Pro Ser
1               5

<210> SEQ ID NO 270
<211> LENGTH: 11
<212> TYPE: PRT
<213> ORGANISM: Homo sapiens
<220> FEATURE:
<223> OTHER INFORMATION: Antibody 27

<400> SEQUENCE: 270

Gln Ser Tyr Asp Ser Pro Thr Gln Thr Ser Pro
1               5                   10

<210> SEQ ID NO 271
<211> LENGTH: 363
<212> TYPE: DNA
<213> ORGANISM: Homo sapiens
<220> FEATURE:
<223> OTHER INFORMATION: Antibody 28

<400> SEQUENCE: 271
caggtccagc tggtgcagtc tggggctgag gtgaagaaac ctggggccac agtgaaactc      60
tcctgcaagg tttatggata cattttcacc gactacaaca tttactgggt gcgccaggcc     120
```

```
cctggaaaag ggcttgagtg gatgggactt attgatcctg acaatggtga gacattttac    180
gcagagaagt tccagggcag agccaccatg accgcggaca cgtcttcaga cagagcctac    240
atggaattga ccagcctgac ctttgaggac acggccactt attattgtgc aacagtgatg    300
gggaagtgga tcaagggggg ctatgactac tggggccggg gcaccctggt caccgtctcg    360
agt                                                                  363
```

<210> SEQ ID NO 272
<211> LENGTH: 121
<212> TYPE: PRT
<213> ORGANISM: Homo sapiens
<220> FEATURE:
<223> OTHER INFORMATION: Antibody 28

<400> SEQUENCE: 272

```
Gln Val Gln Leu Val Gln Ser Gly Ala Glu Val Lys Lys Pro Gly Ala
1               5                  10                  15

Thr Val Lys Leu Ser Cys Lys Val Tyr Gly Tyr Ile Phe Thr Asp Tyr
            20                  25                  30

Asn Ile Tyr Trp Val Arg Gln Ala Pro Gly Lys Gly Leu Glu Trp Met
        35                  40                  45

Gly Leu Ile Asp Pro Asp Asn Gly Glu Thr Phe Tyr Ala Glu Lys Phe
    50                  55                  60

Gln Gly Arg Ala Thr Met Thr Ala Asp Thr Ser Ser Asp Arg Ala Tyr
65                  70                  75                  80

Met Glu Leu Thr Ser Leu Thr Phe Glu Asp Thr Ala Thr Tyr Tyr Cys
                85                  90                  95

Ala Thr Val Met Gly Lys Trp Ile Lys Gly Gly Tyr Asp Tyr Trp Gly
            100                 105                 110

Arg Gly Thr Leu Val Thr Val Ser Ser
        115                 120
```

<210> SEQ ID NO 273
<211> LENGTH: 5
<212> TYPE: PRT
<213> ORGANISM: Homo sapiens
<220> FEATURE:
<223> OTHER INFORMATION: Antibody 28

<400> SEQUENCE: 273

```
Asp Tyr Asn Ile Tyr
1               5
```

<210> SEQ ID NO 274
<211> LENGTH: 17
<212> TYPE: PRT
<213> ORGANISM: Homo sapiens
<220> FEATURE:
<223> OTHER INFORMATION: Antibody 28

<400> SEQUENCE: 274

```
Leu Ile Asp Pro Asp Asn Gly Glu Thr Phe Tyr Ala Glu Lys Phe Gln
1               5                   10                  15

Gly
```

<210> SEQ ID NO 275
<211> LENGTH: 12
<212> TYPE: PRT
<213> ORGANISM: Homo sapiens
<220> FEATURE:
<223> OTHER INFORMATION: Antibody 28

<400> SEQUENCE: 275

Val Met Gly Lys Trp Ile Lys Gly Gly Tyr Asp Tyr
1               5                   10

<210> SEQ ID NO 276
<211> LENGTH: 336
<212> TYPE: DNA
<213> ORGANISM: Homo sapiens
<220> FEATURE:
<223> OTHER INFORMATION: Antibody 28

<400> SEQUENCE: 276

```
cagtctgtgc tgacgcagcc gccctcagtg tctggggccc cagggcagag ggtcaccatc      60
tcctgcactg ggagcagctc caacatcggg gcaggttatg atgtacactg gtatcagcaa     120
cttccaggaa cagcccccaa actcctcatc tatgataatt tcaatcggcc ctcaggggtc     180
cctgaccgat tctctggctc caagtctggc acctcagcct ccctggccat cattgggctc     240
cagactgaag atgaggctga ttattattgc cagtcctatg acagctcctc cctccactcg     300
cccttcggaa ccgggaccaa gctgaccgtc ctaggt                               336
```

<210> SEQ ID NO 277
<211> LENGTH: 112
<212> TYPE: PRT
<213> ORGANISM: Homo sapiens
<220> FEATURE:
<223> OTHER INFORMATION: Antibody 28

<400> SEQUENCE: 277

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
                20                  25                  30

Tyr Asp Val His Trp Tyr Gln Gln Leu Pro Gly Thr Ala Pro Lys Leu
            35                  40                  45

Leu Ile Tyr Asp Asn Phe Asn Arg Pro Ser Gly Val Pro Asp Arg Phe
50                  55                  60

Ser Gly Ser Lys Ser Gly Thr Ser Ala Ser Leu Ala Ile Ile Gly Leu
65                  70                  75                  80

Gln Thr Glu Asp Glu Ala Asp Tyr Tyr Cys Gln Ser Tyr Asp Ser Ser
                85                  90                  95

Ser Leu His Ser Pro Phe Gly Thr Gly Thr Lys Leu Thr Val Leu Gly
            100                 105                 110

<210> SEQ ID NO 278
<211> LENGTH: 14
<212> TYPE: PRT
<213> ORGANISM: Homo sapiens
<220> FEATURE:
<223> OTHER INFORMATION: Antibody 28

<400> SEQUENCE: 278

Thr Gly Ser Ser Ser Asn Ile Gly Ala Gly Tyr Asp Val His
1               5                   10

<210> SEQ ID NO 279
<211> LENGTH: 7
<212> TYPE: PRT
<213> ORGANISM: Homo sapiens
<220> FEATURE:
<223> OTHER INFORMATION: Antibody 28

-continued

<400> SEQUENCE: 279

Asp Asn Phe Asn Arg Pro Ser
1               5

<210> SEQ ID NO 280
<211> LENGTH: 11
<212> TYPE: PRT
<213> ORGANISM: Homo sapiens
<220> FEATURE:
<223> OTHER INFORMATION: Antibody 28

<400> SEQUENCE: 280

Gln Ser Tyr Asp Ser Ser Ser Leu His Ser Pro
1               5                   10

<210> SEQ ID NO 281
<211> LENGTH: 363
<212> TYPE: DNA
<213> ORGANISM: Homo sapiens
<220> FEATURE:
<223> OTHER INFORMATION: Antibody 8 GL

<400> SEQUENCE: 281
gaggtgcagc tggtgcagtc tgggctgag gtgaagaaac ctggggccac agtgaaaatc      60
tcctgcaagg tttatggata cattttcacc gactacaaca tttactgggt gcgacaggcc    120
cctggaaaag ggcttgagtg gatgggactt attgatcctg acaatggtga acatttttac    180
gcagagaagt tccagggcag agccaccatg accgcggaca cgtcttcaga cagagcctac    240
atggaattga gcagcctgag atttgaggac acggccgtgt attattgtgc aacagtcctg    300
ggccggtgga tcaaggggg ctatgactac tggggccggg gcaccctggt caccgtctcc    360
tca                                                                  363

<210> SEQ ID NO 282
<211> LENGTH: 121
<212> TYPE: PRT
<213> ORGANISM: Homo sapiens
<220> FEATURE:
<223> OTHER INFORMATION: Antibody 8 GL

<400> SEQUENCE: 282

Glu Val Gln Leu Val Gln Ser Gly Ala Glu Val Lys Lys Pro Gly Ala
1               5                   10                  15

Thr Val Lys Ile Ser Cys Lys Val Tyr Gly Tyr Ile Phe Thr Asp Tyr
            20                  25                  30

Asn Ile Tyr Trp Val Arg Gln Ala Pro Gly Lys Gly Leu Glu Trp Met
        35                  40                  45

Gly Leu Ile Asp Pro Asp Asn Gly Glu Thr Phe Tyr Ala Glu Lys Phe
    50                  55                  60

Gln Gly Arg Ala Thr Met Thr Ala Asp Thr Ser Ser Asp Arg Ala Tyr
65                  70                  75                  80

Met Glu Leu Ser Ser Leu Arg Phe Glu Asp Thr Ala Val Tyr Tyr Cys
                85                  90                  95

Ala Thr Val Leu Gly Arg Trp Ile Lys Gly Tyr Asp Tyr Trp Gly
            100                 105                 110

Arg Gly Thr Leu Val Thr Val Ser Ser
        115                 120

<210> SEQ ID NO 283
<211> LENGTH: 5
<212> TYPE: PRT

-continued

```
<213> ORGANISM: Homo sapiens
<220> FEATURE:
<223> OTHER INFORMATION: Antibody 8 GL

<400> SEQUENCE: 283

Asp Tyr Asn Ile Tyr
1               5

<210> SEQ ID NO 284
<211> LENGTH: 17
<212> TYPE: PRT
<213> ORGANISM: Homo sapiens
<220> FEATURE:
<223> OTHER INFORMATION: Antibody 8 GL

<400> SEQUENCE: 284

Leu Ile Asp Pro Asp Asn Gly Glu Thr Phe Tyr Ala Glu Lys Phe Gln
1               5                   10                  15
Gly

<210> SEQ ID NO 285
<211> LENGTH: 12
<212> TYPE: PRT
<213> ORGANISM: Homo sapiens
<220> FEATURE:
<223> OTHER INFORMATION: Antibody 8 GL

<400> SEQUENCE: 285

Val Leu Gly Arg Trp Ile Lys Gly Gly Tyr Asp Tyr
1               5                   10

<210> SEQ ID NO 286

<400> SEQUENCE: 286

000

<210> SEQ ID NO 287
<211> LENGTH: 363
<212> TYPE: DNA
<213> ORGANISM: Homo sapiens
<220> FEATURE:
<223> OTHER INFORMATION: Antibody 8 PGL

<400> SEQUENCE: 287
gaggtgcagc tggtgcagtc tggggctgag gtgaagaaac ctggggccac agtgaaaatc      60
tcctgcaagg tttatggata catttttcacc gactacaaca tttactgggt gcaacaggcc    120
cctggaaaag gcttgagtg gatgggactt attgatcctg acaatggtga gacattttac     180
gcagagaagt tccagggcag agccaccatg accgcggaca cgtctacaga cagagcctac    240
atggaattga gcagcctgag atttgaggac acggccgtgt attattgtgc aacagtcctg    300
ggccggtgga tcaagggggg ctatgactac tggggccggg gcaccctggt caccgtctcc    360
tca                                                                  363

<210> SEQ ID NO 288
<211> LENGTH: 121
<212> TYPE: PRT
<213> ORGANISM: Homo sapiens
<220> FEATURE:
<223> OTHER INFORMATION: Antibody 8 PGL

<400> SEQUENCE: 288

Glu Val Gln Leu Val Gln Ser Gly Ala Glu Val Lys Lys Pro Gly Ala
1               5                   10                  15
```

```
Thr Val Lys Ile Ser Cys Lys Val Tyr Gly Tyr Ile Phe Thr Asp Tyr
            20                  25                  30

Asn Ile Tyr Trp Val Gln Gln Ala Pro Gly Lys Gly Leu Glu Trp Met
        35                  40                  45

Gly Leu Ile Asp Pro Asp Asn Gly Glu Thr Phe Tyr Ala Glu Lys Phe
 50                  55                  60

Gln Gly Arg Ala Thr Met Thr Ala Asp Thr Ser Thr Asp Arg Ala Tyr
 65                  70                  75                  80

Met Glu Leu Ser Ser Leu Arg Phe Glu Asp Thr Ala Val Tyr Tyr Cys
                85                  90                  95

Ala Thr Val Leu Gly Arg Trp Ile Lys Gly Gly Tyr Asp Tyr Trp Gly
            100                 105                 110

Arg Gly Thr Leu Val Thr Val Ser Ser
            115                 120

<210> SEQ ID NO 289
<211> LENGTH: 5
<212> TYPE: PRT
<213> ORGANISM: Homo sapiens
<220> FEATURE:
<223> OTHER INFORMATION: Antibody 8 PGL

<400> SEQUENCE: 289

Asp Tyr Asn Ile Tyr
 1               5

<210> SEQ ID NO 290
<211> LENGTH: 17
<212> TYPE: PRT
<213> ORGANISM: Homo sapiens
<220> FEATURE:
<223> OTHER INFORMATION: Antibody 8 PGL

<400> SEQUENCE: 290

Leu Ile Asp Pro Asp Asn Gly Glu Thr Phe Tyr Ala Glu Lys Phe Gln
 1               5                  10                  15

Gly

<210> SEQ ID NO 291
<211> LENGTH: 12
<212> TYPE: PRT
<213> ORGANISM: Homo sapiens
<220> FEATURE:
<223> OTHER INFORMATION: Antibody 8 PGL

<400> SEQUENCE: 291

Val Leu Gly Arg Trp Ile Lys Gly Gly Tyr Asp Tyr
 1               5                  10

<210> SEQ ID NO 292

<400> SEQUENCE: 292

000

<210> SEQ ID NO 293

<400> SEQUENCE: 293

000

<210> SEQ ID NO 294
<211> LENGTH: 336
```

```
<212> TYPE: DNA
<213> ORGANISM: Homo sapiens
<220> FEATURE:
<223> OTHER INFORMATION: Antibody 8 VL GL

<400> SEQUENCE: 294
cagtctgtgc tgacgcagcc gccctcagtg tctggggccc cagggcagag ggtcaccatc      60
tcctgcactg ggagcagctc caacatcggg gcaggttatg atgtacactg gtatcagcaa     120
cttccaggaa cagcccccaa actcctcatc tatgataatt tcaatcggcc ctcagggggtc    180 cctgaccgat tctctggctc caagtctggc acctcagcct ccctggccat cactgggctc    240
caggctgaag atgaggctga ttattattgc cagtcctatg acagccccac ccacacctcc    300
cccttcggaa ccgggaccaa gctgaccgtc ctaggt                              336

<210> SEQ ID NO 295
<211> LENGTH: 112
<212> TYPE: PRT
<213> ORGANISM: Homo sapiens
<220> FEATURE:
<223> OTHER INFORMATION: Antibody 8 VL GL

<400> SEQUENCE: 295

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Asp Asn Phe Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Pro
                85                  90                  95

Thr His Thr Ser Pro Phe Gly Thr Gly Thr Lys Leu Thr Val Leu Gly
            100                 105                 110

<210> SEQ ID NO 296
<211> LENGTH: 14
<212> TYPE: PRT
<213> ORGANISM: Homo sapiens
<220> FEATURE:
<223> OTHER INFORMATION: Antibody 8 VL GL

<400> SEQUENCE: 296

Thr Gly Ser Ser Ser Asn Ile Gly Ala Gly Tyr Asp Val His
1               5                   10

<210> SEQ ID NO 297
<211> LENGTH: 7
<212> TYPE: PRT
<213> ORGANISM: Homo sapiens
<220> FEATURE:
<223> OTHER INFORMATION: Antibody 8 VL GL

<400> SEQUENCE: 297

Asp Asn Phe Asn Arg Pro Ser
1               5

<210> SEQ ID NO 298
<211> LENGTH: 11
<212> TYPE: PRT
```

<213> ORGANISM: Homo sapiens
<220> FEATURE:
<223> OTHER INFORMATION: Antibody 8 VL GL

<400> SEQUENCE: 298

Gln Ser Tyr Asp Ser Pro Thr His Thr Ser Pro
1               5                   10

<210> SEQ ID NO 299
<211> LENGTH: 363
<212> TYPE: DNA
<213> ORGANISM: Homo sapiens
<220> FEATURE:
<223> OTHER INFORMATION: Antibody 11 VH GL

<400> SEQUENCE: 299

```
gaggtgcagc tggtgcagtc tggggctgag gtgaagaaac ctggggccac agtgaaaatc      60
tcctgcaagg tttatggata cattttcacc gactacaaca tttactgggt gcgacaggcc     120
cctggaaaag gcttgagtg gatgggactt attgatcctg acaatggtga gacattttac     180
gcagagaagt tccagggcag agccaccatg accgcggaca cgtcttcaga cagagcctac     240
atggaattga gcagcctgag atttgaggac acggccgtgt attattgtgc aacagtgatg     300
gggaagtgga tcaaggggg ctatgactac tggggccggg gcaccctggt caccgtctcc     360
tca                                                                  363
```

<210> SEQ ID NO 300
<211> LENGTH: 121
<212> TYPE: PRT
<213> ORGANISM: Homo sapiens
<220> FEATURE:
<223> OTHER INFORMATION: Antibody 11 VH GL

<400> SEQUENCE: 300

Glu Val Gln Leu Val Gln Ser Gly Ala Glu Val Lys Lys Pro Gly Ala
1               5                   10                  15

Thr Val Lys Ile Ser Cys Lys Val Tyr Gly Tyr Ile Phe Thr Asp Tyr
                20                  25                  30

Asn Ile Tyr Trp Val Arg Gln Ala Pro Gly Lys Gly Leu Glu Trp Met
            35                  40                  45

Gly Leu Ile Asp Pro Asp Asn Gly Glu Thr Phe Tyr Ala Glu Lys Phe
        50                  55                  60

Gln Gly Arg Ala Thr Met Thr Ala Asp Thr Ser Ser Asp Arg Ala Tyr
65                  70                  75                  80

Met Glu Leu Ser Ser Leu Arg Phe Glu Asp Thr Ala Val Tyr Tyr Cys
                85                  90                  95

Ala Thr Val Met Gly Lys Trp Ile Lys Gly Gly Tyr Asp Tyr Trp Gly
            100                 105                 110

Arg Gly Thr Leu Val Thr Val Ser Ser
        115                 120

<210> SEQ ID NO 301
<211> LENGTH: 5
<212> TYPE: PRT
<213> ORGANISM: Homo sapiens
<220> FEATURE:
<223> OTHER INFORMATION: Antibody 11 VH GL

<400> SEQUENCE: 301

Asp Tyr Asn Ile Tyr
1               5

<210> SEQ ID NO 302
<211> LENGTH: 17
<212> TYPE: PRT
<213> ORGANISM: Homo sapiens
<220> FEATURE:
<223> OTHER INFORMATION: Antibody 11 VH GL

<400> SEQUENCE: 302

Leu Ile Asp Pro Asp Asn Gly Glu Thr Phe Tyr Ala Glu Lys Phe Gln
1               5                   10                  15

Gly

<210> SEQ ID NO 303
<211> LENGTH: 12
<212> TYPE: PRT
<213> ORGANISM: Homo sapiens
<220> FEATURE:
<223> OTHER INFORMATION: Antibody 11 VH GL

<400> SEQUENCE: 303

Val Met Gly Lys Trp Ile Lys Gly Gly Tyr Asp Tyr
1               5                   10

<210> SEQ ID NO 304

<400> SEQUENCE: 304

000

<210> SEQ ID NO 305
<211> LENGTH: 363
<212> TYPE: DNA
<213> ORGANISM: Homo sapiens
<220> FEATURE:
<223> OTHER INFORMATION: Antibody 11 VH PGL

<400> SEQUENCE: 305
gaggtgcagc tggtgcagtc tggggctgag gtgaagaaac ctggggccac agtgaaaatc      60
tcctgcaagg tttatggata cattttcacc gactacaaca tttactgggt gcaacaggcc     120
cctggaaaag ggcttgagtg gatgggactt attgatcctg acaatggtga gacattttac     180
gcagagaagt tccagggcag agccaccatg accgcggaca cgtctacaga cagagcctac     240
atggaattga gcagcctgag atttgaggac acggccgtgt attattgtgc aacagtgatg     300
gggaagtgga tcaaggggggg ctatgactac tggggccggg gcaccctggt caccgtctcc     360
tca                                                                   363

<210> SEQ ID NO 306
<211> LENGTH: 121
<212> TYPE: PRT
<213> ORGANISM: Homo sapiens
<220> FEATURE:
<223> OTHER INFORMATION: Antibody 11 VH PGL

<400> SEQUENCE: 306

Glu Val Gln Leu Val Gln Ser Gly Ala Glu Val Lys Lys Pro Gly Ala
1               5                   10                  15

Thr Val Lys Ile Ser Cys Lys Val Tyr Gly Tyr Ile Phe Thr Asp Tyr
            20                  25                  30

Asn Ile Tyr Trp Val Gln Gln Ala Pro Gly Lys Gly Leu Glu Trp Met
        35                  40                  45

Gly Leu Ile Asp Pro Asp Asn Gly Glu Thr Phe Tyr Ala Glu Lys Phe
    50                  55                  60

Gln Gly Arg Ala Thr Met Thr Ala Asp Thr Ser Thr Asp Ala Tyr
65                  70                  75                  80

Met Glu Leu Ser Ser Leu Arg Phe Glu Asp Thr Ala Val Tyr Tyr Cys
                85                  90                  95

Ala Thr Val Met Gly Lys Trp Ile Lys Gly Gly Tyr Asp Tyr Trp Gly
            100                 105                 110

Arg Gly Thr Leu Val Thr Val Ser Ser
        115                 120

<210> SEQ ID NO 307
<211> LENGTH: 5
<212> TYPE: PRT
<213> ORGANISM: Homo sapiens
<220> FEATURE:
<223> OTHER INFORMATION: Antibody 11 VH PGL

<400> SEQUENCE: 307

Asp Tyr Asn Ile Tyr
1               5

<210> SEQ ID NO 308
<211> LENGTH: 17
<212> TYPE: PRT
<213> ORGANISM: Homo sapiens
<220> FEATURE:
<223> OTHER INFORMATION: Antibody 11 VH PGL

<400> SEQUENCE: 308

Leu Ile Asp Pro Asp Asn Gly Glu Thr Phe Tyr Ala Glu Lys Phe Gln
1               5                   10                  15

Gly

<210> SEQ ID NO 309
<211> LENGTH: 12
<212> TYPE: PRT
<213> ORGANISM: Homo sapiens
<220> FEATURE:
<223> OTHER INFORMATION: Antibody 11 VH PGL

<400> SEQUENCE: 309

Val Met Gly Lys Trp Ile Lys Gly Gly Tyr Asp Tyr
1               5                   10

<210> SEQ ID NO 310

<400> SEQUENCE: 310

000

<210> SEQ ID NO 311

<400> SEQUENCE: 311

000

<210> SEQ ID NO 312
<211> LENGTH: 336
<212> TYPE: DNA
<213> ORGANISM: Homo sapiens
<220> FEATURE:
<223> OTHER INFORMATION: Antibody 11 VL GL

<400> SEQUENCE: 312
cagtctgtgc tgacgcagcc gccctcagtg tctggggccc cagggcagag ggtcaccatc      60

```
tcctgcactg ggagcagctc caacatcggg gcaggttatg atgtacactg gtatcagcaa    120
cttccaggaa cagcccccaa actcctcatc tatgataatt tcaatcggcc ctcagggggtc   180 cctgaccgat tctctggctc caagtctggc acctcagcct ccctggccat cactgggctc    240
caggctgaag atgaggctga ttattattgc cagtcctatg acagccccac cctcacctcc    300
cccttcggaa ccgggaccaa gctgaccgtc ctaggt                              336
```

<210> SEQ ID NO 313
<211> LENGTH: 112
<212> TYPE: PRT
<213> ORGANISM: Homo sapiens
<220> FEATURE:
<223> OTHER INFORMATION: Antibody 11 VL GL

<400> SEQUENCE: 313

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Asp Asn Phe Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Pro
                85                  90                  95

Thr Leu Thr Ser Pro Phe Gly Thr Gly Thr Lys Leu Thr Val Leu Gly
            100                 105                 110
```

<210> SEQ ID NO 314
<211> LENGTH: 14
<212> TYPE: PRT
<213> ORGANISM: Homo sapiens
<220> FEATURE:
<223> OTHER INFORMATION: Antibody 11 VL GL

<400> SEQUENCE: 314

```
Thr Gly Ser Ser Ser Asn Ile Gly Ala Gly Tyr Asp Val His
1               5                   10
```

<210> SEQ ID NO 315
<211> LENGTH: 7
<212> TYPE: PRT
<213> ORGANISM: Homo sapiens
<220> FEATURE:
<223> OTHER INFORMATION: Antibody 11 VL GL

<400> SEQUENCE: 315

```
Asp Asn Phe Asn Arg Pro Ser
1               5
```

<210> SEQ ID NO 316
<211> LENGTH: 11
<212> TYPE: PRT
<213> ORGANISM: Homo sapiens
<220> FEATURE:
<223> OTHER INFORMATION: Antibody 11 VL GL

<400> SEQUENCE: 316

```
Gln Ser Tyr Asp Ser Pro Thr Leu Thr Ser Pro
1               5                   10
```

<210> SEQ ID NO 317
<211> LENGTH: 333
<212> TYPE: DNA
<213> ORGANISM: Homo sapiens
<220> FEATURE:
<223> OTHER INFORMATION: Antibody 1 VL/DNA

<400> SEQUENCE: 317

```
cagtctgtgc tgacgcagcc gccctcagtg tctggggccc cagggcagag ggtcaccatc     60
tcctgcactg ggagcagctc caacatcggg gcaggttatg atgtacactg gtatcagcaa    120
cttccaggaa cagcccccaa actcctcatc tatgataatt tcaatcggcc ctcaggggtc    180
cctgaccgat tctctggctc caagtctggc acctcagcct ccctggccat cattgggctc    240
cagactgaag atgaggctga ttattattgc cagtcctatg acagcagcct gagtggttcc    300
ctcttcggaa ccgggaccaa gctgaccgtc cta                                 333
```

<210> SEQ ID NO 318
<211> LENGTH: 111
<212> TYPE: PRT
<213> ORGANISM: Homo sapiens
<220> FEATURE:
<223> OTHER INFORMATION: Antibody 1 VL/amino acid

<400> SEQUENCE: 318

```
Gln Ser Val Leu Thr Gln Pro Pro Ser Val Ser Gly Ala Pro Gly Gln
1               5                   10                  15
Arg Val Thr Ile Ser Cys Thr Gly Ser Ser Ser Asn Ile Gly Ala Gly
            20                  25                  30
Tyr Asp Val His Trp Tyr Gln Gln Leu Pro Gly Thr Ala Pro Lys Leu
        35                  40                  45
Leu Ile Tyr Asp Asn Phe Asn Arg Pro Ser Gly Val Pro Asp Arg Phe
    50                  55                  60
Ser Gly Ser Lys Ser Gly Thr Ser Ala Ser Leu Ala Ile Ile Gly Leu
65                  70                  75                  80
Gln Thr Glu Asp Glu Ala Asp Tyr Tyr Cys Gln Ser Tyr Asp Ser Ser
                85                  90                  95
Leu Ser Gly Ser Leu Phe Gly Thr Gly Thr Lys Leu Thr Val Leu
            100                 105                 110
```

<210> SEQ ID NO 319
<211> LENGTH: 333
<212> TYPE: DNA
<213> ORGANISM: Homo sapiens
<220> FEATURE:
<223> OTHER INFORMATION: Antibody 2 VL/DNA

<400> SEQUENCE: 319

```
cagtctgtgc tgacgcagcc gccctcagtg tctggggccc cagggcagag ggtcaccatc     60
tcctgcactg ggagcagctc caacatcggg gcaggttatg atgtacactg gtatcagcaa    120
cttccaggaa cagcccccaa actcctcatc tatgataatt tcaatcggcc ctcaggggtc    180
cctgaccgat tctctggctc caagtctggc acctcagcct ccctggccat cattgggctc    240
cagactgaag atgaggctga ttattattgc cagtcctatg acagcagcct gagtggttcc    300
ctcttcggaa ccgggaccaa gctgaccgtc cta                                 333
```

<210> SEQ ID NO 320
<211> LENGTH: 111
<212> TYPE: PRT
<213> ORGANISM: Homo sapiens
<220> FEATURE:
<223> OTHER INFORMATION: Antibody 2 VL/amino acid

<400> SEQUENCE: 320

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Asp Asn Phe Asn Arg Pro Ser Gly Val Pro Asp Arg Phe
    50                  55                  60

Ser Gly Ser Lys Ser Gly Thr Ser Ala Ser Leu Ala Ile Ile Gly Leu
65                  70                  75                  80

Gln Thr Glu Asp Glu Ala Asp Tyr Tyr Cys Gln Ser Tyr Asp Ser Ser
                85                  90                  95

Leu Ser Gly Ser Leu Phe Gly Gly Thr Lys Leu Thr Val Leu
            100                 105                 110
```

<210> SEQ ID NO 321
<211> LENGTH: 333
<212> TYPE: DNA
<213> ORGANISM: Homo sapiens
<220> FEATURE:
<223> OTHER INFORMATION: Antibody 3 VL/DNA

<400> SEQUENCE: 321

```
cagtctgtgc tgacgcagcc gccctcagtg tctggggccc cagggcagag ggtcaccatc     60
tcctgcactg ggagcagctc caacatcggg gcaggttatg atgtacactg gtatcagcaa    120
cttccaggaa cagcccccaa actcctcatc tatgataatt tcaatcggcc ctcagggttc    180
cctgaccgat tctctggctc caagtctggc acctcagcct ccctggccat cattggactc    240
cagactgaag atgaggctga ttattattgc cagtcctatg acagcacgtt caaccacgcc    300
cccttcggaa ccgggaccaa gctgaccgtc cta                                 333
```

<210> SEQ ID NO 322
<211> LENGTH: 111
<212> TYPE: PRT
<213> ORGANISM: Homo sapiens
<220> FEATURE:
<223> OTHER INFORMATION: Antibody 3 VL/amino acid

<400> SEQUENCE: 322

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Asp Asn Phe Asn Arg Pro Ser Gly Val Pro Asp Arg Phe
    50                  55                  60

Ser Gly Ser Lys Ser Gly Thr Ser Ala Ser Leu Ala Ile Ile Gly Leu
65                  70                  75                  80

Gln Thr Glu Asp Glu Ala Asp Tyr Tyr Cys Gln Ser Tyr Asp Ser Thr
                85                  90                  95

Phe Asn His Ala Pro Phe Gly Thr Gly Thr Lys Leu Thr Val Leu
            100                 105                 110
```

<210> SEQ ID NO 323
<211> LENGTH: 333
<212> TYPE: DNA
<213> ORGANISM: Homo sapiens
<220> FEATURE:
<223> OTHER INFORMATION: Antibody 4 VL/DNA

<400> SEQUENCE: 323

```
cagtctgtgc tgacgcagcc gccctcagtg tctggggccc cagggcagag ggtcaccatc    60
tcctgcactg ggagcagctc caacatcggg gcaggttatg atgtacactg gtatcagcaa   120
cttccaggaa cagcccccaa actcctcatc tatgataatt tcaatcggcc ctcaggggtc   180
cctgaccgat tctctggctc caagtctggc acctcagcct ccctggccat cattgggctc   240
cagactgaag atgaggctga ttattattgc cagtcctatg acagccgggg cggccactcc   300
ccgttcggaa ccgggaccaa gctgaccgtc cta                                 333
```

<210> SEQ ID NO 324
<211> LENGTH: 111
<212> TYPE: PRT
<213> ORGANISM: Homo sapiens
<220> FEATURE:
<223> OTHER INFORMATION: Antibody 4 VL/amino acid

<400> SEQUENCE: 324

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Asp Asn Phe Asn Arg Pro Ser Gly Val Pro Asp Arg Phe
    50                  55                  60

Ser Gly Ser Lys Ser Gly Thr Ser Ala Ser Leu Ala Ile Ile Gly Leu
65                  70                  75                  80

Gln Thr Glu Asp Glu Ala Asp Tyr Tyr Cys Gln Ser Tyr Asp Ser Arg
                85                  90                  95

Gly Gly His Ser Pro Phe Gly Thr Gly Thr Lys Leu Thr Val Leu
            100                 105                 110

<210> SEQ ID NO 325
<211> LENGTH: 333
<212> TYPE: DNA
<213> ORGANISM: Homo sapiens
<220> FEATURE:
<223> OTHER INFORMATION: Antibody 5 VL/DNA

<400> SEQUENCE: 325

```
cagtctgtgc tgacgcagcc gccctcagtg tctggggccc cagggcagag ggtcaccatc    60
tcctgcactg ggagcagctc caacatcggg gcaggttatg atgtacactg gtatcagcaa   120
cttccaggaa cagcccccaa actcctcatc tatgataatt tcaatcggcc ctcaggggtc   180
cctgaccgat tctctggctc caagtctggc acctcagcct ccctggccat cattgggctc   240
cagactgaag atgaggctga ttattattgc cagtcctatg acagcaccaa gcacacctcc   300
cccttcggaa ccgggaccaa gctgaccgtc cta                                 333
```

<210> SEQ ID NO 326
<211> LENGTH: 111
<212> TYPE: PRT
<213> ORGANISM: Homo sapiens
<220> FEATURE:

<223> OTHER INFORMATION: Antibody 5 VL/amino acid

<400> SEQUENCE: 326

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Asp Asn Phe Asn Arg Pro Ser Gly Val Pro Asp Arg Phe
    50                  55                  60

Ser Gly Ser Lys Ser Gly Thr Ser Ala Ser Leu Ala Ile Ile Gly Leu
65                  70                  75                  80

Gln Thr Glu Asp Glu Ala Asp Tyr Tyr Cys Gln Ser Tyr Asp Ser Thr
                85                  90                  95

Lys His Thr Ser Pro Phe Gly Thr Gly Thr Lys Leu Thr Val Leu
            100                 105                 110
```

<210> SEQ ID NO 327
<211> LENGTH: 333
<212> TYPE: DNA
<213> ORGANISM: Homo sapiens
<220> FEATURE:
<223> OTHER INFORMATION: Antibody 6 VL/DNA

<400> SEQUENCE: 327

```
cagtctgtgc tgacgcagcc gccctcagtg tctggggccc cagggcagag ggtcaccatc      60
tcctgcactg ggagcagctc caacatcggg gcaggttatg atgtacactg gtatcagcaa     120
cttccaggaa cagcccccaa actcctcatc tatgataatt tcaatcggcc ctcaggggtc     180
cctgaccgat tctctggctc caagtctggc acctcagcct ccctggccat cattgggctc     240
cagactgaag atgaggctga ttattattgc cagtcctatg acagcaccat gaggcacggg     300
ccgttcggaa ccgggaccaa gctgaccgtc cta                                  333
```

<210> SEQ ID NO 328
<211> LENGTH: 111
<212> TYPE: PRT
<213> ORGANISM: Homo sapiens
<220> FEATURE:
<223> OTHER INFORMATION: Antibody 6 VL/amino acid

<400> SEQUENCE: 328

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Asp Asn Phe Asn Arg Pro Ser Gly Val Pro Asp Arg Phe
    50                  55                  60

Ser Gly Ser Lys Ser Gly Thr Ser Ala Ser Leu Ala Ile Ile Gly Leu
65                  70                  75                  80

Gln Thr Glu Asp Glu Ala Asp Tyr Tyr Cys Gln Ser Tyr Asp Ser Thr
                85                  90                  95

Met Arg His Gly Pro Phe Gly Thr Gly Thr Lys Leu Thr Val Leu
            100                 105                 110
```

<210> SEQ ID NO 329

<211> LENGTH: 333
<212> TYPE: DNA
<213> ORGANISM: Homo sapiens
<220> FEATURE:
<223> OTHER INFORMATION: Antibody 7 VL/DNA

<400> SEQUENCE: 329

```
cagtctgtgc tgacgcagcc gccctcagtg tctggggccc cagggcagag ggtcaccatc      60
tcctgcactg ggagcagctc caacatcggg gcaggttatg atgtacactg gtatcagcaa     120
cttccaggaa cagcccccaa actcctcatc tatgataatt tcaatcggcc ctcaggggtc     180
cctgaccgat tctctggctc caagtctggc acctcagcct ccctggccat cattgggctc     240
cagactgaag atgaggctga ttattattgc cagtcctatg acagcgacag gaggaactcc     300
ccgttcggaa ccgggaccaa gctgaccgtc cta                                   333
```

<210> SEQ ID NO 330
<211> LENGTH: 111
<212> TYPE: PRT
<213> ORGANISM: Homo sapiens
<220> FEATURE:
<223> OTHER INFORMATION: Antibody 7 VL/amino acid

<400> SEQUENCE: 330

```
Gln Ser Val Leu Thr Gln Pro Pro Ser Val Ser Gly Ala Pro Gly Gln
 1               5                  10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Asp Asn Phe Asn Arg Pro Ser Gly Val Pro Asp Arg Phe
    50                  55                  60

Ser Gly Ser Lys Ser Gly Thr Ser Ala Ser Leu Ala Ile Ile Gly Leu
65                  70                  75                  80

Gln Thr Glu Asp Glu Ala Asp Tyr Tyr Cys Gln Ser Tyr Asp Ser Asp
                85                  90                  95

Arg Arg Asn Ser Pro Phe Gly Thr Gly Thr Lys Leu Thr Val Leu
            100                 105                 110
```

<210> SEQ ID NO 331
<211> LENGTH: 333
<212> TYPE: DNA
<213> ORGANISM: Homo sapiens
<220> FEATURE:
<223> OTHER INFORMATION: Antibody 8 VL/DNA

<400> SEQUENCE: 331

```
cagtctgtgc tgacgcagcc gccctcagtg tctggggccc cagggcagag ggtcaccatc      60
tcctgcactg ggagcagctc caacatcggg gcaggttatg atgtacactg gtatcagcaa     120
cttccaggaa cagcccccaa actcctcatc tatgataatt tcaatcggcc ctcaggggtc     180
cctgaccgat tctctggctc caagtctggc acctcagcct ccctggccat cattgggctc     240
cagactgaag atgaggctga ttattattgc cagtcctatg acagccccac ccacacctcc     300
cccttcggaa ccgggaccaa gctgaccgtc cta                                   333
```

<210> SEQ ID NO 332
<211> LENGTH: 111
<212> TYPE: PRT
<213> ORGANISM: Homo sapiens
<220> FEATURE:
<223> OTHER INFORMATION: Antibody 8 VL/amino acid

<400> SEQUENCE: 332

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Asp Asn Phe Asn Arg Pro Ser Gly Val Pro Asp Arg Phe
    50                  55                  60

Ser Gly Ser Lys Ser Gly Thr Ser Ala Ser Leu Ala Ile Ile Gly Leu
65                  70                  75                  80

Gln Thr Glu Asp Glu Ala Asp Tyr Tyr Cys Gln Ser Tyr Asp Ser Pro
                85                  90                  95

Thr His Thr Ser Pro Phe Gly Thr Gly Thr Lys Leu Thr Val Leu
            100                 105                 110

<210> SEQ ID NO 333
<211> LENGTH: 333
<212> TYPE: DNA
<213> ORGANISM: Homo sapiens
<220> FEATURE:
<223> OTHER INFORMATION: Antibody 9 VL/DNA

<400> SEQUENCE: 333

```
cagtctgtgc tgacgcagcc gcccctcagtg tctggggccc cagggcagag ggtcaccatc      60
tcctgcactg ggagcagctc caacatcggg gcaggttatg atgtacactg gtatcagcaa     120
cttccaggaa cagcccccaa actcctcatc tatgataatt tcaatcggcc ctcaggggtc     180
cctgaccgat tctctggctc caagtctggc acctcagcct ccctggccat cattgggctc     240
cagactgaag atgaggctga ttattattgc cagtcctatg acagccccct ctccacctcc     300
cccttcggaa ccgggaccaa gctgaccgtc cta                                  333
```

<210> SEQ ID NO 334
<211> LENGTH: 111
<212> TYPE: PRT
<213> ORGANISM: Homo sapiens
<220> FEATURE:
<223> OTHER INFORMATION: Antibody 9 VL/amino acid

<400> SEQUENCE: 334

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Asp Asn Phe Asn Arg Pro Ser Gly Val Pro Asp Arg Phe
    50                  55                  60

Ser Gly Ser Lys Ser Gly Thr Ser Ala Ser Leu Ala Ile Ile Gly Leu
65                  70                  75                  80

Gln Thr Glu Asp Glu Ala Asp Tyr Tyr Cys Gln Ser Tyr Asp Ser Pro
                85                  90                  95

Ser Ser Thr Ser Pro Phe Gly Thr Gly Thr Lys Leu Thr Val Leu
            100                 105                 110

<210> SEQ ID NO 335
<211> LENGTH: 333

```
<212> TYPE: DNA
<213> ORGANISM: Homo sapiens
<220> FEATURE:
<223> OTHER INFORMATION: Antibody 10 VL/DNA

<400> SEQUENCE: 335
cagtctgtgc tgacgcagcc gccctcagtg tctggggccc cagggcagag ggtcaccatc      60
tcctgcactg ggagcagctc caacatcggg gcaggttatg atgtacactg gtatcagcaa    120
cttccaggaa cagcccccaa actcctcatc tatgataatt tcaatcggcc ctcagggggtc   180 cctgaccgat tctctggctc caagtctggc acctcagcct ccctggccat cattgggctc    240
cagactgaag atgaggctga ttattattgc cagtcctatg acagcgagca ggagttggcg    300
ccgttcggaa ccgggaccaa gctgaccgtc cta                                  333

<210> SEQ ID NO 336
<211> LENGTH: 111
<212> TYPE: PRT
<213> ORGANISM: Homo sapiens
<220> FEATURE:
<223> OTHER INFORMATION: Antibody 10 VL/amino acid

<400> SEQUENCE: 336

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Asp Asn Phe Asn Arg Pro Ser Gly Val Pro Asp Arg Phe
    50                  55                  60

Ser Gly Ser Lys Ser Gly Thr Ser Ala Ser Leu Ala Ile Ile Gly Leu
65                  70                  75                  80

Gln Thr Glu Asp Glu Ala Asp Tyr Tyr Cys Gln Ser Tyr Asp Ser Glu
                85                  90                  95

Gln Glu Leu Ala Pro Phe Gly Thr Gly Thr Lys Leu Thr Val Leu
            100                 105                 110

<210> SEQ ID NO 337
<211> LENGTH: 333
<212> TYPE: DNA
<213> ORGANISM: Homo sapiens
<220> FEATURE:
<223> OTHER INFORMATION: Antibody 11 VL/DNA

<400> SEQUENCE: 337
cagtctgtgc tgacgcagcc gccctcagtg tctggggccc cagggcagag ggtcaccatc      60
tcctgcactg ggagcagctc caacatcggg gcaggttatg atgtacactg gtatcagcaa    120
cttccaggaa cagcccccaa actcctcatc tatgataatt tcaatcggcc ctcagggggtc   180 cctgaccgat tctctggctc caagtctggc acctcagcct ccctggccat cattgggctc    240
cagactgaag atgaggctga ttattattgc cagtcctatg acagccccac cctcacctcc    300
cccttcggaa ccgggaccaa gctgaccgtc cta                                  333

<210> SEQ ID NO 338
<211> LENGTH: 111
<212> TYPE: PRT
<213> ORGANISM: Homo sapiens
<220> FEATURE:
<223> OTHER INFORMATION: Antibody 11 VL/amino acid
```

<400> SEQUENCE: 338

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Asp Asn Phe Asn Arg Pro Ser Gly Val Pro Asp Arg Phe
    50                  55                  60

Ser Gly Ser Lys Ser Gly Thr Ser Ala Ser Leu Ala Ile Ile Gly Leu
65                  70                  75                  80

Gln Thr Glu Asp Glu Ala Asp Tyr Tyr Cys Gln Ser Tyr Asp Ser Pro
                85                  90                  95

Thr Leu Thr Ser Pro Phe Gly Thr Gly Thr Lys Leu Thr Val Leu
            100                 105                 110

<210> SEQ ID NO 339
<211> LENGTH: 333
<212> TYPE: DNA
<213> ORGANISM: Homo sapiens
<220> FEATURE:
<223> OTHER INFORMATION: Antibody 12 VL/DNA

<400> SEQUENCE: 339
cagtctgtgc tgacgcagcc gccctcagtg tctggggccc cagggcagag ggtcaccatc      60
tcctgcactg ggagcagctc aacatcggg gcaggttatg atgtacactg gtatcagcaa     120
cttccaggaa cagcccccaa actcctcatc tatgataatt tcaatcggcc ctcaggggtc     180
cctgaccgat tctctggctc caagtctggc acctcagcct ccctggccat cattgggctc     240
cagactgaag atgaggctga ttattattgc cagtcctatg acagctccat cgaccactcc     300
cccttcggaa ccgggaccaa gctgaccgtc cta                                 333

<210> SEQ ID NO 340
<211> LENGTH: 111
<212> TYPE: PRT
<213> ORGANISM: Homo sapiens
<220> FEATURE:
<223> OTHER INFORMATION: Antibody 12 VL/amino acid

<400> SEQUENCE: 340

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Asp Asn Phe Asn Arg Pro Ser Gly Val Pro Asp Arg Phe
    50                  55                  60

Ser Gly Ser Lys Ser Gly Thr Ser Ala Ser Leu Ala Ile Ile Gly Leu
65                  70                  75                  80

Gln Thr Glu Asp Glu Ala Asp Tyr Tyr Cys Gln Ser Tyr Asp Ser Ser
                85                  90                  95

Ile Asp His Ser Pro Phe Gly Thr Gly Thr Lys Leu Thr Val Leu
            100                 105                 110

<210> SEQ ID NO 341
<211> LENGTH: 333
<212> TYPE: DNA

<213> ORGANISM: Homo sapiens
<220> FEATURE:
<223> OTHER INFORMATION: Antibody 13 VL/DNA

<400> SEQUENCE: 341

```
cagtctgtgc tgacgcagcc gccctcagtg tctggggccc cagggcagag ggtcaccatc    60
tcctgcactg ggagcagctc caacatcggg gcaggttatg atgtacactg gtatcagcaa   120
cttccaggaa cagcccccaa actcctcatc tatgataatt tcaatcggcc ctcaggggtc   180
cctgaccgat tctctggctc caagtctggc acctcagcct ccctggccat cattgggctc   240
cagactgaag atgaggctga ttattattgc cagtcctatg acagcaacat cttgtactcc   300
cccttcggaa ccgggaccaa gctgaccgtc cta                                 333
```

<210> SEQ ID NO 342
<211> LENGTH: 111
<212> TYPE: PRT
<213> ORGANISM: Homo sapiens
<220> FEATURE:
<223> OTHER INFORMATION: Antibody 13 VL/amino acid

<400> SEQUENCE: 342

```
Gln Ser Val Leu Thr Gln Pro Pro Ser Val Ser Gly Ala Pro Gly Gln
1               5                   10                  15
Arg Val Thr Ile Ser Cys Thr Gly Ser Ser Ser Asn Ile Gly Ala Gly
            20                  25                  30
Tyr Asp Val His Trp Tyr Gln Gln Leu Pro Gly Thr Ala Pro Lys Leu
        35                  40                  45
Leu Ile Tyr Asp Asn Phe Asn Arg Pro Ser Gly Val Pro Asp Arg Phe
    50                  55                  60
Ser Gly Ser Lys Ser Gly Thr Ser Ala Ser Leu Ala Ile Ile Gly Leu
65                  70                  75                  80
Gln Thr Glu Asp Glu Ala Asp Tyr Tyr Cys Gln Ser Tyr Asp Ser Asn
                85                  90                  95
Ile Leu Tyr Ser Pro Phe Gly Thr Gly Thr Lys Leu Thr Val Leu
            100                 105                 110
```

<210> SEQ ID NO 343
<211> LENGTH: 333
<212> TYPE: DNA
<213> ORGANISM: Homo sapiens
<220> FEATURE:
<223> OTHER INFORMATION: Antibody 14 VL/DNA

<400> SEQUENCE: 343

```
cagtctgtgc tgacgcagcc gccctcagtg tctggggccc cagggcagag ggtcaccatc    60
tcctgcactg ggagcagctc caacatcggg gcaggttatg atgtacactg gtatcagcaa   120
cttccaggaa cagcccccaa actcctcatc tatgataatt tcaatcggcc ctcaggggtc   180
cctgaccgat tctctggctc caagtctggc acctcagcct ccctggccat cattgggctc   240
cagactgaag atgaggctga ttattattgc cagtcctatg acagccacca ccgccactcc   300
cccttcggaa ccgggaccaa gctgaccgtc cta                                 333
```

<210> SEQ ID NO 344
<211> LENGTH: 111
<212> TYPE: PRT
<213> ORGANISM: Homo sapiens
<220> FEATURE:
<223> OTHER INFORMATION: Antibody 14 VL/amino acid

<400> SEQUENCE: 344

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
            35                  40                  45

Leu Ile Tyr Asp Asn Phe Asn Arg Pro Ser Gly Val Pro Asp Arg Phe
50                      55                  60

Ser Gly Ser Lys Ser Gly Thr Ser Ala Ser Leu Ala Ile Ile Gly Leu
65                  70                  75                  80

Gln Thr Glu Asp Glu Ala Asp Tyr Tyr Cys Gln Ser Tyr Asp Ser His
                85                  90                  95

His Arg His Ser Pro Phe Gly Thr Gly Thr Lys Leu Thr Val Leu
            100                 105                 110

<210> SEQ ID NO 345
<211> LENGTH: 333
<212> TYPE: DNA
<213> ORGANISM: Homo sapiens
<220> FEATURE:
<223> OTHER INFORMATION: Antibody 15 VL/DNA

<400> SEQUENCE: 345
cagtctgtgc tgacgcagcc gccctcagtg tctggggccc cagggcagag ggtcaccatc      60
tcctgcactg ggagcagctc caacatcggg gcaggttatg atgtacactg gtatcagcaa     120
cttccaggaa cagcccccaa actcctcatc tatgataatt tcaatcggcc ctcagggg tc     180 cctgaccgat tctctggctc caagtctggc acctcagcct ccctggccat cattgggctc     240
cagactgaag atgaggctga ttattattgc cagtcctatg acagccacaa ggggtacggg     300
gggttcggaa ccgggaccaa gctgaccgtc cta                                   333

<210> SEQ ID NO 346
<211> LENGTH: 111
<212> TYPE: PRT
<213> ORGANISM: Homo sapiens
<220> FEATURE:
<223> OTHER INFORMATION: Antibody 15 VL/amino acid

<400> SEQUENCE: 346

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
            35                  40                  45

Leu Ile Tyr Asp Asn Phe Asn Arg Pro Ser Gly Val Pro Asp Arg Phe
50                      55                  60

Ser Gly Ser Lys Ser Gly Thr Ser Ala Ser Leu Ala Ile Ile Gly Leu
65                  70                  75                  80

Gln Thr Glu Asp Glu Ala Asp Tyr Tyr Cys Gln Ser Tyr Asp Ser His
                85                  90                  95

Lys Gly Tyr Gly Gly Phe Gly Thr Gly Thr Lys Leu Thr Val Leu
            100                 105                 110

<210> SEQ ID NO 347
<211> LENGTH: 333
<212> TYPE: DNA
<213> ORGANISM: Homo sapiens
<220> FEATURE:
<223> OTHER INFORMATION: Antibody 16 VL/DNA

<400> SEQUENCE: 347

```
cagtctgtgc tgacgcagcc gccctcagtg tctggggccc cagggcagag ggtcaccatc    60
tcctgcactg ggagcagctc caacatcggg gcaggttatg atgtacactg gtatcagcaa   120
cttccaggaa cagcccccaa actcctcatc tatgataatt tcaatcggcc ctcaggggtc   180
cctgaccgat tctctggctc caagtctggc acctcagcct ccctggccat cattgggctc   240
cagactgaag atgaggctga ttattattgc cagtcctatg acagccgcca ccaccacgcg   300
ccgttcggaa ccgggaccaa gctgaccgtc cta                                 333
```

<210> SEQ ID NO 348
<211> LENGTH: 111
<212> TYPE: PRT
<213> ORGANISM: Homo sapiens
<220> FEATURE:
<223> OTHER INFORMATION: Antibody 16 VL/amino acid

<400> SEQUENCE: 348

```
Gln Ser Val Leu Thr Gln Pro Pro Ser Val Ser Gly Ala Pro Gly Gln
 1               5                  10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Asp Asn Phe Asn Arg Pro Ser Gly Val Pro Asp Arg Phe
    50                  55                  60

Ser Gly Ser Lys Ser Gly Thr Ser Ala Ser Leu Ala Ile Ile Gly Leu
65                  70                  75                  80

Gln Thr Glu Asp Glu Ala Asp Tyr Tyr Cys Gln Ser Tyr Asp Ser Arg
                85                  90                  95

His His His Ala Pro Phe Gly Thr Gly Thr Lys Leu Thr Val Leu
            100                 105                 110
```

<210> SEQ ID NO 349
<211> LENGTH: 333
<212> TYPE: DNA
<213> ORGANISM: Homo sapiens
<220> FEATURE:
<223> OTHER INFORMATION: Antibody 17 VL/DNA

<400> SEQUENCE: 349

```
cagtctgtgc tgacgcagcc gccctcagtg tctggggccc cagggcagag ggtcaccatc    60
tcctgcactg ggagcagctc caacatcggg gcaggttatg atgtacactg gtatcagcaa   120
cttccaggaa cagcccccaa actcctcatc tatgataatt tcaatcggcc ctcaggggtc   180
cctgaccgat tctctggctc caagtctggc acctcagcct ccctggccat cattgggctc   240
cagactgaag atgaggctga ttattattgc cagtcctatg acagccagag ctccacctcc   300
cccttcggaa ccgggaccaa gctgaccgtc cta                                 333
```

<210> SEQ ID NO 350
<211> LENGTH: 111
<212> TYPE: PRT
<213> ORGANISM: Homo sapiens
<220> FEATURE:
<223> OTHER INFORMATION: Antibody 17 VL/amino acid

<400> SEQUENCE: 350

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
                20                  25                  30

Tyr Asp Val His Trp Tyr Gln Gln Leu Pro Gly Thr Ala Pro Lys Leu
            35                  40                  45

Leu Ile Tyr Asp Asn Phe Asn Arg Pro Ser Gly Val Pro Asp Arg Phe
    50                  55                  60

Ser Gly Ser Lys Ser Gly Thr Ser Ala Ser Leu Ala Ile Ile Gly Leu
65              70                  75                  80

Gln Thr Glu Asp Glu Ala Asp Tyr Tyr Cys Gln Ser Tyr Asp Ser Gln
                85                  90                  95

Ser Ser Thr Ser Pro Phe Gly Thr Gly Thr Lys Leu Thr Val Leu
            100                 105                 110
```

<210> SEQ ID NO 351
<211> LENGTH: 333
<212> TYPE: DNA
<213> ORGANISM: Homo sapiens
<220> FEATURE:
<223> OTHER INFORMATION: Antibody 18 VL/DNA

<400> SEQUENCE: 351

```
cagtctgtgc tgacgcagcc gccctcagtg tctggggccc cagggcagag ggtcaccatc      60
tcctgcactg ggagcagctc caacatcggg gcaggttatg atgtacactg gtatcagcaa     120
cttccaggaa cagcccccaa actcctcatc tatgataatt tcaatcggcc ctcaggggtc     180
cctgaccgat tctctggctc caagtctggc acctcagcct ccctggccat cattgggctc     240
cagactgaag atgaggctga ttattattgc cagtcctatg acagccacct ccagttgagc     300
ccgttcggaa ccgggaccaa gctgaccgtc cta                                  333
```

<210> SEQ ID NO 352
<211> LENGTH: 111
<212> TYPE: PRT
<213> ORGANISM: Homo sapiens
<220> FEATURE:
<223> OTHER INFORMATION: Antibody 18 VL/amino acid

<400> SEQUENCE: 352

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
                20                  25                  30

Tyr Asp Val His Trp Tyr Gln Gln Leu Pro Gly Thr Ala Pro Lys Leu
            35                  40                  45

Leu Ile Tyr Asp Asn Phe Asn Arg Pro Ser Gly Val Pro Asp Arg Phe
    50                  55                  60

Ser Gly Ser Lys Ser Gly Thr Ser Ala Ser Leu Ala Ile Ile Gly Leu
65              70                  75                  80

Gln Thr Glu Asp Glu Ala Asp Tyr Tyr Cys Gln Ser Tyr Asp Ser His
                85                  90                  95

Leu Gln Leu Ser Pro Phe Gly Thr Gly Thr Lys Leu Thr Val Leu
            100                 105                 110
```

<210> SEQ ID NO 353
<211> LENGTH: 333
<212> TYPE: DNA
<213> ORGANISM: Homo sapiens
<220> FEATURE:

<223> OTHER INFORMATION: Antibody 19 VL/DNA

<400> SEQUENCE: 353

```
cagtctgtgc tgacgcagcc gccctcagtg tctggggccc cagggcagag ggtcaccatc    60
tcctgcactg ggagcagctc caacatcggg gcaggttatg atgtacactg gtatcagcaa   120
cttccaggaa cagcccccaa actcctcatc tatgataatt tcaatcggcc ctcaggggtc   180
cctgaccgat tctctggctc caagtctggc acctcagcct ccctggccat cattgggctc   240
cagactgaag atgaggctga ttattattgc cagtcctatg acagcacgtt gtcccactcc   300
cccttcggaa ccgggaccaa gctgaccgtc cta                                333
```

<210> SEQ ID NO 354
<211> LENGTH: 111
<212> TYPE: PRT
<213> ORGANISM: Homo sapiens
<220> FEATURE:
<223> OTHER INFORMATION: Antibody 19 VL/amino acid

<400> SEQUENCE: 354

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Asp Asn Phe Asn Arg Pro Ser Gly Val Pro Asp Arg Phe
50                  55                  60

Ser Gly Ser Lys Ser Gly Thr Ser Ala Ser Leu Ala Ile Ile Gly Leu
65                  70                  75                  80

Gln Thr Glu Asp Glu Ala Asp Tyr Tyr Cys Gln Ser Tyr Asp Ser Thr
                85                  90                  95

Leu Ser His Ser Pro Phe Gly Thr Gly Thr Lys Leu Thr Val Leu
            100                 105                 110
```

<210> SEQ ID NO 355
<211> LENGTH: 333
<212> TYPE: DNA
<213> ORGANISM: Homo sapiens
<220> FEATURE:
<223> OTHER INFORMATION: Antibody 20 VL/DNA

<400> SEQUENCE: 355

```
cagtctgtgc tgacgcagcc gccctcagtg tctggggccc cagggcagag ggtcaccatc    60
tcctgcactg ggagcagctc caacatcggg gcaggttatg atgtacactg gtatcagcaa   120
cttccaggaa cagcccccaa actcctcatc tatgataatt tcaatcggcc ctcaggggtc   180
cctgaccgat tctctggctc caagtctggc acctcagcct ccctggccat cattgggctc   240
cagactgaag atgaggctga ttattattgc cagtcctatg acagctccac gtcctcctcc   300
cccttcggaa ccgggaccaa gctgaccgtc cta                                333
```

<210> SEQ ID NO 356
<211> LENGTH: 111
<212> TYPE: PRT
<213> ORGANISM: Homo sapiens
<220> FEATURE:
<223> OTHER INFORMATION: Antibody 20 VL/amino acid

<400> SEQUENCE: 356

```
Gln Ser Val Leu Thr Gln Pro Pro Ser Val Ser Gly Ala Pro Gly Gln
```

```
                1               5                   10                  15
Arg Val Thr Ile Ser Cys Thr Gly Ser Ser Asn Ile Gly Ala Gly
                    20                  25                  30

Tyr Asp Val His Trp Tyr Gln Gln Leu Pro Gly Thr Ala Pro Lys Leu
            35                  40                  45

Leu Ile Tyr Asp Asn Phe Asn Arg Pro Ser Gly Val Pro Asp Arg Phe
        50                  55                  60

Ser Gly Ser Lys Ser Gly Thr Ser Ala Ser Leu Ala Ile Ile Gly Leu
65                  70                  75                  80

Gln Thr Glu Asp Glu Ala Asp Tyr Tyr Cys Gln Ser Tyr Asp Ser Ser
                85                  90                  95

Thr Ser Ser Ser Pro Phe Gly Thr Gly Thr Lys Leu Thr Val Leu
            100                 105                 110

<210> SEQ ID NO 357
<211> LENGTH: 333
<212> TYPE: DNA
<213> ORGANISM: Homo sapiens
<220> FEATURE:
<223> OTHER INFORMATION: Antibody 21 VL/DNA

<400> SEQUENCE: 357
cagtctgtgc tgacgcagcc gccctcagtg tctggggccc cagggcagag ggtcaccatc      60
tcctgcactg ggagcagctc caacatcggg gcaggttatg atgtacactg gtatcagcaa     120
cttccaggaa cagcccccaa actcctcatc tatgataatt tcaatcggcc ctcaggggtc     180
cctgaccgat tctctggctc caagtctggc acctcagcct ccctggccat cattgggctc     240
cagactgaag atgaggctga ttattattgc cagtcctatg acagctcgtc gcagttgagc     300
ccgttcggaa ccgggaccaa gctgaccgtc cta                                  333

<210> SEQ ID NO 358
<211> LENGTH: 111
<212> TYPE: PRT
<213> ORGANISM: Homo sapiens
<220> FEATURE:
<223> OTHER INFORMATION: Antibody 21 VL/amino acid

<400> SEQUENCE: 358

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
                    20                  25                  30

Tyr Asp Val His Trp Tyr Gln Gln Leu Pro Gly Thr Ala Pro Lys Leu
            35                  40                  45

Leu Ile Tyr Asp Asn Phe Asn Arg Pro Ser Gly Val Pro Asp Arg Phe
        50                  55                  60

Ser Gly Ser Lys Ser Gly Thr Ser Ala Ser Leu Ala Ile Ile Gly Leu
65                  70                  75                  80

Gln Thr Glu Asp Glu Ala Asp Tyr Tyr Cys Gln Ser Tyr Asp Ser Ser
                85                  90                  95

Ser Gln Leu Ser Pro Phe Gly Thr Gly Thr Lys Leu Thr Val Leu
            100                 105                 110

<210> SEQ ID NO 359
<211> LENGTH: 333
<212> TYPE: DNA
<213> ORGANISM: Homo sapiens
<220> FEATURE:
<223> OTHER INFORMATION: Antibody 22 VL/DNA
```

<400> SEQUENCE: 359

```
cagtctgtgc tgacgcagcc gccctcagtg tctggggccc cagggcagag ggtcaccatc      60
tcctgcactg ggagcagctc aacatcgggg gcaggttatg atgtacactg gtatcagcaa     120
cttccaggaa cagcccccaa actcctcatc tatgataatt caatcggcc ctcagggtc       180
cctgaccgat tctctggctc caagtctggc acctcagcct ccctggccat cattgggctc     240
cagactgaag atgaggctga ttattattgc cagtcctatg acagcagcgg ggggtacgcg     300
ccgttcggaa ccgggaccaa gctgaccgtc cta                                   333
```

<210> SEQ ID NO 360
<211> LENGTH: 111
<212> TYPE: PRT
<213> ORGANISM: Homo sapiens
<220> FEATURE:
<223> OTHER INFORMATION: Antibody 22 VL/amino acid

<400> SEQUENCE: 360

```
Gln Ser Val Leu Thr Gln Pro Pro Ser Val Ser Gly Ala Pro Gly Gln
1               5                   10                  15
Arg Val Thr Ile Ser Cys Thr Gly Ser Ser Asn Ile Gly Ala Gly
            20                  25                  30
Tyr Asp Val His Trp Tyr Gln Gln Leu Pro Gly Thr Ala Pro Lys Leu
        35                  40                  45
Leu Ile Tyr Asp Asn Phe Asn Arg Pro Ser Gly Val Pro Asp Arg Phe
    50                  55                  60
Ser Gly Ser Lys Ser Gly Thr Ser Ala Ser Leu Ala Ile Ile Gly Leu
65                  70                  75                  80
Gln Thr Glu Asp Glu Ala Asp Tyr Tyr Cys Gln Ser Tyr Asp Ser Ser
                85                  90                  95
Gly Gly Tyr Ala Pro Phe Gly Thr Gly Thr Lys Leu Thr Val Leu
            100                 105                 110
```

<210> SEQ ID NO 361
<211> LENGTH: 333
<212> TYPE: DNA
<213> ORGANISM: Homo sapiens
<220> FEATURE:
<223> OTHER INFORMATION: Antibody 23 VL/DNA

<400> SEQUENCE: 361

```
cagtctgtgc tgacgcagcc gccctcagtg tctggggccc cagggcagag ggtcaccatc      60
tcctgcactg ggagcagctc aacatcgggg gcaggttatg atgtacactg gtatcagcaa     120
cttccaggaa cagcccccaa actcctcatc tatgataatt caatcggcc ctcagggtc       180
cctgaccgat tctctggctc caagtctggc acctcagcct ccctggccat cattgggctc     240
cagactgaag atgaggctga ttattattgc cagtcctatg acagccacca cctctactcc     300
tccttcggaa ccgggaccaa gctgaccgtc cta                                   333
```

<210> SEQ ID NO 362
<211> LENGTH: 111
<212> TYPE: PRT
<213> ORGANISM: Homo sapiens
<220> FEATURE:
<223> OTHER INFORMATION: Antibody 23 VL/amino acid

<400> SEQUENCE: 362

```
Gln Ser Val Leu Thr Gln Pro Pro Ser Val Ser Gly Ala Pro Gly Gln
1               5                   10                  15
```

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
            35                  40                  45

Leu Ile Tyr Asp Asn Phe Asn Arg Pro Ser Gly Val Pro Asp Arg Phe
 50                  55                  60

Ser Gly Ser Lys Ser Gly Thr Ser Ala Ser Leu Ala Ile Ile Gly Leu
 65                  70                  75                  80

Gln Thr Glu Asp Glu Ala Asp Tyr Tyr Cys Gln Ser Tyr Asp Ser His
                85                  90                  95

His Leu Tyr Ser Ser Phe Gly Thr Gly Thr Lys Leu Thr Val Leu
            100                 105                 110

<210> SEQ ID NO 363
<211> LENGTH: 333
<212> TYPE: DNA
<213> ORGANISM: Homo sapiens
<220> FEATURE:
<223> OTHER INFORMATION: Antibody 24 VL/DNA

<400> SEQUENCE: 363

```
cagtctgtgc tgacgcagcc gccctcagtg tctggggccc cagggcagag ggtcaccatc     60
tcctgcactg ggagcagctc caacatcggg gcaggttatg atgtacactg gtatcagcaa    120
cttccaggaa cagcccccaa actcctcatc tatgataatt tcaatcggcc ctcaggggtc    180
cctgaccgat tctctggctc caagtctggc acctcagcct ccctggccat cattgggctc    240
cagactgaag atgaggctga ttattattgc cagtcctatg acagcaggaa cggctacggc    300
gggttcggaa ccgggaccaa gctgaccgtc cta                                 333
```

<210> SEQ ID NO 364
<211> LENGTH: 111
<212> TYPE: PRT
<213> ORGANISM: Homo sapiens
<220> FEATURE:
<223> OTHER INFORMATION: Antibody 24 VL/amino acid

<400> SEQUENCE: 364

Gln Ser Val Leu Thr Gln Pro Pro Ser Val Ser Gly Ala Pro Gly Gln
 1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
            35                  40                  45

Leu Ile Tyr Asp Asn Phe Asn Arg Pro Ser Gly Val Pro Asp Arg Phe
 50                  55                  60

Ser Gly Ser Lys Ser Gly Thr Ser Ala Ser Leu Ala Ile Ile Gly Leu
 65                  70                  75                  80

Gln Thr Glu Asp Glu Ala Asp Tyr Tyr Cys Gln Ser Tyr Asp Ser Arg
                85                  90                  95

Asn Gly Tyr Gly Gly Phe Gly Thr Gly Thr Lys Leu Thr Val Leu
            100                 105                 110

<210> SEQ ID NO 365
<211> LENGTH: 333
<212> TYPE: DNA
<213> ORGANISM: Homo sapiens
<220> FEATURE:
<223> OTHER INFORMATION: Antibody 25 VL/DNA

<400> SEQUENCE: 365

```
cagtctgtgc tgacgcagcc gccctcagtg tctggggccc cagggcagag ggtcaccatc      60
tcctgcactg ggagcagctc caacatcggg gcaggttatg atgtacactg gtatcagcaa     120
cttccaggaa cagcccccaa actcctcatc tatgataatt tcaatcggcc ctcaggggtc     180
cctgaccgat tctctggctc caagtctggc acctcagcct ccctggccat cattgggctc     240
cagactgaag atgaggctga ttattattgc cagtcctatg acagcaacca caagacctcc     300
cccttcggaa ccgggaccaa gctgaccgtc cta                                  333
```

<210> SEQ ID NO 366
<211> LENGTH: 111
<212> TYPE: PRT
<213> ORGANISM: Homo sapiens
<220> FEATURE:
<223> OTHER INFORMATION: Antibody 25 VL/amino acid

<400> SEQUENCE: 366

```
Gln Ser Val Leu Thr Gln Pro Pro Ser Val Ser Gly Ala Pro Gly Gln
  1               5                  10                  15

Arg Val Thr Ile Ser Cys Thr Gly Ser Ser Ser Asn Ile Gly Ala Gly
                 20                  25                  30

Tyr Asp Val His Trp Tyr Gln Gln Leu Pro Gly Thr Ala Pro Lys Leu
             35                  40                  45

Leu Ile Tyr Asp Asn Phe Asn Arg Pro Ser Gly Val Pro Asp Arg Phe
         50                  55                  60

Ser Gly Ser Lys Ser Gly Thr Ser Ala Ser Leu Ala Ile Ile Gly Leu
 65                  70                  75                  80

Gln Thr Glu Asp Glu Ala Asp Tyr Tyr Cys Gln Ser Tyr Asp Ser Asn
                 85                  90                  95

His Lys Thr Ser Pro Phe Gly Thr Gly Thr Lys Leu Thr Val Leu
                100                 105                 110
```

<210> SEQ ID NO 367
<211> LENGTH: 333
<212> TYPE: DNA
<213> ORGANISM: Homo sapiens
<220> FEATURE:
<223> OTHER INFORMATION: Antibody 26 VL/DNA

<400> SEQUENCE: 367

```
cagtctgtgc tgacgcagcc gccctcagtg tctggggccc cagggcagag ggtcaccatc      60
tcctgcactg ggagcagctc caacatcggg gcaggttatg atgtacactg gtatcagcaa     120
cttccaggaa cagcccccaa actcctcatc tatgataatt tcaatcggcc ctcaggggtc     180
cctgaccgat tctctggctc caagtctggc acctcagcct ccctggccat cattgggctc     240
cagactgaag atgaggctga ttattattgc cagtcctatg acagcgcctc ccgccacgcc     300
cccttcggaa ccgggaccaa gctgaccgtc cta                                  333
```

<210> SEQ ID NO 368
<211> LENGTH: 111
<212> TYPE: PRT
<213> ORGANISM: Homo sapiens
<220> FEATURE:
<223> OTHER INFORMATION: Antibody 26 VL/amino acid

<400> SEQUENCE: 368

```
Gln Ser Val Leu Thr Gln Pro Pro Ser Val Ser Gly Ala Pro Gly Gln
  1               5                  10                  15
```

```
Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Asp Asn Phe Asn Arg Pro Ser Gly Val Pro Asp Arg Phe
50                  55                  60

Ser Gly Ser Lys Ser Gly Thr Ser Ala Ser Leu Ala Ile Ile Gly Leu
65                  70                  75                  80

Gln Thr Glu Asp Glu Ala Asp Tyr Tyr Cys Gln Ser Tyr Asp Ser Ala
                85                  90                  95

Ser Arg His Ala Pro Phe Gly Thr Gly Thr Lys Leu Thr Val Leu
            100                 105                 110

<210> SEQ ID NO 369
<211> LENGTH: 333
<212> TYPE: DNA
<213> ORGANISM: Homo sapiens
<220> FEATURE:
<223> OTHER INFORMATION: Antibody 27 VL/DNA

<400> SEQUENCE: 369
cagtctgtgc tgacgcagcc gccctcagtg tctggggccc cagggcagag ggtcaccatc      60
tcctgcactg ggagcagctc caacatcggg gcaggttatg atgtacactg gtatcagcaa     120
cttccaggaa cagcccccaa actcctcatc tatgataatt tcaatcggcc ctcaggggtc     180
cctgaccgat tctctggctc caagtctggc acctcagcct ccctggccat cattgggctc     240
cagactgaag atgaggctga ttattattgc cagtcctatg acagccccac ccagacctcc     300
cccttcggaa ccgggaccaa gctgaccgtc cta                                   333

<210> SEQ ID NO 370
<211> LENGTH: 111
<212> TYPE: PRT
<213> ORGANISM: Homo sapiens
<220> FEATURE:
<223> OTHER INFORMATION: Antibody 27 VL/amino acid

<400> SEQUENCE: 370

Gln Ser Val Leu Thr Gln Pro Pro Ser Val Ser Gly Ala Pro Gly Gln
1               5                   10                  15

Arg Val Thr Ile Ser Cys Thr Gly Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Asp Asn Phe Asn Arg Pro Ser Gly Val Pro Asp Arg Phe
50                  55                  60

Ser Gly Ser Lys Ser Gly Thr Ser Ala Ser Leu Ala Ile Ile Gly Leu
65                  70                  75                  80

Gln Thr Glu Asp Glu Ala Asp Tyr Tyr Cys Gln Ser Tyr Asp Ser Pro
                85                  90                  95

Thr Gln Thr Ser Pro Phe Gly Thr Gly Thr Lys Leu Thr Val Leu
            100                 105                 110

<210> SEQ ID NO 371
<211> LENGTH: 333
<212> TYPE: DNA
<213> ORGANISM: Homo sapiens
<220> FEATURE:
<223> OTHER INFORMATION: Antibody 28 VL/DNA

<400> SEQUENCE: 371
```

```
cagtctgtgc tgacgcagcc gccctcagtg tctggggccc cagggcagag ggtcaccatc    60
tcctgcactg ggagcagctc caacatcggg gcaggttatg atgtacactg gtatcagcaa   120
cttccaggaa cagcccccaa actcctcatc tatgataatt tcaatcggcc ctcaggggtc   180
cctgaccgat tctctggctc caagtctggc acctcagcct ccctggccat cattgggctc   240
cagactgaag atgaggctga ttattattgc cagtcctatg acagctcctc cctccactcg   300
cccttcggaa ccgggaccaa gctgaccgtc cta                                333

<210> SEQ ID NO 372
<211> LENGTH: 111
<212> TYPE: PRT
<213> ORGANISM: Homo sapiens
<220> FEATURE:
<223> OTHER INFORMATION: Antibody 28 VL/amino acid

<400> SEQUENCE: 372

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Asp Asn Phe Asn Arg Pro Ser Gly Val Pro Asp Arg Phe
    50                  55                  60

Ser Gly Ser Lys Ser Gly Thr Ser Ala Ser Leu Ala Ile Ile Gly Leu
65                  70                  75                  80

Gln Thr Glu Asp Glu Ala Asp Tyr Tyr Cys Gln Ser Tyr Asp Ser Ser
                85                  90                  95

Ser Leu His Ser Pro Phe Gly Thr Gly Thr Lys Leu Thr Val Leu
            100                 105                 110

<210> SEQ ID NO 373
<211> LENGTH: 333
<212> TYPE: DNA
<213> ORGANISM: Homo sapiens
<220> FEATURE:
<223> OTHER INFORMATION: Antibody 8 GL

<400> SEQUENCE: 373
cagtctgtgc tgacgcagcc gccctcagtg tctggggccc cagggcagag ggtcaccatc    60
tcctgcactg ggagcagctc caacatcggg gcaggttatg atgtacactg gtatcagcaa   120
cttccaggaa cagcccccaa actcctcatc tatgataatt tcaatcggcc ctcaggggtc   180
cctgaccgat tctctggctc caagtctggc acctcagcct ccctggccat cactgggctc   240
caggctgaag atgaggctga ttattattgc cagtcctatg acagccccac ccacacctcc   300
cccttcggaa ccgggaccaa gctgaccgtc cta                                333

<210> SEQ ID NO 374
<211> LENGTH: 111
<212> TYPE: PRT
<213> ORGANISM: Homo sapiens
<220> FEATURE:
<223> OTHER INFORMATION: Antibody 8 GL

<400> SEQUENCE: 374

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
```

```
                20                  25                  30
Tyr Asp Val His Trp Tyr Gln Gln Leu Pro Gly Thr Ala Pro Lys Leu
            35                  40                  45

Leu Ile Tyr Asp Asn Phe Asn Arg Pro Ser Gly Val Pro Asp Arg Phe
        50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Pro
                85                  90                  95

Thr His Thr Ser Pro Phe Gly Thr Gly Thr Lys Leu Thr Val Leu
            100                 105                 110

<210> SEQ ID NO 375
<211> LENGTH: 333
<212> TYPE: DNA
<213> ORGANISM: Homo sapiens
<220> FEATURE:
<223> OTHER INFORMATION: Antibody 8 PGL VL/DNA

<400> SEQUENCE: 375
cagtctgtgc tgacgcagcc gccctcagtg tctggggccc cagggcagag ggtcaccatc      60
tcctgcactg ggagcagctc aacatcggg gcaggttatg atgtacactg gtatcagcaa      120
cttccaggaa cagcccccaa actcctcatc tatgataatt tcaatcggcc ctcaggggtc     180
cctgaccgat tctctggctc caagtctggc acctcagcct ccctggccat cactgggctc     240
caggctgaag atgaggctga ttattattgc cagtcctatg acagccccac ccacacctcc     300
cccttcggaa ccgggaccaa gctgaccgtc cta                                  333

<210> SEQ ID NO 376
<211> LENGTH: 111
<212> TYPE: PRT
<213> ORGANISM: Homo sapiens
<220> FEATURE:
<223> OTHER INFORMATION: Antibody 8 PGL VL/amino acid

<400> SEQUENCE: 376

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Asp Asn Phe Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Pro
                85                  90                  95

Thr His Thr Ser Pro Phe Gly Thr Gly Thr Lys Leu Thr Val Leu
            100                 105                 110

<210> SEQ ID NO 377
<211> LENGTH: 333
<212> TYPE: DNA
<213> ORGANISM: Homo sapiens
<220> FEATURE:
<223> OTHER INFORMATION: Antibody 11 GL VL/DNA

<400> SEQUENCE: 377
```

```
cagtctgtgc tgacgcagcc gccctcagtg tctggggccc cagggcagag ggtcaccatc      60
tcctgcactg ggagcagctc caacatcggg gcaggttatg atgtacactg gtatcagcaa     120
cttccaggaa cagcccccaa actcctcatc tatgataatt tcaatcggcc ctcaggggtc     180
cctgaccgat tctctggctc caagtctggc acctcagcct ccctggccat cactgggctc     240
caggctgaag atgaggctga ttattattgc cagtcctatg acagcccac cctcacctcc      300 cccttcggaa ccgggaccaa gctgaccgtc cta                                  333
```

<210> SEQ ID NO 378
<211> LENGTH: 111
<212> TYPE: PRT
<213> ORGANISM: Homo sapiens
<220> FEATURE:
<223> OTHER INFORMATION: Antibody 11 GL VL/DNA

<400> SEQUENCE: 378

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Asp Asn Phe Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Pro
                85                  90                  95

Thr Leu Thr Ser Pro Phe Gly Thr Gly Thr Lys Leu Thr Val Leu
            100                 105                 110
```

<210> SEQ ID NO 379
<211> LENGTH: 333
<212> TYPE: DNA
<213> ORGANISM: Homo sapiens
<220> FEATURE:
<223> OTHER INFORMATION: Antibody 11 PGL VL/DNA

<400> SEQUENCE: 379

```
cagtctgtgc tgacgcagcc gccctcagtg tctggggccc cagggcagag ggtcaccatc      60
tcctgcactg ggagcagctc caacatcggg gcaggttatg atgtacactg gtatcagcaa     120
cttccaggaa cagcccccaa actcctcatc tatgataatt tcaatcggcc ctcaggggtc     180
cctgaccgat tctctggctc caagtctggc acctcagcct ccctggccat cactgggctc     240
caggctgaag atgaggctga ttattattgc cagtcctatg acagcccac cctcacctcc      300 cccttcggaa ccgggaccaa gctgaccgtc cta                                  333
```

<210> SEQ ID NO 380
<211> LENGTH: 111
<212> TYPE: PRT
<213> ORGANISM: Homo sapiens
<220> FEATURE:
<223> OTHER INFORMATION: Antibody 11 PGL VL/amino acid

<400> SEQUENCE: 380

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30
```

| Tyr | Asp | Val | His | Trp | Tyr | Gln | Gln | Leu | Pro | Gly | Thr | Ala | Pro | Lys | Leu |
|---|---|---|---|---|---|---|---|---|---|---|---|---|---|---|---|
| | | | 35 | | | | 40 | | | | 45 | | | | |

Leu Ile Tyr Asp Asn Phe Asn Arg Pro Ser Gly Val Pro Asp Arg Phe
 50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Pro
                 85                  90                  95

Thr Leu Thr Ser Pro Phe Gly Thr Gly Thr Lys Leu Thr Val Leu
             100                 105                 110

<210> SEQ ID NO 381
<211> LENGTH: 789
<212> TYPE: DNA
<213> ORGANISM: Macaca fascicularis
<220> FEATURE:
<223> OTHER INFORMATION: Cynomolgus Ce3-4 FLAG His10 nucleotide

<400> SEQUENCE: 381

```
atgggatgga gttgcattat actgttttg gttgccaccg ctactggtgc gcactctgcg      60
gacccctgtg actctaatcc caggggagtg agcgcatatc tcagcaggcc atcccctttc    120
gatcttttca tcagcaagag cccaacaata acttgcctgg tagtcgatct cgcaccatcc    180
aaggaaaccg tcaatcttac atggagcaga gcatcaggta agcctgttcc tcacatacct    240
gcaactgaaa aaaacagca gaggaacggt actctcacgg tgactagtat ccttccggtg    300
gtcacccagg attggattga gggagagact taccagtgcc gggtcacaca ccctcacctg    360
ccgcgagcac tggtgcgctc catgacaaag acgtccgggc cacgcgcggc tcccgaggtg    420
tacgtttttg ccacccccga gaaactcgag agccgcgaca gcggacact tgcctgcctg    480
atcgagaact ttatgcctga agatatctct gttcagtggc tgcacagtga tgtgcaactt    540
cccgatgcac gccacagtgt tacccagccc aggaagacca aggtagtgg cttcttcgtg    600
tttccccgcc tcgaggtgac caaggcagaa tgggagcaaa aggatgaatt tatctgcaga    660
gcggtgcatg aagccgcgtc cccttcctgg atcgtacagc aggccgtcag tgtgaatcct    720
gggaaggact ataaggatga tgacgacaag gccgcacacc accatcacca tcatcatcac    780
catcactag                                                             789
```

<210> SEQ ID NO 382
<211> LENGTH: 262
<212> TYPE: PRT
<213> ORGANISM: Macaca fascicularis
<220> FEATURE:
<223> OTHER INFORMATION: Cynomolgus Ce3-4 FLAG His10 protein

<400> SEQUENCE: 382

Met Gly Trp Ser Cys Ile Ile Leu Phe Leu Val Ala Thr Ala Thr Gly
1               5                   10                  15

Ala His Ser Ala Asp Pro Cys Asp Ser Asn Pro Arg Gly Val Ser Ala
                 20                  25                  30

Tyr Leu Ser Arg Pro Ser Pro Phe Asp Leu Phe Ile Ser Lys Ser Pro
             35                  40                  45

Thr Ile Thr Cys Leu Val Val Asp Leu Ala Pro Ser Lys Glu Thr Val
         50                  55                  60

Asn Leu Thr Trp Ser Arg Ala Ser Gly Lys Pro Val Pro His Ile Pro
65                  70                  75                  80

Ala Thr Glu Lys Lys Gln Gln Arg Asn Gly Thr Leu Thr Val Thr Ser

```
                    85                  90                  95
Ile Leu Pro Val Val Thr Gln Asp Trp Ile Glu Gly Glu Thr Tyr Gln
            100                 105                 110

Cys Arg Val Thr His Pro His Leu Pro Arg Ala Leu Val Arg Ser Met
            115                 120                 125

Thr Lys Thr Ser Gly Pro Arg Ala Pro Glu Val Tyr Val Phe Ala
130                 135                 140

Thr Pro Glu Lys Leu Glu Ser Arg Asp Lys Arg Thr Leu Ala Cys Leu
145                 150                 155                 160

Ile Glu Asn Phe Met Pro Glu Asp Ile Ser Val Gln Trp Leu His Ser
                165                 170                 175

Asp Val Gln Leu Pro Asp Ala Arg His Ser Val Thr Gln Pro Arg Lys
            180                 185                 190

Thr Lys Gly Ser Gly Phe Phe Val Phe Ser Arg Leu Glu Val Thr Lys
            195                 200                 205

Ala Glu Trp Glu Gln Lys Asp Glu Phe Ile Cys Arg Ala Val His Glu
            210                 215                 220

Ala Ala Ser Pro Ser Trp Ile Val Gln Gln Ala Val Ser Val Asn Pro
225                 230                 235                 240

Gly Lys Asp Tyr Lys Asp Asp Asp Lys Ala Ala His His His
                245                 250                 255

His His His His His His
            260

<210> SEQ ID NO 383
<211> LENGTH: 1701
<212> TYPE: DNA
<213> ORGANISM: Macaca fascicularis
<220> FEATURE:
<223> OTHER INFORMATION: D12_VHcyIgHE TQ nucleotide

<400> SEQUENCE: 383
atgggatgga gctgtatcat cctcttcttg gtagcaacag ctacaggcgc gcactccgag      60
gtgcagctgg tggagtctgg gggaggcttg gtacagcctg gaggtccct  gagactctcc     120 tgtgcagcct ctggagtcac ctttagcagc catgccatga cctgggtccg ccaggctcca    180 gggaagggc  tggaatgggt ctcaggtatc agtggtagtg gtggtgacac ataccacgca    240
gactccgtga agggccggtt caccatctcc aggacaatt  ccaagaacac ggtgtatctg    300
caaatgaaca gcctgcgagc cgaggacacg gccatatatt actgtgcgat tttaggagta    360
ctaaatggtt ttgatatctg gggccaaggg acaatggtca ccgtctcctc agcctccata    420
cagagcccct tcgtcttccc cttgatcccc tgctgcaaac acattgcctc caatgccacc    480
tccgtgaccc tgggctgcct ggccacgggc tacttcccgg agccggtgat ggtgacctgg    540
gacgcaggct ccctcaacag aagcactatg accttaccag ccaccacctt cacgccctcc    600
ggtcactatg ccaccatcag cttgctgacc gtctcgggtg cgtgggccaa ggagacgttc    660
acctgccatg tggtcacac  tccatcgtcc gcagacaaag aggtcaacaa aacctttggc    720
gtctgctcca ggaacttcac cccacctacc gtgaagatct acagtcatc  ctgcgatgac    780 gacgggcact tccccccgac catccagctc ctgtgcctca tctccgggta caccccaggg    840
gccatcaatg tcacctggct ggagaacggg caggtcatga agtgaactc  gcccacccct    900 cctgccacgc aggagggtga gctggcctcc acacaaagtg agttcaccct cgcccagaag    960
cactggctgt cggaccgcac ttacacctgc caggtcacct atcaaggtac cacctataac   1020
gacagcacca agaagtgtgc agattccaac ccgagagggg tgagtgccta cctaagccgg   1080
```

-continued

```
cccagcccgt tgacctgtt catcagcaag tcgcccacga tcacctgtct ggtggtggac    1140
ctggcaccca gcaaggagac cgtgaacctg acctggtccc gggccagtgg gaagcctgtg    1200
ccccacatcc ccgcaacgga gaagaagcag cagcgcaatg gcacgttaac cgttacgtcc    1260
atcctgccgg tggtcaccca agactggatc gaggggagaa cctaccagtg cagggtgacc    1320
cacccccacc tccccagggc cctcgtgcgg tccatgacca agaccagcgg cccgcgtgct    1380
gccccggaag tctatgtgtt tgcaacgcca gagaagctag agagccggga caagcgcacc    1440
ctcgcctgcc tgatccagaa cttcatgcct gaggacatat cggtgcagtg gctgcacagc    1500
gacgtgcagc tcccggacgc ccggcacagc gtgacgcagc cccgcaagac caagggctcc    1560
ggcttcttcg tcttcagccg cctggaggtg accaaggccg aatgggagca gaaagacgag    1620
ttcatctgcc gtgcagtcca tgaggcagcg agcccctcat ggatcgtcca gcaagcggtg    1680
tctgtaaatc ccggtaaatg a                                              1701
```

<210> SEQ ID NO 384
<211> LENGTH: 566
<212> TYPE: PRT
<213> ORGANISM: Macaca fascicularis
<220> FEATURE:
<223> OTHER INFORMATION: D12_VH cyIgHE TQ protein

<400> SEQUENCE: 384

```
Met Gly Trp Ser Cys Ile Ile Leu Phe Leu Val Ala Thr Ala Thr Gly
1               5                   10                  15

Ala His Ser Glu Val Gln Leu Val Glu Ser Gly Gly Gly Leu Val Gln
            20                  25                  30

Pro Gly Arg Ser Leu Arg Leu Ser Cys Ala Ala Ser Gly Val Thr Phe
        35                  40                  45

Ser Ser His Ala Met Thr Trp Val Arg Gln Ala Pro Gly Lys Gly Leu
    50                  55                  60

Glu Trp Val Ser Gly Ile Ser Gly Ser Gly Gly Asp Thr Tyr His Ala
65                  70                  75                  80

Asp Ser Val Lys Gly Arg Phe Thr Ile Ser Arg Asp Asn Ser Lys Asn
                85                  90                  95

Thr Val Tyr Leu Gln Met Asn Ser Leu Arg Ala Glu Asp Thr Ala Ile
            100                 105                 110

Tyr Tyr Cys Ala Ile Leu Gly Val Leu Asn Gly Phe Asp Ile Trp Gly
        115                 120                 125

Gln Gly Thr Met Val Thr Val Ser Ser Ala Ser Ile Gln Ser Pro Phe
    130                 135                 140

Val Phe Pro Leu Ile Pro Cys Cys Lys His Ile Ala Ser Asn Ala Thr
145                 150                 155                 160

Ser Val Thr Leu Gly Cys Leu Ala Thr Gly Tyr Phe Pro Glu Pro Val
                165                 170                 175

Met Val Thr Trp Asp Ala Gly Ser Leu Asn Arg Ser Thr Met Thr Leu
            180                 185                 190

Pro Ala Thr Thr Phe Thr Pro Ser Gly His Tyr Ala Thr Ile Ser Leu
        195                 200                 205

Leu Thr Val Ser Gly Ala Trp Ala Lys Glu Thr Phe Thr Cys His Val
    210                 215                 220

Val His Thr Pro Ser Ser Ala Asp Lys Glu Val Asn Lys Thr Phe Gly
225                 230                 235                 240

Val Cys Ser Arg Asn Phe Thr Pro Pro Thr Val Lys Ile Leu Gln Ser
                245                 250                 255
```

Ser Cys Asp Asp Asp Gly His Phe Pro Pro Thr Ile Gln Leu Leu Cys
        260                 265                 270

Leu Ile Ser Gly Tyr Thr Pro Gly Ala Ile Asn Val Thr Trp Leu Glu
        275                 280                 285

Asn Gly Gln Val Met Lys Val Asn Ser Pro Thr Pro Ala Thr Gln
290                 295                 300

Glu Gly Glu Leu Ala Ser Thr Gln Ser Glu Phe Thr Leu Ala Gln Lys
305                 310                 315                 320

His Trp Leu Ser Asp Arg Thr Tyr Thr Cys Gln Val Thr Tyr Gln Gly
                325                 330                 335

Thr Thr Tyr Asn Asp Ser Thr Lys Lys Cys Ala Asp Ser Asn Pro Arg
                340                 345                 350

Gly Val Ser Ala Tyr Leu Ser Arg Pro Ser Pro Phe Asp Leu Phe Ile
                355                 360                 365

Ser Lys Ser Pro Thr Ile Thr Cys Leu Val Val Asp Leu Ala Pro Ser
370                 375                 380

Lys Glu Thr Val Asn Leu Thr Trp Ser Arg Ala Ser Gly Lys Pro Val
385                 390                 395                 400

Pro His Ile Pro Ala Thr Glu Lys Lys Gln Gln Arg Asn Gly Thr Leu
                405                 410                 415

Thr Val Thr Ser Ile Leu Pro Val Val Thr Gln Asp Trp Ile Glu Gly
                420                 425                 430

Glu Thr Tyr Gln Cys Arg Val Thr His Pro His Leu Pro Arg Ala Leu
                435                 440                 445

Val Arg Ser Met Thr Lys Thr Ser Gly Pro Arg Ala Ala Pro Glu Val
450                 455                 460

Tyr Val Phe Ala Thr Pro Glu Lys Leu Glu Ser Arg Asp Lys Arg Thr
465                 470                 475                 480

Leu Ala Cys Leu Ile Gln Asn Phe Met Pro Glu Asp Ile Ser Val Gln
                485                 490                 495

Trp Leu His Ser Asp Val Gln Leu Pro Asp Ala Arg His Ser Val Thr
                500                 505                 510

Gln Pro Arg Lys Thr Lys Gly Ser Gly Phe Phe Val Phe Ser Arg Leu
                515                 520                 525

Glu Val Thr Lys Ala Glu Trp Glu Gln Lys Asp Glu Phe Ile Cys Arg
                530                 535                 540

Ala Val His Glu Ala Ala Ser Pro Ser Trp Ile Val Gln Gln Ala Val
545                 550                 555                 560

Ser Val Asn Pro Gly Lys
                565

<210> SEQ ID NO 385
<211> LENGTH: 1701
<212> TYPE: DNA
<213> ORGANISM: Macaca fascicularis
<220> FEATURE:
<223> OTHER INFORMATION: D12_VH cyIgHE ME nucleotide

<400> SEQUENCE: 385
atgggatgga gctgtatcat cctcttcttg gtagcaacag ctacaggcgc gcactccgag    60
gtgcagctgg tggagtctgg gggaggcttg gtacagcctg gaggtccct gagactctcc    120 tgtgcagcct ctggagtcac ctttagcagc catgccatga cctgggtccg ccaggctcca    180 gggaagggc tggaatgggt ctcaggtatc agtggtagtg gtggtgacac ataccacgca    240
gactccgtga agggccggtt caccatctcc aggacaatt ccaagaacac ggtgtatctg    300

```
caaatgaaca gcctgcgagc cgaggacacg gccatatatt actgtgcgat tttaggagta      360
ctaaatggtt ttgatatctg gggccaaggg acaatggtca ccgtctcctc agcctccata      420
cagagcccct tcgtcttccc cttgatcccc tgctgcaaac acattgcctc caatgccacc      480
tccgtgaccc tgggctgcct ggccacgggc tacttcccgg agccggtgat ggtgacctgg      540
gacgcaggct ccctcaacag aagcactatg accttaccag ccaccacctt cacgccctcc      600
ggtcactatg ccaccatcag cttgctgacc gtctcgggtg cgtgggccaa ggagatgttc      660
acctgccatg tggtgcacac tccatcgtcc gcagacaaag aggtcaacaa aacctttggc      720
gtctgctcca ggaacttcac cccacctacc gtgaagatct acagtcatc  ctgcgatgac      780 gacgggcact tccccccgac catccagctc ctgtgcctca tctccgggta caccccaggg      840
gccatcaatg tcacctggct ggagaacggg caggtcatga aagtgaactc gcccacccct      900
cctgccacgc aggagggtga gctggcctcc acacaaagtg agttcaccct cgcccagaag      960
cactggctgt cggaccgcac ttacacctgc caggtcacct atcaaggtac cacctataac     1020
gacagcacca agaagtgtgc agattccaac ccgagagggg tgagtgccta cctaagccgg     1080
cccagcccgt ttgacctgtt catcagcaag tcgcccacga tcacctgtct ggtggtggac     1140
ctggcaccca gcaaggagac cgtgaacctg acctggtccc gggccagtgg aagcctgtg      1200 ccccacatcc ccgcaacgga gaagaagcag cagcgcaatg cacgttaac  cgttacgtcc     1260 atcctgccgg tggtcaccca agactggatc gaggggagag cctaccagtg cagggtgacc     1320 caccccacc  tccccaggc  cctcgtgcgg tccatgacca agaccagcgg cccgcgtgct     1380
gccccggaag tctatgtgtt tgcaacgcca gagaagctag agagccggga caagcgcacc     1440
ctcgcctgcc tgatcgagaa cttcatgcct gaggacatat cggtcagtg  gctgcacagc     1500 gacgtgcagc tcccggacgc ccggcacagc gtgacgcagc cccgcaagac caagggctcc     1560
ggcttcttcg tcttcagccg cctggaggtg accaaggccg aatgggagca gaaagacgag     1620
ttcatctgcc gtgcagtcca tgaggcagcg agcccctcat ggatcgtcca gcaagcggtg     1680
tctgtaaatc ccggtaaatg a                                              1701
```

<210> SEQ ID NO 386
<211> LENGTH: 566
<212> TYPE: PRT
<213> ORGANISM: Macaca fascicularis
<220> FEATURE:
<223> OTHER INFORMATION: D12_VH cyIgHE ME protein

<400> SEQUENCE: 386

```
Met Gly Trp Ser Cys Ile Ile Leu Phe Leu Val Ala Thr Ala Thr Gly
1               5                   10                  15

Ala His Ser Glu Val Gln Leu Val Glu Ser Gly Gly Gly Leu Val Gln
                20                  25                  30

Pro Gly Arg Ser Leu Arg Leu Ser Cys Ala Ala Ser Gly Val Thr Phe
            35                  40                  45

Ser Ser His Ala Met Thr Trp Val Arg Gln Ala Pro Gly Lys Gly Leu
        50                  55                  60

Glu Trp Val Ser Gly Ile Ser Gly Ser Gly Gly Asp Thr Tyr His Ala
65                  70                  75                  80

Asp Ser Val Lys Gly Arg Phe Thr Ile Ser Arg Asp Asn Ser Lys Asn
                85                  90                  95

Thr Val Tyr Leu Gln Met Asn Ser Leu Arg Ala Glu Asp Thr Ala Ile
                100                 105                 110
```

```
Tyr Tyr Cys Ala Ile Leu Gly Val Leu Asn Gly Phe Asp Ile Trp Gly
            115                 120                 125

Gln Gly Thr Met Val Thr Val Ser Ser Ala Ser Ile Gln Ser Pro Phe
        130                 135                 140

Val Phe Pro Leu Ile Pro Cys Cys Lys His Ile Ala Ser Asn Ala Thr
145                 150                 155                 160

Ser Val Thr Leu Gly Cys Leu Ala Thr Gly Tyr Phe Pro Glu Pro Val
                165                 170                 175

Met Val Thr Trp Asp Ala Gly Ser Leu Asn Arg Ser Thr Met Thr Leu
            180                 185                 190

Pro Ala Thr Thr Phe Thr Pro Ser Gly His Tyr Ala Thr Ile Ser Leu
        195                 200                 205

Leu Thr Val Ser Gly Ala Trp Ala Lys Glu Met Phe Thr Cys His Val
210                 215                 220

Val His Thr Pro Ser Ser Ala Asp Lys Glu Val Asn Lys Thr Phe Gly
225                 230                 235                 240

Val Cys Ser Arg Asn Phe Thr Pro Pro Thr Val Lys Ile Leu Gln Ser
                245                 250                 255

Ser Cys Asp Asp Asp Gly His Phe Pro Pro Thr Ile Gln Leu Leu Cys
            260                 265                 270

Leu Ile Ser Gly Tyr Thr Pro Gly Ala Ile Asn Val Thr Trp Leu Glu
        275                 280                 285

Asn Gly Gln Val Met Lys Val Asn Ser Pro Thr Pro Pro Ala Thr Gln
290                 295                 300

Glu Gly Glu Leu Ala Ser Thr Gln Ser Glu Phe Thr Leu Ala Gln Lys
305                 310                 315                 320

His Trp Leu Ser Asp Arg Thr Tyr Thr Cys Gln Val Thr Tyr Gln Gly
                325                 330                 335

Thr Thr Tyr Asn Asp Ser Thr Lys Lys Cys Ala Asp Ser Asn Pro Arg
            340                 345                 350

Gly Val Ser Ala Tyr Leu Ser Arg Pro Ser Pro Phe Asp Leu Phe Ile
        355                 360                 365

Ser Lys Ser Pro Thr Ile Thr Cys Leu Val Val Asp Leu Ala Pro Ser
370                 375                 380

Lys Glu Thr Val Asn Leu Thr Trp Ser Arg Ala Ser Gly Lys Pro Val
385                 390                 395                 400

Pro His Ile Pro Ala Thr Glu Lys Lys Gln Gln Arg Asn Gly Thr Leu
                405                 410                 415

Thr Val Thr Ser Ile Leu Pro Val Val Thr Gln Asp Trp Ile Glu Gly
            420                 425                 430

Glu Thr Tyr Gln Cys Arg Val Thr His Pro His Leu Pro Arg Ala Leu
        435                 440                 445

Val Arg Ser Met Thr Lys Thr Ser Gly Pro Arg Ala Ala Pro Glu Val
450                 455                 460

Tyr Val Phe Ala Thr Pro Glu Lys Leu Glu Ser Arg Asp Lys Arg Thr
465                 470                 475                 480

Leu Ala Cys Leu Ile Glu Asn Phe Met Pro Glu Asp Ile Ser Val Gln
                485                 490                 495

Trp Leu His Ser Asp Val Gln Leu Pro Asp Ala Arg His Ser Val Thr
            500                 505                 510

Gln Pro Arg Lys Thr Lys Gly Ser Gly Phe Phe Val Phe Ser Arg Leu
        515                 520                 525

Glu Val Thr Lys Ala Glu Trp Glu Gln Lys Asp Glu Phe Ile Cys Arg
530                 535                 540
```

```
Ala Val His Glu Ala Ala Ser Pro Ser Trp Ile Val Gln Gln Ala Val
545                 550                 555                 560

Ser Val Asn Pro Gly Lys
                565
```

<210> SEQ ID NO 387
<211> LENGTH: 708
<212> TYPE: DNA
<213> ORGANISM: Macaca fascicularis
<220> FEATURE:
<223> OTHER INFORMATION: D12_VL cyIgLC 4 nucleotide

<400> SEQUENCE: 387

```
atgggttgga gttgtataat tctctttctg gtggctaccg ctaccggtgt gcactcccag      60
tcagctctga cgcaaccagc ttccgtttca gggagcccag ggcagagtat aaccatcagt     120
tgcactggca ctagctccga cgttggcgga tacaagtacg tatcttggta tcaacagcac     180
cccggaaaag ctcctaagct gatgattttc gaggtttcca acagaccag cggtgtacct      240
aatcggttct ctggctctaa atccgggaac actgcctcac tcaccatcag cggactgcag     300
gtggaagacg aggcggacta ttattgcagc tctctcacca cgcgttac cgtcatttt       360
ggcggaggca ctaagctgac cgttctcggc caacctaaag ccgccccatc tgtgacccct     420
tttcctccca gcagcgagga actgcaggcc aataaggcca ctctcgtgtg cctcatgtca     480
gactttttacc cagggatcct gaccgtgacc tggaaggccg acggaacccc catcacacag     540
ggcgtggaaa tgaccacgcc aagtaagcag tctaacaaca aatacgccgc atctagctac     600
ttgagcctga ccccagagca gtggcggagt cacaatagct acagctgcca agtgatgcac     660
gagggatcaa tcgtggagaa gactgttgct ccagccgagt gctcctaa                 708
```

<210> SEQ ID NO 388
<211> LENGTH: 235
<212> TYPE: PRT
<213> ORGANISM: Macaca fascicularis
<220> FEATURE:
<223> OTHER INFORMATION: D12_VL cyIgLC 4 protein

<400> SEQUENCE: 388

```
Met Gly Trp Ser Cys Ile Ile Leu Phe Leu Val Ala Thr Ala Thr Gly
1               5                   10                  15

Val His Ser Gln Ser Ala Leu Thr Gln Pro Ala Ser Val Ser Gly Ser
                20                  25                  30

Pro Gly Gln Ser Ile Thr Ile Ser Cys Thr Gly Thr Ser Ser Asp Val
            35                  40                  45

Gly Gly Tyr Lys Tyr Val Ser Trp Tyr Gln Gln His Pro Gly Lys Ala
        50                  55                  60

Pro Lys Leu Met Ile Phe Glu Val Ser Asn Arg Pro Ser Gly Val Pro
65                  70                  75                  80

Asn Arg Phe Ser Gly Ser Lys Ser Gly Asn Thr Ala Ser Leu Thr Ile
                85                  90                  95

Ser Gly Leu Gln Val Glu Asp Glu Ala Asp Tyr Tyr Cys Ser Ser Leu
            100                 105                 110

Thr Arg Arg Val Thr Val Ile Phe Gly Gly Gly Thr Lys Leu Thr Val
        115                 120                 125

Leu Gly Gln Pro Lys Ala Ala Pro Ser Val Thr Leu Phe Pro Pro Ser
    130                 135                 140

Ser Glu Glu Leu Gln Ala Asn Lys Ala Thr Leu Val Cys Leu Met Ser
145                 150                 155                 160
```

Asp Phe Tyr Pro Gly Ile Leu Thr Val Thr Trp Lys Ala Asp Gly Thr
            165                 170                 175

Pro Ile Thr Gln Gly Val Glu Met Thr Thr Pro Ser Lys Gln Ser Asn
            180                 185                 190

Asn Lys Tyr Ala Ala Ser Ser Tyr Leu Ser Leu Thr Pro Glu Gln Trp
            195                 200                 205

Arg Ser His Asn Ser Tyr Ser Cys Gln Val Met His Glu Gly Ser Ile
            210                 215                 220

Val Glu Lys Thr Val Ala Pro Ala Glu Cys Ser
225                 230                 235

<210> SEQ ID NO 389
<211> LENGTH: 708
<212> TYPE: DNA
<213> ORGANISM: Macaca fascicularis
<220> FEATURE:
<223> OTHER INFORMATION: D12_VL cyIgLC 7 nucleotide

<400> SEQUENCE: 389
atgggttgga gttgtataat tctctttctg gtggctaccg ctaccggtgt gcactcccag      60
tcagctctga cgcaaccagc ttccgtttca gggagcccag ggcagagtat aaccatcagt     120
tgcactggca ctagctccga cgttggcgga tacaagtacg tatcttggta tcaacagcac     180
cccggaaaag ctcctaagct gatgattttc gaggtttcca acagacccag cggtgtacct     240
aatcggttct ctggctctaa atccgggaac actgcctcac tcaccatcag cggactgcag     300
gtggaagacg aggcggacta ttattgcagc tctctcacca gacgcgttac cgtcattttt     360
ggcgggggga ctaagctgac cgttctcggc caacctaaag ccgccccctc tgtgaccctt     420
tttcccccta gcagcgagga actgcaggcc aataaggcca ctctcgtgtg cctcatctca     480 gactttttacc caggggccgt ggaggtggcc tggaaggccg acggaagcgc cgtcaacgcg     540
ggcgtggaaa cgaccaagcc aagtaagcag tctaacaaca aatacgccgc atctagctac     600
ttgagcctga cctcagacca gtggaagagt cacaagagct acagctgcca agtgacacac     660
gagggatcaa ccgtggagaa gactgttgct ccaaccgagt gctcctaa                  708

<210> SEQ ID NO 390
<211> LENGTH: 235
<212> TYPE: PRT
<213> ORGANISM: Macaca fascicularis
<220> FEATURE:
<223> OTHER INFORMATION: D12_VL cyIgLC 7 protein

<400> SEQUENCE: 390

Met Gly Trp Ser Cys Ile Ile Leu Phe Leu Val Ala Thr Ala Thr Gly
1               5                   10                  15

Val His Ser Gln Ser Ala Leu Thr Gln Pro Ala Ser Val Ser Gly Ser
            20                  25                  30

Pro Gly Gln Ser Ile Thr Ile Ser Cys Thr Gly Thr Ser Ser Asp Val
            35                  40                  45

Gly Gly Tyr Lys Tyr Val Ser Trp Tyr Gln Gln His Pro Gly Lys Ala
        50                  55                  60

Pro Lys Leu Met Ile Phe Glu Val Ser Asn Arg Pro Ser Gly Val Pro
65                  70                  75                  80

Asn Arg Phe Ser Gly Ser Lys Ser Gly Asn Thr Ala Ser Leu Thr Ile
                85                  90                  95

Ser Gly Leu Gln Val Glu Asp Glu Ala Asp Tyr Tyr Cys Ser Ser Leu
            100                 105                 110

Thr Arg Arg Val Thr Val Ile Phe Gly Gly Gly Thr Lys Leu Thr Val
         115                 120                 125

Leu Gly Gln Pro Lys Ala Ala Pro Ser Val Thr Leu Phe Pro Pro Ser
         130                 135                 140

Ser Glu Glu Leu Gln Ala Asn Lys Ala Thr Leu Val Cys Leu Ile Ser
145                 150                 155                 160

Asp Phe Tyr Pro Gly Ala Val Glu Val Ala Trp Lys Ala Asp Gly Ser
                 165                 170                 175

Ala Val Asn Ala Gly Val Glu Thr Thr Lys Pro Ser Lys Gln Ser Asn
                 180                 185                 190

Asn Lys Tyr Ala Ala Ser Ser Tyr Leu Ser Leu Thr Ser Asp Gln Trp
         195                 200                 205

Lys Ser His Lys Ser Tyr Ser Cys Gln Val Thr His Glu Gly Ser Thr
         210                 215                 220

Val Glu Lys Thr Val Ala Pro Thr Glu Cys Ser
225                 230                 235

<210> SEQ ID NO 391
<211> LENGTH: 1555
<212> TYPE: DNA
<213> ORGANISM: Homo sapiens
<220> FEATURE:
<223> OTHER INFORMATION: FceRI_Fc (NSO) nucleotide

<400> SEQUENCE: 391
gaattcagca cagtaagcac caggagtcca tgaagaagat ggctcctgcc atggaatccc      60
ctactctact gtgtgtagcc ttactgttct tcgctccaga tggcgtgtta gcagtccctc     120
agaaacctaa ggtctccttg aaccctccat ggaataagaat atttaaagga gagaatgtga    180
ctcttacatg taatgggaac aatttctttg aagtcagttc caccaaatgg ttccacaatg     240
gcagcctttc agaagagaca aattcaagtt tgaatattgt gaatgccaaa tttgaagaca     300
gtggagaata caaatgtcag caccaacaag ttaatgagag tgaacctgtg tacctggaag     360
tcttcagtga ctggctgctc cttcaggcct ctgctgaggt ggtgatggag gccagcccc     420 tcttcctcag gtgccatggt tggaggaact gggatgtgta caaggtgatc tattataagg     480
atggtgaagc tctcaagtac tggtatgaga ccacaacat ctccattaca aatgccacag     540
ttgaagacag tggaacctac tactgtacgg gcaaagtgtg gcagctggac tatgagtctg     600 agccctcaa cattactgta ataaaagctc ctcgagagaa gtactggcta gacaaaactc      660
acacatgccc accgtgccca ggtaagccag cccaggcctc gccctccagc tcaaggcggg    720
acaggtgccc tagggtagcc tgcatccagg acaggcccc agccgggtgc tgacacgtcc     780
acctccatct cttcctcagc acctgaactc ctggggggac cgtcagtctt cctcttcccc     840
ccaaaaccca aggacaccct catgatctcc cggacccctg aggtcacatg cgtggtggtg    900
gacgtgagcc acgaagaccc tgaggtcaag ttcaactggt acgtggacgg cgtggaggtg    960
cataatgcca agacaaagcc gcgggaggag cagtacaaca gcacgtaccg tgtggtcagc   1020
gtcctcaccg tcctgcacca ggactggctg aatggcaagg agtacaagtg caaggtctcc   1080
aacaaagccc tcccagcccc catcgagaaa accatctcca agccaaaggt gggacccgt    1140 ggggtgcgag ggccacatgg acagaggccg gctcggccca cctctgcc tgagagtgac     1200 cgctgtacca acctctgtcc ctacagggca gccccgagaa ccacaggtgt acaccctgcc   1260
cccatcccgg gatgagctga ccaagaacca ggtcagcctg acctgcctgg tcaaaggctt   1320
ctatcccagc gacatcgccg tggagtggga gagcaatggg cagccggaga acaactacaa   1380
gaccacgcct cccgtgctgg actccgacgg ctccttcttc ctctacagca agctcaccgt 1440
ggacaagagc aggtggcagc aggggaacgt cttctcatgc tccgtgatgc atgaggctct 1500
gcacaaccac tacacgcaga agagcctctc cttaagtccg ggaaaataat ctaga 1555

<210> SEQ ID NO 392
<211> LENGTH: 431
<212> TYPE: PRT
<213> ORGANISM: Homo sapiens
<220> FEATURE:
<223> OTHER INFORMATION: FceRI_Fc (NSO) protein

<400> SEQUENCE: 392

```
Met Ala Pro Ala Met Glu Ser Pro Thr Leu Leu Cys Val Ala Leu Leu
1               5                   10                  15

Phe Phe Ala Pro Asp Gly Val Leu Ala Val Pro Gln Lys Pro Lys Val
                20                  25                  30

Ser Leu Asn Pro Pro Trp Asn Arg Ile Phe Lys Gly Glu Asn Val Thr
            35                  40                  45

Leu Thr Cys Asn Gly Asn Asn Phe Phe Glu Val Ser Ser Thr Lys Trp
        50                  55                  60

Phe His Asn Gly Ser Leu Ser Glu Glu Thr Asn Ser Ser Leu Asn Ile
65                  70                  75                  80

Val Asn Ala Lys Phe Glu Asp Ser Gly Glu Tyr Lys Cys Gln His Gln
                85                  90                  95

Gln Val Asn Glu Ser Glu Pro Val Tyr Leu Glu Val Phe Ser Asp Trp
            100                 105                 110

Leu Leu Leu Gln Ala Ser Ala Glu Val Val Met Glu Gly Gln Pro Leu
        115                 120                 125

Phe Leu Arg Cys His Gly Trp Arg Asn Trp Asp Val Tyr Lys Val Ile
    130                 135                 140

Tyr Tyr Lys Asp Gly Glu Ala Leu Lys Tyr Trp Tyr Glu Asn His Asn
145                 150                 155                 160

Ile Ser Ile Thr Asn Ala Thr Val Glu Asp Ser Gly Thr Tyr Tyr Cys
                165                 170                 175

Thr Gly Lys Val Trp Gln Leu Asp Tyr Glu Ser Glu Pro Leu Asn Ile
            180                 185                 190

Thr Val Ile Lys Ala Pro Arg Glu Lys Tyr Trp Leu Asp Lys Thr His
        195                 200                 205

Thr Cys Pro Pro Cys Pro Ala Pro Glu Leu Leu Gly Gly Pro Ser Val
    210                 215                 220

Phe Leu Phe Pro Pro Lys Pro Lys Asp Thr Leu Met Ile Ser Arg Thr
225                 230                 235                 240

Pro Glu Val Thr Cys Val Val Asp Val Ser His Glu Asp Pro Glu
                245                 250                 255

Val Lys Phe Asn Trp Tyr Val Asp Gly Val Glu Val His Asn Ala Lys
            260                 265                 270

Thr Lys Pro Arg Glu Glu Gln Tyr Asn Ser Thr Tyr Arg Val Val Ser
        275                 280                 285

Val Leu Thr Val Leu His Gln Asp Trp Leu Asn Gly Lys Glu Tyr Lys
    290                 295                 300

Cys Lys Val Ser Asn Lys Ala Leu Pro Ala Pro Ile Glu Lys Thr Ile
305                 310                 315                 320

Ser Lys Ala Lys Gly Gln Pro Arg Glu Pro Gln Val Tyr Thr Leu Pro
                325                 330                 335
```

-continued

```
Pro Ser Arg Asp Glu Leu Thr Lys Asn Gln Val Ser Leu Thr Cys Leu
            340             345             350

Val Lys Gly Phe Tyr Pro Ser Asp Ile Ala Val Glu Trp Glu Ser Asn
            355             360             365

Gly Gln Pro Glu Asn Asn Tyr Lys Thr Thr Pro Pro Val Leu Asp Ser
    370             375             380

Asp Gly Ser Phe Phe Leu Tyr Ser Lys Leu Thr Val Asp Lys Ser Arg
385             390             395             400

Trp Gln Gln Gly Asn Val Phe Ser Cys Ser Val Met His Glu Ala Leu
                405             410             415

His Asn His Tyr Thr Gln Lys Ser Leu Ser Leu Ser Pro Gly Lys
            420             425             430
```